US005925522A

United States Patent [19]
Wong et al.

[11] Patent Number: 5,925,522
[45] Date of Patent: Jul. 20, 1999

[54] SALMONELLA NUCLEOTIDE SEQUENCES, METHODS OF DETECTION OF SALMONELLA NUCLEOTIDE SEQUENCES, AND METHOD OF DETECTION OF SALMONELLA

[75] Inventors: Kwong-Kwok Wong; Jeffrey D. Saffer, both of Richland, Wash.

[73] Assignee: Battelle Memorial Institute, Richland, Wash.

[21] Appl. No.: 08/853,659

[22] Filed: May 9, 1997

[51] Int. Cl.[6] .............................. C12Q 1/68; C12P 19/34; C07H 21/02; C07H 21/04

[52] U.S. Cl. .......................... 435/6; 435/91.2; 435/320.1; 536/24.32

[58] Field of Search ...................... 536/24.32; 435/320.1, 435/69.1, 6, 91.2

[56] References Cited

U.S. PATENT DOCUMENTS 5,571,639 11/1996 Hubbell et al. ............................ 430/5

OTHER PUBLICATIONS

High–Resolution Restriction Map for a 240–Kilobase Region Spanning 91 to 96 Minutes on the *Salmonella typhimurium* LT2 Chromosome, KK Wong, RM Wong, KE Rudd, M McClelland, Journal of Bacteriology, Sep. 1994, pp. 5729–5734.

Strategies to Accelerate the Applicability of Gene Amplification Protocols for Pathogen Detection in Meat and Meat Products, SD Pillai, SC Ricke, Critical Reviews in Microbiology 21(4):239–261 (1995).

Detection of *Salmonella gallinarum* and *S. typhimurium* DNA in Experimentally Infected Chicks by Polymerase Chain Reaction, LM Tuchili, H Kodama, Y Izumoto, M Mukamoto, T Fukata, T Baba, J Bet Med Sci 57:59–63(1995).

Comparison of the Polymerase Chain Reaction Using Genus–Specific Oligonucleotide Primers and Microbiologic Culture for the Detection of Salmonella in Drag–Swabs from Poultry Houses, ND Cohen, DE Wallis, HL Neibergs, AP McElroy, ED McGruder, JR DeLoach, DE Corrier, BM Hargis, Poult Sci 73:11276–81(1994).

A Simple, Rapid and Sensitive Detection of Salmonella In Food by Polymerase Chain Reaction, S Jitrapakdee, A Tassanakajon, V Boonsaeng, S Piankijagum, S Panyim, Mol Cell Probes 9:375–82(1995).

Combined PCR–Oligonucleotide Ligation Assay for Rapid Detection of Salmonella Serovars, GG Stone, RD Oberst, MP Hays, S McVey, MM Chengappa, J Clin Microbiol 33: 2888–93(1995).

Use of Two 16S DNA Targeted Oligonucleotides as PCR Primers for the Specific Detection of Salmonella in Foods, CK Lin, HY Tsen, J Appl Bacteriol 80:659–66(1996).

*Salmonella typhimurium* Loci Involved in Survival within macrophages, AJ Baumler, JG Kusters, I Stojiljkovic, F Heffron, Infection and Immunity, May, 1994, pp. 1623–1630.

Detection of Salmonella spp. In Eggs: DNA Analyses, Culture Techniques, and Serology, PW Burkhalter, C Muller, J Luthy, U Candrian, J AOAC Int 78:1531–7(1995).

*Primary Examiner*—Kenneth R. Horlick
*Attorney, Agent, or Firm*—Wells, St. John, Roberts, Gregory & Matkin, P.S.

[57] ABSTRACT

The invention encompasses purified and isolated Salmonella nucleotide fragments, methods of expressing and isolating polypeptides coded for by a Salmonella nucleotide sequence, methods for detecting the presence of Salmonella nucleotide sequences, methods for blocking transcription or translation of Salmonella nucleotide sequences, methods for blocking production or activity of polypeptide sequences from Salmonella nucleotide sequences, DNA chips containing Salmonella nucleotide sequences, and purified polypeptides expressed by Salmonella nucleotide sequences.

24 Claims, No Drawings

SALMONELLA NUCLEOTIDE SEQUENCES, METHODS OF DETECTION OF SALMONELLA NUCLEOTIDE SEQUENCES, AND METHOD OF DETECTION OF SALMONELLA

TECHNICAL FIELD

The invention pertains to purified and isolated Salmonella nucleotide fragments, methods of expressing and isolating polypeptides coded for by a Salmonella nucleotide sequence, methods for detecting the presence of Salmonella nucleotide sequences, methods for blocking transcription of Salmonella nucleotide sequences, methods for blocking production of polypeptide sequences from Salmonella nucleotide sequences, DNA chips containing Salmonella nucleotide sequences, and purified polypeptides expressed by Salmonella nucleotide sequences.

BACKGROUND OF THE INVENTION

Members of the genus Salmonella are ubiquitous pathogens found in humans and livestock, as well as in wild animals, reptiles, birds, insects and in the environment. Salmonella causes diseases such as gastroenteritis and enteric fever in both humans and animals. The World Health Organization (WHO) estimated that in the year 1980 Salmonella caused more than one billion cases of acute diarrhea in children under five years of age in developing countries, and that five million of these children died. (Garthright W. E., Archer D. L., Kvenberg J. E. (1988) *Estimates of Incidence and Costs of Intestinal Infectious Diseases in United States*. Public-Health Rep 103:107–115.) The worldwide incidents of Salmonellosis (food poisoning of humans infected with Salmonella) has been increasing during the 1980's and 1990's (Todd E. (1990) *Epidemiology of Food Borne Illness: North America*. Lancet 336:788–790; and Cooke E. M. (1990) *Epidemiology of Food Borne Illness: UK*. Lancet 336:790–793.) The costs of food borne gastroenteritis in the U.S. are astonishing. There are five different estimates summarized by Todd (1990) which range from 4.8 to 23 billion dollars per year; Salmonella infections are a major component of these costs.

The incidence of Salmonellosis has changed dramatically in the last few years. The incidence of typhoid fever caused by *S. typhi* has been greatly reduced in the developed world in the last 50 years. However, it is still a major disease in developing countries. At the same time, there has been a marked increase in the incidence of non-typhoid Salmonellosis in the United States and worldwide. Although non-typhoid Salmonellosis is often a self-limiting event, including symptoms like non-bloody diarrheal stools, nausea, abdominal pain, and vomiting, it can proceed to more serious complications in patients with underlying diseases such as HIV-AIDS, sickle cell anemia, liver and gall bladder diseases. *S. typhimurium* most commonly causes infections and disease in both humans and animals. *S. typhi* only infects humans, and causes the dreadful illness typhoid fever. Typhoid fever kills about 10% of all people infected.

Infection by non-typhoid Salmonella is usually caused by contaminated food or via animals or pets. Infection by *S. typhi* is frequently caused by food mishandling or by carriers, who may themselves appear healthy. Such apparently healthy carriers are referred to as "asymptomatic carriers" of *S. typhi*. Development into an asymptomatic carrier state is well known in the Salmonella infection progression. When employed as food handlers, chronic asymptomatic carriers can pose a serious threat to the public health. A classic example is Typhoid Mary, a New York City cook who spread typhoid fever to many people before she was apprehended and imprisoned for life. (Salyers A. A., and Whitt D. D. (1994) *In Bacterial Pathogenesis, a Molecular Approach* A.S.M. Press, Washington, D.C.)

It would be desirable to create a monitoring system for virulent strains of Salmonella utilizing modern comparative molecular genomic approaches.

Various current typing techniques that can distinguish between strains of microorganisms can be divided into two major categories: those based on phenotypic characteristics and those based on genotypic characteristics. The former techniques include isozyme electrophoresis, whole-cell protein profiling (Senior B. W., and Voros S. (1990) *Protein Profile Typing—a New Method of Typing Morganella morganii Strains* J. Medical Microbiol. 33:259–64), sugar metabolism profiling, total fatty acids profiling (Guerrant G., Lambert M. A., Moss C. W. (1982) *Analysis of Short-Chain Acids From Anaerobic Bacteria by High-Performance Liquid Chromatography* J. Clin. Microbiol. 16:355–360), and various immunoblotting techniques (Persing D., Smith T. F., Tenover F. C., White J. (eds.) (1993) *Diagnostic Molecular Microbiology* American Society For Microbiology, Washington, D.C.).

Typing techniques based on genotype characteristics include DNA-DNA hybridization, restriction enzyme analysis (RFLP), ribotyping (Bingen E. H., Denamur E., Elion J. (1994) *Use of Ribotyping in Epidemiological Surveillance of Nosocomial Outbreaks* Clin. Microbiol. Rev. 7:311–327), plasma profiling (Grattard F., Pozzetto B., Berthelot P., Rayet I., Ros A., Lauras B., Gaudian O. G. (1994) *Arbitrarily Primed PCR, Ribotyping, and Plasmid Pattern Analysis Applied to Investigation of a Nosocomial Outbreak Due to Enterobacter cloacae in a Neonatal Intensive Care Unit* J. Clin. Microbiol. 32:596–602), DNA fingerprinting by Arbitrarily Primed PCR (APPCR), (Welsh J., McClelland M. (1990) *Fingerprinting Genomes Usiniz PCR with Arbitrary Primers* Nucleic Acids, Res. 18:7213–7218), random amplified polymorphic DNA (RAPDs) (Williams J. G. K., Kubelik A. R., Livak K. J., Rafiliski J. A., Tingey S. V. (1990) *DNA Polymorphisms Amplified by Arbitrary Primers Are Useful as Genetic Markers* Nucleic Acids, Res. 18:6531–6535), and rep-PCR (Versalovic J., Koeuth T., Lupski J. R. (1991) *Distribution of Repetitive DNA Sequences in Eubacteria and Application to Fingerprinting of Bacterial Genomes* Nucleic Acids, Res. 19:6823–6831).

Among the currently available commercial diagnostic assays for Salmonella are miniaturized biochemical tests utilizing nucleic acid-based assays (Aabo S., Andersen J. K., Olsen J. E. (1995) *Research Note: Detection of Salmonella in Minced Meat by the Polymerase Chain Reaction Method* Lett. Appl. Microbiol. 21:180–2); Lin C. K., Tsen H. Y. (1995) *Development and Evaluation of Two Novel Oligonucleotide Probes Based on 16S rRNA Sequence in the Identification of Salmonella in Foods* J. Applied Bacteriol. 78:507–520); and Olsen J. E., Aabo S., Rasmussen O. F., Rossen L., (1995) *Oligonucleotide Probes Specific for the Genus Salmonella and for Salmonella typhimurium* Lett. Appl. Microbiol. 20:160–163), and antibody-based assays (Feng P. (1992) *Commercial Assay Systems for Detecting Food Borne Salmonella* J. Food Prot. 56:927).

Regardless of whether a phenotypically-based typing method is used or a genotypic-based typing method is used, a relatively pure culture of microorganisms is required. Currently available Salmonella typing procedures are generally not applicable for the detection of a single pathogen in a complex microbial flora due to limitations of the specificity and sensitivity of the typing procedures. For instance, Salmonella has a high degree of homogeneity with *E. coli*. Accordingly, a high degree of specificity is required to identify Salmonella in environments in which *E. coli* is also present. To overcome the specificity limitations of current Salmonella detection procedures, the procedures frequently require that a sample in which Salmonella is to be detected be subjected to Salmonella-specific growth conditions before subjecting the sample to DNA identification methods. (See, Quinn C., Ward J., Griffin M., Yearsley D., Egan J. (1995) *The Comparison of a Conventional Culture and Three Rapid Methods for the Detection of Salmonella in Poultry Feeds and Environmental Samples* Appl. Microbiol. 20:89–91; Cudjoe K. S., Hagtubeet, T., Dainty R. (1995) *Immunomagnetic Separation of Salmonella from Foods and their Detection Using Immunomagnetic Particle (IMP)-ELISA* Int. J. Food Microbiol. 27:11–25); and (Meer R. R., Park D. L. (1995) *Immunochemical Detection Methods for Salmonella SPP, Escherichia coli O157:87 and Listeria Monocytogenes in Foods* Rev. Environmental Contam. Toxicol. 142:1–12).

The Salmonella-specific growth conditions amplify the relative amount of Salmonella within the sample and thereby enrich the sample in Salmonella. However, such Salmonella enrichment procedures undesirably add time and expense to Salmonella detection methods. Accordingly, it would be desirable to develop Salmonella detection methods which could be used to identify Salmonella in a complex microbial flora without requiring Salmonella enrichment procedures. It would further be desirable to develop a method which could detect or recognize a Salmonella pathogen in sample directly obtained from tissues, food materials or the environment without requiring prior selective amplification of Salmonella within the sample.

A PCR-gene-probe based assay has potential for improving routine monitoring of Salmonella (Hanes D. E., Koch W. H., Miliotis M. D., Lampel K. A. (1995) *DNA Probe for Detecting Salmonella Enteritidis in Food*. Mol. Cellular Probes:9–18). However, more Salmonella-specific determinants have to be discovered before useful PCR-gene-probe assays can be utilized. Accordingly, it would be desirable to identify Salmonella-specific sequences which could be utilized as Salmonella-specific determinants.

Once a Salmonella-specific sequence is identified, a number of in-vitro gene amplification protocols may be utilized for detecting the determinant. Such gene application protocols include: polymerase chain reaction (PCR), ligase chain reaction (LCR), Qβ replicase amplifications, 3SR amplifications, and transcription-based amplification systems (TAS). (See, Pillai S. D. and Ricke S. C. (1995) *Strategies to Accelerate the Applicability of Gene Amplification Protocols for Pathogen Detection in Meat and Meat Products* Crit. Reviews in Microbiology, 21(4):239–261.) While gene amplification approaches have shown some promise, they also have shortcomings which have detracted from their usefulness inasmuch as the existing protocols require the time consuming and costly step of culture enrichment.

Also, once a Salmonella-specific sequence is identified and isolated it is conceivable that it could be attached to a chip to form a DNA chip. This could be subsequently utilized for detecting the presence of the identified Salmonella-specific determinant. (See, Chee M., Yang R., Hubbel E., Berno et al (1996) *Accessing Genetic Information With High-Density DNA Arrays* Science 274:610–614).

Currently, several efforts are underway to sequence various Salmonella species. For instance, a *Salmonella typhimurium* sequence, shown below as SEQ ID NO:1, has been identified by Baumler et. al. (See, Baumler A. J., Kusters J. G., Stojiljkovic I., Heffron F. (1994) *Salmonella typhimurium Loci Involved in Survival within Macrophages*, Infect. Immun. 62:1623–30.)

Other identified sequences of a Salmonella species are described by Wong et. al. (Wong K. K., Wong R. M., Rudd K. E., McClelland M. (1994) *High-Resolution Restriction Map for a 240-Kilobase Region Spanning 91 to 96 Minutes on the Salmonella typhimurium LT2 Chromosome* Journ. of Bacteriology, p. 5729–5734). Wong et. al. provides a restriction map for a 240-kilobase region of a *Salmonella typhimurium* LT2 chromosome.

It would be desirable to develop a means by which the genus Salmonella may be readily identified by gene amplification or other procedures, and which avoids the shortcoming attendant to the prior art techniques and practices.

Further, as Salmonella is responsible for much illness throughout the world, it would be desirable to develop procedures which block the virulence of Salmonella.

BRIEF DESCRIPTION OF THE BELOW-LISTED DNA SEQUENCES

SEQ ID NO:1 is a prior art Salmonella nucleotide sequence.

SEQ ID NO:2 is a Salmonella nucleotide (DNA) sequence of the present invention.

SEQ ID NO:3 is a Salmonella nucleotide (DNA) sequence which is complementary to SEQ ID NO:2.

SEQ ID NO:4 is a middle nucleotide (DNA) segment of SEQ ID NO:2 and which is somewhat complementary to SEQ ID NO: 1.

SEQ ID NO:5 is a nucleotide (DNA) segment of SEQ ID NO:2 and which is upstream from SEQ ID. NO:4.

SEQ ID NO:6 is a nucleotide (DNA) segment of SEQ ID NO:2 and which is downstream from SEQ ID. NO:4.

SEQ ID NO:7 is a nucleotide (DNA) segment of SEQ ID NO:3 and which is somewhat homologous to SEQ ID NO:1 and which is complementary to SEQ ID NO:4.

SEQ ID NO:8 is a nucleotide (DNA) segment of SEQ ID NO:3 and which is complementary to SEQ ID NO:5.

SEQ ID NO:9 is a nucleotide (DNA) segment of SEQ ID NO:3 and which is complementary to SEQ ID NO:6.

SEQ ID NO:10 is a coding region of SEQ ID NO:2.

SEQ ID NO:11 is a coding region of SEQ ID NO:2.

SEQ ID NO:12 is a coding region of SEQ ID NO:2.

SEQ ID NO:13 is a coding region of SEQ ID NO:2.

SEQ ID NO:14 is a coding region of SEQ ID NO:2.

SEQ ID NO:15 is a coding region of SEQ ID NO:2.

SEQ ID NO:16 is a coding region of SEQ ID NO:2.

SEQ ID NO:17 is a coding region of SEQ ID NO:2.

SEQ ID NO:18 is a coding region of SEQ ID NO:2.

SEQ ID NO:19 is a coding region of SEQ ID NO:2.

SEQ ID NO:20 is a coding region of SEQ ID NO:2.

SEQ ID NO:21 is a coding region of SEQ ID NO:2.

SEQ ID NO:22 is a coding region of SEQ ID NO:2.

SEQ ID NO:23 is a coding region of SEQ ID NO:2.

SEQ ID NO:24 is a coding region of SEQ ID NO:2.

SEQ ID NO:25 is a coding region of SEQ ID NO:2.

SEQ ID NO:26 is a coding region of SEQ ID NO:2.

SEQ ID NO:27 is a coding region of SEQ ID NO:2.

SEQ ID NO:28 is a coding region of SEQ ID NO:2.

SEQ ID NO:29 is a coding region of SEQ ID NO:3.

SEQ ID NO:30 is a coding region of SEQ ID NO:3.

SEQ ID NO:31 is a coding region of SEQ ID NO:3.

SEQ ID NO:32 is a coding region of SEQ ID NO:3.

SEQ ID NO:33 is a coding region of SEQ ID NO:3.

SEQ ID NO:34 is a coding region of SEQ ID NO:3.

SEQ ID NO:35 is a peptide sequence coded for by SEQ ID NO:10.

SEQ ID NO:36 is a peptide sequence coded for by SEQ ID NO:11.

SEQ ID NO:37 is a peptide sequence coded for by SEQ ID NO:12.

SEQ ID NO:38 is a peptide sequence coded for by SEQ ID NO:13.

SEQ ID NO:39 is a peptide sequence coded for by SEQ ID NO:14.

SEQ ID NO:40 is a peptide sequence coded for by SEQ ID NO:15.

SEQ ID NO:41 is a peptide sequence coded for by SEQ ID NO:16.

SEQ ID NO:42 is a peptide sequence coded for by SEQ ID NO:17.

SEQ ID NO:43 is a peptide sequence coded for by SEQ ID NO:18.

SEQ ID NO:44 is a peptide sequence coded for by SEQ ID NO:19.

SEQ ID NO:45 is a peptide sequence coded for by SEQ ID NO:20.

SEQ ID NO:46 is a peptide sequence coded for by SEQ ID NO:21.

SEQ ID NO:47 is a peptide sequence coded for by SEQ ID NO:22.

SEQ ID NO:48 is a peptide sequence coded for by SEQ ID NO:23.

SEQ ID NO:49 is a peptide sequence coded for by SEQ ID NO:24.

SEQ ID NO:50 is a peptide sequence coded for by SEQ ID NO:25.

SEQ ID NO:51 is a peptide sequence coded for by SEQ ID NO:26.

SEQ ID NO:52 is a peptide sequence coded for by SEQ ID NO:27.

SEQ ID NO:53 is a peptide sequence coded for by SEQ ID NO:28.

SEQ ID NO:54 is a peptide sequence coded for by SEQ ID NO:29.

SEQ ID NO:55 is a peptide sequence coded for by SEQ ID NO:30.

SEQ ID NO:56 is a peptide sequence coded for by SEQ ID NO:31.

SEQ ID NO:57 is a peptide sequence coded for by SEQ ID NO:32.

SEQ ID NO:58 is a peptide sequence coded for by SEQ ID NO:33.

SEQ ID NO:59 is a peptide sequence coded for by SEQ ID NO:34.

SEQ ID NO:60 is a nucleotide (RNA) sequence complementary to the DNA sequence of SEQ ID NO:3 and which contains codons corresponding to peptide sequences 35–53.

SEQ ID NO:61 is a nucleotide (RNA) sequence complementary to the DNA sequence of SEQ ID NO:2 and which contains codons corresponding to peptide sequences 54–59.

SEQ ID NO:62 is a nucleotide (RNA) sequence complementary to the DNA sequence of SEQ ID NO:7.

SEQ ID NO:63 is a nucleotide (RNA) sequence complementary to the DNA sequence of SEQ ID NO:8.

SEQ ID NO:64 is a nucleotide (RNA) sequence complementary to the DNA sequence of SEQ ID NO:9.

SEQ ID NO:65 is a nucleotide (RNA) sequence complementary to the DNA sequence of SEQ ID NO:4.

SEQ ID NO:66 is a nucleotide (RNA) sequence complementary to the DNA sequence of SEQ ID NO:5.

SEQ ID NO:67 is a nucleotide (RNA) sequence complementary to the DNA sequence of SEQ ID NO:6.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

Referring to SEQ ID NOs:2 and 3, these are complementary Salmonella nucleotide sequences of the present invention. For purposes of the following discussion, SEQ ID NO:2 may be referred to as a "first strand", and SEQ ID NO:3 may be referred to as a "second strand". SEQ ID NOs:2 and 3 are substantially specific to Salmonella, i.e., do not exist in, for example, *E. coli*, and therefore can be utilized in detection methods for Salmonella. SEQ ID NOs:2 and 3 are within the 240 kilobase region mapped by Wong, et. al. and described above in the background section of this application. Specifically, SEQ ID NOs:2 and 3 lie within a region between the uvrA and soxS gene loci. The region is covered by lambda clones 12A5 and 4F12.

A central portion of the second strand (SEQ ID NO:3) is referred to herein as SEQ ID NO:7. SEQ ID NO:7 is substantially homologous to the prior art SEQ ID NO:1 (SEQ ID NO:1 is discussed above in the background section of the application). The portion of SEQ ID NO:3 upstream of SEQ ID NO:7 is identified as SEQ ID NO:9, and the portion of SEQ ID NO:3 downstream of SEQ ID NO:7 is identified as SEQ ID NO:8. An important aspect of the present invention is the recognition that the entire SEQ ID NO:3 is a Salmonella specific sequence which can be utilized to distinguish Salmonella from, for example, *E. coli*. Another important aspect of the present invention is the identification of the novel sequences SEQ ID NO:8 and SEQ ID NO:9 which flank SEQ ID NO:7.

Referring to SEQ ID NO:4, SEQ ID NO:5 and SEQ ID NO:6, these are portions of the first strand (SEQ ID NO:2) which are complementary to SEQ ID NO:7, SEQ ID NO:8 and SEQ ID NO:9, respectively, of the second strand (SEQ ID NO:3).

As will be recognized by persons of ordinary skill in the art, the prior art SEQ ID NO:1 is a 223 base sequence. Accordingly, any sequence of at least 224 bases of SEQ ID NO:2 or SEQ ID NO:3 is novel over the prior art SEQ ID NO:1.

Referring to SEQ ID NOs:60–67, these are RNA fragments complementary to SEQ ID NOs:3, 2, 7–9 and 4–6, respectively.

One aspect of the present invention is to purify and isolate nucleotide fragments comprising portions of one or more of the nucleotide sequences SEQ ID NOs:2, 3, 60 and 61, and thereafter utilize such portions for the subsequent identification of Salmonella. For instance, purified nucleotide fragments comprising at least 10 bases of one or more of the SEQ ID NOs:5, 6, 8, 9, 63, 64, 66 or 67 may be utilized in hybridization assays. (General methods for performing a hybridization assay are described in, for example, *Molecular Cloning—a Laboratory Manual*, 1989, 2nd edition, edited by Sambrook J., Fritsch E. F., and Maniatis T. Cold Spring Harbor Laboratory Press, New York.) Alternatively, larger fragments, such as fragments comprising at least 224 bases of a purified nucleotide fragment comprising a portion of one of the nucleotide sequences of SEQ ID NOs:2, 3, 60 or 61 may be utilized in hybridization assays for identifying Salmonella. Larger sequences can provide significant advantages in hybridization assays. For instance, assay conditions can become more stringent with larger sequences to provide higher specificity for the sequences which are sought.

An exemplary hybridization method utilizing a portion of one of the nucleotide sequences of SEQ ID NOs:2, 3, 60 or 61 would comprise forming a nucleotide fragment complementary to at least a 10 base pair portion of one or more of SEQ ID NOs:5, 6, 8, 9, 63, 64, 66 or 67. Such nucleotide fragment could then be incubated with a sample under conditions suitable for hybridization of the nucleotide fragment to one or more of the nucleotide sequences of SEQ ID NOs:5, 6, 8, 9, 63, 64, 66 or 67. After the incubation of the nucleotide fragment with the sample, hybridization of the nucleotide fragment with one or more of the nucleotide sequences SEQ ID NOs:5, 6, 8, 9, 63, 64, 66 or 67 could be detected by methods known to persons of ordinary skill in the art.

As the nucleotide sequences SEQ ID NOs:2, 3, 60 and 61 are substantially specific for Salmonella, detection of hybridization with one or more of nucleotide fragments SEQ ID NOs:5, 6, 8, 9, 63, 64, 66 or 67 can be utilized for detecting the presence of Salmonella in a sample.

An alternative method for detecting the presence Salmonella is to form primers specific for one or more portions of SEQ ID NOs:2, 3, 60 or 61. The primers can be utilized in an in vitro gene amplification procedure, such as, for example, a PCR procedure, Tas procedure, 3SR procedure, Qβ procedure, or LCR procedure discussed, above, in the background section of this application, to detect the presence of Salmonella.

Also, the above-discussed in vitro gene application procedures can be utilized for detecting the presence of one or more nucleotide sequences, such as SEQ ID NOs:2, 3, 60 or 61, or a portion of SEQ ID NOs:2, 3, 60 or 61 in a sample. Such detection may have application in methods other than methods of detection of Salmonella. For instance, detection of all or a portion of one or more of the nucleotide sequences of SEQ ID NOs:2, 3, 60 or 61 may have application, for example, in procedures for expressing proteins from one or more of such sequences. SEQ ID NOs:2, 3, 60 and 61 code for a number of different proteins, as will be discussed below.

The primers utilized for detection of nucleotide sequences SEQ ID NOs:2, 3, 60 and 61 will typically have a length of at least about 10 bases to provide adequate specificity. If higher specificity is desired, the primers may be longer. For instance, high-specificity primers may be formed having a length of from about 15 to about 35 bases.

The methods of the present invention are considered to be highly specific for detection of Salmonella, and therefore are thought to be applicable for samples which have not been enriched in Salmonella. However, in applications in which the relative amount of Salmonella is very low, it may be desirable to enrich the sample in Salmonella before attempting to detect Salmonella. Methods for enriching a sample in Salmonella include growing the sample in a broth-comprising 5 grams tryptone, 4 grams lactose, 10 grams sodium hydrogen phosphate, and 4 grams sodium hydrogen selenite (per liter) in water, as discussed in *Manual of Methods for General Bacteriology* (1981) edited by Gerhardt et al., American Society For Microbiology, Washington D.C. Such conditions advantageously permit Salmonella to grow relatively rapidly in relation to other microorganisms.

An alternative method for detecting for the presence of one or more of the nucleotide sequences of SEQ ID NOs:2, 3, 60 and 61 comprises detecting for the presence of at least a portion of one or more amino acid sequences coded for by the sequences of SEQ ID NOs:2, 3, 60 and 61. Amino acid sequences coded for by SEQ ID NOs:2, 3, 60 and 61 are listed herein as SEQ ID NOs:35–59. For purposes of the following discussion and for interpreting the claims which follow, a polypeptide substantially comprises an amino acid sequence when the polypeptide either exactly comprises the amino acid sequence, or differs from the amino acid sequence by only conservative amino acid substitutions. Conservative amino acid substitutions are defined to encompass, for example, the substitution of charged side chains for alternative charged side chains; non-polar side chains for alternative non-polar side chains; aliphatic hydroxyl containing side chains for alternative aliphatic hydroxyl containing side chains; and sulfur containing side chains for alternative sulfur containing side chains.

An exemplary method for detecting one or more of the amino acid sequences of SEQ ID NOs:35–59 is to form antibodies to one or more of such amino acid sequences. The antibodies can be incubated with a sample under conditions suitable for binding of the antibodies to one or more of the amino acid sequences of SEQ ID NOs:35–59. The binding of antibodies with one or more of the amino acid sequences of SEQ ID NOs:35–59 can be detected by methods known to persons of ordinary skill in the art. (Methods for forming and utilizing antibodies are described generally in, for example, *Antibodies—A laboratory Manual* (1988), edited by Harlow E. and Lane D., Cold Spring Harbor Press, New York.)

A comparison of amino acid SEQ ID NOs:35–59 with known protein sequences has been performed. The comparison utilized the program BLAST of Gish et. al. (The program BLAST is described in: Gish W. and States D. J. (1993) *Identification of Protein Coating Regions by Data Base Similarity Search* Nat. Genet. 3:266–72; and Altschul S. F., Gish W., Miller W., Myers E. W. and Lipman D. J. (1990) *Basic Local Alignment Search Tool* J. Mol. Biol. 215:403–10.) The BLAST comparison indicates that some of the amino acids are significantly homologous to toxins and ATP binding proteins. The homology of the amino acid SEQ ID NOs:35–59 with toxins indicates that amino acids may comprise toxins produced by Salmonella. Accordingly, a method for alleviating the symptoms of Salmonella infected victims may be to block production of one or more of the polypeptide sequences of SEQ ID NOs:35–59 in vivo. Methods for in vivo blocking of production or activity of polypeptide sequences could include, for example, using drugs which bind to and interfere with such polypeptide sequences. For instance, the production of one or more of the polypeptide sequences of SEQ ID NOs:35–59 could be accomplished by blocking transcription or translation of one or more portions of the nucleotide SEQ ID NOs:2, 3, 60 and 61. Such blocking of transcription and/or translation could be accomplished by designing drugs to interfere with regulatory factors required for such processes, as has been done for mammalian cells.

The present invention encompasses methods of expressing and isolating polypeptides comprising the amino acid sequences of SEQ ID NOs:35–59. The invention further encompasses methods of purifying polypeptides comprising portions of the amino acid sequences of SEQ ID NOs:35–59.

Such methods encompass, for example expressing and purifying at least a portion of at least one of the amino acid sequences of SEQ ID NOs:35–59. An exemplary portion would be a 10 amino acid length segment for utilization as an antigen to generate antibodies for the antibody-based Salmonella detection method described above.

An exemplary method for expressing a polypeptide coded for by one of the nucleotide sequences of SEQ ID NOs:2 and 3 would be to clone a coding sequence, such as a sequence complementary to one of the coding sequences of SEQ ID NOs:10–34 into an expression system. Such expression system could comprise, for example, a bacteria modified to express the cloned coding sequence. Methods for incorporating a coding sequence into an expression system are known to persons of skill in the art, and could include, for example, incorporating portions of the nucleotide sequences into recombinant DNA vectors. The incorporated portions would preferably be at least 10 bases in length, and more preferably be at least 30 bases in length to correspond to a 10 amino acid length segment. A general description of methods for incorporating nucleotide fragments into expression systems is provided in *Methods of Enzymology*, Vol. 185, *Gene Expression Technology*, edited by David Goeddess, (1991). A general description of methods for purifying expressed proteins is provided in *Current Protocols In Molecular Biology* (1987), edited by F. Ausubel el al, Greene Publishing Associates and Wiley-Interscience.

Significant portions of the sequences of SEQ ID NOs:2 and 3 are thought to be prevalent throughout the genus Salmonella, as evidence by experiments indicating that a 7.46 kb EcoR1 fragment within SEQ ID NOs:2 and 3 can be utilized as a probe which hybridizes with ten diverse Salmonella strains—*Salmonella dublin, Salmonella enteritidis, Salmonella gallinarum, Salmonella Minnesota, Salmonella paratyphi A, Salmonella paratyphi B, Salmonella paratyphi C, Salmonella pullorum, Salmonella typh ty21a*, and *Salmonella typhimurium*. Accordingly, the above-discussed methods of detection of Salmonella should apply to many, and possibly all, Salmonella species. Certainly, the methods of detection should apply to the Salmonella species *Salmonella typhimurium*, from which the sequences SEQ ID NO:2 and SEQ ID NO:3 have been isolated. Also, the method should have application to the species *Salmonella typhi* which is thought to be genetically very similar to *Salmonella typhimurium.*

Alternative methods for detecting SEQ ID NOs:2, 3, 60 or 61 could comprise incorporating a portion of one or both of the nucleotide sequences SEQ ID NO:2 or SEQ ID NO:3 onto a DNA chip, utilizing, for instance, the procedure of Chee M., Yang R., Hubbel E., Berno et al (1996) *Accessing Genetic Information With High-Density DNA Arrays* Science 274:610–614. The portions provided in the DNA chip will preferably comprise at least a 10 base pair segment of one or both of the nucleotide sequences SEQ ID NO:2 or SEQ ID NO:3 for adequate specificity. Such segment could be from one or more of the portions corresponding to SEQ ID NO:5, SEQ ID NO:6, SEQ ID NO:8 or SEQ ID NO:9.

Operational Aspects of the Invention

Operational aspects of the present invention are believed to be readily apparent to persons of skill in the art. However, for clarity, they will be briefly summarized here.

In a first aspect, the invention encompasses a purified nucleotide comprising at least a portion of at least one of SEQ ID NOs:2, 3, 60 or 61.

In another aspect, the invention encompasses a purified nucleotide fragment comprising a portion of one of the nucleotide sequences SEQ ID NOs:2, 3, 60 or 61, said portion comprising at least 224 bases.

In another aspect, the invention encompasses a purified DNA fragment comprising a portion of one of the nucleotide sequences SEQ ID NO:5, SEQ ID NO:6, SEQ ID NO:8 or SEQ ID NO:9, said portion comprising at least 150 bases.

In another aspect, the invention encompasses a purified oligonucleotide complementary to a segment of at least one of the nucleotide sequences SEQ ID NOs:5, 6, 8, 9, 63, 4, 66 and 67, said oligonucleotide having a length of at least about ten bases.

In another aspect, the invention encompasses a recombinant DNA vector comprising a portion of one of the nucleotide sequences SEQ ID NO:5, SEQ ID NO:6, SEQ ID NO:8 or SEQ ID NO:9, said portion being at least about 10 bases in length.

In another aspect, the invention encompasses a method of expressing and isolating a polypeptide coded for by a nucleotide SEQ ID NO:2 or SEQ ID NO:3.

In another aspect, the invention encompasses a purified polypeptide comprising a ten amino acid length segment of at least one of the amino acid sequences of SEQ ID NOs:35–59.

In another aspect, the invention encompasses a hybridization method for detecting the presence of one of the nucleotide sequences SEQ ID NOs:5, 6, 8, 9, 63, 64, 66 and 67 in a sample comprising the following steps:

forming a nucleotide fragment complementary to at least a 10 base pair portion of one or more of the nucleotide sequences SEQ ID NOs:5, 6, 8, 9, 63, 64, 66 and 67;

incubating the nucleotide fragment with the sample under conditions suitable for hybridization of the nucleotide fragment to one or more of the nucleotide sequences SEQ ID NOs:5, 6, 8, 9, 63, 64, 66 and 67; and detecting for hybridization of the nucleotide fragment with one or more of the nucleotide sequences SEQ ID NOs:5, 6, 8, 9, 63, 64, 66 and 67.

In another aspect, an in vitro gene amplification method for amplifying at least a portion of SEQ ID NO:2, or at least a portion of a sequence complementary to SEQ ID NO:2, within a sample, the method comprising the following steps:

forming primers complementary to segments of one or more of the nucleotide sequences SEQ ID NO:2 and SEQ ID NO:3; and utilizing the primers in an in vitro gene amplification procedure to amplify a concentration of at least a portion of one or more of the nucleotide sequences SEQ ID NO:2 and SEQ ID NO:3 within the sample, wherein the at least a portion of one or more of the nucleotide sequences SEQ ID NO:2 and SEQ ID NO:3 which is amplified does not correspond solely to either SEQ ID NO:4 or SEQ ID: NO:7.

In another aspect, the invention encompasses a method for detecting the presence of one or more of the nucleotide sequences SEQ ID NOs:5, 6, 8, 9, 63, 64, 66 and 67 in a sample comprising the following steps:

forming primers complementary to segments of one or more of the nucleotide sequences SEQ ID NOs:5, 6, 8, 9, 63, 64, 66 and 67;

utilizing the primers in an in vitro gene amplification procedure to amplify a concentration of at least a portion of one or more of the nucleotide sequences SEQ ID NOs:5, 6, 8, 9, 63, 64, 66 and 67; and detecting the amplified concentration of the amplified portion of one or more of the nucleotide sequences SEQ ID NOs:5, 6, 8, 9, 63, 64, 66 and 67 within the sample.

In another aspect, the invention encompasses a method for detecting the presence of Salmonella in a sample comprising detecting for the presence of at least a portion of one of the nucleotide sequences SEQ ID NOs:2, 3, 60 or 61.

In another aspect, the invention encompasses a method for blocking transcription from one or both of the nucleotide sequences SEQ ID NO:2 and SEQ ID NO:3 in Salmonella.

In another aspect, the invention encompasses a method for blocking production of one or more of the polypeptide sequences of SEQ ID NOs:35–59 in Salmonella.

In another aspect, the invention encompasses a DNA chip comprising a 10 base pair segment of one or both of the nucleotide sequences SEQ ID NO:2 or SEQ ID NO:3.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

We claim:

1. A purified nucleotide strand comprising SEQ ID NO:2 or a sequence complementary thereto.

2. A purified nucleotide strand comprising SEQ ID NO:3 or a sequence complementary thereto.

3. A purified RNA strand complementary to a portion of one of the nucleotide sequences SEQ ID NO:2 or SEQ ID NO:3, said portion comprising at least 224 bases.

4. A purified DNA fragment comprising a portion of one of the nucleotide sequences SEQ ID NO:2 or SEQ ID NO:3, said portion comprising at least 224 bases.

5. A purified DNA fragment comprising a portion of one of the nucleotide sequences SEQ ID NO:5, SEQ ID NO:6, SEQ ID NO:8 or SEQ ID NO:9, said portion comprising at least 150 bases.

6. A purified RNA fragment complementary to a portion of one of the nucleotide sequences SEQ ID NO:5, SEQ ID NO:6, SEQ ID NO:8 or SEQ ID NO:9, said portion comprising at least 150 bases.

7. A purified oligonucleotide complementary to a segment of one of the nucleotide sequences SEQ ID NO:5, SEQ ID NO:6, SEQ ID NO:8 or SEQ ID NO:9, said oligonucleotide having a length of at least about ten bases.

8. The oligonucleotide of claim 7 having a length of from about 15 to about 35 bases.

9. A purified RNA fragment complementary to a segment of one of the nucleotide sequences SEQ ID NO:5, SEQ ID NO:6, SEQ ID NO:8 or SEQ ID NO:9, said RNA fragment having a length of at least about ten bases.

10. A recombinant DNA vector comprising a portion of at least one of the nucleotide sequences SEQ ID NO:5, SEQ ID NO:6, SEQ ID NO:8, SEQ ID NO:9, SEQ ID NO:63, SEQ ID NO:64, SEQ ID NO:66, or SEQ ID NO:67, said portion being at least about 10 bases in length.

11. A hybridization method for detecting the presence of at least one of the nucleotide sequences SEQ ID NO:5, SEQ ID NO:6, SEQ ID NO:8, SEQ ID NO:9, SEQ ID NO:63, SEQ ID NO:64, SEQ ID NO:66, or SEQ ID NO:67 in a sample comprising the following steps:

forming a nucleotide fragment complementary to at least a 10 base pair portion of one or more of the nucleotide sequences SEQ ID NO:5, SEQ ID NO:6, SEQ ID NO:8, SEQ ID NO:9, SEQ ID NO:63, SEQ ID NO:64, SEQ ID NO:66, or SEQ ID NO:67;

incubating the nucleotide fragment with the sample under conditions suitable for hybridization of the nucleotide fragment to one or more of the nucleotide sequences SEQ ID NO:5, SEQ ID NO:6, SEQ ID NO:8, SEQ ID NO:9, SEQ ID NO:63, SEQ ID NO:64, SEQ ID NO:66, or SEQ ID NO:67; and detecting for hybridization of the nucleotide fragment with one or more of the nucleotide sequences SEQ ID NO:5, SEQ ID NO:6, SEQ ID NO:8, SEQ ID NO:9, SEQ ID NO:63, SEQ ID NO:64, SEQ ID NO:66, or SEQ ID NO:67.

12. The method of claim 11 wherein the formed nucleotide fragment comprises an RNA strand.

13. The method of claim 11 wherein the formed nucleotide fragment comprises a DNA strand.

14. An in vitro gene amplification method for amplifying at least a portion of at least one of SEQ ID NO:2 or SEQ ID NO:3 within a sample, the method comprising the following steps:

forming primers complementary to segments of at least one of the nucleotide sequences SEQ ID NO:2 or SEQ ID NO:3; and utilizing the primers in an in vitro gene amplification procedure to amplify a concentration of at least a portion of at least one of the nucleotide sequences SEQ ID NO:2 or SEQ ID NO:3 within the sample, wherein the at least a portion of at least one of the nucleotide sequences SEQ ID NO:2 or SEQ ID NO:3 which is amplified does not correspond solely to either SEQ ID NO:4 or SEQ ID NO:7.

15. The method of claim 14 wherein the formed primers comprise DNA strands.

16. The method of claim 14 wherein the at least a portion which is amplified corresponds to at least one of the nucleotide sequences of SEQ ID NOs:10–34.

17. The method of claim 14 wherein the primers comprise lengths of at least about 10 base pairs.

18. A method for detecting the presence of one or more of the nucleotide sequences SEQ ID NO:5, SEQ ID NO:6, SEQ ID NO:8, SEQ ID NO:9, SEQ ID NO:63, SEQ ID NO:64, SEQ ID NO:66, or SEQ ID NO:67 in a sample comprising the following steps:

forming primers complementary to segments of one or more of the nucleotide sequences SEQ ID NO:5, SEQ ID NO:6, SEQ ID NO:8, SEQ ID NO:9, SEQ ID NO:63, SEQ ID NO:64, SEQ ID NO:66, or SEQ ID NO:67;

utilizing the primers in an in vitro gene amplification procedure to amplify a concentration of at least a portion of one or more of the nucleotide sequences SEQ ID NO:5, SEQ ID NO:6, SEQ ID NO:8, SEQ ID NO:9, SEQ ID NO:63, SEQ ID NO:64, SEQ ID NO:66, or SEQ ID NO:67; and detecting the amplified concentration of the amplified portion of one or more of the nucleotide sequences SEQ ID NO:5, SEQ ID NO:6, SEQ ID NO:8, SEQ ID NO:9, SEQ ID NO:63, SEQ ID NO:64, SEQ ID NO:66, or SEQ ID NO:67.

19. The method of claim 18 wherein the in vitro gene amplification procedure comprises a PCR procedure.

20. The method of claim 18 wherein the in vitro gene amplification procedure comprises a TAS procedure.

21. The method of claim 18 wherein the in vitro gene amplification procedure comprises a 3SR procedure.

22. The method of claim 18 wherein the in vitro gene amplification procedure comprises a Qβ procedure.

23. The method of claim 18 wherein the in vitro gene amplification procedure comprises an LCR procedure.

24. A method for detecting the presence of Salmonella in a sample comprising detecting for the presence of at least a portion of one of the nucleotide sequences SEQ ID NO:2, SEQ ID NO:3, SEQ ID NO:60 or SEQ ID NO:61, wherein the detecting comprises a hybridization method comprising the following steps:

forming a nucleotide fragment complementary to at least about a 10 base pair portion of one or more of the nucleotide sequences SEQ ID NO:5, SEQ ID NO:6, SEQ ID NO:8, SEQ ID NO:9, SEQ ID NO:63, SEQ ID NO:64, SEQ ID NO:66, or SEQ ID NO:67;

incubating the nucleotide fragment with the sample under conditions suitable for hybridization of the nucleotide fragment to one or more of the nucleotide sequences SEQ ID NO:5, SEQ ID NO:6, SEQ ID NO:8, SEQ ID NO:9, SEQ ID NO:63, SEQ ID NO:64, SEQ ID NO:66, or SEQ ID NO:67; and detecting for the presence of Salmonella by detecting for hybridization of the nucleotide fragment with one or more of the nucleotide sequences SEQ ID NO:5, SEQ ID NO:6, SEQ ID NO:8, SEQ ID NO:9, SEQ ID NO:63, SEQ ID NO:64, SEQ ID NO:66, or SEQ ID NO:67.

* * * * *

```
                         SEQUENCE LISTING


(1) GENERAL INFORMATION:

   (iii) NUMBER OF SEQUENCES: 67


(2) INFORMATION FOR SEQ ID NO:1:

     (i) SEQUENCE CHARACTERISTICS:
          (A) LENGTH: 223 bases
          (B) TYPE: nucleotide
          (C) STRANDEDNESS: double stranded
          (D) TOPOLOGY: linear

    (xi) SEQUENCE DESCRIPTION: SEQ ID NO:1:

GGTTACGCGT ACCTGGACGA CATCACCGGG AACGTCAATT CTGAATGACG GTTTGGCAAC     60

ATTCGTTAAT TGATCATTCT GCACGCCGGT ATCATTAAGC AATACGATAT TGTTAATGGT    120

TGTCGTGGTA TCAATACGCA CCTCAAACGG CGCAGACTCT TTTACATTCC CCGCCAAGAT    180

CTTCCACCAC AACGGCTAAC TGATATGAGC CATCAGCCCA GCT                      223


(2) INFORMATION FOR SEQ ID NO:2:

     (i) SEQUENCE CHARACTERISTICS:
          (A) LENGTH: 24701 bases
          (B) TYPE: nucleotide
          (C) STRANDEDNESS: double stranded
          (D) TOPOLOGY: linear

    (xi) SEQUENCE DESCRIPTION: SEQ ID NO:2:

ACTCAAAGCG TTATTTGCAT TTTCGCTATA GTTCTCGTCT GCTGAAATGC CTGGTGTAAA     60

CCAGGCATTT TCTTACCTGG TATTATTGTC TTTGTATCCC TTTCAAAAAA GAGAAGCGCA    120

TATCTTACGG AAAAATGTCG CTTATCGCCT CTGGCCGACT CGCCTCGGCA CATCATTATC    180

CAGCCGAAGT TCATAAATGT ACTGCAATAA CCCGGATTGT CTTAAATATG AAAGAGAAAT    240

CTCATCTGCA AAATATATAA TTTATAGCCA TTTTTTGACA ACAAAAAGAT ATTATAAAAT    300

AACGGTAGAG AATGGTCGGT ATTATCAATG GTTAATTAAA TGTTTGCTTT AGCTTGTGAT    360

GAGCTCAAAT ATGATATGTG TATCTTGCTT TATTTTTAAT TGCTGAAGAT AAAATTGTTA    420

CTTATAGCTG GCTTTATATA AAAAATGGTT TTATTTGTGT ATTTTTTTAC ACAATTCTGA    480

TTTTTTACTC CCCACTTATT ATATTTTCAA TGATTTAAGT TATATTGAAG TCCATATGAC    540

CCTATGTTTT AATTGTGAAA ATTAATTTTA TCCTCTGGAG GCAAATTTAT TAAATACGTA    600

TGGTTATAAC GCGTATTAAA AAGAAATATG TCCTTAAAAT GATTTAGAGT TTCAATGATT    660

AGCTAACAAA TCTATTTATC GGCGGGTGGT TTTAATTTGC TGATGACTAT TTTTTATTTA    720

TGAGTTGAGA GCTTATGCGA TACCTATTAT TGGGGAGGAT ATAGTTAGTG CAATAATTGA    780

TGTCTACCTA ATTAAAAAAA TGAAGAGTGT TTTTAATTAA AGCACTCATC TTTGTTGTGG    840
```

-continued

```
GCGCATAAAA ATGGCGTCGT TGTTTTTATT TTTCTGATTA CGAGATGTAA GAAAACTGAA    900
ATCTATAAAG CGTATTGGTA GCAGGAAGCC AAGGGCGGTA GCGTTCACTT TCTGAATAAG    960
TTGAGCATCC TTTATCCTTT CTAATCCACA AAAACATTTT ATTCACAATG TAATATCAGG   1020
AGACAACATG GAAGACGAAA GTAATCCGTG GCCTAGTTTT GTTGATACAT TCTCTACGGT   1080
ATTGTGCATT TTTATATTTC TTATGTTGGT GTTTGCACTT AATAATATGA TTATTATGTA   1140
TGACAACTCA ATTAAAGTTT ATAAAGCAAA TATAGAGAAT AAGACTAAAT CTACTGCTCA   1200
AAATAGCGGA GCCAATGACG ATTCAAATCC TAATGAAATA GTTAATAAGG AAGTGAATAC   1260
TCAAGATGTG TCGGACGGAA TGACTACAAT GTCAGGTAAG GAGGTTGGAG TATACGATAT   1320
CGCCGATGGT CAGAAAACTG ATATAACGTC TACAAAAAAT GAGCTTGTTA TTACGTATCA   1380
TGGCAGGCTG AGAAGCTTTT CAGAAGAGGA CACTTATAAA ATAAAGGCTT GGTTAGAAGA   1440
CAAAATCAAT AGTAATTTAT TGATAGAAAT GGTTATTCCT CAGGCAGACA TCTCTTTCTC   1500
TGACTCTCTA CGACTGGGAT ATGAACGGGG AATTATTTTG ATGAAAGAGA TTAAGAAAAT   1560
ATATCCTGAT GTAGTTATTG ACATGAGTGT TAACTCCGCA GCATCAAGTA CAACGAGTAA   1620
AGCTATTATC ACGACTATTA ATAAAAGGTG TCAGAGTGAA ATATATAAAT CATTACCGCT   1680
ATTTGTTGTC TGTTCTTTCC TTGCCATACT CCCTTTTTTT GCTTTATCTT TTCCCGGTAT   1740
AAGAGAGTAT GTTTTTGATA ACTTCATGGT TTCTGCAATT TACAATGGAG TCATTATTGC   1800
CATTTATATT ACAGGTTCTT TGTGTGCATT ATTCACTATT CTTAAAAATA TTTCAGCAAA   1860
AGACATATTA ATAGCTCAGG ACGCCAGTAG AAAAAATAGC ATTCTTTCTA ACCTCAATCA   1920
GGTTTTGTTT GCCGGGGAGT CCAAACAGTG TGATTTCAAT TTACTGATGG AATTAGATGA   1980
CAATGTGTCT ACCGCCCGTA ATCAACGATT GTCATTTATT ATGAGCTGTA GCAATGTGTC   2040
GACGCTTGTT GGCCTGTTGG GGACGTTTGC GGGTCTGTCT ATTACGATTG GTTCAATCGG   2100
GAACTTATTG AGCTCGCCAT CAGATGTTGG CGGTGATAAT GCAAGTAATA CACTCAATAT   2160
GATCGTGACA ATGGTAGCGT CGCTTTCTGA ACCATTGAAA GGGATGAATA CCGCATTTGT   2220
ATCTTCTATC TATGGTGTTG TTTGCGCCAT ACTCCTGACC TCACAAAGTG TTTTTGTTCG   2280
CAGCTCCTAT TCCCTTGTTT CTACGGAAAT CAAAAAATTA AAAATCATAA GCAACAGAGC   2340
CAATAATAAA CAGCGAAGCC TGCGGGTTGA ATCAGAGACG CTTGTAGAAT TTAAAGAGTT   2400
GTTTAAAGCG TTTTTTGATA ACTACCTGAC AGTTGAAAAC TTACGGACGC AGGATGAAGA   2460
AAAGAAACGA GAGATGCTAT CAGATAGCTT TGTCACTTTG CAAAACCGAC TATTGGATAA   2520
CTCAGCAAAA CTGGAACAAA TTTTTACGCT GATTGATGGT TATCTGGTAA GCAGTAACGG   2580
AAAATCTCAA AAAATTATCT GACGGTGTAA TAACAATTAC CTCTCGTTTA TCTGAAGGTA   2640
ATATCCTGCT TGCTGATAAT AATGCACGAC TGGAGGCAAT GAGTACAATA CAAAATATTA   2700
TAGATAAAAA GAATGATTCA ATAATGACAT CAGTTGATAA ATGTTATCAG GAATCTCTTT   2760
CACATGGTAA GACCATAAAC GATATTGCCG CTGGCAGTGC CGATATTTCT CATACTCTCG   2820
ATGGGCTGAG AAAAGAAATG GATGAGGATA TGAATAATGT TCATTTAGCG CTATCCGATC   2880
TATCGGCTAC TGATAAAAAG ATTATTGCCA ATACTAAAGA GATTAGTGCT GAAATGGTTA   2940
GCTACCGTGA TACCTATATG CCATTAATGG AAAAAATAAC ATCTATGCAT CAGGAAATAG   3000
TAAAGCAACG TTTGTTAAAC AAGGAGGAAA AAAATGAAGA TTAAGATGTT TTTTCTGACG   3060
ACTGCTTTTA TTACACAAAG CACATACGCC AGCGAGCTTC CGGTCATTCC TCTAAGAGAT   3120
TTAGTTAATG CCGCATTAAC GCATCAGCCC TCTGTTGCTG TTTCATATTA TGAGACTGAA   3180
AAGAAAAACA GTGACTTAGA TCTTTCACGG GCAGCACTTT ATCCTACCCT GGATCTAACA   3240
```

-continued

```
TCTGGCCTTA ATAATAACAG GAAAGAGTCA TCAGGTACCG AGAGGAACGT TGAAAATAAG   3300

GTGTCTTTAT CATACCGAAT AACGGATTTT GGAGTGAGGG GGCTAATAT CAGGAAATCT    3360

GAATATGAAA GAGATAATAG TAAAACTGAC TATGAAAAAA CAAAGAATAT AGTGTCTCAG   3420

GAGGTTGTGA CAACCTATTA CAACATCAGT AAATATCGTG AAATGATTGA TGGCGTAAAT   3480

CTGGAGAAAG AGTTTTATAA AAAGATGCTG GAACCTTTTT CGTTGCTGGT ATCTTCCGGT   3540

GTAGCTATGC AATCTGATAT GCGTAAAGTA CAAGTATCTA TCGATGCATT AAATACCAGA   3600

AGCATTATGT ATCAGTCGAT GTTGGATGAT GAAATGTATA AATGCAGAA TATGACTGGT    3660

CTGAATTTAT CGCCAGTTCA GATTCAAAGC GATGAAAAAT TCAACCTCTT CAAAAAATAT   3720

ATCTTTGTCG AAAGCCCTGA AAAACTTATG GACATGGTGA TGAAATACAA CGATGACTAT   3780

AAGATGCTTG TCAATACCCG AAAAGCCGCG ACCGAAGATA TTAATGCCGC AAAATCATCC   3840

TATTTTCCGA CTGTAGATCT TGTTTCCAGC TATGTACAGA ATAACCCAAG CGGTAGTGCC   3900

AAAAAAAGTG ATTATGAAGA TGAATTTAAA ACGGGTATCA ATGTCAGTTT CAACATTTTT   3960

AATGGGTTCA GAAATTCAGC CCAGGAAAGA AAAATGGTGG CAAGTTACTC GCAGGCTAAG   4020

CTGCAAATTG ACGATTTTTT GATTAAAACG CGTTATAACA TTGATTCACA ACTTTCAAGA   4080

TACGCCGCTG CAAAAGAGAC TTACTCAGTG GCGGAACGTT CACATACAAA CGCGTTACAG   4140

CTTACTGAAT TATATGAGCA GGAGTTTCAG TTAGGGCAAA AAAGTTTGCT TGATTTAATT   4200

TCAAGCCGTA ATGAAGCATT TCAGGCATAT GTAAGCATGA TCGACAGCAA ATATAGCCTG   4260

TATATTTTAA AGCTACAGCA ACTCTCATTG ATTTTTCATT TAATGGATTA TTTAAAAGGA   4320

AATACTGAAA GTGAGTTAAA TGTAATGAAA TGAATAGAAG ACAAAGCGAT CATCTCATGA   4380

TGATAATTAT TTCTTTGACG ATCTTAATTA TTATCCTTAC CTACTTTATA GAAATTAATT   4440

CAGTGGTTCA TGGTCAGGGC GTTATCACTA CTAAAGATAA TGCTCAGTTA ATATCTCTTT   4500

CTAAAGGAGG GACGATACAA GATATTTATG TAGCCGAGGG TGATACTGTA AAAAAAGGAG   4560

AACTCCTTGC AAAGGTCGTT AACCTTGATC TGCAAAAAGA ATATCAAAGG TATAGAACTC   4620

AAAAAGGGTA TCTGGATAAA GATGTTAACG AAATATCTTT CATTCTTGAT AAAGAAAATG   4680

AGAGTGGGTT GATTACCCTG GATGGCACCC GTTCTTTAAG CAATAAAGAG GTAAAAGCGA   4740

ATATTGAATT AGTGCATAGT CAGATAAGAG CTAAAGAGTT AAAAAAAACC TCTCTTGATT   4800

CTGAGATTAG CGGATTACAA GAGAAGCTGA GTTCGAAAGA AAAAGAACTC GCATTGCTTG   4860

CCGAAGAAAT AAATATTCTT TCCCCACTGG TAAAAAAAGG AATTAGCCCA TATACCAATT   4920

TTCTTAACAA GAAACAGGCG TATATAAAAG TTAAGTCTGA AATTAATGAT ATTGAAAGTA   4980

GCATCACTTT AAAAAAAGAT GATATTGAGT TGGTTGTTAA TGATATTGAG GCGCTTAATA   5040

ATGAATTGCG ACTATCTTTA TCTAAAATAA TATCTAAAAA TCTTCAGGAA CTTGAGGTTG   5100

TTAACTCTAC ATTAAAAGTA ATAGAGAAGC AGATAAATGA GGAGGATATC TATTCACCGG   5160

TTGACGGTGT AATTTATAAA ATCAATAAAA GTGCCACTAC TCATGGTGGT GTGATTCAGG   5220

CGGCGGACTT ACTTTTTGAA ATAAAACCAA AAGTAAGGAC TATGCTGGCC GATGTGAAAA   5280

TATTACCCAA ATACCGTGAC CAAATATATG TAGATGAAGC CGTTAAACTG GATGTGCAGT   5340

CAATTATCCA ACCAAAGATA AAATCGTATA ATGCGACTAT CGATAATATT AGCCCTGATT   5400

CCTATGAGGA AAATACCGGA GGAACAATTC AGCGTTATTA TAAAGTAATT ATTGCATTCG   5460

ATGTTAATGA AGATGATTTA CGGTGGTTAA AACCAGGTAT GACTGTTGAC GCCAGTGTAA   5520

TTACCGGAAA ACACAGCATT ATGGAATACC TGTTATCTCC CTTGATGAAA GGCGTGGACA   5580

AAGCCTTTTC AGAACCAGTT AATACTAAAC GATTAGATAC ACCTTGAGAG TGAATATAAT   5640
```

-continued

```
ATTATGGGAA ATAAAAGCAT ACAAAAGTTT TTTGCCGATC AAAATTCTGT AATTGATTTA   5700
TCTTCTTTGG GTAATGCCAA AGGCGCAAAA GTTTCTCTTT CCGGGCCAGA CATGAACATT   5760
ACCACGCCGC GTGGTTCAGT GATCATTGTC AATGGCGCTC TTTATTCAAG TATCAAAGGC   5820
AATAACCTCG CTGTTAAATT TAAAGATAAG ACTATTACCG GCGCTAAAAT TCTGGGCAGC   5880
GTAGATTTAA AAGATATTCA ACTGGAGAGA ATTGACAGCT CATTGGTTGA TTCTGCTCAG   5940
GTAGAAAAGA AAGGTAATGG CAAACGACGA AATAAGAAGG AAGAAGAGGA ATTAAAAAGC   6000
AGCTTGACGA TGCTGAAAAC GCAAGAAAGA AGCTGATAAG GCGAAGGAAG AAGCAGAGAA   6060
AGCTAAGGAG GCTGCAGAAA AAGCGCTCAA TGAAGCGTTT GAAGTACAGA ACTCGTCAAA   6120
GCAAATTGAA GAAATGCTGC AGAACTTTTT GGCTGACAAT GTAGCAAAAG ACAATCTGGC   6180
TCAGCAAAGC GATGCTTCCC AGCAAAATAC ACAGGCTAAA GCAACGCAGG CTTCTAAACA   6240
GAACGATGCT GAAAAAGTTC TTCCTCAACC TATTAATAAA AATACCAGTA CTGGCAAAAG   6300
TAATAGCAGT AAAAATGAGG AAAATAAGCT CGATGCCGAG TCTGTTAAAG AGCCGCTTAA   6360
AGTCACATTA GCGCGTGCGG CCGAGAGTAA CAGCGGTAGC AAAGATGATA GTATAACTAA   6420
TTTTACCAAA CCTCAGTTTG TAGTTAGCAC TGCTCCCAAT GCCACGGTTA TTATTAAAAT   6480
TAATGGTATT GCTGTCGGTC AGGCTGTAAC GGATAGTTTG GGTAACTTCA CCTTTACAGC   6540
GCCTGAAACA TTGACTGATG GAACATATAA TCTGGAGGCA GAGGCCAAGA CTGCTGATGG   6600
GAGCGGTAGC GCCAAACTTG TCATTACTAT CGATTCCGTT ACCGATAAAC CAACATTTGA   6660
ACTTTCGCCT GAAAGTAGTG TGTCCGGTCA TAAGGGCTTA ACGCCGACCT TGACGCCTTC   6720
AATTGTTGGT ACGGCGGAAG AGAATGCTAA GGTTGACATT TATGTAGATA ATAAACTGGT   6780
TGCCAGCGTT GATGTCGATA AAGATGGAAA CTGGAGTTAT GAATTTAAGG ATAATGAATT   6840
ATCTGAGGGC GAAAATAGTA TAAAAGTCGT TGCTGTAGAT AAAGCAGGTA ATAAAAAACGA   6900
AACGACGGAT AGTATCATAA CCGACACCAT TGCTCCAGAA AAGCCGACGA TTGAGCTGGA   6960
TGATAGTAGT GATTCCGGCA TTAAAAATGA CAACATTACA AATAGCACCC TGCCAACATT   7020
TATTGGTGTG GCGGAACCCG GTTCTACAGT CTCTATTTAT CTTGGACTTA AACATCTTGG   7080
TGAGGTCATT GTTGCTAAAG ATGGGACATG GAGCTATACG CTTACTACGC CGCTCAAGGA   7140
TGGCGAATAC AATATAACAG CAACAGCTAC TGATATTGCC GGGCATACCT CAGCGACGGC   7200
AAATCTGCCT TTTACTATTG ATACACGTAT CAGCTATTTC AGCGCTGAGA TTGAAACGAC   7260
GAATGATAGC GGTATTGTCG GAGATAACGT TACTAACAAT ACTCGCCCAA CCTTTACAGG   7320
TAAAACTGAG CCAAATGCTA TTATCAGTGT CATAAATAGT GAGACTGGCG AAGAGGTTAT   7380
TTTTAAAGCG AATGACAAGG GCGAATGGAC GTTCAATTTC ACTTCCGACT CAGTGGAAGG   7440
GATTAACAAT CTTACGTTCA CTGTTGAAGA TGTCGCTGGC AACAAAAAGG ATTTTTCCTT   7500
TAGTTACGTT ATTGATACTA TTGCCCCTGT ACCTCCGACG GCTTCTTTGG AGGATTATGT   7560
TGTTTTGCCG AATGGTATAA TTTTATCAGG GAATGATTTA CCGGCTTTAG TCGGTACGGC   7620
AGAACCAAAG TCTACCATCT TATTGATGCG AGATGGTAAA TTATATGACA GCATTGAAGT   7680
TGACTCAAAC GGGACCTGGA AATTATCAGT TTAGTAATAA ATTCTTCAGG GCGCCTATGA   7740
TATTGAAATC ATTCTCAGGA TGCCGCCGGC AATAAATCCT CTACTGTTAA ATATTCTTTT   7800
ACTATTCAAA CTGAAGTTGT ACCTCCAAAA GCGGAACTCG ATGCCAGTGA TGATTCCGGT   7860
GCAAAAGGCG ACTGGATTAC CAATAAACAT AATGCTCTGA CATTACTGGG AACAGCGGAT   7920
AGGTTTGCTA CCGTAAATAT CCTTATTGAC GGTAAAACGA TAGGCGTGAC GACTGCGGAT   7980
GCAGACGGTA ACTGGAATTT TGATATTTCC AGAAATCTGT CTGACAATGT TTATAAGATT   8040
```

-continued

```
ACGGTTGAAT CCATCGATCC TTTAGGAAGA ACGTCATCTG TAGATTATCA GCTTACCATT    8100
GATAGCTTTA CGCCGATCCC TACTGTTATG TTGCATGATA GCGCTGACTC TGGCGTTAAA    8160
GGCGATATGA TTACTAAAAT TAATACACCG TTGTTTACCG GGATGGCTGA AGCTAATGCT    8220
AAGGTTTCCA TCTATGTTGA CGGTGTGTTA AGTGGTGAGG CTATTGCTGG CGATGATGGT    8280
GTATGGAATT TTCAATTTAC CACAGCGTTA TCCGATGGCT CGCATGACGT AACGGTAAAG    8340
GTAGAAGATA TTGCCGGTAA TACTGCCTCC TCATCAGCGT ATAATTTCCA AATCGTAACG    8400
CAAACGCAAA AACCAACAAT AGAGTTGGTC AACGATACGG GGGTTGATAA TACAGACCAT    8460
ATTATTAATG AAAAGAATCC TGCACTGACA GGAACCGCTG CACCCTATTC AACGGTTAAA    8520
CTCTATATTG ATGGTGCACT GATCGCTGAG GTCAGAACAA ATAAAGATGG CAGATGGGAG    8580
TATACCCTGA AAGCCGATCA AGGTTTGGTT GATGGCGATC ATAGAATAAC CGCTTCAGTT    8640
GAAGATATCG CTGGCAACAT TGCTCATTCG GATCCTTTCT TAATTAGCGT CGATACTGCT    8700
ATTTCAATAC CGATAGTTTC ATTGAGCCCG GATTCAGATT CGGGAATTTC AGATGATAAT    8760
TTAACGAATA TCGTTAAACC TACCTTGCAC CTAAAAGATA TTGATCCGGA CATTATCAGT    8820
GTTCAGGTAT GGGATGCCAT GTCTGATACG CAGATCGGTG TTGCCACGCA ACAACCTGAT    8880
GGTTCATGGG CCTATACCTT TACTTCAGAT TTAACGGAAG GCTTGCATCA GGTTTATGTC    8940
AAGGTTGAGG ACATTGCGGG TAATAAAGCG AACAGCGCGA TATTCGATTT TACTATCGAT    9000
ACCACAGTAT CAACGCCGGT GATTTCCCTG CTTTCTAAGG ATGATACGGG GGTTACAGGC    9060
GATAACCTGA CCAATATCAA TAAGCCAGGT TTTGCTATTT CCGGTGTTGA TGCCGATGCG    9120
CATCGGGTCG TCGTACAGGT GATGCACAAT GGCGTGAGCG AAGAGATCGA ACTTTCCCAC    9180
CTCAATGGGA GTTGGTTATT TATACCAGGG GAATACGTGG GCGGATGGCA GCTACACGTT    9240
AACGGTGAAA GTAGAAGATA AGGCAGGAAA TACCAACTAC TCGGCGCCGC TGACGGTCGT    9300
TATCGATACC CAAATCGCCA TTGATGGGGT GGAACTGGTC AACGATAGCG GCGTGAAAGG    9360
CGATAATATG ACCAACGACG ACCGTCCCCA CTTTCGTGTG ACGGTACCTA CGGATGTCAA    9420
TGAAGTCCGT CTGAGCATTG ACGGTGGTAA TTCGTGGGTT CAGGCAACTC CGGGCGTGGC    9480
AGGAAGCTGG GAGTATATCT GGCCGACAGA CCTGGCAGAT GGTCCTACAC GCTAACGGTG    9540
GAAGCGACTG ATAAAGCAGC AATACATGAC GAAGACCATC GATTTCGCGG TGGATACCAC    9600
GCTGTCAGTG CCGGTCATCG TACTGGATAG CGCGGACGAC ACCGGCATCC AGGGCGATAA    9660
CATGACGAAT AGCACCCAGC CGACATTTGC CTTGCAGCAT ATTGATGATG ATGCCGTTCG    9720
CGTTACGGTC AGCGTGGAGC ATGGCGGCGT CACCACCACA TTTGACGCCA CGAAAGGCAC    9780
AGGCGGATGG ACCTTTACGC CGCCGACATC ATGGGCGGAT GGTGATTATA CCCTGAGTGT    9840
GTCAGTCGAA GATAAAGCGG GGAACACCAG CCATTCTGCA TCGCTGACGG TGACGGTGGA    9900
CACGCAAATC GCCATTAATA ACATTGAACT GGTCAATGAC AGCGGTATTC CCGACGATAA    9960
TCTGACTAAT AATGTGCGTC CGCACTTCCA GGTGACGGTA CCGACGGATG TCAACGTGGT   10020
GCGCCTGAGC ATTGACGGCG GCAAGACGTG GTTCAACGCT ACCCAGAGCG CGACGCCAGG   10080
CGTCTGGGAT TATATCTGGC CGGATGATGT GGCCGACGGA GGCTATACCC TGACGGTAGA   10140
AGCGACCGAT GAGGCAGGAA ATAAGGCAAC ACAGACCTCG ATTTCACCAT CGATACCACT   10200
CTGTCTGTGC CGACCCTCTC GCTGGACAGC GCAGATGACA GCGGCATCGC GGGCGATAAT   10260
ATCACCAATG TTAAAACGCC GGGCTTTACC CTCAACAATA TTGATACCGA TGTCAGCCGG   10320
GTGATAGTGG AGGTAATGCA CAATGGCATT AAGCAGGAGG TGCCACTGGT TCAGACCGGC   10380
GGACAGTGGC GCTTTGCGCC GACCAGCGAC TGGGCGGACG GCGACTATAT CCTGACGGTG   10440
```

-continued

```
AAGGTAGAAG ATAGGACCGG AAATGTGAAG CAGTCCGCGC CGTTGACGGT GACAGTAGAC  10500
ACGCATATCG CCATTGACCG TATTGAACTG GTTAACGACA GCGGTATCCC CGGCGATAAT  10560
CTGACCAATG AAGCGCGCCC GCACTTTCAG GTGACAGTAC CGGCGGATGT TAACGGCGTA  10620
AGACTGAGCA TTGATGGCGG CAAAACGTGG TTTGACGCCA CGCAGCAGCG CGACGTCGGG  10680
CGTCTGGGAT TACACCTGGC TGACGAATGT GGCTAACGGC CCTCACACCC TGATGGTGGA  10740
AGCGTCCGAC AAGGCGGGAA ACAAAACGAC GCAGAAACTG GACTTCACCA TCGATACCAT  10800
TCTGTCAGAA CCGACGATTA CCCTGGACAG CGCGGATGAT AGCGCCGCTG GCGATAACAT  10860
CACCAACGTT AAGATGCCAG GCTTTACCCT CGGTAATATC GACGCCGACG TGACCAAAGT  10920
GGTGGTGACG GTGGCGCATG ATGGTAAGAA CCAACAGATA GAGTTGATTA AGAACGGCGG  10980
TGTGTGGCGC TTTACGCCGG GCGCAGCCTG GACCGATGGC GACTATACGT TGACGGTAAA  11040
GGTAGAAGAT AAGGCGGGTA ATACAAATTA TTCTGCGCCG CTGACGGTGA CTATCGATAC  11100
GCAAACGTCT ATTGATCGCA TTGAGCTTCT TAATGACACG GGTATTGTCG GGGATAACCT  11160
GACCAATGAA GCACGTCCAC AGTTTCATAT TACGGTACCG ACGGACGTGA ACTCTGTGCA  11220
ACTGAGTCTT GATGGCGGCA TCAACTGGGT TAACGCAACG CTGACGTCTG ACGGCGTTTG  11280
GGAGTATATA TGGCCGACAG ATCTGGTCGA AAATACGTAT ACCCTGACAG TGAAAGCAAC  11340
CGATGTTGCA GGCAACACGG CGACGGAAAC GCTCAATTTT ACCATTGATA CCACATTGTC  11400
GACACCGACC ATCACGCTGG ATAGCGCAGA TGATAGCGGC ACCGCCAACG ATAATAAGAC  11460
TAACGTTAAA ACGCCGGGTT TTATTATCGG CGGTATTGAT TCTGACGTGA CTCAGGTCGT  11520
CGTGCAGGTG ATGCGCGATG GTCACAGCGA GGAGGTGGAG CTGACGCAGA CTAACGGGCA  11580
GTGGCGTTTT GTACCCGGCA GCGCGTGGAC TGATGGCGAC TATACGCTGA CGGTAACGGT  11640
GAAAGATGAG GCGGGTAATA TTCGCCACTC AGCGCCGTTG ACGGTCACCA TCGATACGCA  11700
AATCACCATT GACCATATTG AACTGGTCAA TGACAGCGGT ATTCCGGACG ATAATCTGAC  11760
TAATAATGTG CGTCCGCAAC TTCCAGGTGA CGGTACCGAC GGATGTCAAC GTGGTGCGCC  11820
TGAGCATTGA CGGCGGTAAG ACGTGGTTCA ACGTTACCCA GAGCGCGACG CCGGGCGTCT  11880
GGGATTATAC CTGGCTGGCT GATGTGGGAG AGGGTAAGCA TACCCTGACA GTGGAGGCGA  11940
CCGACAAGGC GGGAAACAAA ACGACGCAGC AACTGGACTT CATCATCGAT ACCCTACTGT  12000
CAGAACCGAC TATCGTGCTG GACAGCACGG ACGACAGCGG AACAAAAGGC GATCACCTGA  12060
CCAACGTAAA TAAGCCGACG TTTTTACTGG GCAATATTGA CGCAGACGCG CGGTATGTCA  12120
CGGTTGAGGT ACAGCATGGC GGCACGAAAG AGGTGCTGAC GGCCACCAAA GACGCGACCG  12180
GCAACTGGAG CGTGACACCG ACCGGCACAT GGGCAGATGG CGACTATACG CTGACAGTGA  12240
GGGTGGAAGA TGAGGCGGGG AACGAAAAAC ACTCAGGTCG CTGACGGTCA CTGTTGATAC  12300
CCAAATCACC ATTGATGTTA TTGAACTGGT TAATGATAAC GGTATTCCCG GCGACAATAT  12360
GACTAACGAC GCCCATCCGC AGTTCCGCGT GACGGTACCG GGGGACGTTA ACGAAGTCAG  12420
TCTGAGCATT GACGGTGGCG TGACCTGGGT TAAGGCGACA CAGAGCGCGA CGCCGGGCGT  12480
CTGGAATTAT ACCTGGCCGG GCACCGTGCC GGATGGCGAC TATACGCTGA ATGTGAAAGC  12540
GACTGACAAT GCGGGTAATA CGGTGACGGA GACACTCCAC TTCACTATTG ATACTACGTT  12600
GTCGACGCCG GTGATCGTAC TGGATAGCGC GGACGACAGT GGTGTCCATG GCGATAACAT  12660
GACGAATAGC ACCCAGCCGA CATTTGCCCT GCAGCATATT GATGATGATG CCGTTCGCGT  12720
TACGGTCAGC GTAGAGCATG GCGGCGTCAC CACCACATTT GACGCCACGA AAGACGCAGG  12780
CGGATGGACC TTTACGCCGA CAGGGGCGTG GCGGATGGT GATTATACCC TGAGTGTGTC  12840
```

-continued

```
AGTCGAAGAT AAAGCGGGGA ACACCAGCCA TTCTGCATCG CTGACGGTGA CGGTGGACAC  12900
GCAAATCGCC ATTAATAACA TTGAACTGGT CAATGACAGC GGTATTCCCG ACGATAATCT  12960
GACTAATAAT GTGCGTCCGC ACTTCCAGGT GACGGTACCG ACGGATGTCA ACGTGGTGCG  13020
CCTGAGCATT GACGGCGGCA AGACGTGGTT CAACGCTACC CAGAGCGCGA CGCCGGGCGT  13080
CTGGGATTAT ACCTGGCTGG CTGATGTGGG AGAGGGTAAG CATACCCTGA CAGTGGGGGC  13140
GACCGACAAG GCGGGAAACA AAACGACGCA GCAACTGGAC TTCATCATCG ATACCCTACT  13200
GTCAGAACCG ACTATCGTGC TGGACAACAC GGACTACAGC GGAAACAAAA GGCGATCACC  13260
TGACCAACGT AAATAAGCCG ACGTTTTTAC TGGGCAATAT TGACGCAGAC GCGCGGTATG  13320
TCACGGTTGA GGTGCAACAT GGCGGCACGA AAGAAGTGCT GACGGCCACC AAAGGCGCGA  13380
CCGGCATCTG GAGCGTGACA CCGACCGGCA CATGGGCAGA TGGCGACTAT ACGCTGACGG  13440
TGAGGGTGGA GGATGATGCG GGGAACGTAA AATACTCAGC GCCGCTGACG GTCACGGTTG  13500
ACACCCAAAT CACCATCGAT GTTATTGAAC TGGTTAATGA TAACGGTATT CCCGGCGACA  13560
ACCTGACCAA TGACGTTCGT CCACACTTCC GCGTCACGGT GCCAGGGGAT GTCAACGAAG  13620
TACGTCTGAG TATCGACGGC GGTAATACGT GGGTTCGTGC AACACAGGGC ACGGCAGGGA  13680
TCTGGGATTA CACCTGGCCG AAAGATGTGA CCGACGGGCT ACATACCCTG ACGGTAGAAG  13740
CGACCGATAA GGCGGGAAAT AAGACGACGC AGACGCTCGA TTTTACCATT GATACCCGGC  13800
TGTCAACGCC TACCATCGCT ATGGATAGCA GGGACGATAC AGGTGCCATT GGCGATCATA  13860
TTACGAGCGT CAAAAGACCG GGCTTTACTA TTGGCAATAT TGACGCCGAT GCGCACTCGG  13920
TCATTTTGCG GATCACACAG GGCGGCAATA GCCAGGAAGT GACACTAACC CAGGTTGGAG  13980
GACAGTGGCG CTTTACGCCA GATGCTGACT GGGCGGACGG TAGCTATACG CTGACGGTAG  14040
AGGTAACGGA TAACGCAGGA AACGTTCGTC AGTCCACGCC GCTGGTGGTG ACGGTGGACA  14100
CGCAAACCAG CATTACTGAT ATTACATTGG TCAATGATCA TGGCGTGCCT GATGACAATC  14160
TAACTAATAG CACCCGTCCG CAGTTTGAGA TCACGGTGCC GGCGGATGTG AATTCTGTGC  14220
AACTGAGCAT TGATGGGGGC GCAAACTGGG TGAGCGCGAC GCAGGGTATC GAAGGCGTCT  14280
GGGGCTATAC CTGGCCAACG GATATGGGCG ATGGAAAACA CACCCTAACC GTCATGGTCA  14340
CCGACAGAGC GGGCAATACG GCGACGCAAA CGCTTGAATT TTTCATCGAC ACCCGGTTGT  14400
CGACGCCGAC CATTGCGCTG GATAGCACGG ATGATACCGG TACGCCTGGC GATGATATGA  14460
CCAATCGCAC CCGACCGACC TTTATTCTGC AGAATATCGA TTCGGATGTT ATCAACGTTA  14520
CAGTCAGCGT CACGCATAAT GGAACGACAA CCTCGTTTAC TGCGACACAG GGGGCTGGAG  14580
GATGGAGCTT TACACCGCCA GCGCCGTGGG GCGACGGTGA TTATACGCTG ACGGTGACAG  14640
TGGAGGATCG GGCGGGAAAT ACGCGTCCGT CTACGCCGCT GACGGTGACA GTGGATACGC  14700
AAATAGCCAT TGATCGTATT GAATTAGTCA ACGATAGCGG CGTCCCTGGC GATAATGTGA  14760
CAAAACATGT GCGTCCGCAG TTCCAGATCT CGGTACCGGA TGATGTGGAA AAGTTCTTCT  14820
GAGTATTGAC GGCGGCACGA CCTGGGTTAC TGCAATCAAG AGTTCGACGG CTGGCATTTG  14880
GGATTACACC TGGCCGACGG ATATGCCAGA GGGACAGCAT ACCCTGACCG TGGAAGTGAC  14940
TGACGGTGCG GGTAATAAGA TGACGGAGAC GCTCAATTTC ACTATCGATA TCACGTTGTT  15000
AACGCCAACC ATTGAGCTAG CGCCCGATCA GGATACCGGA CAGAATAAGA ACGATAATCT  15060
GACCAGCGTC ACTCAGCCGG TATTTGTGTT GGGGAGTATC GATAAAGATG TTCGACACGT  15120
GGAATTGAGT ATTGAGCATA ACGGCACGTT TAAAACGGTG GTACTCACCG AATCAGCCGA  15180
CGGCTGGCGC TATCGACCGG ATTCTGCTTT GGCGGACGGT AGCTACACAT TCACCGTGAC  15240
```

-continued

```
GGTAACAGAT GTGGCAGGCA ACCAGCAAAC ATCCGCGCCT TTAAAGGTGA CGATAGACGG  15300
TACGTTGACT ACGCCGGTGA TTGAACTGGC AGCTGGCGAA GATAGCGGTA CTGTTGGCGA  15360
TCGCCTCACC AATCACGATC GGCCTGTGTT CGACATACAT CAGGTTGATT CTGACGTTAC  15420
GCGCGTGATG GTCAAAGTAA CTTACAACGG TAAAACGCAC GAAGAAGCGG CGGTATTCAC  15480
CAATGGTCAA TGGCGCTTTA CGCCTTCTGC GAAGCTGGGC TGATGGCTCA TATCAGTTAG  15540
CCGTTGTGGT GGAAGATCTG GCGGGGAATG TAAAAGAGTC TGCGCCGTTT GAGGTGCGTA  15600
TTGATACCAC GACAACCATT AACAATATCG TATTGCTTAA TGATACCGGC GTGCAGAATG  15660
ATCAATTAAC GAATGTTGCC AAACCGTCAT TCAGAATTGA CGTTCCCGGT GATGTCGTCC  15720
AGGTACGTGT AACCCTGGAT GGTGGCGCTA ACTGGAATGT GATACGCAAA AATGCCGACG  15780
GACAGTGGAT TTTTGACAGC CCGAATACTC TGGTTGACGG CACATATACC CTTCGCGTAG  15840
AGGCCACGGG ATGAGGCAGG TAATATTGCG AATAAAGATT TAGTATTTAA TATCGATACT  15900
AATATACAGG TTCCTACTAT TGCTTTAGAC GCAGGACAAG ATACCGGAGC GAATACCGCC  15960
GATAATATTA CTAATATTTC ACGACCCACC TTTACGATTG GTAATGTTGA CCCCGATGTT  16020
ATCAAAGTCG TGGTGACGAT TGATGGTCAT GATTATAACG CGACTAAGGT TGGGGCTGGT  16080
TGGCAATTTA CACCAGGCAA TGCCATTCCG GATGGCTCTT ATAATATTAC CGTTACGGTT  16140
GAAGATAAGG CCGGAAATAC CGCGACATCG AAACCATTAC CTGTTGTGAT AGATACGACG  16200
GCTGAAATTG AAAGCGTCAC GTTGGTTACA GATAGCGGTG ATAGCGATGT AGATAACATT  16260
ACCAAAGTCG ACAGCCGCAG TTTAGTATTG TTACCGCTGA TGATATAACC CATGTGCGCG  16320
TTAAAATCGA TAACGCCGCT AATTGGATTG AACTCACAAA AGGAGGGATG GCCGCTGGAT  16380
ATTTAATGTC GGTTCGGCAT TACCTGATGG GCAACACACT CTCTTGGTTG ATGTGACTGA  16440
TATCGCCGGC AACGTTGCGC AAGAAACGCT GCAGTTTACG ATTGATACGA CTCTGCGAGA  16500
GCCGACAATT GTACTCGATC CCACCCATGA TACTGGTGAT GATACTAATG ATAATCTTAC  16560
CAGGATTAAC AAACCGGTGT TTATTATCGG TAATGTCGAT AATGATGTAT CACACATTGT  16620
GGTTCATATT GATGGTCGGG ATTACACCAT TGAAAACACA GGGGGGAATT TAACCTTTAC  16680
GCCGGATCAA CCGCTGTCTG ACGGTCAGCA TACGATCTCT GTTACCGTAA CGGATATTGC  16740
TGGTAATACC AAAACATCGG CCGAACTGCG GATTGAAATC GACACGCAGG TTCAGATTGA  16800
CAGTGTTACG TTAACAACAG ATAGCGGCGT CAACGATCAC GATAATGTCA CCAATGCTAC  16860
CCGTCCCTCT TTTGAAATTG CAACGCCTGA TGATGTGACA TCGGTGCTGG TTTCTTTCGA  16920
TGGCGTAAAC TGGACGCCCA TCAGTAAAAA TGCGGCCGGG CAGTGGGAAT TTACTGCAGG  16980
TAGCGCATTG CCTGATGGTC ATTATACTCT CCATGTCCAG GCGACGGATC GGGCAGGGAA  17040
TACGGCAAAT TCCACGCTGG GCTTCACCGT GGATACGCAG ATTGACGGCC TGAGCGTCGT  17100
GATGCTGGAC GACGCCGGAA AGGATTCTAC GGATGGTATT ACGAATATTA CCTCTCCACG  17160
TTTTGAAATT TCAGCCAGAG AACCGCTGCA GAGCGTGACG GTAATTTTAA ACGGGAAATC  17220
CAGCACACTG ACTCAGGGGG CAGGTAATAA ATGGCTGTTT ACCCCTGATA CACCGTTAGT  17280
GGATGGAACT TACAAAATAG AAATAGTGGC TGAAGATATC GCAGGTAATA AAATTAGCAA  17340
AGAGGTATCA TTCACAATAG ACACTATTGT TTCTGATCCC AGTATTGATT TGCTGGATGC  17400
GGATGATACT GGCGAAAGCG CTGTTGATAA TATTACGAGT GTCACTACAC CACGTTTCGT  17460
TATTGGCAAT GTACCCGCCG ATATTGATAC TGTTGTTATC AGAATTAACG GCGTTTCTTA  17520
TCCGGTTACG GCAAATGGCA ATAACCTCTG GGAATTTCAG GTTCCCGTTG CGTTAAACGA  17580
TGGCGTATAT GAAGCCGTTG TTGTCTTCAG AGATATTGCC GGAAATATTT CTGAAATTAA  17640
```

```
GCTGCCCTTT ACCATTGATA CCACGACAAG CGTCAGTGTC AGAATGGAGC TAGCGTCTGA  17700

TACCGGAAAT TCCAATAGCG ATAACCTTAC GAATAAGCAA AATCCCAAAT TCGAAGGTAC  17760

TGCAGAGCCC AATGCGAAAC TGGTGATTAC CATTGTTGAC GATAAGTCAG GTCAGGAGGT  17820

TTTAAAACAA ACGATTACGG TTGGCGCTGA TGGCAACTGG AGTGTGACGC CGAATATACT  17880

GCCGGATGGC ATGTATACCA TCAACGTCGT CGCAACAGAT GTCGCGGGAA ATACTGCGCA  17940

AACGCAGGAA AGATTCACTA TCGATACGGT TACGATCGAT CCCACCATTC GCCTTTCGGA  18000

TCCATCTATT GATGATCAGC ATGAAGCAAC CAGCCTGCGT CCTGAGTTCA AAGGGTTTGC  18060

CGAAGCGTTC TCGACGATTA TGATTCAGTG GGATGGGAAA GTGGTCGGCT CGGCAAACGC  18120

CAATGCGAAT GGCGAATGGA GTTGGACGCC GCCATCAGTA TTAGCGCCAG GCTCCTATGT  18180

TGTGAGCATT GTTGCCAAAG ATAAAGCGGG TAATGATTCG TCGCAGGTCG ACTTTCCTGT  18240

CGTAATACCT GTTATTGATG TCACGCCTCC AACCATAAAG CTCAGCGAGG AGAGCGATAG  18300

TGGCGCCTTA GGAGACTTTA CCACGAATAA TAAAACGCCG ACCCTGATTG GGAGCACGTT  18360

ACCTAATACG ATTGTGAGTA TTTATGTGGA TGGCGTGAAG GTCGGCGAGG CGACAGCGGA  18420

TACAGCGGGT CGATATACTT TCCAGTTATC GGAAATGAAA GATGGCCATT ATGTCGTCCA  18480

GGTGGGTATC GTCAACCCTC GCGATAATAG CGAACTGCGT TCTACCGCCG TTGATGTCAC  18540

TATCGATACC GAGGTTGCTG AACTGGTATG GAATATATCT GGAATGCATG AGGGCGGATA  18600

TATCAATACG GTGACGCCGG AGATTGGCGG CACCAGTGAG CCAAACAGCA AAATCACTAT  18660

CTTTGTGAAT GGCGTTGGAA AAGCGATTGC TTATACGACA GGCGCAGGAC ACTGGGGCGT  18720

AGTATTACCC GCTTTGGGTA ATGACGGTAA TTATGAATTA ACGTTTAAAG TTGAAGACGT  18780

TGCCGGTAAT ATCAGAGAGT TTGGTCCGCA GAATGTAATA CTGGATACAG TAATTTCGCC  18840

GTTAACCGTG GTATTACGCG AAGCTGATGA CAGTGGCAAA GTTGGCGACT GGATCACCAA  18900

TAAATCTCAT GTCACCATCG ATGGTACTGC CGAAGCCGGA AGTACTTTAA CCATCAGGAA  18960

TCCGCAGGGA GTGGTTATTG CTACCCTGGT GGTAGGCAAT GATGGTCGAT GGAGCGCAGA  19020

ATTAGATCTG CGTGAAGGTA GTAATGCCTT TGTCGTGGTA TCGGAAGATA AAGCGGGCAA  19080

CAGTCAACAA AAAGAGATTC TGATAGAACA TGATACGCAG ATTGAAATCA GCGATATTTC  19140

ATTAAGTCGG GATACTAATA GCGGTGATAA ATATGATCTG ATTACCAATA ATAAGTCTCC  19200

GGTACTGGTT GCCAGGACCG ATCCCGGCGC GACGGTACAG GTTTATATTA ATGGTGTGTT  19260

ACAAGGCACA GTAGAGGCGA GTTCGTCAGG TAATATTAGC TATACCATGC CGGCAAATAG  19320

CGCCGACGGC GAGTATCAGG TGCAATTTGT TGCTACGGAT ACTGCTGGTA ACCGGGTTGA  19380

GTCTGCGATT ACAACCGTGA CAATCGATTC TCAAATTGCT GTCTTTGATA TTGATGAAGA  19440

TTCATTACCG GCCCTCTCTA ATAACCGAGC GTTGTCAGTC TCAGGTGTCG GGGAGGCTGG  19500

TTCTCAGGTC AGCATCTTTG TCGACGGTAA ATTAGTCAAC GTTGTTATGG TTGAGGCTGA  19560

TGGCACATGG CGCGCGCCGA TACTGCTGCA AGATGATGGT ACGTTTAATA TTCATTTCAG  19620

CATTACTGAC GTTGCTGGCA ACACTGAAGT GAGCAAGGAT TATAGCGTGG ATGTCGATTC  19680

ATCAACCGAC TTCCCAACGC TCAACCTTGA AGATGCAAGC AACTCTGGTT CACTTGACGA  19740

TCTGATTACT AATCACAACA AGCCTGTATT AGTTGGCACC GCAGAAGCGG GAGCCACAAT  19800

CCATATTTAT GTGGATGAAA AGATCGTGGC AAATGTTCTT GTGCTTGAAG ATGGAACCTG  19860

GTCCTATCAG TTTGATAATG CGTTAAAAGA TGGTGAATAT TCTATCCGTG TGGTTGCCGA  19920

AGACCCGGCA GGTAATACGG CAGAATCGCC TCGCTTACTC GTCACGATAG ATACCAGTAC  19980

GTTTATCGAT AATCCTGCTA TGGTGGCAGG TTCTGATAAT GGTATTTTCA GTAATGATAG  20040
```

```
TATAACGAGT CAGACCCGGC CTACGTTTAG TATTTTTGGA GAAATGAACC AGAGTGTTCA  20100
GATTTTCATT GATGGAGTGC TAGTCGATAC GATCACGGTG ACCGACAGAA ATCAAGTTTA  20160
TCGACCTGAG TCACCGTTGG GCGATGGTTC CCATAGCATT TATTATGTTA TCACCGATAA  20220
AGCAGGCAAC ACGGCTACCT CGAAAACGCT AAACTTTACT ATCGATACCT TTAATACGAC  20280
GCCTGTCGCC ATTGATTCTA TCGGTGGACA AACGTTAGCA GAGATGACCG GTAGTGATGG  20340
CAAAATATAT ATAACGGACA CGACGCGTAA CTTATTGTTT AGTGGCAGTG CCGAGCCCAA  20400
TAGCAAAATA GAAATCATCA TTAATGGCTT AAATGTGGGG GAAGTTTGGG TTAATGAAAA  20460
AGGCCACTGG CAGATGCCGG TGAACCCGCT TTATTTCACA GAAGGCCAAC TGGATATCAC  20520
TGTTAAATCT ACGGACCGTG CTGGTAACGT AAATCAGGAA AAGTATTCCA TTTGGGTTGA  20580
TACGCATATC AAGGTATTTA CCAGCGAGCT TGATGACAAT AAATCATCAT CGAAAACGGA  20640
ATGGTGGAGT AATAGCGATC TCATTACCAT GCGAGGCACG GGTGAAATTG GCGCTACGGT  20700
ATCATTAATC GTGGCTGGCG TCACGCTGGC AACTGCTGTT GTGGCGGCAA CAGGACGATG  20760
GGAATTATCA ACAGACAAGC TTCCAGAAGG GACTTACGAT ATTAGTTTGG TCATTGAAGA  20820
TAGCCCGGAA ATCGTTGGGA AGATGTGCGT GAAATATTTA TTGACCGAAC CCGCCAAATG  20880
CTCCGGTCGT AACGTATTCA GATATTGTCA ACGATCTAAT TATTATGCAG GGGACGGCGG  20940
AAGCCAAATC TCAGCTAATA ATAACCGATA GTGAGGGGAA TACTTATACG TTAACCGTTC  21000
CTGATAATGG TAAATGGAGT ATGGCTATCC CGTATCCATC AGAAGGGAAG TTTACCATTA  21060
CGAGTGTGGA TGCTATTGGT AACCGGAGTG ATGATGTCCC TCTCGATATC ATGAAAGAGG  21120
TTCCCGTTAT TTCATTATCT CCAGACTCAG ACAGTGGTAC GGTGGGCGAT AATATTACGC  21180
GAGATAAGCA ACCTACCTTT ATTATCGGGA ATCTGGAAAG CGATGTTGTG GTCGTTCAGG  21240
TCGATATCAA TGGGACCGTA TATAATGCTG AAAAAAATGC CGATGGCGTT TGGTTCTTTA  21300
CGCCAGGTAC ACCGTTAGCT GATGGTTCCT ATACGATATC GGTAATCGCA AGCGATGCCG  21360
CGGGTAATCA GAAAAACTCG TTACCCATTA CTGTCACGAT CGACAGCACG CTGACGGTGC  21420
CGGAGATTGC GTTGGCAGCA GGTGAAGACA ATGGCGCTTC AGACAGCGAT AACGTGACGA  21480
ATCACACCCA GCCTAAGTTC ACGCTGCAGC ATATTGATGC TGATGTGACC GGGGTGACCG  21540
TAAACGTGAC GCATAATGGC GTGACAGACA TCTATCAGGC GACGCAAGGC GCGGATGGCT  21600
GGACCTTCAC GCCGCCAGCC GCCTGGAATG ACGGTAACTA CACGCTGAGC GTGACGGTGG  21660
TGGATCGCGC GGGGAATTCA CAGCAATCTG CTTCGCTAGC GGTGACGGTT GACTCAACGG  21720
TGACGGTAAC AGCGGATAGC CAGCATGACG ATGCGAGCGA TGACGCCACG GCAACAGCGG  21780
TTACTCCACC GGAGTCTGAA ACAGTGAATG CCGAAAGCGC TACGCATCTT CGTACAGAGC  21840
CGTCTGCGGC GGAAGAAAGC GTGGTGAAGG TGACAGCCTA TAGTATTACA TTGTTAAACG  21900
CTGACTCTGG GGATGAAATA GATCGTTCAA TTAGTCAGAC ACCTTCTTTT GAAATATCAG  21960
TACCTGAGAA TATTGTTAAT GTCAGTATTA TGTTTGAAGG AGAAGAGTTT ACTCTGCCGA  22020
TAACTAACCA GAAAGCAATA TTCGAAGTTC CGCTATCTTT GGAAGATGGT GAATATACTA  22080
TGGACGTGAA ATTCATTGAT AAAGACAATG ATTTCCTGAT TAAGGAGAAA ACATTCTCAG  22140
TCGATCACTC CTCGGCGGAT ATTGTGAACG CAATGAATGT AAGAGGAAAG ACCGAGGATG  22200
ATATTAATGA TTCCCCTTCC ACGAGTTCTG TAGGGCACAA CAATAACGGC GCTATTGATG  22260
TTTTCGCCGT TAATGAAGTT ACGCTACCTG TAGATAATCA AGAAGAACAC GCATAATAAC  22320
GGAGGCCCCT CACCTTTGGG TTGAAGGGGG TTTACTTATG GATAAAAAAC TAGAACCTTA  22380
TTATTTAAGT GCGGAAACGG CATTATCTAT AGTGTCTACA AAATTCAACA TAAAAATTGA  22440
```

-continued

CATCCGAGAA GATGATATAC ATTTGAAGAT TTAGAAAGTA CGACTGAAAT AACACTGACG 22500

ACCTATACGA ATGAAGAATT TCTTTTTGTC GTTAGGGCTT TCTCTACAGG ATATATTATT 22560

TAATAATGGT GAGGATTTAC TAAATGAGCC TATGCCGATT TTACTATTAA CACCAGAAAA 22620

TGAAAGTGGA TGGTGTGTGT GAGTGGCGGG CAAAAAATAA AGTTGGTAAA CGCGCGCGGT 22680

GAACTCTGTT ATGTTGAAAT TGAAGATGAA TATTTAAAAG AGTTATCTGC ATTTAGTATA 22740

CTACCTTTAA ATAAAGTTGT TGATAGTATA AGAGTAAAAA ATATCATAAA AAACTCTTTA 22800

TCGATGAACA AGATTTTTTA TACTAAATAC TTTTTTTCAT CTCTTTTTAT GGCAATTTTT 22860

GCGTTAACTA TCCCAGTATT TAGTAATCTG TTCTATGATA AGCTTGTTCC AAGCGCTTCG 22920

GTTTCATCTT TATTTGGCGT GGCTATAATT GTTGCTGTAT TTATTGTTTT TGAGTTTATC 22980

CTTCGTACTT CGAAAGATAT TTATCAGTCT ATCACAGCAA GGCAGGATGA CGTCGATATT 23040

GATATCGCAT TTCTTGAAGC GGTACTTTAT AGTAAAAAGA AAAATGGCAG ATCCATGTCA 23100

TCAGCATTTG TGCTATGGAA TGAGTTTCAG AAAATTAAAC CCGTTTTATT AAACTCGATC 23160

TTTCAACGTA TAGCCGATAT TCCAATATTT ATTATATTTC TCATTGTTAT ATATGTAAAT 23220

TTAGGTCTGG TTGTTATTGT ACCTATTACC ATGTTTATCG TCTCTATTAT TATTTCCCTC 23280

GTTAACCACC ATTATACTAA TGAGTTAATG AACAAACAAA AAGAAGGACA GAAGAACAGG 23340

AATATTTTTA TCTCAGAAGT TTTCTTATCT ATTAAAATGA TCCATACCTT AAATAATCAA 23400

GGTTTACTTT TTGATTGGGT TAATACATCA AATGAACAGT CGTATCTTAA CCTGAAGATA 23460

AGGAAATTAA ATCTTATCTA TCAATCTATA TTGGGGAGTA TGTCATCTAT TACCCAAATA 23520

ACTATTATGG TAATAGCCTT TTTTATGGTA ATCAAGGGTG ATGTTACTAC TGGCGCAATT 23580

GTTTCATCTG TCATTGTCTC TGGCCGTATT TCCGGGATCA TTTCGAATTT TTCTTCTACA 23640

TTAATCTCTA TTTTATCAGC AGAAAAAACC GGTAAGGATC TGCTTTCTTT TTTTGATGAA 23700

GATCAGGCAG AAAAAACACC GGCATTACAG TCAATATCAA AGTGCAATGG CGATATCTCT 23760

ATCCGGGGCG TGAGTTATCA GTATGATGCT CAATCTCCGA TGATTATTAA CCGACTGTCT 23820

ATAGACATAC CTGCGGGGCA ACGTGTCGCG GTGGTAGGCG AATGCGGAGC AGGAAAAAGC 23880

TCATTACTGG GAATGCTATC TGGCTACCTT TCGCCAACAG ACGGTGCCAT TTTATATGAT 23940

GGATATAACT TAGGACATTT ATCGCAGAAC TTTTTTTCTC AGCATTTAAG CGTGGTGACG 24000

ACACATGATG TTTTATTCAC CGGAACCATT GAAAGTAATT TCGCGTTAAA ACCGCAAAAC 24060

GACAGGGGCC GGGTACTCAA GGCGCTTCAG CTGGCGAACT GTGGTTTTAT CTTGCAACAT 24120

CCTATGGGGC TGAAGTTTCC GGTGAATTTT ATGGCTAAAA ACCTGTCATC CGGACAGCAG 24180

CAGCAGTTAT TATTAGCACG TAGTCTGAGT AGTGACGCCA GCGTCTTTTT ATGGGATGAA 24240

CCAACATCAA ATCTGGATGA GAATACCGAG AAGCAAATTT TTGATAACTT AGATGAGTTT 24300

ATTCATGGGA AAACGTTGAT CATGGTGACG CATCGTCGAT ATCTGATAAA GTATTTTGAC 24360

CGGGTCCTGG TAATGAAAGG TGGAAAAATA ATCCGTGATT GTTCTCCGGA TAAATTATTA 24420

ATGTAAAATA AGCAGCGCTT GTCGCTGTTA TCAGGTGGTA CTGCTTAATA AAAAAGACCC 24480

GTTGCACAAA CGGGTCTTTT TTGTCATTTA ACGGAGTCGG CAACGTCTTC AATAAGTTTA 24540

GCTCGATTCT GTTAGGGCTA TTCCACTTGC CATTTTTGGA TAACCACACC TGGCGGCCTT 24600

CATCAACGGC AATGCGAGGG ACGTGATGGT GCGCAAGGCT AACCCCTGGC GCGCGATTCC 24660

GCGTTGAGAT AACCGGTGGG CGGCTTCAGC GGCAGCGATA G 24701

(2) INFORMATION FOR SEQ ID NO:3:

(i) SEQUENCE CHARACTERISTICS:

(A) LENGTH: 24701 bases
(B) TYPE: nucleotide
(C) STRANDEDNESS: double stranded
(D) TOPOLOGY: linear (xi) SEQUENCE DESCRIPTION: SEQ ID NO:3:

```
CTATCGCTGC CGCTGAAGCC GCCCACCGGT TATCTCAACG CGGAATCGCG CGCCAGGGGT     60
TAGCCTTGCG CACCATCACG TCCCTCGCAT TGCCGTTGAT GAAGGCCGCC AGGTGTGGTT    120
ATCCAAAAAT GGCAAGTGGA ATAGCCCTAA CAGAATCGAG CTAAACTTAT TGAAGACGTT    180
GCCGACTCCG TTAAATGACA AAAAAGACCC GTTTGTGCAA CGGGTCTTTT TTATTAAGCA    240
GTACCACCTG ATAACAGCGA CAAGCGCTGC TTATTTTACA TTAATAATTT ATCCGGAGAA    300
CAATCACGGA TTATTTTTCC ACCTTTCATT ACCAGGACCC GGTCAAAATA CTTTATCAGA    360
TATCGACGAT GCGTCACCAT GATCAACGTT TTCCCATGAA TAAACTCATC TAAGTTATCA    420
AAAATTTGCT TCTCGGTATT CTCATCCAGA TTTGATGTTG GTTCATCCCA TAAAAAGACG    480
CTGGCGTCAC TACTCAGACT ACGTGCTAAT AATAACTGCT GCTGCTGTCC GGATGACAGG    540
TTTTTAGCCA TAAAATTCAC CGGAAACTTC AGCCCCATAG GATGTTGCAA GATAAAACCA    600
CAGTTCGCCA GCTGAAGCGC CTTGAGTACC CGGCCCCTGT CGTTTTGCGG TTTTAACGCG    660
AAATTACTTT CAATGGTTCC GGTGAATAAA ACATCATGTG TCGTCACCAC GCTTAAATGC    720
TGAGAAAAAA AGTTCTGCGA TAAATGTCCT AAGTTATATC CATCATATAA AATGGCACCG    780
TCTGTTGGCG AAAGGTAGCC AGATAGCATT CCCAGTAATG AGCTTTTTCC TGCTCCGCAT    840
TCGCCTACCA CCGCGACACG TTGCCCCGCA GGTATGTCTA TAGACAGTCG GTTAATAATC    900
ATCGGAGATT GAGCATCATA CTGATAACTC ACGCCCCGGA TAGAGATATC GCCATTGCAC    960
TTTGATATTG ACTGTAATGC CGGTGTTTTT TCTGCCTGAT CTTCATCAAA AAAAGAAAGC   1020
AGATCCTTAC CGGTTTTTTC TGCTGATAAA ATAGAGATTA ATGTAGAAGA AAAATTCGAA   1080
ATGATCCCGG AAATACGGCC AGAGACAATG ACAGATGAAA CAATTGCGCC AGTAGTAACA   1140
TCACCCTTGA TTACCATAAA AAAGGCTATT ACCATAATAG TTATTTGGGT AATAGATGAC   1200
ATACTCCCCA ATATAGATTG ATAGATAAGA TTTAATTTCC TTATCTTCAG GTTAAGATAC   1260
GACTGTTCAT TTGATGTATT AACCCAATCA AAAAGTAAAC CTTGATTATT TAAGGTATGG   1320
ATCATTTTAA TAGATAAGAA AACTTCTGAG ATAAAAATAT TCCTGTTCTT CTGTCCTTCT   1380
TTTTGTTTGT TCATTAACTC ATTAGTATAA TGGTGGTTAA CGAGGGAAAT AATAATAGAG   1440
ACGATAAACA TGGTAATAGG TACAATAACA ACCAGACCTA AATTTACATA TATAACAATG   1500
AGAAATATAA TAAATATTGG AATATCGGCT ATACGTTGAA AGATCGAGTT TAATAAAACG   1560
GGTTTAATTT TCTGAAACTC ATTCCATAGC ACAAATGCTG ATGACATGGA TCTGCCATTT   1620
TTCTTTTTAC TATAAAGTAC CGCTTCAAGA AATGCGATAT CAATATCGAC GTCATCCTGC   1680
CTTGCTGTGA TAGACTGATA AATATCTTTC GAAGTACGAA GGATAAACTC AAAAACAATA   1740
AATACAGCAA CAATTATAGC CACGCCAAAT AAAGATGAAA CCGAAGCGCT TGGAACAAGC   1800
TTATCATAGA ACAGATTACT AAATACTGGG ATAGTTAACG CAAAAATTGC CATAAAAAGA   1860
GATGAAAAAA AGTATTTAGT ATAAAAAATC TTGTTCATCG ATAAAGAGTT TTTTATGATA   1920
TTTTTTACTC TTATACTATC AACAACTTTA TTTAAAGGTA GTATACTAAA TGCAGATAAC   1980
TCTTTTAAAT ATTCATCTTC AATTTCAACA TAACAGAGTT CACCGCGCGC GTTTACCAAC   2040
TTTATTTTTT GCCCGCCACT CACACACACC ATCCACTTTC ATTTTCTGGT GTTAATAGTA   2100
AAATCGGCAT AGGCTCATTT AGTAAATCCT CACCATTATT AAATAATATA TCCTGTAGAG   2160
AAAGCCCTAA CGACAAAAAG AAATTCTTCA TTCGTATAGG TCGTCAGTGT TATTTCAGTC   2220
```

GTACTTTCTA AATCTTCAAA TGTATATCAT CTTCTCGGAT GTCAATTTTT ATGTTGAATT 2280

TTGTAGACAC TATAGATAAT GCCGTTTCCG CACTTAAATA ATAAGGTTCT AGTTTTTTAT 2340

CCATAAGTAA ACCCCCTTCA ACCCAAAGGT GAGGGGCCTC CGTTATTATG CGTGTTCTTC 2400

TTGATTATCT ACAGGTAGCG TAACTTCATT AACGGCGAAA ACATCAATAG CGCCGTTATT 2460

GTTGTGCCCT ACAGAACTCG TGGAAGGGGA ATCATTAATA TCATCCTCGG TCTTTCCTCT 2520

TACATTCATT GCGTTCACAA TATCCGCCGA GGAGTGATCG ACTGAGAATG TTTTCTCCTT 2580

AATCAGGAAA TCATTGTCTT TATCAATGAA TTTCACGTCC ATAGTATATT CACCATCTTC 2640

CAAAGATAGC GGAACTTCGA ATATTGCTTT CTGGTTAGTT ATCGGCAGAG TAAACTCTTC 2700

TCCTTCAAAC ATAATACTGA CATTAACAAT ATTCTCAGGT ACTGATATTT CAAAAGAAGG 2760

TGTCTGACTA ATTGAACGAT CTATTTCATC CCCAGAGTCA GCGTTTAACA ATGTAATACT 2820

ATAGGCTGTC ACCTTCACCA CGCTTTCTTC CGCCGCAGAC GGCTCTGTAC GAAGATGCGT 2880

AGCGCTTTCG GCATTCACTG TTTCAGACTC CGGTGGAGTA ACCGCTGTTG CCGTGGCGTC 2940

ATCGCTCGCA TCGTCATGCT GGCTATCCGC TGTTACCGTC ACCGTTGAGT CAACCGTCAC 3000

CGCTAGCGAA GCAGATTGCT GTGAATTCCC CGCGCGATCC ACCACCGTCA CGCTCAGCGT 3060

GTAGTTACCG TCATTCCAGG CGGCTGGCGG CGTGAAGGTC CAGCCATCCG CGCCTTGCGT 3120

CGCCTGATAG ATGTCTGTCA CGCCATTATG CGTCACGTTT ACGGTCACCC CGGTCACATC 3180

AGCATCAATA TGCTGCAGCG TGAACTTAGG CTGGGTGTGA TTCGTCACGT TATCGCTGTC 3240

TGAAGCGCCA TTGTCTTCAC CTGCTGCCAA CGCAATCTCC GGCACCGTCA GCGTGCTGTC 3300

GATCGTGACA GTAATGGGTA ACGAGTTTTT CTGATTACCC GCGGCATCGC TTGCGATTAC 3360

CGATATCGTA TAGGAACCAT CAGCTAACGG TGTACCTGGC GTAAAGAACC AAACGCCATC 3420

GGCATTTTTT TCAGCATTAT ATACGGTCCC ATTGATATCG ACCTGAACGA CCACAACATC 3480

GCTTTCCAGA TTCCCGATAA TAAAGGTAGG TTGCTTATCT CGCGTAATAT TATCGCCCAC 3540

CGTACCACTG TCTGAGTCTG GAGATAATGA AATAACGGGA ACCTCTTTCA TGATATCGAG 3600

AGGGACATCA TCACTCCGGT TACCAATAGC ATCCACACTC GTAATGGTAA ACTTCCCTTC 3660

TGATGGATAC GGGATAGCCA TACTCCATTT ACCATTATCA GGAACGGTTA ACGTATAAGT 3720

ATTCCCCTCA CTATCGGTTA TTATTAGCTG AGATTTGGCT TCCGCCGTCC CCTGCATAAT 3780

AATTAGATCG TTGACAATAT CTGAATACGT TACGACCGGA GCATTTGGCG GGTTCGGTCA 3840

ATAAATATTT CACGCACATC TTCCCAACGA TTTCCGGGCT ATCTTCAATG ACCAAACTAA 3900

TATCGTAAGT CCCTTCTGGA AGCTTGTCTG TTGATAATTC CCATCGTCCT GTTGCCGCCA 3960

CAACAGCAGT TGCCAGCGTG ACGCCAGCCA CGATTAATGA TACCGTAGCG CCAATTTCAC 4020

CCGTGCCTCG CATGGTAATG AGATCGCTAT TACTCCACCA TTCCGTTTTC GATGATGATT 4080

TATTGTCATC AAGCTCGCTG GTAAATACCT TGATATGCGT ATCAACCCAA ATGGAATACT 4140

TTTCCTGATT TACGTTACCA GCACGGTCCG TAGATTTAAC AGTGATATCC AGTTGGCCTT 4200

CTGTGAAATA AAGCGGGTTC ACCGGCATCT GCCAGTGGCC TTTTTCATTA ACCCAAACTT 4260

CCCCCACATT TAAGCCATTA ATGATGATTT CTATTTTGCT ATTGGGCTCG GCACTGCCAC 4320

TAAACAATAA GTTACGCGTC GTGTCCGTTA TATATATTTT GCCATCACTA CCGGTCATCT 4380

CTGCTAACGT TTGTCCACCG ATAGAATCAA TGGCGACAGG CGTCGTATTA AAGGTATCGA 4440

TAGTAAAGTT TAGCGTTTTC GAGGTAGCCG TGTTGCCTGC TTTATCGGTG ATAACATAAT 4500

AAATGCTATG GGAACCATCG CCCAACGGTG ACTCAGGTCG ATAAACTTGA TTTCTGTCGG 4560

TCACCGTGAT CGTATCGACT AGCACTCCAT CAATGAAAAT CTGAACACTC TGGTTCATTT 4620

```
CTCCAAAAAT ACTAAACGTA GGCCGGGTCT GACTCGTTAT ACTATCATTA CTGAAAATAC   4680
CATTATCAGA ACCTGCCACC ATAGCAGGAT TATCGATAAA CGTACTGGTA TCTATCGTGA   4740
CGAGTAAGCG AGGCGATTCT GCCGTATTAC CTGCCGGGTC TTCGGCAACC ACACGGATAG   4800
AATATTCACC ATCTTTTAAC GCATTATCAA ACTGATAGGA CCAGGTTCCA TCTTCAAGCA   4860
CAAGAACATT TGCCACGATC TTTTCATCCA CATAAATATG GATTGTGGCT CCCGCTTCTG   4920
CGGTGCCAAC TAATACAGGC TTGTTGTGAT TAGTAATCAG ATCGTCAAGT GAACCAGAGT   4980
TGCTTGCATC TTCAAGGTTG AGCGTTGGGA AGTCGGTTGA TGAATCGACA TCCACGCTAT   5040
AATCCTTGCT CACTTCAGTG TTGCCAGCAA CGTCAGTAAT GCTGAAATGA ATATTAAACG   5100
TACCATCATC TTGCAGCAGT ATCGGCGCGC GCCATGTGCC ATCAGCCTCA ACCATAACAA   5160
CGTTGACTAA TTTACCGTCG ACAAAGATGC TGACCTGAGA ACCAGCCTCC CCGACACCTG   5220
AGACTGACAA CGCTCGGTTA TTAGAGAGGG CCGGTAATGA ATCTTCATCA ATATCAAAGA   5280
CAGCAATTTG AGAATCGATT GTCACGGTTG TAATCGCAGA CTCAACCCGG TTACCAGCAG   5340
TATCCGTAGC AACAAATTGC ACCTGATACT CGCCGTCGGC GCTATTTGCC GGCATGGTAT   5400
AGCTAATATT ACCTGACGAA CTCGCCTCTA CTGTGCCTTG TAACACACCA TTAATATAAA   5460
CCTGTACCGT CGCGCCGGGA TCGGTCCTGG CAACCAGTAC CGGAGACTTA TTATTGGTAA   5520
TCAGATCATA TTTATCACCG CTATTAGTAT CCCGACTTAA TGAAATATCG CTGATTTCAA   5580
TCTGCGTATC ATGTTCTATC AGAATCTCTT TTTGTTGACT GTTGCCCGCT TTATCTTCCG   5640
ATACCACGAC AAAGGCATTA CTACCTTCAC GCAGATCTAA TTCTGCGCTC CATCGACCAT   5700
CATTGCCTAC CACCAGGGTA GCAATAACCA CTCCCTGCGG ATTCCTGATG GTTAAAGTAC   5760
TTCCGGCTTC GGCAGTACCA TCGATGGTGA CATGAGATTT ATTGGTGATC CAGTCGCCAA   5820
CTTTGCCACT GTCATCAGCT TCGCGTAATA CCACGGTTAA CGGCGAAATT ACTGTATCCA   5880
GTATTACATT CTGCGGACCA AACTCTCTGA TATTACCGGC AACGTCTTCA ACTTTAAACG   5940
TTAATTCATA ATTACCGTCA TTACCCAAAG CGGGTAATAC TACGCCCCAG TGTCCTGCGC   6000
CTGTCGTATA AGCAATCGCT TTTCCAACGC CATTCACAAA GATAGTGATT TTGCTGTTTG   6060
GCTCACTGGT GCCGCCAATC TCCGGCGTCA CCGTATTGAT ATATCCGCCC TCATGCATTC   6120
CAGATATATT CCATACCAGT TCAGCAACCT CGGTATCGAT AGTGACATCA ACGGCGGTAG   6180
AACGCAGTTC GCTATTATCG CGAGGGTTGA CGATACCCAC CTGGACGACA TAATGGCCAT   6240
CTTTCATTTC CGATAACTGG AAAGTATATC GACCCGCTGT ATCCGCTGTC GCCTCGCCGA   6300
CCTTCACGCC ATCCACATAA ATACTCACAA TCGTATTAGG TAACGTGCTC CCAATCAGGG   6360
TCGGCGTTTT ATTATTCGTG GTAAAGTCTC CTAAGGCGCC ACTATCGCTC TCCTCGCTGA   6420
GCTTTATGGT TGGAGGCGTG ACATCAATAA CAGGTATTAC GACAGGAAAG TCGACCTGCG   6480
ACGAATCATT ACCCGCTTTA TCTTTGGCAA CAATGCTCAC AACATAGGAG CCTGGCGCTA   6540
ATACTGATGG CGGCGTCCAA CTCCATTCGC CATTCGCATT GGCGTTTGCC GAGCCGACCA   6600
CTTTCCCATC CCACTGAATC ATAATCGTCG AGAACGCTTC GGCAAACCCT TTGAACTCAG   6660
GACGCAGGCT GGTTGCTTCA TGCTGATCAT CAATAGATGG ATCCGAAAGG CGAATGGTGG   6720
GATCGATCGT AACCGTATCG ATAGTGAATC TTTCCTGCGT TTGCGCAGTA TTTCCCGCGA   6780
CATCTGTTGC GACGACGTTG ATGGTATACA TGCCATCCGG CAGTATATTC GGCGTCACAC   6840
TCCAGTTGCC ATCAGCGCCA ACCGTAATCG TTTGTTTTAA AACCTCCTGA CCTGACTTAT   6900
CGTCAACAAT GGTAATCACC AGTTTCGCAT TGGGCTCTGC AGTACCTTCG AATTTGGGAT   6960
TTTGCTTATT CGTAAGGTTA TCGCTATTGG AATTTCCGGT ATCAGACGCT AGCTCCATTC   7020
```

-continued

```
TGACACTGAC GCTTGTCGTG GTATCAATGG TAAAGGGCAG CTTAATTTCA GAAATATTTC   7080
CGGCAATATC TCTGAAGACA ACAACGGCTT CATATACGCC ATCGTTTAAC GCAACGGGAA   7140
CCTGAAATTC CCAGAGGTTA TTGCCATTTG CCGTAACCGG ATAAGAAACG CCGTTAATTC   7200
TGATAACAAC AGTATCAATA TCGGCGGGTA CATTGCCAAT AACGAAACGT GGTGTAGTGA   7260
CACTCGTAAT ATTATCAACA GCGCTTTCGC CAGTATCATC CGCATCCAGC AAATCAATAC   7320
TGGGATCAGA AACAATAGTG TCTATTGTGA ATGATACCTC TTTGCTAATT TTATTACCTG   7380
CGATATCTTC AGCCACTATT TCTATTTTGT AAGTTCCATC CACTAACGGT GTATCAGGGG   7440
TAAACAGCCA TTTATTACCT GCCCCCTGAG TCAGTGTGCT GGATTTCCCG TTTAAAATTA   7500
CCGTCACGCT CTGCAGCGGT TCTCTGGCTG AAATTTCAAA ACGTGGAGAG GTAATATTCG   7560
TAATACCATC CGTAGAATCC TTTCCGGCGT CGTCCAGCAT CACGACGCTC AGGCCGTCAA   7620
TCTGCGTATC CACGGTGAAG CCCAGCGTGG AATTTGCCGT ATTCCCTGCC CGATCCGTCG   7680
CCTGGACATG GAGAGTATAA TGACCATCAG GCAATGCGCT ACCTGCAGTA AATTCCCACT   7740
GCCCGGCCGC ATTTTTACTG ATGGGCGTCC AGTTTACGCC ATCGAAAGAA ACCAGCACCG   7800
ATGTCACATC ATCAGGCGTT GCAATTTCAA AAGAGGGACG GGTAGCATTG GTGACATTAT   7860
CGTGATCGTT GACGCCGCTA TCTGTTGTTA ACGTAACACT GTCAATCTGA ACCTGCGTGT   7920
CGATTTCAAT CCGCAGTTCG GCCGATGTTT TGGTATTACC AGCAATATCC GTTACGGTAA   7980
CAGAGATCGT ATGCTGACCG TCAGACAGCG GTTGATCCGG CGTAAAGGTT AAATTCCCCC   8040
CTGTGTTTTC AATGGTGTAA TCCCGACCAT CAATATGAAC CACAATGTGT GATACATCAT   8100
TATCGACATT ACCGATAATA AACACCGGTT TGTTAATCCT GGTAAGATTA TCATTAGTAT   8160
CATCACCAGT ATCATGGGTG GGATCGAGTA CAATTGTCGG CTCTCGCAGA GTCGTATCAA   8220
TCGTAAACTG CAGCGTTTCT TGCGCAACGT TGCCGGCGAT ATCAGTCACA TCAACCAAGA   8280
GAGTGTGTTG CCCATCAGGT AATGCCGAAC CGACATTAAA TATCCAGCGG CCATCCCTCC   8340
TTTTGTGAGT TCAATCCAAT TAGCGGCGTT ATCGATTTTA ACGCGCACAT GGGTTATATC   8400
ATCAGCGGTA ACAATACTAA ACTGCGGCTG TCGACTTTGG TAATGTTATC TACATCGCTA   8460
TCACCGCTAT CTGTAACCAA CGTGACGCTT TCAATTTCAG CCGTCGTATC TATCACAACA   8520
GGTAATGGTT TCGATGTCGC GGTATTTCCG GCCTTATCTT CAACCGTAAC GGTAATATTA   8580
TAAGAGCCAT CCGGAATGGC ATTGCCTGGT GTAAATTGCC AACCAGCCCC AACCTTAGTC   8640
GCGTTATAAT CATGACCATC AATCGTCACC ACGACTTTGA TAACATCGGG GTCAACATTA   8700
CCAATCGTAA AGGTGGGTCG TGAAATATTA GTAATATTAT CGGCGGTATT CGCTCCGGTA   8760
TCTTGTCCTG CGTCTAAAGC AATAGTAGGA ACCTGTATAT TAGTATCGAT ATTAAATACT   8820
AAATCTTTAT TCGCAATATT ACCTGCCTCA TCCCGTGGCC TCTACGCGAA GGGTATATGT   8880
GCCGTCAACC AGAGTATTCG GGCTGTCAAA AATCCACTGT CCGTCGGCAT TTTTGCGTAT   8940
CACATTCCAG TTAGCGCCAC CATCCAGGGT TACACGTACC TGGACGACAT CACCGGGAAC   9000
GTCAATTCTG AATGACGGTT TGGCAACATT CGTTAATTGA TCATTCTGCA CGCCGGTATC   9060
ATTAAGCAAT ACGATATTGT TAATGGTTGT CGTGGTATCA ATACGCACCT CAAACGGCGC   9120
AGACTCTTTT ACATTCCCCG CCAGATCTTC CACCACAACG GCTAACTGAT ATGAGCCATC   9180
AGCCCAGCTT CGCAGAAGGC GTAAAGCGCC ATTGACCATT GGTGAATACC GCCGCTTCTT   9240
CGTGCGTTTT ACCGTTGTAA GTTACTTTGA CCATCACGCG CGTAACGTCA GAATCAACCT   9300
GATGTATGTC GAACACAGGC CGATCGTGAT TGGTGAGGCG ATCGCCAACA GTACCGCTAT   9360
CTTCGCCAGC TGCCAGTTCA ATCACCGGCG TAGTCAACGT ACCGTCTATC GTCACCTTTA   9420
```

```
AAGGCGCGGA TGTTTGCTGG TTGCCTGCCA CATCTGTTAC CGTCACGGTG AATGTGTAGC   9480
TACCGTCCGC CAAAGCAGAA TCCGGTCGAT AGCGCCAGCC GTCGGCTGAT TCGGTGAGTA   9540
CCACCGTTTT AAACGTGCCG TTATGCTCAA TACTCAATTC CACGTGTCGA ACATCTTTAT   9600
CGATACTCCC CAACACAAAT ACCGGCTGAG TGACGCTGGT CAGATTATCG TTCTTATTCT   9660
GTCCGGTATC CTGATCGGGC GCTAGCTCAA TGGTTGGCGT TAACAACGTG ATATCGATAG   9720
TGAAATTGAG CGTCTCCGTC ATCTTATTAC CCGCACCGTC AGTCACTTCC ACGGTCAGGG   9780
TATGCTGTCC CTCTGGCATA TCCGTCGGCC AGGTGTAATC CCAAATGCCA GCCGTCGAAC   9840
TCTTGATTGC AGTAACCCAG GTCGTGCCGC CGTCAATACT CAGAAGAACT TTTCCACATC   9900
ATCCGGTACC GAGATCTGGA ACTGCGGACG CACATGTTTT GTCACATTAT CGCCAGGGAC   9960
GCCGCTATCG TTGACTAATT CAATACGATC AATGGCTATT TGCGTATCCA CTGTCACCGT  10020
CAGCGGCGTA GACGGACGCG TATTTCCCGC CCGATCCTCC ACTGTCACCG TCAGCGTATA  10080
ATCACCGTCG CCCCACGGCG CTGGCGGTGT AAAGCTCCAT CCTCCAGCCC CCTGTGTCGC  10140
AGTAAACGAG GTTGTCGTTC CATTATGCGT GACGCTGACT GTAACGTTGA TAACATCCGA  10200
ATCGATATTC TGCAGAATAA AGGTCGGTCG GGTGCGATTG GTCATATCAT CGCCAGGCGT  10260
ACCGGTATCA TCCGTGCTAT CCAGCGCAAT GGTCGGCGTC GACAACCGGG TGTCGATGAA  10320
AAATTCAAGC GTTTGCGTCG CCGTATTGCC CGCTCTGTCG GTGACCATGA CGGTTAGGGT  10380
GTGTTTTCCA TCGCCCATAT CCGTTGGCCA GGTATAGCCC CAGACGCCTT CGATACCCTG  10440
CGTCGCGCTC ACCCAGTTTG CGCCCCCATC AATGCTCAGT TGCACAGAAT TCACATCCGC  10500
CGGCACCGTG ATCTCAAACT GCGGACGGGT GCTATTAGTT AGATTGTCAT CAGGCACGCC  10560
ATGATCATTG ACCAATGTAA TATCAGTAAT GCTGGTTTGC GTGTCCACCG TCACCACCAG  10620
CGGCGTGGAC TGACGAACGT TTCCTGCGTT ATCCGTTACC TCTACCGTCA GCGTATAGCT  10680
ACCGTCCGCC CAGTCAGCAT CTGGCGTAAA GCGCCACTGT CCTCCAACCT GGGTTAGTGT  10740
CACTTCCTGG CTATTGCCGC CCTGTGTGAT CCGCAAAATG ACCGAGTGCG CATCGGCGTC  10800
AATATTGCCA ATAGTAAAGC CCGGTCTTTT GACGCTCGTA ATATGATCGC CAATGGCACC  10860
TGTATCGTCC CTGCTATCCA TAGCGATGGT AGGCGTTGAC AGCCGGGTAT CAATGGTAAA  10920
ATCGAGCGTC TGCGTCGTCT TATTTCCCGC CTTATCGGTC GCTTCTACCG TCAGGGTATG  10980
TAGCCCGTCG GTCACATCTT TCGGCCAGGT GTAATCCCAG ATCCCTGCCG TGCCCTGTGT  11040
TGCACGAACC CACGTATTAC CGCCGTCGAT ACTCAGACGT ACTTCGTTGA CATCCCCTGG  11100
CACCGTGACG CGGAAGTGTG GACGAACGTC ATTGGTCAGG TTGTCGCCGG GAATACCGTT  11160
ATCATTAACC AGTTCAATAA CATCGATGGT GATTTGGGTG TCAACCGTGA CCGTCAGCGG  11220
CGCTGAGTAT TTTACGTTCC CCGCATCATC CTCCACCCTC ACCGTCAGCG TATAGTCGCC  11280
ATCTGCCCAT GTGCCGGTCG GTGTCACGCT CCAGATGCCG GTCGCGCCTT TGGTGGCCGT  11340
CAGCACTTCT TTCGTGCCGC CATGTTGCAC CTCAACCGTG ACATACCGCG CGTCTGCGTC  11400
AATATTGCCC AGTAAAAACG TCGGCTTATT TACGTTGGTC AGGTGATCGC CTTTTGTTTC  11460
CGCTGTAGTC CGTGTTGTCC AGCACGATAG TCGGTTCTGA CAGTAGGGTA TCGATGATGA  11520
AGTCCAGTTG CTGCGTCGTT TTGTTTCCCG CCTTGTCGGT CGCCCCCACT GTCAGGGTAT  11580
GCTTACCCTC TCCCACATCA GCCAGCCAGG TATAATCCCA GACGCCCGGC GTCGCGCTCT  11640
GGGTAGCGTT GAACCACGTC TTGCCGCCGT CAATGCTCAG GCGCACCACG TTGACATCCG  11700
TCGGTACCGT CACCTGGAAG TGCGGACGCA CATTATTAGT CAGATTATCG TCGGGAATAC  11760
CGCTGTCATT GACCAGTTCA ATGTTATTAA TGGCGATTTG CGTGTCCACC GTCACCGTCA  11820
```

```
GCGATGCAGA ATGGCTGGTG TTCCCCGCTT TATCTTCGAC TGACACACTC AGGGTATAAT  11880
CACCATCCGC CCACGCCCCT GTCGGCGTAA AGGTCCATCC GCCTGCGTCT TTCGTGGCGT  11940
CAAATGTGGT GGTGACGCCG CCATGCTCTA CGCTGACCGT AACGCGAACG GCATCATCAT  12000
CAATATGCTG CAGGGCAAAT GTCGGCTGGG TGCTATTCGT CATGTTATCG CCATGGACAC  12060
CACTGTCGTC CGCGCTATCC AGTACGATCA CCGGCGTCGA CAACGTAGTA TCAATAGTGA  12120
AGTGGAGTGT CTCCGTCACC GTATTACCCG CATTGTCAGT CGCTTTCACA TTCAGCGTAT  12180
AGTCGCCATC CGGCACGGTG CCCGGCCAGG TATAATTCCA GACGCCCGGC GTCGCGCTCT  12240
GTGTCGCCTT AACCCAGGTC ACGCCACCGT CAATGCTCAG ACTGACTTCG TTAACGTCCC  12300
CCGGTACCGT CACGCGGAAC TGCGGATGGG CGTCGTTAGT CATATTGTCG CCGGGAATAC  12360
CGTTATCATT AACCAGTTCA ATAACATCAA TGGTGATTTG GGTATCAACA GTGACCGTCA  12420
GCGACCTGAG TGTTTTTCGT TCCCCGCCTC ATCTTCCACC CTCACTGTCA GCGTATAGTC  12480
GCCATCTGCC CATGTGCCGG TCGGTGTCAC GCTCCAGTTG CCGGTCGCGT CTTTGGTGGC  12540
CGTCAGCACC TCTTTCGTGC CGCCATGCTG TACCTCAACC GTGACATACC GCGCGTCTGC  12600
GTCAATATTG CCCAGTAAAA ACGTCGGCTT ATTTACGTTG GTCAGGTGAT CGCCTTTTGT  12660
TCCGCTGTCG TCCGTGCTGT CCAGCACGAT AGTCGGTTCT GACAGTAGGG TATCGATGAT  12720
GAAGTCCAGT TGCTGCGTCG TTTTGTTTCC CGCCTTGTCG GTCGCCTCCA CTGTCAGGGT  12780
ATGCTTACCC TCTCCCACAT CAGCCAGCCA GGTATAATCC CAGACGCCCG GCGTCGCGCT  12840
CTGGGTAACG TTGAACCACG TCTTACCGCC GTCAATGCTC AGGCGCACCA CGTTGACATC  12900
CGTCGGTACC GTCACCTGGA AGTTGCGGAC GCACATTATT AGTCAGATTA TCGTCCGGAA  12960
TACCGCTGTC ATTGACCAGT TCAATATGGT CAATGGTGAT TTGCGTATCG ATGGTGACCG  13020
TCAACGGCGC TGAGTGGCGA ATATTACCCG CCTCATCTTT CACCGTTACC GTCAGCGTAT  13080
AGTCGCCATC AGTCCACGCG CTGCCGGGTA CAAAACGCCA CTGCCCGTTA GTCTGCGTCA  13140
GCTCCACCTC CTCGCTGTGA CCATCGCGCA TCACCTGCAC GACGACCTGA GTCACGTCAG  13200
AATCAATACC GCCGATAATA AAACCCGGCG TTTTAACGTT AGTCTTATTA TCGTTGGCGG  13260
TGCCGCTATC ATCTGCGCTA TCCAGCGTGA TGGTCGGTGT CGACAATGTG GTATCAATGG  13320
TAAAATTGAG CGTTTCCGTC GCCGTGTTGC CTGCAACATC GGTTGCTTTC ACTGTCAGGG  13380
TATACGTATT TTCGACCAGA TCTGTCGGCC ATATATACTC CCAAACGCCG TCAGACGTCA  13440
GCGTTGCGTT AACCCAGTTG ATGCCGCCAT CAAGACTCAG TTGCACAGAG TTCACGTCCG  13500
TCGGTACCGT AATATGAAAC TGTGGACGTG CTTCATTGGT CAGGTTATCC CCGACAATAC  13560
CCGTGTCATT AAGAAGCTCA ATGCGATCAA TAGACGTTTG CGTATCGATA GTCACCGTCA  13620
GCGGCGCAGA ATAATTTGTA TTACCCGCCT TATCTTCTAC CTTTACCGTC AACGTATAGT  13680
CGCCATCGGT CCAGGCTGCG CCCGGCGTAA AGCGCCACAC ACCGCCGTTC TTAATCAACT  13740
CTATCTGTTG GTTCTTACCA TCATGCGCCA CCGTCACCAC CACTTTGGTC ACGTCGGCGT  13800
CGATATTACC GAGGGTAAAG CCTGGCATCT TAACGTTGGT GATGTTATCG CCAGCGGCGC  13860
TATCATCCGC GCTGTCCAGG GTAATCGTCG GTTCTGACAG AATGGTATCG ATGGTGAAGT  13920
CCAGTTTCTG CGTCGTTTTG TTTCCCGCCT TGTCGGACGC TTCCACCATC AGGGTGTGAG  13980
GGCCGTTAGC CACATTCGTC AGCCAGGTGT AATCCCAGAC GCCCGACGTC GCGCTGCTGC  14040
GTGGCGTCAA ACCACGTTTT GCCGCCATCA ATGCTCAGTC TTACGCCGTT AACATCCGCC  14100
GGTACTGTCA CCTGAAAGTG CGGGCGCGCT TCATTGGTCA GATTATCGCC GGGGATACCG  14160
CTGTCGTTAA CCAGTTCAAT ACGGTCAATG GCGATATGCG TGTCTACTGT CACCGTCAAC  14220
```

```
GGCGCGGACT GCTTCACATT TCCGGTCCTA TCTTCTACCT TCACCGTCAG GATATAGTCG  14280
CCGTCCGCCC AGTCGCTGGT CGGCGCAAAG CGCCACTGTC CGCCGGTCTG AACCAGTGGC  14340
ACCTCCTGCT TAATGCCATT GTGCATTACC TCCACTATCA CCCGGCTGAC ATCGGTATCA  14400
ATATTGTTGA GGGTAAAGCC CGGCGTTTTA ACATTGGTGA TATTATCGCC CGCGATGCCG  14460
CTGTCATCTG CGCTGTCCAG CGAGAGGGTC GGCACAGACA GAGTGGTATC GATGGTGAAA  14520
TCGAGGTCTG TGTTGCCTTA TTTCCTGCCT CATCGGTCGC TTCTACCGTC AGGGTATAGC  14580
CTCCGTCGGC CACATCATCC GGCCAGATAT AATCCCAGAC GCCTGGCGTC GCGCTCTGGG  14640
TAGCGTTGAA CCACGTCTTG CCGCCGTCAA TGCTCAGGCG CACCACGTTG ACATCCGTCG  14700
GTACCGTCAC CTGGAAGTGC GGACGCACAT TATTAGTCAG ATTATCGTCG GGAATACCGC  14760
TGTCATTGAC CAGTTCAATG TTATTAATGG CGATTTGCGT GTCCACCGTC ACCGTCAGCG  14820
ATGCAGAATG GCTGGTGTTC CCCGCTTTAT CTTCGACTGA CACACTCAGG GTATAATCAC  14880
CATCCGCCCA TGATGTCGGC GGCGTAAAGG TCCATCCGCC TGTGCCTTTC GTGGCGTCAA  14940
ATGTGGTGGT GACGCCGCCA TGCTCCACGC TGACCGTAAC GCGAACGGCA TCATCATCAA  15000
TATGCTGCAA GGCAAATGTC GGCTGGGTGC TATTCGTCAT GTTATCGCCC TGGATGCCGG  15060
TGTCGTCCGC GCTATCCAGT ACGATGACCG GCACTGACAG CGTGGTATCC ACCGCGAAAT  15120
CGATGGTCTT CGTCATGTAT TGCTGCTTTA TCAGTCGCTT CCACCGTTAG CGTGTAGGAC  15180
CATCTGCCAG GTCTGTCGGC CAGATATACT CCCAGCTTCC TGCCACGCCC GGAGTTGCCT  15240
GAACCCACGA ATTACCACCG TCAATGCTCA GACGGACTTC ATTGACATCC GTAGGTACCG  15300
TCACACGAAA GTGGGGACGG TCGTCGTTGG TCATATTATC GCCTTTCACG CCGCTATCGT  15360
TGACCAGTTC CACCCCATCA ATGGCGATTT GGGTATCGAT AACGACCGTC AGCGGCGCCG  15420
AGTAGTTGGT ATTTCCTGCC TTATCTTCTA CTTTCACCGT TAACGTGTAG CTGCCATCCG  15480
CCCACGTATT CCCCTGGTAT AAATAACCAA CTCCCATTGA GGTGGGAAAG TTCGATCTCT  15540
TCGCTCACGC CATTGTGCAT CACCTGTACG ACGACCCGAT GCGCATCGGC ATCAACACCG  15600
GAAATAGCAA AACCTGGCTT ATTGATATTG GTCAGGTTAT CGCCTGTAAC CCCCGTATCA  15660
TCCTTAGAAA GCAGGGAAAT CACCGGCGTT GATACTGTGG TATCGATAGT AAAATCGAAT  15720
ATCGCGCTGT TCGCTTTATT ACCCGCAATG TCCTCAACCT TGACATAAAC CTGATGCAAG  15780
CCTTCCGTTA AATCTGAAGT AAAGGTATAG GCCCATGAAC CATCAGGTTG TTGCGTGGCA  15840
ACACCGATCT GCGTATCAGA CATGGCATCC CATACCTGAA CACTGATAAT GTCCGGATCA  15900
ATATCTTTTA GGTGCAAGGT AGGTTTAACG ATATTCGTTA AATTATCATC TGAAATTCCC  15960
GAATCTGAAT CCGGGCTCAA TGAAACTATC GGTATTGAAA TAGCAGTATC GACGCTAATT  16020
AAGAAAGGAT CCGAATGAGC AATGTTGCCA GCGATATCTT CAACTGAAGC GGTTATTCTA  16080
TGATCGCCAT CAACCAAACC TTGATCGGCT TTCAGGGTAT ACTCCCATCT GCCATCTTTA  16140
TTTGTTCTGA CCTCAGCGAT CAGTGCACCA TCAATATAGA GTTTAACCGT TGAATAGGGT  16200
GCAGCGGTTC CTGTCAGTGC AGGATTCTTT TCATTAATAA TATGGTCTGT ATTATCAACC  16260
CCCGTATCGT TGACCAACTC TATTGTTGGT TTTTGCGTTT GCGTTACGAT TTGGAAATTA  16320
TACGCTGATG AGGAGGCAGT ATTACCGGCA ATATCTTCTA CCTTTACCGT TACGTCATGC  16380
GAGCCATCGG ATAACGCTGT GGTAAATTGA AAATTCCATA CACCATCATC GCCAGCAATA  16440
GCCTCACCAC TTAACACACC GTCAACATAG ATGGAAACCT TAGCATTAGC TTCAGCCATC  16500
CCGGTAAACA ACGGTGTATT AATTTTAGTA ATCATATCGC CTTTAACGCC AGAGTCAGCG  16560
CTATCATGCA ACATAACAGT AGGGATCGGC GTAAAGCTAT CAATGGTAAG CTGATAATCT  16620
```

ACAGATGACG TTCTTCCTAA AGGATCGATG GATTCAACCG TAATCTTATA AACATTGTCA 16680

GACAGATTTC TGGAAATATC AAAATTCCAG TTACCGTCTG CATCCGCAGT CGTCACGCCT 16740

ATCGTTTTAC CGTCAATAAG GATATTTACG GTAGCAAACC TATCCGCTGT TCCCAGTAAT 16800

GTCAGAGCAT TATGTTTATT GGTAATCCAG TCGCCTTTTG CACCGGAATC ATCACTGGCA 16860

TCGAGTTCCG CTTTTGGAGG TACAACTTCA GTTTGAATAG TAAAAGAATA TTTAACAGTA 16920

GAGGATTTAT TGCCGGCGGC ATCCTGAGAA TGATTTCAAT ATCATAGGCG CCCTGAAGAA 16980

TTTATTACTA AACTGATAAT TTCCAGGTCC CGTTTGAGTC AACTTCAATG CTGTCATATA 17040

ATTTACCATC TCGCATCAAT AAGATGGTAG ACTTTGGTTC TGCCGTACCG ACTAAAGCCG 17100

GTAAATCATT CCCTGATAAA ATTATACCAT TCGGCAAAAC AACATAATCC TCCAAAGAAG 17160

CCGTCGGAGG TACAGGGGCA ATAGTATCAA TAACGTAACT AAAGGAAAAA TCCTTTTTGT 17220

TGCCAGCGAC ATCTTCAACA GTGAACGTAA GATTGTTAAT CCCTTCCACT GAGTCGGAAG 17280

TGAAATTGAA CGTCCATTCG CCCTTGTCAT TCGCTTTAAA AATAACCTCT TCGCCAGTCT 17340

CACTATTTAT GACACTGATA ATAGCATTTG GCTCAGTTTT ACCTGTAAAG GTTGGGCGAG 17400

TATTGTTAGT AACGTTATCT CCGACAATAC CGCTATCATT CGTCGTTTCA ATCTCAGCGC 17460

TGAAATAGCT GATACGTGTA TCAATAGTAA AAGGCAGATT TGCCGTCGCT GAGGTATGCC 17520

CGGCAATATC AGTAGCTGTT GCTGTTATAT TGTATTCGCC ATCCTTGAGC GGCGTAGTAA 17580

GCGTATAGCT CCATGTCCCA TCTTTAGCAA CAATGACCTC ACCAAGATGT TTAAGTCCAA 17640

GATAAATAGA GACTGTAGAA CCGGGTTCCG CCACACCAAT AAATGTTGGC AGGGTGCTAT 17700

TTGTAATGTT GTCATTTTTA ATGCCGGAAT CACTACTATC ATCCAGCTCA ATCGTCGGCT 17760

TTTCTGGAGC AATGGTGTCG GTTATGATAC TATCCGTCGT TTCGTTTTTA TTACCTGCTT 17820

TATCTACAGC AACGACTTTT ATACTATTTT CGCCCTCAGA TAATTCATTA TCCTTAAATT 17880

CATAACTCCA GTTTCCATCT TTATCGACAT CAACGCTGGC AACCAGTTTA TTATCTACAT 17940

AAATGTCAAC CTTAGCATTC TCTTCCGCCG TACCAACAAT TGAAGGCGTC AAGGTCGGCG 18000

TTAAGCCCTT ATGACCGGAC ACACTACTTT CAGGCGAAAG TTCAAATGTT GGTTTATCGG 18060

TAACGGAATC GATAGTAATG ACAAGTTTGG CGCTACCGCT CCCATCAGCA GTCTTGGCCT 18120

CTGCCTCCAG ATTATATGTT CCATCAGTCA ATGTTTCAGG CGCTGTAAAG GTGAAGTTAC 18180

CCAAACTATC CGTTACAGCC TGACCGACAG CAATACCATT AATTTTAATA ATAACCGTGG 18240

CATTGGGAGC AGTGCTAACT ACAAACTGAG GTTTGGTAAA ATTAGTTATA CTATCATCTT 18300

TGCTACCGCT GTTACTCTCG GCCGCACGCG CTAATGTGAC TTTAAGCGGC TCTTTAACAG 18360

ACTCGGCATC GAGCTTATTT TCCTCATTTT TACTGCTATT ACTTTTGCCA GTACTGGTAT 18420

TTTTATTAAT AGGTTGAGGA AGAACTTTTT CAGCATCGTT CTGTTTAGAA GCCTGCGTTG 18480

CTTTAGCCTG TGTATTTTGC TGGGAAGCAT CGCTTTGCTG AGCCAGATTG TCTTTTGCTA 18540

CATTGTCAGC CAAAAAGTTC TGCAGCATTT CTTCAATTTG CTTTGACGAG TTCTGTACTT 18600

CAAACGCTTC ATTGAGCGCT TTTTCTGCAG CCTCCTTAGC TTTCTCTGCT TCTTCCTTCG 18660

CCTTATCAGC TTCTTTCTTG CGTTTTCAGC ATCGTCAAGC TGCTTTTTAA TTCCTCTTCT 18720

TCCTTCTTAT TTCGTCGTTT GCCATTACCT TTCTTTTCTA CCTGAGCAGA ATCAACCAAT 18780

GAGCTGTCAA TTCTCTCCAG TTGAATATCT TTTAAATCTA CGCTGCCCAG AATTTTAGCG 18840

CCGGTAATAG TCTTATCTTT AAATTTAACA GCGAGGTTAT TGCCTTTGAT ACTTGAATAA 18900

AGAGCGCCAT TGACAATGAT CACTGAACCA CGCGGCGTGG TAATGTTCAT GTCTGGCCCG 18960

GAAAGAGAAA CTTTTGCGCC TTTGGCATTA CCCAAAGAAG ATAAATCAAT TACAGAATTT 19020

```
TGATCGGCAA AAAACTTTTG TATGCTTTTA TTTCCCATAA TATTATATTC ACTCTCAAGG  19080
TGTATCTAAT CGTTTAGTAT TAACTGGTTC TGAAAAGGCT TTGTCCACGC CTTTCATCAA  19140
GGGAGATAAC AGGTATTCCA TAATGCTGTG TTTTCCGGTA ATTACACTGG CGTCAACAGT  19200
CATACCTGGT TTTAACCACC GTAAATCATC TTCATTAACA TCGAATGCAA TAATTACTTT  19260
ATAATAACGC TGAATTGTTC CTCCGGTATT TTCCTCATAG GAATCAGGGC TAATATTATC  19320
GATAGTCGCA TTATACGATT TTATCTTTGG TTGGATAATT GACTGCACAT CCAGTTTAAC  19380
GGCTTCATCT ACATATATTT GGTCACGGTA TTTGGGTAAT ATTTTCACAT CGGCCAGCAT  19440
AGTCCTTACT TTTGGTTTTA TTTCAAAAAG TAAGTCCGCC GCCTGAATCA CACCACCATG  19500
AGTAGTGGCA CTTTTATTGA TTTTATAAAT TACACCGTCA ACCGGTGAAT AGATATCCTC  19560
CTCATTTATC TGCTTCTCTA TTACTTTTAA TGTAGAGTTA ACAACCTCAA GTTCCTGAAG  19620
ATTTTTAGAT ATTATTTTAG ATAAAGATAG TCGCAATTCA TTATTAAGCG CCTCAATATC  19680
ATTAACAACC AACTCAATAT CATCTTTTTT TAAAGTGATG CTACTTTCAA TATCATTAAT  19740
TTCAGACTTA ACTTTTATAT ACGCCTGTTT CTTGTTAAGA AAATTGGTAT ATGGGCTAAT  19800
TCCTTTTTTT ACCAGTGGGG AAAGAATATT TATTTCTTCG GCAAGCAATG CGAGTTCTTT  19860
TTCTTTCGAA CTCAGCTTCT CTTGTAATCC GCTAATCTCA GAATCAAGAG AGGTTTTTTT  19920
TAACTCTTTA GCTCTTATCT GACTATGCAC TAATTCAATA TTCGCTTTTA CCTCTTTATT  19980
GCTTAAAGAA CGGGTGCCAT CCAGGGTAAT CAACCCACTC TCATTTTCTT TATCAAGAAT  20040
GAAAGATATT TCGTTAACAT CTTTATCCAG ATACCCTTTT TGAGTTCTAT ACCTTTGATA  20100
TTCTTTTTGC AGATCAAGGT TAACGACCTT TGCAAGGAGT TCTCCTTTTT TTACAGTATC  20160
ACCCTCGGCT ACATAAATAT CTTGTATCGT CCCTCCTTTA GAAAGAGATA TTAACTGAGC  20220
ATTATCTTTA GTAGTGATAA CGCCCTGACC ATGAACCACT GAATTAATTT CTATAAAGTA  20280
GGTAAGGATA ATAATTAAGA TCGTCAAAGA AATAATTATC ATCATGAGAT GATCGCTTTG  20340
TCTTCTATTC ATTTCATTAC ATTTAACTCA CTTTCAGTAT TTCCTTTTAA ATAATCCATT  20400
AAATGAAAAA TCAATGAGAG TTGCTGTAGC TTTAAAATAT ACAGGCTATA TTTGCTGTCG  20460
ATCATGCTTA CATATGCCTG AAATGCTTCA TTACGGCTTG AAATTAAATC AAGCAAACTT  20520
TTTTGCCCTA ACTGAAACTC CTGCTCATAT AATTCAGTAA GCTGTAACGC GTTTGTATGT  20580
GAACGTTCCG CCACTGAGTA AGTCTCTTTT GCAGCGGCGT ATCTTGAAAG TTGTGAATCA  20640
ATGTTATAAC GCGTTTTAAT CAAAAAATCG TCAATTTGCA GCTTAGCCTG CGAGTAACTT  20700
GCCACCATTT TTCTTTCCTG GGCTGAATTT CTGAACCCAT TAAAAATGTT GAAACTGACA  20760
TTGATACCCG TTTTAAATTC ATCTTCATAA TCACTTTTTT TGGCACTACC GCTTGGGTTA  20820
TTCTGTACAT AGCTGGAAAC AAGATCTACA GTCGGAAAAT AGGATGATTT TGCGGCATTA  20880
ATATCTTCGG TCGCGGCTTT TCGGGTATTG ACAAGCATCT TATAGTCATC GTTGTATTTC  20940
ATCACCATGT CCATAAGTTT TTCAGGGCTT TCGACAAAGA TATATTTTTT GAAGAGGTTG  21000
AATTTTTCAT CGCTTTGAAT CTGAACTGGC GATAAATTCA GACCAGTCAT ATTCTGCATT  21060
TTATACATTT CATCATCCAA CATCGACTGA TACATAATGC TTCTGGTATT TAATGCATCG  21120
ATAGATACTT GTACTTTACG CATATCAGAT TGCATAGCTA CACCGGAAGA TACCAGCAAC  21180
GAAAAAGGTT CCAGCATCTT TTTATAAAAC TCTTTCTCCA GATTTACGCC ATCAATCATT  21240
TCACGATATT TACTGATGTT GTAATAGGTT GTCACAACCT CCTGAGACAC TATATTCTTT  21300
GTTTTTTCAT AGTCAGTTTT ACTATTATCT CTTTCATATT CAGATTTCCT GATATTAGCC  21360
CCCCTCACTC CAAAATCCGT TATTCGGTAT GATAAAGACA CCTTATTTTC AACGTTCCTC  21420
```

```
TCGGTACCTG ATGACTCTTT CCTGTTATTA TTAAGGCCAG ATGTTAGATC CAGGGTAGGA  21480
TAAAGTGCTG CCCGTGAAAG ATCTAAGTCA CTGTTTTTCT TTTCAGTCTC ATAATATGAA  21540
ACAGCAACAG AGGGCTGATG CGTTAATGCG GCATTAACTA AATCTCTTAG AGGAATGACC  21600
GGAAGCTCGC TGGCGTATGT GCTTTGTGTA ATAAAAGCAG TCGTCAGAAA AAACATCTTA  21660
ATCTTCATTT TTTTCCTCCT TGTTTAACAA ACGTTGCTTT ACTATTTCCT GATGCATAGA  21720
TGTTATTTTT TCCATTAATG GCATATAGGT ATCACGGTAG CTAACCATTT CAGCACTAAT  21780
CTCTTTAGTA TTGGCAATAA TCTTTTTATC AGTAGCCGAT AGATCGGATA GCGCTAAATG  21840
AACATTATTC ATATCCTCAT CCATTTCTTT TCTCAGCCCA TCGAGAGTAT GAGAAATATC  21900
GGCACTGCCA GCGGCAATAT CGTTTATGGT CTTACCATGT GAAAGAGATT CCTGATAACA  21960
TTTATCAACT GATGTCATTA TTGAATCATT CTTTTTATCT ATAATATTTT GTATTGTACT  22020
CATTGCCTCC AGTCGTGCAT TATTATCAGC AAGCAGGATA TTACCTTCAG ATAAACGAGA  22080
GGTAATTGTT ATTACACCGT CAGATAATTT TTTGAGATTT TCCGTTACTG CTTACCAGAT  22140
AACCATCAAT CAGCGTAAAA ATTTGTTCCA GTTTTGCTGA GTTATCCAAT AGTCGGTTTT  22200
GCAAAGTGAC AAAGCTATCT GATAGCATCT CTCGTTTCTT TTCTTCATCC TGCGTCCGTA  22260
AGTTTTCAAC TGTCAGGTAG TTATCAAAAA ACGCTTTAAA CAACTCTTTA AATTCTACAA  22320
GCGTCTCTGA TTCAACCCGC AGGCTTCGCT GTTTATTATT GGCTCTGTTG CTTATGATTT  22380
TTAATTTTTT GATTTCCGTA GAAACAAGGG AATAGGAGCT GCGAACAAAA ACACTTTGTG  22440
AGGTCAGGAG TATGGCGCAA ACAACACCAT AGATAGAAGA TACAAATGCG GTATTCATCC  22500
CTTTCAATGG TTCAGAAAGC GACGCTACCA TTGTCACGAT CATATTGAGT GTATTACTTG  22560
CATTATCACC GCCAACATCT GATGGCGAGC TCAATAAGTT CCCGATTGAA CCAATCGTAA  22620
TAGACAGACC CGCAAACGTC CCCAACAGGC CAACAAGCGT CGACACATTG CTACAGCTCA  22680
TAATAAATGA CAATCGTTGA TTACGGGCGG TAGACACATT GTCATCTAAT TCCATCAGTA  22740
AATTGAAATC ACACTGTTTG GACTCCCCGG CAAACAAAAC CTGATTGAGG TTAGAAAGAA  22800
TGCTATTTTT TCTACTGGCG TCCTGAGCTA TTAATATGTC TTTTGCTGAA ATATTTTTAA  22860
GAATAGTGAA TAATGCACAC AAAGAACCTG TAATATAAAT GGCAATAATG ACTCCATTGT  22920
AAATTGCAGA AACCATGAAG TTATCAAAAA CATACTCTCT TATACCGGGA AAAGATAAAG  22980
CAAAAAAAGG GAGTATGGCA AGGAAAGAAC AGACAACAAA TAGCGGTAAT GATTTATATA  23040
TTTCACTCTG ACACCTTTTA TTAATAGTCG TGATAATAGC TTTACTCGTT GTACTTGATG  23100
CTGCGGAGTT AACACTCATG TCAATAACTA CATCAGGATA TATTTTCTTA ATCTCTTTCA  23160
TCAAAATAAT TCCCCGTTCA TATCCCAGTC GTAGAGAGTC AGAGAAAGAG ATGTCTGCCT  23220
GAGGAATAAC CATTTCTATC AATAAATTAC TATTGATTTT GTCTTCTAAC CAAGCCTTTA  23280
TTTTATAAGT GTCCTCTTCT GAAAAGCTTC TCAGCCTGCC ATGATACGTA ATAACAAGCT  23340
CATTTTTTGT AGACGTTATA TCAGTTTTCT GACCATCGGC GATATCGTAT ACTCCAACCT  23400
CCTTACCTGA CATTGTAGTC ATTCCGTCCG ACACATCTTG AGTATTCACT TCCTTATTAA  23460
CTATTTCATT AGGATTTGAA TCGTCATTGG CTCCGCTATT TTGAGCAGTA GATTTAGTCT  23520
TATTCTCTAT ATTTGCTTTA TAAACTTTAA TTGAGTTGTC ATACATAATA ATCATATTAT  23580
TAAGTGCAAA CACCAACATA AGAAATATAA AAATGCACAA TACCGTAGAG AATGTATCAA  23640
CAAAACTAGG CCACGGATTA CTTTCGTCTT CCATGTTGTC TCCTGATATT ACATTGTGAA  23700
TAAAATGTTT TTGTGGATTA GAAAGGATAA AGGATGCTCA ACTTATTCAG AAAGTGAACG  23760
CTACCGCCCT TGGCTTCCTG CTACCAATAC GCTTTATAGA TTTCAGTTTT CTTACATCTC  23820
```

GTAATCAGAA AAATAAAAAC AACGACGCCA TTTTTATGCG CCCACAACAA AGATGAGTGC 23880

TTTAATTAAA AACACTCTTC ATTTTTTTAA TTAGGTAGAC ATCAATTATT GCACTAACTA 23940

TATCCTCCCC AATAATAGGT ATCGCATAAG CTCTCAACTC ATAAATAAAA AATAGTCATC 24000

AGCAAATTAA AACCACCCGC CGATAAATAG ATTTGTTAGC TAATCATTGA AACTCTAAAT 24060

CATTTTAAGG ACATATTTCT TTTTAATACG CGTTATAACC ATACGTATTT AATAAATTTG 24120

CCTCCAGAGG ATAAAATTAA TTTTCACAAT TAAAACATAG GGTCATATGG ACTTCAATAT 24180

AACTTAAATC ATTGAAAATA TAATAAGTGG GGAGTAAAAA ATCAGAATTG TGTAAAAAAA 24240

TACACAAATA AAACCATTTT TTATATAAAG CCAGCTATAA GTAACAATTT TATCTTCAGC 24300

AATTAAAAAT AAAGCAAGAT ACACATATCA TATTTGAGCT CATCACAAGC TAAAGCAAAC 24360

ATTTAATTAA CCATTGATAA TACCGACCAT TCTCTACCGT TATTTTATAA TATCTTTTTG 24420

TTGTCAAAAA ATGGCTATAA ATTATATATT TTGCAGATGA GATTTCTCTT TCATATTTAA 24480

GACAATCCGG GTTATTGCAG TACATTTATG AACTTCGGCT GGATAATGAT GTGCCGAGGC 24540

GAGTCGGCCA GAGGCGATAA GCGACATTTT TCCGTAAGAT ATGCGCTTCT CTTTTTTGAA 24600

AGGGATACAA AGACAATAAT ACCAGGTAAG AAAATGCCTG GTTTACACCA GGCATTTCAG 24660

CAGACGAGAA CTATAGCGAA AATGCAAATA ACGCTTTGAG T 24701

(2) INFORMATION FOR SEQ ID NO:4:

(i) SEQUENCE CHARACTERISTICS:
(A) LENGTH: 222 bases
(B) TYPE: nucleotide
(C) STRANDEDNESS: double stranded
(D) TOPOLOGY: linear (ix) FEATURE:
(D) OTHER INFORMATION: SEQ ID NO:4 corresponds to nucleotides 15513 through 15734 of SEQ ID NO:2

(xi) SEQUENCE DESCRIPTION: SEQ ID NO:4:

AGCTGGGCTG ATGGCTCATA TCAGTTAGCC GTTGTGGTGG AAGATCTGGC GGGGAATGTA 60

AAAGAGTCTG CGCCGTTTGA GGTGCGTATT GATACCACGA CAACCATTAA CAATATCGTA 120

TTGCTTAATG ATACCGGCGT GCAGAATGAT CAATTAACGA ATGTTGCCAA ACCGTCATTC 180

AGAATTGACG TTCCCGGTGA TGTCGTCCAG GTACGTGTAA CC 222

(2) INFORMATION FOR SEQ ID NO:5:

(i) SEQUENCE CHARACTERISTICS:
(A) LENGTH: 15512 bases
(B) TYPE: nucleotide
(C) STRANDEDNESS: double stranded
(D) TOPOLOGY: linear (xi) SEQUENCE DESCRIPTION: SEQ ID NO:5:

ACTCAAAGCG TTATTTGCAT TTTCGCTATA GTTCTCGTCT GCTGAAATGC CTGGTGTAAA 60

CCAGGCATTT TCTTACCTGG TATTATTGTC TTTGTATCCC TTTCAAAAAA GAGAAGCGCA 120

TATCTTACGG AAAAATGTCG CTTATCGCCT CTGGCCGACT CGCCTCGGCA CATCATTATC 180

CAGCCGAAGT TCATAAATGT ACTGCAATAA CCCGGATTGT CTTAAATATG AAAGAGAAAT 240

CTCATCTGCA AAATATATAA TTTATAGCCA TTTTTTGACA ACAAAAAGAT ATTATAAAAT 300

AACGGTAGAG AATGGTCGGT ATTATCAATG GTTAATTAAA TGTTTGCTTT AGCTTGTGAT 360

GAGCTCAAAT ATGATATGTG TATCTTGCTT TATTTTTAAT TGCTGAAGAT AAAATTGTTA 420

CTTATAGCTG GCTTTATATA AAAAATGGTT TTATTTGTGT ATTTTTTTAC ACAATTCTGA 480

```
TTTTTTACTC CCCACTTATT ATATTTTCAA TGATTTAAGT TATATTGAAG TCCATATGAC    540
CCTATGTTTT AATTGTGAAA ATTAATTTTA TCCTCTGGAG GCAAATTTAT TAAATACGTA    600
TGGTTATAAC GCGTATTAAA AAGAAATATG TCCTTAAAAT GATTTAGAGT TTCAATGATT    660
AGCTAACAAA TCTATTTATC GGCGGGTGGT TTTAATTTGC TGATGACTAT TTTTTATTTA    720
TGAGTTGAGA GCTTATGCGA TACCTATTAT TGGGGAGGAT ATAGTTAGTG CAATAATTGA    780
TGTCTACCTA ATTAAAAAAA TGAAGAGTGT TTTTAATTAA AGCACTCATC TTTGTTGTGG    840
GCGCATAAAA ATGGCGTCGT TGTTTTTATT TTTCTGATTA CGAGATGTAA GAAAACTGAA    900
ATCTATAAAG CGTATTGGTA GCAGGAAGCC AAGGGCGGTA GCGTTCACTT TCTGAATAAG    960
TTGAGCATCC TTTATCCTTT CTAATCCACA AAAACATTTT ATTCACAATG TAATATCAGG   1020
AGACAACATG GAAGACGAAA GTAATCCGTG GCCTAGTTTT GTTGATACAT TCTCTACGGT   1080
ATTGTGCATT TTTATATTTC TTATGTTGGT GTTTGCACTT AATAATATGA TTATTATGTA   1140
TGACAACTCA ATTAAAGTTT ATAAAGCAAA TATAGAGAAT AAGACTAAAT CTACTGCTCA   1200
AAATAGCGGA GCCAATGACG ATTCAAATCC TAATGAAATA GTTAATAAGG AAGTGAATAC   1260
TCAAGATGTG TCGGACGGAA TGACTACAAT GTCAGGTAAG GAGGTTGGAG TATACGATAT   1320
CGCCGATGGT CAGAAAACTG ATATAACGTC TACAAAAAAT GAGCTTGTTA TTACGTATCA   1380
TGGCAGGCTG AGAAGCTTTT CAGAAGAGGA CACTTATAAA ATAAAGGCTT GGTTAGAAGA   1440
CAAAATCAAT AGTAATTTAT TGATAGAAAT GGTTATTCCT CAGGCAGACA TCTCTTTCTC   1500
TGACTCTCTA CGACTGGGAT ATGAACGGGG AATTATTTTG ATGAAAGAGA TTAAGAAAAT   1560
ATATCCTGAT GTAGTTATTG ACATGAGTGT TAACTCCGCA GCATCAAGTA CAACGAGTAA   1620
AGCTATTATC ACGACTATTA ATAAAAGGTG TCAGAGTGAA ATATATAAAT CATTACCGCT   1680
ATTTGTTGTC TGTTCTTTCC TTGCCATACT CCCTTTTTTT GCTTTATCTT TTCCCGGTAT   1740
AAGAGAGTAT GTTTTTGATA ACTTCATGGT TTCTGCAATT TACAATGGAG TCATTATTGC   1800
CATTTATATT ACAGGTTCTT TGTGTGCATT ATTCACTATT CTTAAAAATA TTTCAGCAAA   1860
AGACATATTA ATAGCTCAGG ACGCCAGTAG AAAAAATAGC ATTCTTTCTA ACCTCAATCA   1920
GGTTTTGTTT GCCGGGGAGT CCAAACAGTG TGATTTCAAT TTACTGATGG AATTAGATGA   1980
CAATGTGTCT ACCGCCCGTA ATCAACGATT GTCATTTATT ATGAGCTGTA GCAATGTGTC   2040
GACGCTTGTT GGCCTGTTGG GGACGTTTGC GGGTCTGTCT ATTACGATTG GTTCAATCGG   2100
GAACTTATTG AGCTCGCCAT CAGATGTTGG CGGTGATAAT GCAAGTAATA CACTCAATAT   2160
GATCGTGACA ATGGTAGCGT CGCTTTCTGA ACCATTGAAA GGGATGAATA CCGCATTTGT   2220
ATCTTCTATC TATGGTGTTG TTTGCGCCAT ACTCCTGACC TCACAAAGTG TTTTTGTTCG   2280
CAGCTCCTAT TCCCTTGTTT CTACGGAAAT CAAAAAATTA AAAATCATAA GCAACAGAGC   2340
CAATAATAAA CAGCGAAGCC TGCGGGTTGA ATCAGAGACG CTTGTAGAAT TTAAAGAGTT   2400
GTTTAAAGCG TTTTTTGATA ACTACCTGAC AGTTGAAAAC TTACGGACGC AGGATGAAGA   2460
AAAGAAACGA GAGATGCTAT CAGATAGCTT TGTCACTTTG CAAAACCGAC TATTGGATAA   2520
CTCAGCAAAA CTGGAACAAA TTTTTACGCT GATTGATGGT TATCTGGTAA GCAGTAACGG   2580
AAAATCTCAA AAAATTATCT GACGGTGTAA TAACAATTAC CTCTCGTTTA TCTGAAGGTA   2640
ATATCCTGCT TGCTGATAAT AATGCACGAC TGGAGGCAAT GAGTACAATA CAAAATATTA   2700
TAGATAAAAA GAATGATTCA ATAATGACAT CAGTTGATAA ATGTTATCAG GAATCTCTTT   2760
CACATGGTAA GACCATAAAC GATATTGCCG CTGGCAGTGC CGATATTTCT CATACTCTCG   2820
ATGGGCTGAG AAAAGAAATG GATGAGGATA TGAATAATGT TCATTTAGCG CTATCCGATC   2880
```

```
TATCGGCTAC TGATAAAAAG ATTATTGCCA ATACTAAAGA GATTAGTGCT GAAATGGTTA   2940
GCTACCGTGA TACCTATATG CCATTAATGG AAAAAATAAC ATCTATGCAT CAGGAAATAG   3000
TAAAGCAACG TTTGTTAAAC AAGGAGGAAA AAAATGAAGA TTAAGATGTT TTTTCTGACG   3060
ACTGCTTTTA TTACACAAAG CACATACGCC AGCGAGCTTC CGGTCATTCC TCTAAGAGAT   3120
TTAGTTAATG CCGCATTAAC GCATCAGCCC TCTGTTGCTG TTTCATATTA TGAGACTGAA   3180
AAGAAAAACA GTGACTTAGA TCTTTCACGG GCAGCACTTT ATCCTACCCT GGATCTAACA   3240
TCTGGCCTTA ATAATAACAG GAAAGAGTCA TCAGGTACCG AGAGGAACGT TGAAAATAAG   3300
GTGTCTTTAT CATACCGAAT AACGGATTTT GGAGTGAGGG GGGCTAATAT CAGGAAATCT   3360
GAATATGAAA GAGATAATAG TAAAACTGAC TATGAAAAAA CAAAGAATAT AGTGTCTCAG   3420
GAGGTTGTGA CAACCTATTA CAACATCAGT AAATATCGTG AAATGATTGA TGGCGTAAAT   3480
CTGGAGAAAG AGTTTTATAA AAAGATGCTG GAACCTTTTT CGTTGCTGGT ATCTTCCGGT   3540
GTAGCTATGC AATCTGATAT GCGTAAAGTA CAAGTATCTA TCGATGCATT AAATACCAGA   3600
AGCATTATGT ATCAGTCGAT GTTGGATGAT GAAATGTATA AAATGCAGAA TATGACTGGT   3660
CTGAATTTAT CGCCAGTTCA GATTCAAAGC GATGAAAAAT TCAACCTCTT CAAAAAATAT   3720
ATCTTTGTCG AAAGCCCTGA AAAACTTATG GACATGGTGA TGAAATACAA CGATGACTAT   3780
AAGATGCTTG TCAATACCCG AAAAGCCGCG ACCGAAGATA TTAATGCCGC AAAATCATCC   3840
TATTTTCCGA CTGTAGATCT TGTTTCCAGC TATGTACAGA ATAACCCAAG CGGTAGTGCC   3900
AAAAAAAGTG ATTATGAAGA TGAATTTAAA ACGGGTATCA ATGTCAGTTT CAACATTTTT   3960
AATGGGTTCA GAAATTCAGC CCAGGAAAGA AAAATGGTGG CAAGTTACTC GCAGGCTAAG   4020
CTGCAAATTG ACGATTTTTT GATTAAAACG CGTTATAACA TTGATTCACA ACTTTCAAGA   4080
TACGCCGCTG CAAAAGAGAC TTACTCAGTG GCGGAACGTT CACATACAAA CGCGTTACAG   4140
CTTACTGAAT TATATGAGCA GGAGTTTCAG TTAGGGCAAA AAAGTTTGCT TGATTTAATT   4200
TCAAGCCGTA ATGAAGCATT TCAGGCATAT GTAAGCATGA TCGACAGCAA ATATAGCCTG   4260
TATATTTTAA AGCTACAGCA ACTCTCATTG ATTTTTCATT TAATGGATTA TTTAAAAGGA   4320
AATACTGAAA GTGAGTTAAA TGTAATGAAA TGAATAGAAG ACAAAGCGAT CATCTCATGA   4380
TGATAATTAT TTCTTTGACG ATCTTAATTA TTATCCTTAC CTACTTTATA GAAATTAATT   4440
CAGTGGTTCA TGGTCAGGGC GTTATCACTA CTAAAGATAA TGCTCAGTTA ATATCTCTTT   4500
CTAAAGGAGG GACGATACAA GATATTTATG TAGCCGAGGG TGATACTGTA AAAAAAGGAG   4560
AACTCCTTGC AAAGGTCGTT AACCTTGATC TGCAAAAAGA ATATCAAAGG TATAGAACTC   4620
AAAAAGGGTA TCTGGATAAA GATGTTAACG AAATATCTTT CATTCTTGAT AAAGAAAATG   4680
AGAGTGGGTT GATTACCCTG GATGGCACCC GTTCTTTAAG CAATAAAGAG GTAAAAGCGA   4740
ATATTGAATT AGTGCATAGT CAGATAAGAG CTAAAGAGTT AAAAAAAACC TCTCTTGATT   4800
CTGAGATTAG CGGATTACAA GAGAAGCTGA GTTCGAAAGA AAAAGAACTC GCATTGCTTG   4860
CCGAAGAAAT AAATATTCTT TCCCCACTGG TAAAAAAAGG AATTAGCCCA TATACCAATT   4920
TTCTTAACAA GAAACAGGCG TATATAAAAG TTAAGTCTGA AATTAATGAT ATTGAAAGTA   4980
GCATCACTTT AAAAAAAGAT GATATTGAGT TGGTTGTTAA TGATATTGAG GCGCTTAATA   5040
ATGAATTGCG ACTATCTTTA TCTAAAATAA TATCTAAAAA TCTTCAGGAA CTTGAGGTTG   5100
TTAACTCTAC ATTAAAAGTA ATAGAGAAGC AGATAAATGA GGAGGATATC TATTCACCGG   5160
TTGACGGTGT AATTTATAAA ATCAATAAAA GTGCCACTAC TCATGGTGGT GTGATTCAGG   5220
CGGCGGACTT ACTTTTTGAA ATAAAACCAA AAGTAAGGAC TATGCTGGCC GATGTGAAAA   5280
```

```
TATTACCCAA ATACCGTGAC CAAATATATG TAGATGAAGC CGTTAAACTG GATGTGCAGT   5340
CAATTATCCA ACCAAAGATA AAATCGTATA ATGCGACTAT CGATAATATT AGCCCTGATT   5400
CCTATGAGGA AAATACCGGA GGAACAATTC AGCGTTATTA TAAAGTAATT ATTGCATTCG   5460
ATGTTAATGA AGATGATTTA CGGTGGTTAA AACCAGGTAT GACTGTTGAC GCCAGTGTAA   5520
TTACCGGAAA ACACAGCATT ATGGAATACC TGTTATCTCC CTTGATGAAA GGCGTGGACA   5580
AAGCCTTTTC AGAACCAGTT AATACTAAAC GATTAGATAC ACCTTGAGAG TGAATATAAT   5640
ATTATGGGAA ATAAAAGCAT ACAAAAGTTT TTTGCCGATC AAAATTCTGT AATTGATTTA   5700
TCTTCTTTGG GTAATGCCAA AGGCGCAAAA GTTTCTCTTT CCGGGCCAGA CATGAACATT   5760
ACCACGCCGC GTGGTTCAGT GATCATTGTC AATGGCGCTC TTTATTCAAG TATCAAAGGC   5820
AATAACCTCG CTGTTAAATT TAAAGATAAG ACTATTACCG GCGCTAAAAT TCTGGGCAGC   5880
GTAGATTTAA AAGATATTCA ACTGGAGAGA ATTGACAGCT CATTGGTTGA TTCTGCTCAG   5940
GTAGAAAAGA AAGGTAATGG CAAACGACGA AATAAGAAGG AAGAAGAGGA ATTAAAAAGC   6000
AGCTTGACGA TGCTGAAAAC GCAAGAAAGA AGCTGATAAG GCGAAGGAAG AAGCAGAGAA   6060
AGCTAAGGAG GCTGCAGAAA AAGCGCTCAA TGAAGCGTTT GAAGTACAGA ACTCGTCAAA   6120
GCAAATTGAA GAAATGCTGC AGAACTTTTT GGCTGACAAT GTAGCAAAAG ACAATCTGGC   6180
TCAGCAAAGC GATGCTTCCC AGCAAAATAC ACAGGCTAAA GCAACGCAGG CTTCTAAACA   6240
GAACGATGCT GAAAAAGTTC TTCCTCAACC TATTAATAAA AATACCAGTA CTGGCAAAAG   6300
TAATAGCAGT AAAAATGAGG AAAATAAGCT CGATGCCGAG TCTGTTAAAG AGCCGCTTAA   6360
AGTCACATTA GCGCGTGCGG CCGAGAGTAA CAGCGGTAGC AAAGATGATA GTATAACTAA   6420
TTTTACCAAA CCTCAGTTTG TAGTTAGCAC TGCTCCCAAT GCCACGGTTA TTATTAAAAT   6480
TAATGGTATT GCTGTCGGTC AGGCTGTAAC GGATAGTTTG GGTAACTTCA CCTTTACAGC   6540
GCCTGAAACA TTGACTGATG GAACATATAA TCTGGAGGCA GAGGCCAAGA CTGCTGATGG   6600
GAGCGGTAGC GCCAAACTTG TCATTACTAT CGATTCCGTT ACCGATAAAC CAACATTTGA   6660
ACTTTCGCCT GAAAGTAGTG TGTCCGGTCA TAAGGGCTTA ACGCCGACCT TGACGCCTTC   6720
AATTGTTGGT ACGGCGGAAG AGAATGCTAA GGTTGACATT TATGTAGATA ATAAACTGGT   6780
TGCCAGCGTT GATGTCGATA AAGATGGAAA CTGGAGTTAT GAATTTAAGG ATAATGAATT   6840
ATCTGAGGGC GAAAATAGTA TAAAAGTCGT TGCTGTAGAT AAAGCAGGTA ATAAAAACGA   6900
AACGACGGAT AGTATCATAA CCGACACCAT TGCTCCAGAA AAGCCGACGA TTGAGCTGGA   6960
TGATAGTAGT GATTCCGGCA TTAAAAATGA CAACATTACA AATAGCACCC TGCCAACATT   7020
TATTGGTGTG GCGGAACCCG GTTCTACAGT CTCTATTTAT CTTGGACTTA AACATCTTGG   7080
TGAGGTCATT GTTGCTAAAG ATGGGACATG GAGCTATACG CTTACTACGC CGCTCAAGGA   7140
TGGCGAATAC AATATAACAG CAACAGCTAC TGATATTGCC GGGCATACCT CAGCGACGGC   7200
AAATCTGCCT TTTACTATTG ATACACGTAT CAGCTATTTC AGCGCTGAGA TTGAAACGAC   7260
GAATGATAGC GGTATTGTCG GAGATAACGT TACTAACAAT ACTCGCCCAA CCTTTACAGG   7320
TAAAACTGAG CCAAATGCTA TTATCAGTGT CATAAATAGT GAGACTGGCG AAGAGGTTAT   7380
TTTTAAAGCG AATGACAAGG GCGAATGGAC GTTCAATTTC ACTTCCGACT CAGTGGAAGG   7440
GATTAACAAT CTTACGTTCA CTGTTGAAGA TGTCGCTGGC AACAAAAAGG ATTTTTCCTT   7500
TAGTTACGTT ATTGATACTA TTGCCCCTGT ACCTCCGACG GCTTCTTTGG AGGATTATGT   7560
TGTTTTGCCG AATGGTATAA TTTTATCAGG GAATGATTTA CCGGCTTTAG TCGGTACGGC   7620
AGAACCAAAG TCTACCATCT TATTGATGCG AGATGGTAAA TTATATGACA GCATTGAAGT   7680
```

```
TGACTCAAAC GGGACCTGGA AATTATCAGT TTAGTAATAA ATTCTTCAGG GCGCCTATGA   7740
TATTGAAATC ATTCTCAGGA TGCCGCCGGC AATAAATCCT CTACTGTTAA ATATTCTTTT   7800
ACTATTCAAA CTGAAGTTGT ACCTCCAAAA GCGGAACTCG ATGCCAGTGA TGATTCCGGT   7860
GCAAAAGGCG ACTGGATTAC CAATAAACAT AATGCTCTGA CATTACTGGG AACAGCGGAT   7920
AGGTTTGCTA CCGTAAATAT CCTTATTGAC GGTAAAACGA TAGGCGTGAC GACTGCGGAT   7980
GCAGACGGTA ACTGGAATTT TGATATTTCC AGAAATCTGT CTGACAATGT TTATAAGATT   8040
ACGGTTGAAT CCATCGATCC TTTAGGAAGA ACGTCATCTG TAGATTATCA GCTTACCATT   8100
GATAGCTTTA CGCCGATCCC TACTGTTATG TTGCATGATA GCGCTGACTC TGGCGTTAAA   8160
GGCGATATGA TTACTAAAAT TAATACACCG TTGTTTACCG GGATGGCTGA AGCTAATGCT   8220
AAGGTTTCCA TCTATGTTGA CGGTGTGTTA AGTGGTGAGG CTATTGCTGG CGATGATGGT   8280
GTATGGAATT TTCAATTTAC CACAGCGTTA TCCGATGGCT CGCATGACGT AACGGTAAAG   8340
GTAGAAGATA TTGCCGGTAA TACTGCCTCC TCATCAGCGT ATAATTTCCA AATCGTAACG   8400
CAAACGCAAA AACCAACAAT AGAGTTGGTC AACGATACGG GGGTTGATAA TACAGACCAT   8460
ATTATTAATG AAAAGAATCC TGCACTGACA GGAACCGCTG CACCCTATTC AACGGTTAAA   8520
CTCTATATTG ATGGTGCACT GATCGCTGAG GTCAGAACAA ATAAAGATGG CAGATGGGAG   8580
TATACCCTGA AAGCCGATCA AGGTTTGGTT GATGGCGATC ATAGAATAAC CGCTTCAGTT   8640
GAAGATATCG CTGGCAACAT TGCTCATTCG GATCCTTTCT TAATTAGCGT CGATACTGCT   8700
ATTTCAATAC CGATAGTTTC ATTGAGCCCG GATTCAGATT CGGGAATTTC AGATGATAAT   8760
TTAACGAATA TCGTTAAACC TACCTTGCAC CTAAAAGATA TTGATCCGGA CATTATCAGT   8820
GTTCAGGTAT GGGATGCCAT GTCTGATACG CAGATCGGTG TTGCCACGCA ACAACCTGAT   8880
GGTTCATGGG CCTATACCTT TACTTCAGAT TTAACGGAAG GCTTGCATCA GGTTTATGTC   8940
AAGGTTGAGG ACATTGCGGG TAATAAAGCG AACAGCGCGA TATTCGATTT TACTATCGAT   9000
ACCACAGTAT CAACGCCGGT GATTTCCCTG CTTTCTAAGG ATGATACGGG GGTTACAGGC   9060
GATAACCTGA CCAATATCAA TAAGCCAGGT TTTGCTATTT CCGGTGTTGA TGCCGATGCG   9120
CATCGGGTCG TCGTACAGGT GATGCACAAT GGCGTGAGCG AAGAGATCGA ACTTTCCCAC   9180
CTCAATGGGA GTTGGTTATT TATACCAGGG GAATACGTGG GCGGATGGCA GCTACACGTT   9240
AACGGTGAAA GTAGAAGATA AGGCAGGAAA TACCAACTAC TCGGCGCCGC TGACGGTCGT   9300
TATCGATACC CAAATCGCCA TTGATGGGGT GGAACTGGTC AACGATAGCG GCGTGAAAGG   9360
CGATAATATG ACCAACGACG ACCGTCCCCA CTTTCGTGTG ACGGTACCTA CGGATGTCAA   9420
TGAAGTCCGT CTGAGCATTG ACGGTGGTAA TTCGTGGGTT CAGGCAACTC CGGGCGTGGC   9480
AGGAAGCTGG GAGTATATCT GGCCGACAGA CCTGGCAGAT GGTCCTACAC GCTAACGGTG   9540
GAAGCGACTG ATAAAGCAGC AATACATGAC GAAGACCATC GATTTCGCGG TGGATACCAC   9600
GCTGTCAGTG CCGGTCATCG TACTGGATAG CGCGGACGAC ACCGGCATCC AGGGCGATAA   9660
CATGACGAAT AGCACCCAGC CGACATTTGC CTTGCAGCAT ATTGATGATG ATGCCGTTCG   9720
CGTTACGGTC AGCGTGGAGC ATGGCGGCGT CACCACCACA TTTGACGCCA CGAAAGGCAC   9780
AGGCGGATGG ACCTTTACGC CGCCGACATC ATGGGCGGAT GGTGATTATA CCCTGAGTGT   9840
GTCAGTCGAA GATAAAGCGG GGAACACCAG CCATTCTGCA TCGCTGACGG TGACGGTGGA   9900
CACGCAAATC GCCATTAATA ACATTGAACT GGTCAATGAC AGCGGTATTC CCGACGATAA   9960
TCTGACTAAT AATGTGCGTC CGCACTTCCA GGTGACGGTA CCGACGGATG TCAACGTGGT  10020
GCGCCTGAGC ATTGACGGCG GCAAGACGTG GTTCAACGCT ACCCAGAGCG CGACGCCAGG  10080
```

```
CGTCTGGGAT TATATCTGGC CGGATGATGT GGCCGACGGA GGCTATACCC TGACGGTAGA  10140
AGCGACCGAT GAGGCAGGAA ATAAGGCAAC ACAGACCTCG ATTTCACCAT CGATACCACT  10200
CTGTCTGTGC CGACCCTCTC GCTGGACAGC GCAGATGACA GCGGCATCGC GGGCGATAAT  10260
ATCACCAATG TTAAAACGCC GGGCTTTACC CTCAACAATA TTGATACCGA TGTCAGCCGG  10320
GTGATAGTGG AGGTAATGCA CAATGGCATT AAGCAGGAGG TGCCACTGGT TCAGACCGGC  10380
GGACAGTGGC GCTTTGCGCC GACCAGCGAC TGGGCGGACG GCGACTATAT CCTGACGGTG  10440
AAGGTAGAAG ATAGGACCGG AAATGTGAAG CAGTCCGCGC CGTTGACGGT GACAGTAGAC  10500
ACGCATATCG CCATTGACCG TATTGAACTG GTTAACGACA GCGGTATCCC CGGCGATAAT  10560
CTGACCAATG AAGCGCGCCC GCACTTTCAG GTGACAGTAC CGGCGGATGT TAACGGCGTA  10620
AGACTGAGCA TTGATGGCGG CAAAACGTGG TTTGACGCCA CGCAGCAGCG CGACGTCGGG  10680
CGTCTGGGAT TACACCTGGC TGACGAATGT GGCTAACGGC CCTCACACCC TGATGGTGGA  10740
AGCGTCCGAC AAGGCGGGAA ACAAAACGAC GCAGAAACTG GACTTCACCA TCGATACCAT  10800
TCTGTCAGAA CCGACGATTA CCCTGGACAG CGCGGATGAT AGCGCCGCTG GCGATAACAT  10860
CACCAACGTT AAGATGCCAG GCTTTACCCT CGGTAATATC GACGCCGACG TGACCAAAGT  10920
GGTGGTGACG GTGGCGCATG ATGGTAAGAA CCAACAGATA GAGTTGATTA AGAACGGCGG  10980
TGTGTGGCGC TTTACGCCGG GCGCAGCCTG GACCGATGGC GACTATACGT TGACGGTAAA  11040
GGTAGAAGAT AAGGCGGGTA ATACAAATTA TTCTGCGCCG CTGACGGTGA CTATCGATAC  11100
GCAAACGTCT ATTGATCGCA TTGAGCTTCT TAATGACACG GGTATTGTCG GGGATAACCT  11160
GACCAATGAA GCACGTCCAC AGTTTCATAT TACGGTACCG ACGGACGTGA ACTCTGTGCA  11220
ACTGAGTCTT GATGGCGGCA TCAACTGGGT TAACGCAACG CTGACGTCTG ACGGCGTTTG  11280
GGAGTATATA TGGCCGACAG ATCTGGTCGA AAATACGTAT ACCCTGACAG TGAAAGCAAC  11340
CGATGTTGCA GGCAACACGG CGACGGAAAC GCTCAATTTT ACCATTGATA CCACATTGTC  11400
GACACCGACC ATCACGCTGG ATAGCGCAGA TGATAGCGGC ACCGCCAACG ATAATAAGAC  11460
TAACGTTAAA ACGCCGGGTT TTATTATCGG CGGTATTGAT TCTGACGTGA CTCAGGTCGT  11520
CGTGCAGGTG ATGCGCGATG GTCACAGCGA GGAGGTGGAG CTGACGCAGA CTAACGGGCA  11580
GTGGCGTTTT GTACCCGGCA GCGCGTGGAC TGATGGCGAC TATACGCTGA CGGTAACGGT  11640
GAAAGATGAG GCGGGTAATA TTCGCCACTC AGCGCCGTTG ACGGTCACCA TCGATACGCA  11700
AATCACCATT GACCATATTG AACTGGTCAA TGACAGCGGT ATTCCGGACG ATAATCTGAC  11760
TAATAATGTG CGTCCGCAAC TTCCAGGTGA CGGTACCGAC GGATGTCAAC GTGGTGCGCC  11820
TGAGCATTGA CGGCGGTAAG ACGTGGTTCA ACGTTACCCA GAGCGCGACG CCGGGCGTCT  11880
GGGATTATAC CTGGCTGGCT GATGTGGGAG AGGGTAAGCA TACCCTGACA GTGGAGGCGA  11940
CCGACAAGGC GGGAAACAAA ACGACGCAGC AACTGGACTT CATCATCGAT ACCCTACTGT  12000
CAGAACCGAC TATCGTGCTG GACAGCACGG ACGACAGCGG AACAAAAGGC GATCACCTGA  12060
CCAACGTAAA TAAGCCGACG TTTTTACTGG GCAATATTGA CGCAGACGCG CGGTATGTCA  12120
CGGTTGAGGT ACAGCATGGC GGCACGAAAG AGGTGCTGAC GGCCACCAAA GACGCGACCG  12180
GCAACTGGAG CGTGACACCG ACCGGCACAT GGGCAGATGG CGACTATACG CTGACAGTGA  12240
GGGTGGAAGA TGAGGCGGGG AACGAAAAAC ACTCAGGTCG CTGACGGTCA CTGTTGATAC  12300
CCAAATCACC ATTGATGTTA TTGAACTGGT TAATGATAAC GGTATTCCCG GCGACAATAT  12360
GACTAACGAC GCCCATCCGC AGTTCCGCGT GACGGTACCG GGGGACGTTA ACGAAGTCAG  12420
TCTGAGCATT GACGGTGGCG TGACCTGGGT TAAGGCGACA CAGAGCGCGA CGCCGGGCGT  12480
```

CTGGAATTAT ACCTGGCCGG GCACCGTGCC GGATGGCGAC TATACGCTGA ATGTGAAAGC 12540

GACTGACAAT GCGGGTAATA CGGTGACGGA GACACTCCAC TTCACTATTG ATACTACGTT 12600

GTCGACGCCG GTGATCGTAC TGGATAGCGC GGACGACAGT GGTGTCCATG GCGATAACAT 12660

GACGAATAGC ACCCAGCCGA CATTTGCCCT GCAGCATATT GATGATGATG CCGTTCGCGT 12720

TACGGTCAGC GTAGAGCATG GCGGCGTCAC CACCACATTT GACGCCACGA AAGACGCAGG 12780

CGGATGGACC TTTACGCCGA CAGGGGCGTG GCGGATGGT GATTATACCC TGAGTGTGTC 12840

AGTCGAAGAT AAAGCGGGGA ACACCAGCCA TTCTGCATCG CTGACGGTGA CGGTGGACAC 12900

GCAAATCGCC ATTAATAACA TTGAACTGGT CAATGACAGC GGTATTCCCG ACGATAATCT 12960

GACTAATAAT GTGCGTCCGC ACTTCCAGGT GACGGTACCG ACGGATGTCA ACGTGGTGCG 13020

CCTGAGCATT GACGGCGGCA AGACGTGGTT CAACGCTACC CAGAGCGCGA CGCCGGGCGT 13080

CTGGGATTAT ACCTGGCTGG CTGATGTGGG AGAGGGTAAG CATACCCTGA CAGTGGGGGC 13140

GACCGACAAG GCGGGAAACA AAACGACGCA GCAACTGGAC TTCATCATCG ATACCCTACT 13200

GTCAGAACCG ACTATCGTGC TGGACAACAC GGACTACAGC GGAAACAAAA GGCGATCACC 13260

TGACCAACGT AAATAAGCCG ACGTTTTTAC TGGGCAATAT TGACGCAGAC GCGCGGTATG 13320

TCACGGTTGA GGTGCAACAT GGCGGCACGA AAGAAGTGCT GACGGCCACC AAAGGCGCGA 13380

CCGGCATCTG GAGCGTGACA CCGACCGGCA CATGGGCAGA TGGCGACTAT ACGCTGACGG 13440

TGAGGGTGGA GGATGATGCG GGGAACGTAA AATACTCAGC GCCGCTGACG GTCACGGTTG 13500

ACACCCAAAT CACCATCGAT GTTATTGAAC TGGTTAATGA TAACGGTATT CCCGGCGACA 13560

ACCTGACCAA TGACGTTCGT CCACACTTCC GCGTCACGGT GCCAGGGGAT GTCAACGAAG 13620

TACGTCTGAG TATCGACGGC GGTAATACGT GGGTTCGTGC AACACAGGGC ACGGCAGGGA 13680

TCTGGGATTA CACCTGGCCG AAAGATGTGA CCGACGGGCT ACATACCCTG ACGGTAGAAG 13740

CGACCGATAA GGCGGGAAAT AAGACGACGC AGACGCTCGA TTTTACCATT GATACCCGGC 13800

TGTCAACGCC TACCATCGCT ATGGATAGCA GGGACGATAC AGGTGCCATT GGCGATCATA 13860

TTACGAGCGT CAAAAGACCG GGCTTTACTA TTGGCAATAT TGACGCCGAT GCGCACTCGG 13920

TCATTTTGCG GATCACACAG GGCGGCAATA GCCAGGAAGT GACACTAACC CAGGTTGGAG 13980

GACAGTGGCG CTTTACGCCA GATGCTGACT GGGCGGACGG TAGCTATACG CTGACGGTAG 14040

AGGTAACGGA TAACGCAGGA AACGTTCGTC AGTCCACGCC GCTGGTGGTG ACGGTGGACA 14100

CGCAAACCAG CATTACTGAT ATTACATTGG TCAATGATCA TGGCGTGCCT GATGACAATC 14160

TAACTAATAG CACCCGTCCG CAGTTTGAGA TCACGGTGCC GGCGGATGTG AATTCTGTGC 14220

AACTGAGCAT TGATGGGGGC GCAAACTGGG TGAGCGCGAC GCAGGGTATC GAAGGCGTCT 14280

GGGGCTATAC CTGGCCAACG GATATGGGCG ATGGAAAACA CACCCTAACC GTCATGGTCA 14340

CCGACAGAGC GGGCAATACG GCGACGCAAA CGCTTGAATT TTTCATCGAC ACCCGGTTGT 14400

CGACGCCGAC CATTGCGCTG GATAGCACGG ATGATACCGG TACGCCTGGC GATGATATGA 14460

CCAATCGCAC CCGACCGACC TTTATTCTGC AGAATATCGA TTCGGATGTT ATCAACGTTA 14520

CAGTCAGCGT CACGCATAAT GGAACGACAA CCTCGTTTAC TGCGACACAG GGGGCTGGAG 14580

GATGGAGCTT TACACCGCCA GCGCCGTGGG GCGACGGTGA TTATACGCTG ACGGTGACAG 14640

TGGAGGATCG GGCGGGAAAT ACGCGTCCGT CTACGCCGCT GACGGTGACA GTGGATACGC 14700

AAATAGCCAT TGATCGTATT GAATTAGTCA ACGATAGCGG CGTCCCTGGC GATAATGTGA 14760

CAAAACATGT GCGTCCGCAG TTCCAGATCT CGGTACCGGA TGATGTGGAA AAGTTCTTCT 14820

GAGTATTGAC GGCGGCACGA CCTGGGTTAC TGCAATCAAG AGTTCGACGG CTGGCATTTG 14880

```
GGATTACACC TGGCCGACGG ATATGCCAGA GGGACAGCAT ACCCTGACCG TGGAAGTGAC  14940

TGACGGTGCG GGTAATAAGA TGACGGAGAC GCTCAATTTC ACTATCGATA TCACGTTGTT  15000

AACGCCAACC ATTGAGCTAG CGCCCGATCA GGATACCGGA CAGAATAAGA ACGATAATCT  15060

GACCAGCGTC ACTCAGCCGG TATTTGTGTT GGGGAGTATC GATAAAGATG TTCGACACGT  15120

GGAATTGAGT ATTGAGCATA ACGGCACGTT TAAAACGGTG GTACTCACCG AATCAGCCGA  15180

CGGCTGGCGC TATCGACCGG ATTCTGCTTT GGCGGACGGT AGCTACACAT TCACCGTGAC  15240

GGTAACAGAT GTGGCAGGCA ACCAGCAAAC ATCCGCGCCT TTAAAGGTGA CGATAGACGG  15300

TACGTTGACT ACGCCGGTGA TTGAACTGGC AGCTGGCGAA GATAGCGGTA CTGTTGGCGA  15360

TCGCCTCACC AATCACGATC GGCCTGTGTT CGACATACAT CAGGTTGATT CTGACGTTAC  15420

GCGCGTGATG GTCAAAGTAA CTTACAACGG TAAAACGCAC GAAGAAGCGG CGGTATTCAC  15480

CAATGGTCAA TGGCGCTTTA CGCCTTCTGC GA                                15512
```

(2) INFORMATION FOR SEQ ID NO:6:

(i) SEQUENCE CHARACTERISTICS:
(A) LENGTH: 8967 bases
(B) TYPE: nucleotide
(C) STRANDEDNESS: double stranded
(D) TOPOLOGY: linear (ix) FEATURE:
(D) OTHER INFORMATION: SEQ ID NO:6 corresponds to nucleotides 15735 through 24701 of SEQ ID NO:2

(xi) SEQUENCE DESCRIPTION: SEQ ID NO:6:

```
CTGGATGGTG GCGCTAACTG GAATGTGATA CGCAAAAATG CCGACGGACA GTGGATTTTT    60

GACAGCCCGA ATACTCTGGT TGACGGCACA TATACCCTTC GCGTAGAGGC CACGGGATGA   120

GGCAGGTAAT ATTGCGAATA AAGATTTAGT ATTTAATATC GATACTAATA TACAGGTTCC   180

TACTATTGCT TTAGACGCAG GACAAGATAC CGGAGCGAAT ACCGCCGATA ATATTACTAA   240

TATTTCACGA CCCACCTTTA CGATTGGTAA TGTTGACCCC GATGTTATCA AAGTCGTGGT   300

GACGATTGAT GGTCATGATT ATAACGCGAC TAAGGTTGGG GCTGGTTGGC AATTTACACC   360

AGGCAATGCC ATTCCGGATG GCTCTTATAA TATTACCGTT ACGGTTGAAG ATAAGGCCGG   420

AAATACCGCG ACATCGAAAC CATTACCTGT TGTGATAGAT ACGACGGCTG AAATTGAAAG   480

CGTCACGTTG GTTACAGATA GCGGTGATAG CGATGTAGAT AACATTACCA AAGTCGACAG   540

CCGCAGTTTA GTATTGTTAC CGCTGATGAT ATAACCCATG TGCGCGTTAA AATCGATAAC   600

GCCGCTAATT GGATTGAACT CACAAAAGGA GGGATGGCCG CTGGATATTT AATGTCGGTT   660

CGGCATTACC TGATGGGCAA CACACTCTCT TGGTTGATGT GACTGATATC GCCGGCAACG   720

TTGCGCAAGA AACGCTGCAG TTTACGATTG ATACGACTCT GCGAGAGCCG ACAATTGTAC   780

TCGATCCCAC CCATGATACT GGTGATGATA CTAATGATAA TCTTACCAGG ATTAACAAAC   840

CGGTGTTTAT TATCGGTAAT GTCGATAATG ATGTATCACA CATTGTGGTT CATATTGATG   900

GTCGGGATTA CACCATTGAA AACACAGGGG GGAATTTAAC CTTTACGCCG GATCAACCGC   960

TGTCTGACGG TCAGCATACG ATCTCTGTTA CCGTAACGGA TATTGCTGGT AATACCAAAA  1020

CATCGGCCGA ACTGCGGATT GAAATCGACA CGCAGGTTCA GATTGACAGT GTTACGTTAA  1080

CAACAGATAG CGGCGTCAAC GATCACGATA ATGTCACCAA TGCTACCCGT CCCTCTTTTG  1140

AAATTGCAAC GCCTGATGAT GTGACATCGG TGCTGGTTTC TTTCGATGGC GTAAACTGGA  1200

CGCCCATCAG TAAAAATGCG GCCGGGCAGT GGGAATTTAC TGCAGGTAGC GCATTGCCTG  1260
```

```
ATGGTCATTA TACTCTCCAT GTCCAGGCGA CGGATCGGGC AGGGAATACG GCAAATTCCA   1320
CGCTGGGCTT CACCGTGGAT ACGCAGATTG ACGGCCTGAG CGTCGTGATG CTGGACGACG   1380
CCGGAAAGGA TTCTACGGAT GGTATTACGA ATATTACCTC TCCACGTTTT GAAATTTCAG   1440
CCAGAGAACC GCTGCAGAGC GTGACGGTAA TTTTAAACGG GAAATCCAGC ACACTGACTC   1500
AGGGGGCAGG TAATAAATGG CTGTTTACCC CTGATACACC GTTAGTGGAT GGAACTTACA   1560
AAATAGAAAT AGTGGCTGAA GATATCGCAG GTAATAAAAT TAGCAAAGAG GTATCATTCA   1620
CAATAGACAC TATTGTTTCT GATCCCAGTA TTGATTTGCT GGATGCGGAT GATACTGGCG   1680
AAAGCGCTGT TGATAATATT ACGAGTGTCA CTACACCACG TTTCGTTATT GGCAATGTAC   1740
CCGCCGATAT TGATACTGTT GTTATCAGAA TTAACGGCGT TTCTTATCCG GTTACGGCAA   1800
ATGGCAATAA CCTCTGGGAA TTTCAGGTTC CCGTTGCGTT AAACGATGGC GTATATGAAG   1860
CCGTTGTTGT CTTCAGAGAT ATTGCCGGAA ATATTTCTGA AATTAAGCTG CCCTTTACCA   1920
TTGATACCAC GACAAGCGTC AGTGTCAGAA TGGAGCTAGC GTCTGATACC GGAAATTCCA   1980
ATAGCGATAA CCTTACGAAT AAGCAAAATC CCAAATTCGA AGGTACTGCA GAGCCCAATG   2040
CGAAACTGGT GATTACCATT GTTGACGATA AGTCAGGTCA GGAGGTTTTA AAACAAACGA   2100
TTACGGTTGG CGCTGATGGC AACTGGAGTG TGACGCCGAA TATACTGCCG GATGGCATGT   2160
ATACCATCAA CGTCGTCGCA ACAGATGTCG CGGGAAATAC TGCGCAAACG CAGGAAAGAT   2220
TCACTATCGA TACGGTTACG ATCGATCCCA CCATTCGCCT TTCGGATCCA TCTATTGATG   2280
ATCAGCATGA AGCAACCAGC CTGCGTCCTG AGTTCAAAGG GTTTGCCGAA GCGTTCTCGA   2340
CGATTATGAT TCAGTGGGAT GGGAAAGTGG TCGGCTCGGC AAACGCCAAT GCGAATGGCG   2400
AATGGAGTTG GACGCCGCCA TCAGTATTAG CGCCAGGCTC CTATGTTGTG AGCATTGTTG   2460
CCAAAGATAA AGCGGGTAAT GATTCGTCGC AGGTCGACTT TCCTGTCGTA ATACCTGTTA   2520
TTGATGTCAC GCCTCCAACC ATAAAGCTCA GCGAGGAGAG CGATAGTGGC GCCTTAGGAG   2580
ACTTTACCAC GAATAATAAA ACGCCGACCC TGATTGGGAG CACGTTACCT AATACGATTG   2640
TGAGTATTTA TGTGGATGGC GTGAAGGTCG GCGAGGCGAC AGCGGATACA GCGGGTCGAT   2700
ATACTTTCCA GTTATCGGAA ATGAAAGATG GCCATTATGT CGTCCAGGTG GGTATCGTCA   2760
ACCCTCGCGA TAATAGCGAA CTGCGTTCTA CCGCCGTTGA TGTCACTATC GATACCGAGG   2820
TTGCTGAACT GGTATGGAAT ATATCTGGAA TGCATGAGGG CGGATATATC AATACGGTGA   2880
CGCCGGAGAT TGGCGGCACC AGTGAGCCAA ACAGCAAAAT CACTATCTTT GTGAATGGCG   2940
TTGGAAAAGC GATTGCTTAT ACGACAGGCG CAGGACACTG GGGCGTAGTA TTACCCGCTT   3000
TGGGTAATGA CGGTAATTAT GAATTAACGT TTAAAGTTGA AGACGTTGCC GGTAATATCA   3060
GAGAGTTTGG TCCGCAGAAT GTAATACTGG ATACAGTAAT TTCGCCGTTA ACCGTGGTAT   3120
TACGCGAAGC TGATGACAGT GGCAAAGTTG GCGACTGGAT CACCAATAAA TCTCATGTCA   3180
CCATCGATGG TACTGCCGAA GCCGGAAGTA CTTTAACCAT CAGGAATCCG CAGGGAGTGG   3240
TTATTGCTAC CCTGGTGGTA GGCAATGATG GTCGATGGAG CGCAGAATTA GATCTGCGTG   3300
AAGGTAGTAA TGCCTTTGTC GTGGTATCGG AAGATAAAGC GGGCAACAGT CAACAAAAAG   3360
AGATTCTGAT AGAACATGAT ACGCAGATTG AAATCAGCGA TATTTCATTA AGTCGGGATA   3420
CTAATAGCGG TGATAAATAT GATCTGATTA CCAATAATAA GTCTCCGGTA CTGGTTGCCA   3480
GGACCGATCC CGGCGCGACG GTACAGGTTT ATATTAATGG TGTGTTACAA GGCACAGTAG   3540
AGGCGAGTTC GTCAGGTAAT ATTAGCTATA CCATGCCGGC AAATAGCGCC GACGGCGAGT   3600
ATCAGGTGCA ATTTGTTGCT ACGGATACTG CTGGTAACCG GGTTGAGTCT GCGATTACAA   3660
```

-continued

```
CCGTGACAAT CGATTCTCAA ATTGCTGTCT TTGATATTGA TGAAGATTCA TTACCGGCCC   3720
TCTCTAATAA CCGAGCGTTG TCAGTCTCAG GTGTCGGGGA GGCTGGTTCT CAGGTCAGCA   3780
TCTTTGTCGA CGGTAAATTA GTCAACGTTG TTATGGTTGA GGCTGATGGC ACATGGCGCG   3840
CGCCGATACT GCTGCAAGAT GATGGTACGT TTAATATTCA TTTCAGCATT ACTGACGTTG   3900
CTGGCAACAC TGAAGTGAGC AAGGATTATA GCGTGGATGT CGATTCATCA ACCGACTTCC   3960
CAACGCTCAA CCTTGAAGAT GCAAGCAACT CTGGTTCACT TGACGATCTG ATTACTAATC   4020
ACAACAAGCC TGTATTAGTT GGCACCGCAG AAGCGGGAGC CACAATCCAT ATTTATGTGG   4080
ATGAAAAGAT CGTGGCAAAT GTTCTTGTGC TTGAAGATGG AACCTGGTCC TATCAGTTTG   4140
ATAATGCGTT AAAAGATGGT GAATATTCTA TCCGTGTGGT TGCCGAAGAC CCGGCAGGTA   4200
ATACGGCAGA ATCGCCTCGC TTACTCGTCA CGATAGATAC CAGTACGTTT ATCGATAATC   4260
CTGCTATGGT GGCAGGTTCT GATAATGGTA TTTTCAGTAA TGATAGTATA ACGAGTCAGA   4320
CCCGGCCTAC GTTTAGTATT TTTGGAGAAA TGAACCAGAG TGTTCAGATT TTCATTGATG   4380
GAGTGCTAGT CGATACGATC ACGGTGACCG ACAGAAATCA AGTTTATCGA CCTGAGTCAC   4440
CGTTGGGCGA TGGTTCCCAT AGCATTTATT ATGTTATCAC CGATAAAGCA GGCAACACGG   4500
CTACCTCGAA AACGCTAAAC TTTACTATCG ATACCTTTAA TACGACGCCT GTCGCCATTG   4560
ATTCTATCGG TGGACAAACG TTAGCAGAGA TGACCGGTAG TGATGGCAAA ATATATATAA   4620
CGGACACGAC GCGTAACTTA TTGTTTAGTG GCAGTGCCGA GCCCAATAGC AAAATAGAAA   4680
TCATCATTAA TGGCTTAAAT GTGGGGGAAG TTTGGGTTAA TGAAAAAGGC CACTGGCAGA   4740
TGCCGGTGAA CCCGCTTTAT TTCACAGAAG GCCAACTGGA TATCACTGTT AAATCTACGG   4800
ACCGTGCTGG TAACGTAAAT CAGGAAAAGT ATTCCATTTG GGTTGATACG CATATCAAGG   4860
TATTTACCAG CGAGCTTGAT GACAATAAAT CATCATCGAA AACGGAATGG TGGAGTAATA   4920
GCGATCTCAT TACCATGCGA GGCACGGGTG AAATTGGCGC TACGGTATCA TTAATCGTGG   4980
CTGGCGTCAC GCTGGCAACT GCTGTTGTGG CGGCAACAGG ACGATGGGAA TTATCAACAG   5040
ACAAGCTTCC AGAAGGGACT TACGATATTA GTTTGGTCAT TGAAGATAGC CCGGAAATCG   5100
TTGGGAAGAT GTGCGTGAAA TATTTATTGA CCGAACCCGC CAAATGCTCC GGTCGTAACG   5160
TATTCAGATA TTGTCAACGA TCTAATTATT ATGCAGGGGA CGGCGGAAGC CAAATCTCAG   5220
CTAATAATAA CCGATAGTGA GGGGAATACT TATACGTTAA CCGTTCCTGA TAATGGTAAA   5280
TGGAGTATGG CTATCCCGTA TCCATCAGAA GGGAAGTTTA CCATTACGAG TGTGGATGCT   5340
ATTGGTAACC GGAGTGATGA TGTCCCTCTC GATATCATGA AAGAGGTTCC CGTTATTTCA   5400
TTATCTCCAG ACTCAGACAG TGGTACGGTG GGCGATAATA TTACGCGAGA TAAGCAACCT   5460
ACCTTTATTA TCGGGAATCT GGAAAGCGAT GTTGTGGTCG TTCAGGTCGA TATCAATGGG   5520
ACCGTATATA ATGCTGAAAA AAATGCCGAT GGCGTTTGGT TCTTTACGCC AGGTACACCG   5580
TTAGCTGATG GTTCCTATAC GATATCGGTA ATCGCAAGCG ATGCCGCGGG TAATCAGAAA   5640
AACTCGTTAC CCATTACTGT CACGATCGAC AGCACGCTGA CGGTGCCGGA GATTGCGTTG   5700
GCAGCAGGTG AAGACAATGG CGCTTCAGAC AGCGATAACG TGACGAATCA CACCCAGCCT   5760
AAGTTCACGC TGCAGCATAT TGATGCTGAT GTGACCGGGG TGACCGTAAA CGTGACGCAT   5820
AATGGCGTGA CAGACATCTA TCAGGCGACG CAAGGCGCGG ATGGCTGGAC CTTCACGCCG   5880
CCAGCCGCCT GGAATGACGG TAACTACACG CTGAGCGTGA CGGTGGTGGA TCGCGCGGGG   5940
AATTCACAGC AATCTGCTTC GCTAGCGGTG ACGGTTGACT CAACGGTGAC GGTAACAGCG   6000
GATAGCCAGC ATGACGATGC GAGCGATGAC GCCACGGCAA CAGCGGTTAC TCCACCGGAG   6060
```

```
TCTGAAACAG TGAATGCCGA AAGCGCTACG CATCTTCGTA CAGAGCCGTC TGCGGCGGAA   6120
GAAAGCGTGG TGAAGGTGAC AGCCTATAGT ATTACATTGT TAAACGCTGA CTCTGGGGAT   6180
GAAATAGATC GTTCAATTAG TCAGACACCT TCTTTTGAAA TATCAGTACC TGAGAATATT   6240
GTTAATGTCA GTATTATGTT TGAAGGAGAA GAGTTTACTC TGCCGATAAC TAACCAGAAA   6300
GCAATATTCG AAGTTCCGCT ATCTTTGGAA GATGGTGAAT ATACTATGGA CGTGAAATTC   6360
ATTGATAAAG ACAATGATTT CCTGATTAAG GAGAAAACAT TCTCAGTCGA TCACTCCTCG   6420
GCGGATATTG TGAACGCAAT GAATGTAAGA GGAAAGACCG AGGATGATAT TAATGATTCC   6480
CCTTCCACGA GTTCTGTAGG GCACAACAAT AACGGCGCTA TTGATGTTTT CGCCGTTAAT   6540
GAAGTTACGC TACCTGTAGA TAATCAAGAA GAACACGCAT AATAACGGAG GCCCCTCACC   6600
TTTGGGTTGA AGGGGGTTTA CTTATGGATA AAAAACTAGA ACCTTATTAT TTAAGTGCGG   6660
AAACGGCATT ATCTATAGTG TCTACAAAAT TCAACATAAA AATTGACATC CGAGAAGATG   6720
ATATACATTT GAAGATTTAG AAAGTACGAC TGAAATAACA CTGACGACCT ATACGAATGA   6780
AGAATTTCTT TTTGTCGTTA GGGCTTTCTC TACAGGATAT ATTATTTAAT AATGGTGAGG   6840
ATTTACTAAA TGAGCCTATG CCGATTTTAC TATTAACACC AGAAAATGAA AGTGGATGGT   6900
GTGTGTGAGT GGCGGGCAAA AAATAAAGTT GGTAAACGCG CGCGGTGAAC TCTGTTATGT   6960
TGAAATTGAA GATGAATATT TAAAAGAGTT ATCTGCATTT AGTATACTAC CTTTAAATAA   7020
AGTTGTTGAT AGTATAAGAG TAAAAAATAT CATAAAAAAC TCTTTATCGA TGAACAAGAT   7080
TTTTTATACT AAATACTTTT TTTCATCTCT TTTTATGGCA ATTTTTGCGT TAACTATCCC   7140
AGTATTTAGT AATCTGTTCT ATGATAAGCT TGTTCCAAGC GCTTCGGTTT CATCTTTATT   7200
TGGCGTGGCT ATAATTGTTG CTGTATTTAT TGTTTTTGAG TTTATCCTTC GTACTTCGAA   7260
AGATATTTAT CAGTCTATCA CAGCAAGGCA GGATGACGTC GATATTGATA TCGCATTTCT   7320
TGAAGCGGTA CTTTATAGTA AAAAGAAAAA TGGCAGATCC ATGTCATCAG CATTTGTGCT   7380
ATGGAATGAG TTTCAGAAAA TTAAACCCGT TTTATTAAAC TCGATCTTTC AACGTATAGC   7440
CGATATTCCA ATATTTATTA TATTTCTCAT TGTTATATAT GTAAATTTAG GTCTGGTTGT   7500
TATTGTACCT ATTACCATGT TTATCGTCTC TATTATTATT TCCCTCGTTA ACCACCATTA   7560
TACTAATGAG TTAATGAACA AACAAAAAGA AGGACAGAAG AACAGGAATA TTTTTATCTC   7620
AGAAGTTTTC TTATCTATTA AAATGATCCA TACCTTAAAT AATCAAGGTT TACTTTTTGA   7680
TTGGGTTAAT ACATCAAATG AACAGTCGTA TCTTAACCTG AAGATAAGGA AATTAAATCT   7740
TATCTATCAA TCTATATTGG GGAGTATGTC ATCTATTACC CAAATAACTA TTATGGTAAT   7800
AGCCTTTTTT ATGGTAATCA AGGGTGATGT TACTACTGGC GCAATTGTTT CATCTGTCAT   7860
TGTCTCTGGC CGTATTTCCG GGATCATTTC GAATTTTTCT TCTACATTAA TCTCTATTTT   7920
ATCAGCAGAA AAAACCGGTA AGGATCTGCT TTCTTTTTTT GATGAAGATC AGGCAGAAAA   7980
AACACCGGCA TTACAGTCAA TATCAAAGTG CAATGGCGAT ATCTCTATCC GGGGCGTGAG   8040
TTATCAGTAT GATGCTCAAT CTCCGATGAT TATTAACCGA CTGTCTATAG ACATACCTGC   8100
GGGGCAACGT GTCGCGGTGG TAGGCGAATG CGGAGCAGGA AAAAGCTCAT TACTGGGAAT   8160
GCTATCTGGC TACCTTTCGC CAACAGACGG TGCCATTTTA TATGATGGAT ATAACTTAGG   8220
ACATTTATCG CAGAACTTTT TTTCTCAGCA TTTAAGCGTG GTGACGACAC ATGATGTTTT   8280
ATTCACCGGA ACCATTGAAA GTAATTTCGC GTTAAAACCG CAAAACGACA GGGGCCGGGT   8340
ACTCAAGGCG CTTCAGCTGG CGAACTGTGG TTTTATCTTG CAACATCCTA TGGGGCTGAA   8400
GTTTCCGGTG AATTTTATGG CTAAAAACCT GTCATCCGGA CAGCAGCAGC AGTTATTATT   8460
```

```
AGCACGTAGT CTGAGTAGTG ACGCCAGCGT CTTTTTATGG GATGAACCAA CATCAAATCT   8520

GGATGAGAAT ACCGAGAAGC AAATTTTTGA TAACTTAGAT GAGTTTATTC ATGGGAAAAC   8580

GTTGATCATG GTGACGCATC GTCGATATCT GATAAAGTAT TTTGACCGGG TCCTGGTAAT   8640

GAAAGGTGGA AAAATAATCC GTGATTGTTC TCCGGATAAA TTATTAATGT AAAATAAGCA   8700

GCGCTTGTCG CTGTTATCAG GTGGTACTGC TTAATAAAAA AGACCCGTTG CACAAACGGG   8760

TCTTTTTTGT CATTTAACGG AGTCGGCAAC GTCTTCAATA AGTTTAGCTC GATTCTGTTA   8820

GGGCTATTCC ACTTGCCATT TTTGGATAAC CACACCTGGC GGCCTTCATC AACGGCAATG   8880

CGAGGGACGT GATGGTGCGC AAGGCTAACC CCTGGCGCGC GATTCCGCGT TGAGATAACC   8940

GGTGGGCGGC TTCAGCGGCA GCGATAG                                      8967
```

(2) INFORMATION FOR SEQ ID NO:7:

(i) SEQUENCE CHARACTERISTICS:
(A) LENGTH: 222 bases
(B) TYPE: nucleotide
(C) STRANDEDNESS: double stranded
(D) TOPOLOGY: linear (ix) FEATURE:
(D) OTHER INFORMATION: SEQ ID NO:7 corresponds to nucleotides 9366 through 9587 of SEQ ID NO:3

(xi) SEQUENCE DESCRIPTION: SEQ ID NO:7:

```
GGTTACACGT ACCTGGACGA CATCACCGGG AACGTCAATT CTGAATGACG GTTTGGCAAC     60

ATTCGTTAAT TGATCATTCT GCACGCCGGT ATCATTAAGC AATACGATAT TGTTAATGGT    120

TGTCGTGGTA TCAATACGCA CCTCAAACGG CGCAGACTCT TTTACATTCC CCGCCAGATC    180

TTCCACCACA ACGGCTAACT GATATGAGCC ATCAGCCCAG CT                       222
```

(2) INFORMATION FOR SEQ ID NO:8:

(i) SEQUENCE CHARACTERISTICS:
(A) LENGTH: 15512 bases
(B) TYPE: nucleotide
(C) STRANDEDNESS: double stranded
(D) TOPOLOGY: linear (ix) FEATURE:
(D) OTHER INFORMATION: SEQ ID NO:8 corresponds to nucleotides 9190 through 24701 of SEQ ID NO:3

(xi) SEQUENCE DESCRIPTION: SEQ ID NO:8:

```
TCGCAGAAGG CGTAAAGCGC CATTGACCAT TGGTGAATAC CGCCGCTTCT TCGTGCGTTT     60

TACCGTTGTA AGTTACTTTG ACCATCACGC GCGTAACGTC AGAATCAACC TGATGTATGT    120

CGAACACAGG CCGATCGTGA TTGGTGAGGC GATCGCCAAC AGTACCGCTA TCTTCGCCAG    180

CTGCCAGTTC AATCACCGGC GTAGTCAACG TACCGTCTAT CGTCACCTTT AAAGGCGCGG    240

ATGTTTGCTG GTTGCCTGCC ACATCTGTTA CCGTCACGGT GAATGTGTAG CTACCGTCCG    300

CCAAAGCAGA ATCCGGTCGA TAGCGCCAGC CGTCGGCTGA TTCGGTGAGT ACCACCGTTT    360

TAAACGTGCC GTTATGCTCA ATACTCAATT CCACGTGTCG AACATCTTTA TCGATACTCC    420

CCAACACAAA TACCGGCTGA GTGACGCTGG TCAGATTATC GTTCTTATTC TGTCCGGTAT    480

CCTGATCGGG CGCTAGCTCA ATGGTTGGCG TTAACAACGT GATATCGATA GTGAAATTGA    540

GCGTCTCCGT CATCTTATTA CCCGCACCGT CAGTCACTTC CACGGTCAGG GTATGCTGTC    600

CCTCTGGCAT ATCCGTCGGC CAGGTGTAAT CCCAAATGCC AGCCGTCGAA CTCTTGATTG    660

CAGTAACCCA GGTCGTGCCG CCGTCAATAC TCAGAAGAAC TTTTCCACAT CATCCGGTAC    720
```

-continued

```
CGAGATCTGG AACTGCGGAC GCACATGTTT TGTCACATTA TCGCCAGGGA CGCCGCTATC    780
GTTGACTAAT TCAATACGAT CAATGGCTAT TTGCGTATCC ACTGTCACCG TCAGCGGCGT    840
AGACGGACGC GTATTTCCCG CCCGATCCTC CACTGTCACC GTCAGCGTAT AATCACCGTC    900
GCCCCACGGC GCTGGCGGTG TAAAGCTCCA TCCTCCAGCC CCCTGTGTCG CAGTAAACGA    960
GGTTGTCGTT CCATTATGCG TGACGCTGAC TGTAACGTTG ATAACATCCG AATCGATATT   1020
CTGCAGAATA AAGGTCGGTC GGGTGCGATT GGTCATATCA TCGCCAGGCG TACCGGTATC   1080
ATCCGTGCTA TCCAGCGCAA TGGTCGGCGT CGACAACCGG GTGTCGATGA AAAATTCAAG   1140
CGTTTGCGTC GCCGTATTGC CCGCTCTGTC GGTGACCATG ACGGTTAGGG TGTGTTTTCC   1200
ATCGCCCATA TCCGTTGGCC AGGTATAGCC CCAGACGCCT TCGATACCCT GCGTCGCGCT   1260
CACCCAGTTT GCGCCCCCAT CAATGCTCAG TTGCACAGAA TTCACATCCG CCGGCACCGT   1320
GATCTCAAAC TGCGGACGGG TGCTATTAGT TAGATTGTCA TCAGGCACGC CATGATCATT   1380
GACCAATGTA ATATCAGTAA TGCTGGTTTG CGTGTCCACC GTCACCACCA GCGGCGTGGA   1440
CTGACGAACG TTTCCTGCGT TATCCGTTAC CTCTACCGTC AGCGTATAGC TACCGTCCGC   1500
CCAGTCAGCA TCTGGCGTAA AGCGCCACTG TCCTCCAACC TGGGTTAGTG TCACTTCCTG   1560
GCTATTGCCG CCCTGTGTGA TCCGCAAAAT GACCGAGTGC GCATCGGCGT CAATATTGCC   1620
AATAGTAAAG CCCGGTCTTT TGACGCTCGT AATATGATCG CCAATGGCAC CTGTATCGTC   1680
CCTGCTATCC ATAGCGATGG TAGGCGTTGA CAGCCGGGTA TCAATGGTAA AATCGAGCGT   1740
CTGCGTCGTC TTATTTCCCG CCTTATCGGT CGCTTCTACC GTCAGGGTAT GTAGCCCGTC   1800
GGTCACATCT TTCGGCCAGG TGTAATCCCA GATCCCTGCC GTGCCCTGTG TTGCACGAAC   1860
CCACGTATTA CCGCCGTCGA TACTCAGACG TACTTCGTTG ACATCCCCTG GCACCGTGAC   1920
GCGGAAGTGT GGACGAACGT CATTGGTCAG GTTGTCGCCG GGAATACCGT TATCATTAAC   1980
CAGTTCAATA ACATCGATGG TGATTTGGGT GTCAACCGTG ACCGTCAGCG GCGCTGAGTA   2040
TTTTACGTTC CCCGCATCAT CCTCCACCCT CACCGTCAGC GTATAGTCGC CATCTGCCCA   2100
TGTGCCGGTC GGTGTCACGC TCCAGATGCC GGTCGCGCCT TTGGTGGCCG TCAGCACTTC   2160
TTTCGTGCCG CCATGTTGCA CCTCAACCGT GACATACCGC GCGTCTGCGT CAATATTGCC   2220
CAGTAAAAAC GTCGGCTTAT TTACGTTGGT CAGGTGATCG CCTTTTGTTT CCGCTGTAGT   2280
CCGTGTTGTC CAGCACGATA GTCGGTTCTG ACAGTAGGGT ATCGATGATG AAGTCCAGTT   2340
GCTGCGTCGT TTTGTTTCCC GCCTTGTCGG TCGCCCCCAC TGTCAGGGTA TGCTTACCCT   2400
CTCCCACATC AGCCAGCCAG GTATAATCCC AGACGCCCGG CGTCGCGCTC TGGGTAGCGT   2460
TGAACCACGT CTTGCCGCCG TCAATGCTCA GGCGCACCAC GTTGACATCC GTCGGTACCG   2520
TCACCTGGAA GTGCGGACGC ACATTATTAG TCAGATTATC GTCGGGAATA CCGCTGTCAT   2580
TGACCAGTTC AATGTTATTA ATGGCGATTT GCGTGTCCAC CGTCACCGTC AGCGATGCAG   2640
AATGGCTGGT GTTCCCCGCT TTATCTTCGA CTGACACACT CAGGGTATAA TCACCATCCG   2700
CCCACGCCCC TGTCGGCGTA AAGGTCCATC CGCCTGCGTC TTTCGTGGCG TCAAATGTGG   2760
TGGTGACGCC GCCATGCTCT ACGCTGACCG TAACGCGAAC GGCATCATCA TCAATATGCT   2820
GCAGGGCAAA TGTCGGCTGG GTGCTATTCG TCATGTTATC GCCATGGACA CCACTGTCGT   2880
CCGCGCTATC CAGTACGATC ACCGGCGTCG ACAACGTAGT ATCAATAGTG AAGTGGAGTG   2940
TCTCCGTCAC CGTATTACCC GCATTGTCAG TCGCTTTCAC ATTCAGCGTA TAGTCGCCAT   3000
CCGGCACGGT GCCCGGCCAG GTATAATTCC AGACGCCCGG CGTCGCGCTC TGTGTCGCCT   3060
TAACCCAGGT CACGCCACCG TCAATGCTCA GACTGACTTC GTTAACGTCC CCCGGTACCG   3120
```

-continued

```
TCACGCGGAA CTGCGGATGG GCGTCGTTAG TCATATTGTC GCCGGGAATA CCGTTATCAT   3180
TAACCAGTTC AATAACATCA ATGGTGATTT GGGTATCAAC AGTGACCGTC AGCGACCTGA   3240
GTGTTTTTCG TTCCCCGCCT CATCTTCCAC CCTCACTGTC AGCGTATAGT CGCCATCTGC   3300
CCATGTGCCG GTCGGTGTCA CGCTCCAGTT GCCGGTCGCG TCTTTGGTGG CCGTCAGCAC   3360
CTCTTTCGTG CCGCCATGCT GTACCTCAAC CGTGACATAC CGCGCGTCTG CGTCAATATT   3420
GCCCAGTAAA AACGTCGGCT TATTTACGTT GGTCAGGTGA TCGCCTTTTG TTCCGCTGTC   3480
GTCCGTGCTG TCCAGCACGA TAGTCGGTTC TGACAGTAGG GTATCGATGA TGAAGTCCAG   3540
TTGCTGCGTC GTTTTGTTTC CCGCCTTGTC GGTCGCCTCC ACTGTCAGGG TATGCTTACC   3600
CTCTCCCACA TCAGCCAGCC AGGTATAATC CCAGACGCCC GGCGTCGCGC TCTGGGTAAC   3660
GTTGAACCAC GTCTTACCGC CGTCAATGCT CAGGCGCACC ACGTTGACAT CCGTCGGTAC   3720
CGTCACCTGG AAGTTGCGGA CGCACATTAT TAGTCAGATT ATCGTCCGGA ATACCGCTGT   3780
CATTGACCAG TTCAATATGG TCAATGGTGA TTTGCGTATC GATGGTGACC GTCAACGGCG   3840
CTGAGTGGCG AATATTACCC GCCTCATCTT TCACCGTTAC CGTCAGCGTA TAGTCGCCAT   3900
CAGTCCACGC GCTGCCGGGT ACAAAACGCC ACTGCCCGTT AGTCTGCGTC AGCTCCACCT   3960
CCTCGCTGTG ACCATCGCGC ATCACCTGCA CGACGACCTG AGTCACGTCA GAATCAATAC   4020
CGCCGATAAT AAAACCCGGC GTTTTAACGT TAGTCTTATT ATCGTTGGCG GTGCCGCTAT   4080
CATCTGCGCT ATCCAGCGTG ATGGTCGGTG TCGACAATGT GGTATCAATG GTAAAATTGA   4140
GCGTTTCCGT CGCCGTGTTG CCTGCAACAT CGGTTGCTTT CACTGTCAGG GTATACGTAT   4200
TTTCGACCAG ATCTGTCGGC CATATATACT CCCAAACGCC GTCAGACGTC AGCGTTGCGT   4260
TAACCCAGTT GATGCCGCCA TCAAGACTCA GTTGCACAGA GTTCACGTCC GTCGGTACCG   4320
TAATATGAAA CTGTGGACGT GCTTCATTGG TCAGGTTATC CCCGACAATA CCCGTGTCAT   4380
TAAGAAGCTC AATGCGATCA ATAGACGTTT GCGTATCGAT AGTCACCGTC AGCGGCGCAG   4440
AATAATTTGT ATTACCCGCC TTATCTTCTA CCTTTACCGT CAACGTATAG TCGCCATCGG   4500
TCCAGGCTGC GCCCGGCGTA AAGCGCCACA CACCGCCGTT CTTAATCAAC TCTATCTGTT   4560
GGTTCTTACC ATCATGCGCC ACCGTCACCA CCACTTTGGT CACGTCGGCG TCGATATTAC   4620
CGAGGGTAAA GCCTGGCATC TTAACGTTGG TGATGTTATC GCCAGCGGCG CTATCATCCG   4680
CGCTGTCCAG GGTAATCGTC GGTTCTGACA GAATGGTATC GATGGTGAAG TCCAGTTTCT   4740
GCGTCGTTTT GTTTCCCGCC TTGTCGGACG CTTCCACCAT CAGGGTGTGA GGGCCGTTAG   4800
CCACATTCGT CAGCCAGGTG TAATCCCAGA CGCCCGACGT CGCGCTGCTG CGTGGCGTCA   4860
AACCACGTTT TGCCGCCATC AATGCTCAGT CTTACGCCGT TAACATCCGC CGGTACTGTC   4920
ACCTGAAAGT GCGGGCGCGC TTCATTGGTC AGATTATCGC CGGGGATACC GCTGTCGTTA   4980
ACCAGTTCAA TACGGTCAAT GGCGATATGC GTGTCTACTG TCACCGTCAA CGGCGCGGAC   5040
TGCTTCACAT TTCCGGTCCT ATCTTCTACC TTCACCGTCA GGATATAGTC GCCGTCCGCC   5100
CAGTCGCTGG TCGGCGCAAA GCGCCACTGT CCGCCGGTCT GAACCAGTGG CACCTCCTGC   5160
TTAATGCCAT TGTGCATTAC CTCCACTATC ACCCGGCTGA CATCGGTATC AATATTGTTG   5220
AGGGTAAAGC CCGGCGTTTT AACATTGGTG ATATTATCGC CCGCGATGCC GCTGTCATCT   5280
GCGCTGTCCA GCGAGAGGGT CGGCACAGAC AGAGTGGTAT CGATGGTGAA ATCGAGGTCT   5340
GTGTTGCCTT ATTTCCTGCC TCATCGGTCG CTTCTACCGT CAGGGTATAG CCTCCGTCGG   5400
CCACATCATC CGGCCAGATA TAATCCCAGA CGCCTGGCGT CGCGCTCTGG GTAGCGTTGA   5460
ACCACGTCTT GCCGCCGTCA ATGCTCAGGC GCACCACGTT GACATCCGTC GGTACCGTCA   5520
```

```
CCTGGAAGTG CGGACGCACA TTATTAGTCA GATTATCGTC GGGAATACCG CTGTCATTGA   5580
CCAGTTCAAT GTTATTAATG GCGATTTGCG TGTCCACCGT CACCGTCAGC GATGCAGAAT   5640
GGCTGGTGTT CCCCGCTTTA TCTTCGACTG ACACACTCAG GGTATAATCA CCATCCGCCC   5700
ATGATGTCGG CGGCGTAAAG GTCCATCCGC CTGTGCCTTT CGTGGCGTCA AATGTGGTGG   5760
TGACGCCGCC ATGCTCCACG CTGACCGTAA CGCGAACGGC ATCATCATCA ATATGCTGCA   5820
AGGCAAATGT CGGCTGGGTG CTATTCGTCA TGTTATCGCC CTGGATGCCG GTGTCGTCCG   5880
CGCTATCCAG TACGATGACC GGCACTGACA GCGTGGTATC CACCGCGAAA TCGATGGTCT   5940
TCGTCATGTA TTGCTGCTTT ATCAGTCGCT TCCACCGTTA GCGTGTAGGA CCATCTGCCA   6000
GGTCTGTCGG CCAGATATAC TCCCAGCTTC CTGCCACGCC CGGAGTTGCC TGAACCCACG   6060
AATTACCACC GTCAATGCTC AGACGGACTT CATTGACATC CGTAGGTACC GTCACACGAA   6120
AGTGGGGACG GTCGTCGTTG GTCATATTAT CGCCTTTCAC GCCGCTATCG TTGACCAGTT   6180
CCACCCCATC AATGGCGATT TGGGTATCGA TAACGACCGT CAGCGGCGCC GAGTAGTTGG   6240
TATTTCCTGC CTTATCTTCT ACTTTCACCG TTAACGTGTA GCTGCCATCC GCCCACGTAT   6300
TCCCCTGGTA TAAATAACCA ACTCCCATTG AGGTGGGAAA GTTCGATCTC TTCGCTCACG   6360
CCATTGTGCA TCACCTGTAC GACGACCCGA TGCGCATCGG CATCAACACC GGAAATAGCA   6420
AAACCTGGCT TATTGATATT GGTCAGGTTA TCGCCTGTAA CCCCCGTATC ATCCTTAGAA   6480
AGCAGGGAAA TCACCGGCGT TGATACTGTG GTATCGATAG TAAAATCGAA TATCGCGCTG   6540
TTCGCTTTAT TACCCGCAAT GTCCTCAACC TTGACATAAA CCTGATGCAA GCCTTCCGTT   6600
AAATCTGAAG TAAAGGTATA GGCCCATGAA CCATCAGGTT GTTGCGTGGC AACACCGATC   6660
TGCGTATCAG ACATGGCATC CCATACCTGA ACACTGATAA TGTCCGGATC AATATCTTTT   6720
AGGTGCAAGG TAGGTTTAAC GATATTCGTT AAATTATCAT CTGAAATTCC CGAATCTGAA   6780
TCCGGGCTCA ATGAAACTAT CGGTATTGAA ATAGCAGTAT CGACGCTAAT TAAGAAAGGA   6840
TCCGAATGAG CAATGTTGCC AGCGATATCT TCAACTGAAG CGGTTATTCT ATGATCGCCA   6900
TCAACCAAAC CTTGATCGGC TTTCAGGGTA TACTCCCATC TGCCATCTTT ATTTGTTCTG   6960
ACCTCAGCGA TCAGTGCACC ATCAATATAG AGTTTAACCG TTGAATAGGG TGCAGCGGTT   7020
CCTGTCAGTG CAGGATTCTT TTCATTAATA ATATGGTCTG TATTATCAAC CCCCGTATCG   7080
TTGACCAACT CTATTGTTGG TTTTTGCGTT TGCGTTACGA TTTGGAAATT ATACGCTGAT   7140
GAGGAGGCAG TATTACCGGC AATATCTTCT ACCTTTACCG TTACGTCATG CGAGCCATCG   7200
GATAACGCTG TGGTAAATTG AAAATTCCAT ACACCATCAT CGCCAGCAAT AGCCTCACCA   7260
CTTAACACAC CGTCAACATA GATGGAAACC TTAGCATTAG CTTCAGCCAT CCCGGTAAAC   7320
AACGGTGTAT TAATTTTAGT AATCATATCG CCTTTAACGC CAGAGTCAGC GCTATCATGC   7380
AACATAACAG TAGGGATCGG CGTAAAGCTA TCAATGGTAA GCTGATAATC TACAGATGAC   7440
GTTCTTCCTA AAGGATCGAT GGATTCAACC GTAATCTTAT AAACATTGTC AGACAGATTT   7500
CTGGAAATAT CAAAATTCCA GTTACCGTCT GCATCCGCAG TCGTCACGCC TATCGTTTTA   7560
CCGTCAATAA GGATATTTAC GGTAGCAAAC CTATCCGCTG TTCCCAGTAA TGTCAGAGCA   7620
TTATGTTTAT TGGTAATCCA GTCGCCTTTT GCACCGGAAT CATCACTGGC ATCGAGTTCC   7680
GCTTTTGGAG GTACAACTTC AGTTTGAATA GTAAAAGAAT ATTTAACAGT AGAGGATTTA   7740
TTGCCGGCGG CATCCTGAGA ATGATTTCAA TATCATAGGC GCCCTGAAGA ATTTATTACT   7800
AAACTGATAA TTTCCAGGTC CCGTTTGAGT CAACTTCAAT GCTGTCATAT AATTTACCAT   7860
CTCGCATCAA TAAGATGGTA GACTTTGGTT CTGCCGTACC GACTAAAGCC GGTAAATCAT   7920
```

```
TCCCTGATAA AATTATACCA TTCGGCAAAA CAACATAATC CTCCAAAGAA GCCGTCGGAG   7980
GTACAGGGGC AATAGTATCA ATAACGTAAC TAAAGGAAAA ATCCTTTTTG TTGCCAGCGA   8040
CATCTTCAAC AGTGAACGTA AGATTGTTAA TCCCTTCCAC TGAGTCGGAA GTGAAATTGA   8100
ACGTCCATTC GCCCTTGTCA TTCGCTTTAA AAATAACCTC TTCGCCAGTC TCACTATTTA   8160
TGACACTGAT AATAGCATTT GGCTCAGTTT TACCTGTAAA GGTTGGGCGA GTATTGTTAG   8220
TAACGTTATC TCCGACAATA CCGCTATCAT TCGTCGTTTC AATCTCAGCG CTGAAATAGC   8280
TGATACGTGT ATCAATAGTA AAAGGCAGAT TTGCCGTCGC TGAGGTATGC CCGGCAATAT   8340
CAGTAGCTGT TGCTGTTATA TTGTATTCGC CATCCTTGAG CGGCGTAGTA AGCGTATAGC   8400
TCCATGTCCC ATCTTTAGCA ACAATGACCT CACCAAGATG TTTAAGTCCA AGATAAATAG   8460
AGACTGTAGA ACCGGGTTCC GCCACACCAA TAAATGTTGG CAGGGTGCTA TTTGTAATGT   8520
TGTCATTTTT AATGCCGGAA TCACTACTAT CATCCAGCTC AATCGTCGGC TTTTCTGGAG   8580
CAATGGTGTC GGTTATGATA CTATCCGTCG TTTCGTTTTT ATTACCTGCT TTATCTACAG   8640
CAACGACTTT TATACTATTT TCGCCCTCAG ATAATTCATT ATCCTTAAAT TCATAACTCC   8700
AGTTTCCATC TTTATCGACA TCAACGCTGG CAACCAGTTT ATTATCTACA TAAATGTCAA   8760
CCTTAGCATT CTCTTCCGCC GTACCAACAA TTGAAGGCGT CAAGGTCGGC GTTAAGCCCT   8820
TATGACCGGA CACACTACTT TCAGGCGAAA GTTCAAATGT TGGTTTATCG GTAACGGAAT   8880
CGATAGTAAT GACAAGTTTG GCGCTACCGC TCCCATCAGC AGTCTTGGCC TCTGCCTCCA   8940
GATTATATGT TCCATCAGTC AATGTTTCAG GCGCTGTAAA GGTGAAGTTA CCCAAACTAT   9000
CCGTTACAGC CTGACCGACA GCAATACCAT TAATTTTAAT AATAACCGTG GCATTGGGAG   9060
CAGTGCTAAC TACAAACTGA GGTTTGGTAA AATTAGTTAT ACTATCATCT TTGCTACCGC   9120
TGTTACTCTC GGCCGCACGC GCTAATGTGA CTTTAAGCGG CTCTTTAACA GACTCGGCAT   9180
CGAGCTTATT TTCCTCATTT TTACTGCTAT TACTTTTGCC AGTACTGGTA TTTTTATTAA   9240
TAGGTTGAGG AAGAACTTTT TCAGCATCGT TCTGTTTAGA AGCCTGCGTT GCTTTAGCCT   9300
GTGTATTTTG CTGGGAAGCA TCGCTTTGCT GAGCCAGATT GTCTTTTGCT ACATTGTCAG   9360
CCAAAAAGTT CTGCAGCATT TCTTCAATTT GCTTTGACGA GTTCTGTACT TCAAACGCTT   9420
CATTGAGCGC TTTTTCTGCA GCCTCCTTAG CTTTCTCTGC TTCTTCCTTC GCCTTATCAG   9480
CTTCTTTCTT GCGTTTTCAG CATCGTCAAG CTGCTTTTTA ATTCCTCTTC TTCCTTCTTA   9540
TTTCGTCGTT TGCCATTACC TTTCTTTTCT ACCTGAGCAG AATCAACCAA TGAGCTGTCA   9600
ATTCTCTCCA GTTGAATATC TTTTAAATCT ACGCTGCCCA GAATTTTAGC GCCGGTAATA   9660
GTCTTATCTT TAAATTTAAC AGCGAGGTTA TTGCCTTTGA TACTTGAATA AAGAGCGCCA   9720
TTGACAATGA TCACTGAACC ACGCGGCGTG GTAATGTTCA TGTCTGGCCC GGAAAGAGAA   9780
ACTTTTGCGC CTTTGGCATT ACCCAAAGAA GATAAATCAA TTACAGAATT TTGATCGGCA   9840
AAAAACTTTT GTATGCTTTT ATTTCCCATA ATATTATATT CACTCTCAAG GTGTATCTAA   9900
TCGTTTAGTA TTAACTGGTT CTGAAAAGGC TTTGTCCACG CCTTTCATCA AGGGAGATAA   9960
CAGGTATTCC ATAATGCTGT GTTTTCCGGT AATTACACTG GCGTCAACAG TCATACCTGG  10020
TTTTAACCAC CGTAAATCAT CTTCATTAAC ATCGAATGCA ATAATTACTT TATAATAACG  10080
CTGAATTGTT CCTCCGGTAT TTTCCTCATA GGAATCAGGG CTAATATTAT CGATAGTCGC  10140
ATTATACGAT TTTATCTTTG GTTGGATAAT TGACTGCACA TCCAGTTTAA CGGCTTCATC  10200
TACATATATT TGGTCACGGT ATTTGGGTAA TATTTTCACA TCGGCCAGCA TAGTCCTTAC  10260
TTTTGGTTTT ATTTCAAAAA GTAAGTCCGC CGCCTGAATC ACACCACCAT GAGTAGTGGC  10320
```

```
ACTTTTATTG ATTTTATAAA TTACACCGTC AACCGGTGAA TAGATATCCT CCTCATTTAT  10380

CTGCTTCTCT ATTACTTTTA ATGTAGAGTT AACAACCTCA AGTTCCTGAA GATTTTTAGA  10440

TATTATTTTA GATAAAGATA GTCGCAATTC ATTATTAAGC GCCTCAATAT CATTAACAAC  10500

CAACTCAATA TCATCTTTTT TTAAAGTGAT GCTACTTTCA ATATCATTAA TTTCAGACTT  10560

AACTTTTATA TACGCCTGTT TCTTGTTAAG AAAATTGGTA TATGGGCTAA TTCCTTTTTT  10620

TACCAGTGGG GAAAGAATAT TTATTTCTTC GGCAAGCAAT GCGAGTTCTT TTTCTTTCGA  10680

ACTCAGCTTC TCTTGTAATC CGCTAATCTC AGAATCAAGA GAGGTTTTTT TTAACTCTTT  10740

AGCTCTTATC TGACTATGCA CTAATTCAAT ATTCGCTTTT ACCTCTTTAT TGCTTAAAGA  10800

ACGGGTGCCA TCCAGGGTAA TCAACCCACT CTCATTTTCT TTATCAAGAA TGAAAGATAT  10860

TTCGTTAACA TCTTTATCCA GATACCCTTT TTGAGTTCTA TACCTTTGAT ATTCTTTTTG  10920

CAGATCAAGG TTAACGACCT TTGCAAGGAG TTCTCCTTTT TTTACAGTAT CACCCTCGGC  10980

TACATAAATA TCTTGTATCG TCCCTCCTTT AGAAAGAGAT ATTAACTGAG CATTATCTTT  11040

AGTAGTGATA ACGCCCTGAC CATGAACCAC TGAATTAATT TCTATAAAGT AGGTAAGGAT  11100

AATAATTAAG ATCGTCAAAG AAATAATTAT CATCATGAGA TGATCGCTTT GTCTTCTATT  11160

CATTTCATTA CATTTAACTC ACTTTCAGTA TTTCCTTTTA AATAATCCAT TAAATGAAAA  11220

ATCAATGAGA GTTGCTGTAG CTTTAAAATA TACAGGCTAT ATTTGCTGTC GATCATGCTT  11280

ACATATGCCT GAAATGCTTC ATTACGGCTT GAAATTAAAT CAAGCAAACT TTTTTGCCCT  11340

AACTGAAACT CCTGCTCATA TAATTCAGTA AGCTGTAACG CGTTTGTATG TGAACGTTCC  11400

GCCACTGAGT AAGTCTCTTT TGCAGCGGCG TATCTTGAAA GTTGTGAATC AATGTTATAA  11460

CGCGTTTTAA TCAAAAAATC GTCAATTTGC AGCTTAGCCT GCGAGTAACT TGCCACCATT  11520

TTTCTTTCCT GGGCTGAATT TCTGAACCCA TTAAAAATGT TGAAACTGAC ATTGATACCC  11580

GTTTTAAATT CATCTTCATA ATCACTTTTT TTGGCACTAC CGCTTGGGTT ATTCTGTACA  11640

TAGCTGGAAA CAAGATCTAC AGTCGGAAAA TAGGATGATT TTGCGGCATT AATATCTTCG  11700

GTCGCGGCTT TTCGGGTATT GACAAGCATC TTATAGTCAT CGTTGTATTT CATCACCATG  11760

TCCATAAGTT TTTCAGGGCT TTCGACAAAG ATATATTTTT TGAAGAGGTT GAATTTTTCA  11820

TCGCTTTGAA TCTGAACTGG CGATAAATTC AGACCAGTCA TATTCTGCAT TTTATACATT  11880

TCATCATCCA ACATCGACTG ATACATAATG CTTCTGGTAT TTAATGCATC GATAGATACT  11940

TGTACTTTAC GCATATCAGA TTGCATAGCT ACACCGGAAG ATACCAGCAA CGAAAAAGGT  12000

TCCAGCATCT TTTTATAAAA CTCTTTCTCC AGATTTACGC CATCAATCAT TTCACGATAT  12060

TTACTGATGT TGTAATAGGT TGTCACAACC TCCTGAGACA CTATATTCTT TGTTTTTTCA  12120

TAGTCAGTTT TACTATTATC TCTTTCATAT TCAGATTTCC TGATATTAGC CCCCCTCACT  12180

CCAAAATCCG TTATTCGGTA TGATAAAGAC ACCTTATTTT CAACGTTCCT CTCGGTACCT  12240

GATGACTCTT TCCTGTTATT ATTAAGGCCA GATGTTAGAT CCAGGGTAGG ATAAAGTGCT  12300

GCCCGTGAAA GATCTAAGTC ACTGTTTTTC TTTTCAGTCT CATAATATGA AACAGCAACA  12360

GAGGGCTGAT GCGTTAATGC GGCATTAACT AAATCTCTTA GAGGAATGAC CGGAAGCTCG  12420

CTGGCGTATG TGCTTTGTGT AATAAAAGCA GTCGTCAGAA AAAACATCTT AATCTTCATT  12480

TTTTTCCTCC TTGTTTAACA AACGTTGCTT TACTATTTCC TGATGCATAG ATGTTATTTT  12540

TTCCATTAAT GGCATATAGG TATCACGGTA GCTAACCATT TCAGCACTAA TCTCTTTAGT  12600

ATTGGCAATA ATCTTTTTAT CAGTAGCCGA TAGATCGGAT AGCGCTAAAT GAACATTATT  12660

CATATCCTCA TCCATTTCTT TTCTCAGCCC ATCGAGAGTA TGAGAAATAT CGGCACTGCC  12720
```

```
AGCGGCAATA TCGTTTATGG TCTTACCATG TGAAAGAGAT TCCTGATAAC ATTTATCAAC  12780

TGATGTCATT ATTGAATCAT TCTTTTTATC TATAATATTT TGTATTGTAC TCATTGCCTC  12840

CAGTCGTGCA TTATTATCAG CAAGCAGGAT ATTACCTTCA GATAAACGAG AGGTAATTGT  12900

TATTACACCG TCAGATAATT TTTTGAGATT TTCCGTTACT GCTTACCAGA TAACCATCAA  12960

TCAGCGTAAA AATTTGTTCC AGTTTTGCTG AGTTATCCAA TAGTCGGTTT TGCAAAGTGA  13020

CAAAGCTATC TGATAGCATC TCTCGTTTCT TTTCTTCATC CTGCGTCCGT AAGTTTTCAA  13080

CTGTCAGGTA GTTATCAAAA AACGCTTTAA ACAACTCTTT AAATTCTACA AGCGTCTCTG  13140

ATTCAACCCG CAGGCTTCGC TGTTTATTAT TGGCTCTGTT GCTTATGATT TTTAATTTTT  13200

TGATTTCCGT AGAAACAAGG GAATAGGAGC TGCGAACAAA AACACTTTGT GAGGTCAGGA  13260

GTATGGCGCA AACAACACCA TAGATAGAAG ATACAAATGC GGTATTCATC CCTTTCAATG  13320

GTTCAGAAAG CGACGCTACC ATTGTCACGA TCATATTGAG TGTATTACTT GCATTATCAC  13380

CGCCAACATC TGATGGCGAG CTCAATAAGT TCCCGATTGA ACCAATCGTA ATAGACAGAC  13440

CCGCAAACGT CCCCAACAGG CCAACAAGCG TCGACACATT GCTACAGCTC ATAATAAATG  13500

ACAATCGTTG ATTACGGGCG GTAGACACAT TGTCATCTAA TTCCATCAGT AAATTGAAAT  13560

CACACTGTTT GGACTCCCCG GCAAACAAAA CCTGATTGAG GTTAGAAAGA ATGCTATTTT  13620

TTCTACTGGC GTCCTGAGCT ATTAATATGT CTTTTGCTGA AATATTTTTA AGAATAGTGA  13680

ATAATGCACA CAAAGAACCT GTAATATAAA TGGCAATAAT GACTCCATTG TAAATTGCAG  13740

AAACCATGAA GTTATCAAAA ACATACTCTC TTATACCGGG AAAAGATAAA GCAAAAAAAG  13800

GGAGTATGGC AAGGAAAGAA CAGACAACAA ATAGCGGTAA TGATTTATAT ATTTCACTCT  13860

GACACCTTTT ATTAATAGTC GTGATAATAG CTTTACTCGT TGTACTTGAT GCTGCGGAGT  13920

TAACACTCAT GTCAATAACT ACATCAGGAT ATATTTTCTT AATCTCTTTC ATCAAAATAA  13980

TTCCCCGTTC ATATCCCAGT CGTAGAGAGT CAGAGAAAGA GATGTCTGCC TGAGGAATAA  14040

CCATTTCTAT CAATAAATTA CTATTGATTT TGTCTTCTAA CCAAGCCTTT ATTTTATAAG  14100

TGTCCTCTTC TGAAAAGCTT CTCAGCCTGC CATGATACGT AATAACAAGC TCATTTTTTG  14160

TAGACGTTAT ATCAGTTTTC TGACCATCGG CGATATCGTA TACTCCAACC TCCTTACCTG  14220

ACATTGTAGT CATTCCGTCC GACACATCTT GAGTATTCAC TTCCTTATTA ACTATTTCAT  14280

TAGGATTTGA ATCGTCATTG GCTCCGCTAT TTTGAGCAGT AGATTTAGTC TTATTCTCTA  14340

TATTTGCTTT ATAAACTTTA ATTGAGTTGT CATACATAAT AATCATATTA TTAAGTGCAA  14400

ACACCAACAT AAGAAATATA AAAATGCACA ATACCGTAGA GAATGTATCA ACAAAACTAG  14460

GCCACGGATT ACTTTCGTCT TCCATGTTGT CTCCTGATAT TACATTGTGA ATAAAATGTT  14520

TTTGTGGATT AGAAAGGATA AAGGATGCTC AACTTATTCA GAAAGTGAAC GCTACCGCCC  14580

TTGGCTTCCT GCTACCAATA CGCTTTATAG ATTTCAGTTT TCTTACATCT CGTAATCAGA  14640

AAAATAAAAA CAACGACGCC ATTTTTATGC GCCCACAACA AAGATGAGTG CTTTAATTAA  14700

AAACACTCTT CATTTTTTTA ATTAGGTAGA CATCAATTAT TGCACTAACT ATATCCTCCC  14760

CAATAATAGG TATCGCATAA GCTCTCAACT CATAAATAAA AAATAGTCAT CAGCAAATTA  14820

AAACCACCCG CCGATAAATA GATTTGTTAG CTAATCATTG AAACTCTAAA TCATTTTAAG  14880

GACATATTTC TTTTTAATAC GCGTTATAAC CATACGTATT TAATAAATTT GCCTCCAGAG  14940

GATAAAATTA ATTTTCACAA TTAAAACATA GGGTCATATG GACTTCAATA TAACTTAAAT  15000

CATTGAAAAT ATAATAAGTG GGGAGTAAAA AATCAGAATT GTGTAAAAAA ATACACAAAT  15060

AAAACCATTT TTTATATAAA GCCAGCTATA AGTAACAATT TTATCTTCAG CAATTAAAAA  15120
```

```
TAAAGCAAGA TACACATATC ATATTTGAGC TCATCACAAG CTAAAGCAAA CATTTAATTA  15180

ACCATTGATA ATACCGACCA TTCTCTACCG TTATTTTATA ATATCTTTTT GTTGTCAAAA  15240

AATGGCTATA AATTATATAT TTTGCAGATG AGATTTCTCT TTCATATTTA AGACAATCCG  15300

GGTTATTGCA GTACATTTAT GAACTTCGGC TGGATAATGA TGTGCCGAGG CGAGTCGGCC  15360

AGAGGCGATA AGCGACATTT TTCCGTAAGA TATGCGCTTC TCTTTTTTGA AAGGGATACA  15420

AAGACAATAA TACCAGGTAA GAAAATGCCT GGTTTACACC AGGCATTTCA GCAGACGAGA  15480

ACTATAGCGA AAATGCAAAT AACGCTTTGA GT                                15512
```

(2) INFORMATION FOR SEQ ID NO:9:

(i) SEQUENCE CHARACTERISTICS:
(A) LENGTH: 8967 bases
(B) TYPE: nucleotide
(C) STRANDEDNESS: double stranded
(D) TOPOLOGY: linear (xi) SEQUENCE DESCRIPTION: SEQ ID NO:9:

```
CTATCGCTGC CGCTGAAGCC GCCCACCGGT TATCTCAACG CGGAATCGCG CGCCAGGGGT     60

TAGCCTTGCG CACCATCACG TCCCTCGCAT TGCCGTTGAT GAAGGCCGCC AGGTGTGGTT    120

ATCCAAAAAT GGCAAGTGGA ATAGCCCTAA CAGAATCGAG CTAAACTTAT TGAAGACGTT    180

GCCGACTCCG TTAAATGACA AAAAAGACCC GTTTGTGCAA CGGGTCTTTT TTATTAAGCA    240

GTACCACCTG ATAACAGCGA CAAGCGCTGC TTATTTTACA TTAATAATTT ATCCGGAGAA    300

CAATCACGGA TTATTTTTCC ACCTTTCATT ACCAGGACCC GGTCAAAATA CTTTATCAGA    360

TATCGACGAT GCGTCACCAT GATCAACGTT TTCCCATGAA TAAACTCATC TAAGTTATCA    420

AAAATTTGCT TCTCGGTATT CTCATCCAGA TTTGATGTTG GTTCATCCCA TAAAAAGACG    480

CTGGCGTCAC TACTCAGACT ACGTGCTAAT AATAACTGCT GCTGCTGTCC GGATGACAGG    540

TTTTTAGCCA TAAAATTCAC CGGAAACTTC AGCCCCATAG GATGTTGCAA GATAAAACCA    600

CAGTTCGCCA GCTGAAGCGC CTTGAGTACC CGGCCCCTGT CGTTTTGCGG TTTTAACGCG    660

AAATTACTTT CAATGGTTCC GGTGAATAAA ACATCATGTG TCGTCACCAC GCTTAAATGC    720

TGAGAAAAAA AGTTCTGCGA TAAATGTCCT AAGTTATATC CATCATATAA AATGGCACCG    780

TCTGTTGGCG AAAGGTAGCC AGATAGCATT CCCAGTAATG AGCTTTTTCC TGCTCCGCAT    840

TCGCCTACCA CCGCGACACG TTGCCCCGCA GGTATGTCTA TAGACAGTCG GTTAATAATC    900

ATCGGAGATT GAGCATCATA CTGATAACTC ACGCCCCGGA TAGAGATATC GCCATTGCAC    960

TTTGATATTG ACTGTAATGC CGGTGTTTTT TCTGCCTGAT CTTCATCAAA AAAAGAAAGC   1020

AGATCCTTAC CGGTTTTTTC TGCTGATAAA ATAGAGATTA ATGTAGAAGA AAAATTCGAA   1080

ATGATCCCGG AAATACGGCC AGAGACAATG ACAGATGAAA CAATTGCGCC AGTAGTAACA   1140

TCACCCTTGA TTACCATAAA AAAGGCTATT ACCATAATAG TTATTTGGGT AATAGATGAC   1200

ATACTCCCCA ATATAGATTG ATAGATAAGA TTTAATTTCC TTATCTTCAG GTTAAGATAC   1260

GACTGTTCAT TTGATGTATT AACCCAATCA AAAAGTAAAC CTTGATTATT TAAGGTATGG   1320

ATCATTTTAA TAGATAAGAA AACTTCTGAG ATAAAAATAT TCCTGTTCTT CTGTCCTTCT   1380

TTTTGTTTGT TCATTAACTC ATTAGTATAA TGGTGGTTAA CGAGGGAAAT AATAATAGAG   1440

ACGATAAACA TGGTAATAGG TACAATAACA ACCAGACCTA AATTTACATA TATAACAATG   1500

AGAAATATAA TAAATATTGG AATATCGGCT ATACGTTGAA AGATCGAGTT TAATAAAACG   1560

GGTTTAATTT TCTGAAACTC ATTCCATAGC ACAAATGCTG ATGACATGGA TCTGCCATTT   1620

TTCTTTTTAC TATAAAGTAC CGCTTCAAGA AATGCGATAT CAATATCGAC GTCATCCTGC   1680
```

```
CTTGCTGTGA TAGACTGATA AATATCTTTC GAAGTACGAA GGATAAACTC AAAAACAATA   1740
AATACAGCAA CAATTATAGC CACGCCAAAT AAAGATGAAA CCGAAGCGCT TGGAACAAGC   1800
TTATCATAGA ACAGATTACT AAATACTGGG ATAGTTAACG CAAAAATTGC CATAAAAAGA   1860
GATGAAAAAA AGTATTTAGT ATAAAAAATC TTGTTCATCG ATAAAGAGTT TTTTATGATA   1920
TTTTTTACTC TTATACTATC AACAACTTTA TTTAAAGGTA GTATACTAAA TGCAGATAAC   1980
TCTTTTAAAT ATTCATCTTC AATTTCAACA TAACAGAGTT CACCGCGCGC GTTTACCAAC   2040
TTTATTTTTT GCCCGCCACT CACACACACC ATCCACTTTC ATTTTCTGGT GTTAATAGTA   2100
AAATCGGCAT AGGCTCATTT AGTAAATCCT CACCATTATT AAATAATATA TCCTGTAGAG   2160
AAAGCCCTAA CGACAAAAAG AAATTCTTCA TTCGTATAGG TCGTCAGTGT TATTTCAGTC   2220
GTACTTTCTA AATCTTCAAA TGTATATCAT CTTCTCGGAT GTCAATTTTT ATGTTGAATT   2280
TTGTAGACAC TATAGATAAT GCCGTTTCCG CACTTAAATA ATAAGGTTCT AGTTTTTTAT   2340
CCATAAGTAA ACCCCCTTCA ACCCAAAGGT GAGGGGCCTC CGTTATTATG CGTGTTCTTC   2400
TTGATTATCT ACAGGTAGCG TAACTTCATT AACGGCGAAA ACATCAATAG CGCCGTTATT   2460
GTTGTGCCCT ACAGAACTCG TGGAAGGGGA ATCATTAATA TCATCCTCGG TCTTTCCTCT   2520
TACATTCATT GCGTTCACAA TATCCGCCGA GGAGTGATCG ACTGAGAATG TTTTCTCCTT   2580
AATCAGGAAA TCATTGTCTT TATCAATGAA TTTCACGTCC ATAGTATATT CACCATCTTC   2640
CAAAGATAGC GGAACTTCGA ATATTGCTTT CTGGTTAGTT ATCGGCAGAG TAAACTCTTC   2700
TCCTTCAAAC ATAATACTGA CATTAACAAT ATTCTCAGGT ACTGATATTT CAAAAGAAGG   2760
TGTCTGACTA ATTGAACGAT CTATTTCATC CCCAGAGTCA GCGTTTAACA ATGTAATACT   2820
ATAGGCTGTC ACCTTCACCA CGCTTTCTTC CGCCGCAGAC GGCTCTGTAC GAAGATGCGT   2880
AGCGCTTTCG GCATTCACTG TTTCAGACTC CGGTGGAGTA ACCGCTGTTG CCGTGGCGTC   2940
ATCGCTCGCA TCGTCATGCT GGCTATCCGC TGTTACCGTC ACCGTTGAGT CAACCGTCAC   3000
CGCTAGCGAA GCAGATTGCT GTGAATTCCC CGCGCGATCC ACCACCGTCA CGCTCAGCGT   3060
GTAGTTACCG TCATTCCAGG CGGCTGGCGG CGTGAAGGTC CAGCCATCCG CGCCTTGCGT   3120
CGCCTGATAG ATGTCTGTCA CGCCATTATG CGTCACGTTT ACGGTCACCC CGGTCACATC   3180
AGCATCAATA TGCTGCAGCG TGAACTTAGG CTGGGTGTGA TTCGTCACGT TATCGCTGTC   3240
TGAAGCGCCA TTGTCTTCAC CTGCTGCCAA CGCAATCTCC GGCACCGTCA GCGTGCTGTC   3300
GATCGTGACA GTAATGGGTA ACGAGTTTTT CTGATTACCC GCGGCATCGC TTGCGATTAC   3360
CGATATCGTA TAGGAACCAT CAGCTAACGG TGTACCTGGC GTAAAGAACC AAACGCCATC   3420
GGCATTTTTT TCAGCATTAT ATACGGTCCC ATTGATATCG ACCTGAACGA CCACAACATC   3480
GCTTTCCAGA TTCCCGATAA TAAAGGTAGG TTGCTTATCT CGCGTAATAT TATCGCCCAC   3540
CGTACCACTG TCTGAGTCTG GAGATAATGA AATAACGGGA ACCTCTTTCA TGATATCGAG   3600
AGGGACATCA TCACTCCGGT TACCAATAGC ATCCACACTC GTAATGGTAA ACTTCCCTTC   3660
TGATGGATAC GGGATAGCCA TACTCCATTT ACCATTATCA GGAACGGTTA ACGTATAAGT   3720
ATTCCCCTCA CTATCGGTTA TTATTAGCTG AGATTTGGCT TCCGCCGTCC CCTGCATAAT   3780
AATTAGATCG TTGACAATAT CTGAATACGT TACGACCGGA GCATTTGGCG GGTTCGGTCA   3840
ATAAATATTT CACGCACATC TTCCCAACGA TTTCCGGGCT ATCTTCAATG ACCAAACTAA   3900
TATCGTAAGT CCCTTCTGGA AGCTTGTCTG TTGATAATTC CCATCGTCCT GTTGCCGCCA   3960
CAACAGCAGT TGCCAGCGTG ACGCCAGCCA CGATTAATGA TACCGTAGCG CCAATTTCAC   4020
CCGTGCCTCG CATGGTAATG AGATCGCTAT TACTCCACCA TTCCGTTTTC GATGATGATT   4080
```

```
TATTGTCATC AAGCTCGCTG GTAAATACCT TGATATGCGT ATCAACCCAA ATGGAATACT   4140
TTTCCTGATT TACGTTACCA GCACGGTCCG TAGATTTAAC AGTGATATCC AGTTGGCCTT   4200
CTGTGAAATA AAGCGGGTTC ACCGGCATCT GCCAGTGGCC TTTTTCATTA ACCCAAACTT   4260
CCCCCACATT TAAGCCATTA ATGATGATTT CTATTTTGCT ATTGGGCTCG GCACTGCCAC   4320
TAAACAATAA GTTACGCGTC GTGTCCGTTA TATATATTTT GCCATCACTA CCGGTCATCT   4380
CTGCTAACGT TTGTCCACCG ATAGAATCAA TGGCGACAGG CGTCGTATTA AAGGTATCGA   4440
TAGTAAAGTT TAGCGTTTTC GAGGTAGCCG TGTTGCCTGC TTTATCGGTG ATAACATAAT   4500
AAATGCTATG GGAACCATCG CCCAACGGTG ACTCAGGTCG ATAAACTTGA TTTCTGTCGG   4560
TCACCGTGAT CGTATCGACT AGCACTCCAT CAATGAAAAT CTGAACACTC TGGTTCATTT   4620
CTCCAAAAAT ACTAAACGTA GGCCGGGTCT GACTCGTTAT ACTATCATTA CTGAAAATAC   4680
CATTATCAGA ACCTGCCACC ATAGCAGGAT TATCGATAAA CGTACTGGTA TCTATCGTGA   4740
CGAGTAAGCG AGGCGATTCT GCCGTATTAC CTGCCGGGTC TTCGGCAACC ACACGGATAG   4800
AATATTCACC ATCTTTTAAC GCATTATCAA ACTGATAGGA CCAGGTTCCA TCTTCAAGCA   4860
CAAGAACATT TGCCACGATC TTTTCATCCA CATAAATATG GATTGTGGCT CCCGCTTCTG   4920
CGGTGCCAAC TAATACAGGC TTGTTGTGAT TAGTAATCAG ATCGTCAAGT GAACCAGAGT   4980
TGCTTGCATC TTCAAGGTTG AGCGTTGGGA AGTCGGTTGA TGAATCGACA TCCACGCTAT   5040
AATCCTTGCT CACTTCAGTG TTGCCAGCAA CGTCAGTAAT GCTGAAATGA ATATTAAACG   5100
TACCATCATC TTGCAGCAGT ATCGGCGCGC GCCATGTGCC ATCAGCCTCA ACCATAACAA   5160
CGTTGACTAA TTTACCGTCG ACAAAGATGC TGACCTGAGA ACCAGCCTCC CCGACACCTG   5220
AGACTGACAA CGCTCGGTTA TTAGAGAGGG CCGGTAATGA ATCTTCATCA ATATCAAAGA   5280
CAGCAATTTG AGAATCGATT GTCACGGTTG TAATCGCAGA CTCAACCCGG TTACCAGCAG   5340
TATCCGTAGC AACAAATTGC ACCTGATACT CGCCGTCGGC GCTATTTGCC GGCATGGTAT   5400
AGCTAATATT ACCTGACGAA CTCGCCTCTA CTGTGCCTTG TAACACACCA TTAATATAAA   5460
CCTGTACCGT CGCGCCGGGA TCGGTCCTGG CAACCAGTAC CGGAGACTTA TTATTGGTAA   5520
TCAGATCATA TTTATCACCG CTATTAGTAT CCCGACTTAA TGAAATATCG CTGATTTCAA   5580
TCTGCGTATC ATGTTCTATC AGAATCTCTT TTTGTTGACT GTTGCCCGCT TTATCTTCCG   5640
ATACCACGAC AAAGGCATTA CTACCTTCAC GCAGATCTAA TTCTGCGCTC CATCGACCAT   5700
CATTGCCTAC CACCAGGGTA GCAATAACCA CTCCCTGCGG ATTCCTGATG GTTAAAGTAC   5760
TTCCGGCTTC GGCAGTACCA TCGATGGTGA CATGAGATTT ATTGGTGATC CAGTCGCCAA   5820
CTTTGCCACT GTCATCAGCT TCGCGTAATA CCACGGTTAA CGGCGAAATT ACTGTATCCA   5880
GTATTACATT CTGCGGACCA AACTCTCTGA TATTACCGGC AACGTCTTCA ACTTTAAACG   5940
TTAATTCATA ATTACCGTCA TTACCCAAAG CGGGTAATAC TACGCCCCAG TGTCCTGCGC   6000
CTGTCGTATA AGCAATCGCT TTTCCAACGC CATTCACAAA GATAGTGATT TTGCTGTTTG   6060
GCTCACTGGT GCCGCCAATC TCCGGCGTCA CCGTATTGAT ATATCCGCCC TCATGCATTC   6120
CAGATATATT CCATACCAGT TCAGCAACCT CGGTATCGAT AGTGACATCA ACGGCGGTAG   6180
AACGCAGTTC GCTATTATCG CGAGGGTTGA CGATACCCAC CTGGACGACA TAATGGCCAT   6240
CTTTCATTTC CGATAACTGG AAAGTATATC GACCCGCTGT ATCCGCTGTC GCCTCGCCGA   6300
CCTTCACGCC ATCCACATAA ATACTCACAA TCGTATTAGG TAACGTGCTC CCAATCAGGG   6360
TCGGCGTTTT ATTATTCGTG GTAAAGTCTC CTAAGGCGCC ACTATCGCTC TCCTCGCTGA   6420
GCTTTATGGT TGGAGGCGTG ACATCAATAA CAGGTATTAC GACAGGAAAG TCGACCTGCG   6480
```

```
ACGAATCATT ACCCGCTTTA TCTTTGGCAA CAATGCTCAC AACATAGGAG CCTGGCGCTA   6540
ATACTGATGG CGGCGTCCAA CTCCATTCGC CATTCGCATT GGCGTTTGCC GAGCCGACCA   6600
CTTTCCCATC CCACTGAATC ATAATCGTCG AGAACGCTTC GGCAAACCCT TTGAACTCAG   6660
GACGCAGGCT GGTTGCTTCA TGCTGATCAT CAATAGATGG ATCCGAAAGG CGAATGGTGG   6720
GATCGATCGT AACCGTATCG ATAGTGAATC TTTCCTGCGT TTGCGCAGTA TTTCCCGCGA   6780
CATCTGTTGC GACGACGTTG ATGGTATACA TGCCATCCGG CAGTATATTC GGCGTCACAC   6840
TCCAGTTGCC ATCAGCGCCA ACCGTAATCG TTTGTTTTAA AACCTCCTGA CCTGACTTAT   6900
CGTCAACAAT GGTAATCACC AGTTTCGCAT TGGGCTCTGC AGTACCTTCG AATTTGGGAT   6960
TTTGCTTATT CGTAAGGTTA TCGCTATTGG AATTTCCGGT ATCAGACGCT AGCTCCATTC   7020
TGACACTGAC GCTTGTCGTG GTATCAATGG TAAAGGGCAG CTTAATTTCA GAAATATTTC   7080
CGGCAATATC TCTGAAGACA ACAACGGCTT CATATACGCC ATCGTTTAAC GCAACGGGAA   7140
CCTGAAATTC CCAGAGGTTA TTGCCATTTG CCGTAACCGG ATAAGAAACG CCGTTAATTC   7200
TGATAACAAC AGTATCAATA TCGGCGGGTA CATTGCCAAT AACGAAACGT GGTGTAGTGA   7260
CACTCGTAAT ATTATCAACA GCGCTTTCGC CAGTATCATC CGCATCCAGC AAATCAATAC   7320
TGGGATCAGA AACAATAGTG TCTATTGTGA ATGATACCTC TTTGCTAATT TTATTACCTG   7380
CGATATCTTC AGCCACTATT TCTATTTTGT AAGTTCCATC CACTAACGGT GTATCAGGGG   7440
TAAACAGCCA TTTATTACCT GCCCCCTGAG TCAGTGTGCT GGATTTCCCG TTTAAAATTA   7500
CCGTCACGCT CTGCAGCGGT TCTCTGGCTG AAATTTCAAA ACGTGGAGAG GTAATATTCG   7560
TAATACCATC CGTAGAATCC TTTCCGGCGT CGTCCAGCAT CACGACGCTC AGGCCGTCAA   7620
TCTGCGTATC CACGGTGAAG CCCAGCGTGG AATTTGCCGT ATTCCCTGCC CGATCCGTCG   7680
CCTGGACATG GAGAGTATAA TGACCATCAG GCAATGCGCT ACCTGCAGTA AATTCCCACT   7740
GCCCGGCCGC ATTTTTACTG ATGGGCGTCC AGTTTACGCC ATCGAAAGAA ACCAGCACCG   7800
ATGTCACATC ATCAGGCGTT GCAATTTCAA AAGAGGGACG GGTAGCATTG GTGACATTAT   7860
CGTGATCGTT GACGCCGCTA TCTGTTGTTA ACGTAACACT GTCAATCTGA ACCTGCGTGT   7920
CGATTTCAAT CCGCAGTTCG GCCGATGTTT TGGTATTACC AGCAATATCC GTTACGGTAA   7980
CAGAGATCGT ATGCTGACCG TCAGACAGCG GTTGATCCGG CGTAAAGGTT AAATTCCCCC   8040
CTGTGTTTTC AATGGTGTAA TCCCGACCAT CAATATGAAC CACAATGTGT GATACATCAT   8100
TATCGACATT ACCGATAATA AACACCGGTT TGTTAATCCT GGTAAGATTA TCATTAGTAT   8160
CATCACCAGT ATCATGGGTG GGATCGAGTA CAATTGTCGG CTCTCGCAGA GTCGTATCAA   8220
TCGTAAACTG CAGCGTTTCT TGCGCAACGT TGCCGGCGAT ATCAGTCACA TCAACCAAGA   8280
GAGTGTGTTG CCCATCAGGT AATGCCGAAC CGACATTAAA TATCCAGCGG CCATCCCTCC   8340
TTTTGTGAGT TCAATCCAAT TAGCGGCGTT ATCGATTTTA ACGCGCACAT GGGTTATATC   8400
ATCAGCGGTA ACAATACTAA ACTGCGGCTG TCGACTTTGG TAATGTTATC TACATCGCTA   8460
TCACCGCTAT CTGTAACCAA CGTGACGCTT TCAATTTCAG CCGTCGTATC TATCACAACA   8520
GGTAATGGTT TCGATGTCGC GGTATTTCCG GCCTTATCTT CAACCGTAAC GGTAATATTA   8580
TAAGAGCCAT CCGGAATGGC ATTGCCTGGT GTAAATTGCC AACCAGCCCC AACCTTAGTC   8640
GCGTTATAAT CATGACCATC AATCGTCACC ACGACTTTGA TAACATCGGG GTCAACATTA   8700
CCAATCGTAA AGGTGGGTCG TGAAATATTA GTAATATTAT CGGCGGTATT CGCTCCGGTA   8760
TCTTGTCCTG CGTCTAAAGC AATAGTAGGA ACCTGTATAT TAGTATCGAT ATTAAATACT   8820
AAATCTTTAT TCGCAATATT ACCTGCCTCA TCCCGTGGCC TCTACGCGAA GGGTATATGT   8880
```

```
GCCGTCAACC AGAGTATTCG GGCTGTCAAA AATCCACTGT CCGTCGGCAT TTTTGCGTAT   8940

CACATTCCAG TTAGCGCCAC CATCCAG                                       8967
```

(2) INFORMATION FOR SEQ ID NO:10:

(i) SEQUENCE CHARACTERISTICS:
(A) LENGTH: 1575 bases
(B) TYPE: nucleotide
(C) STRANDEDNESS: double stranded
(D) TOPOLOGY: linear (ix) FEATURE:
(D) OTHER INFORMATION: the coding nucleotides of SEQ ID NO:10 correspond to nucleotides 1028 through 2602 of SEQ ID NO:2

(xi) SEQUENCE DESCRIPTION: SEQ ID NO:10:

```
ATG GAA GAC GAA AGT AAT CCG TGG CCT AGT TTT GTT GAT ACA TTC TCT       48
Met Glu Asp Glu Ser Asn Pro Trp Pro Ser Phe Val Asp Thr Phe Ser
 1               5                  10                  15

ACG GTA TTG TGC ATT TTT ATA TTT CTT ATG TTG GTG TTT GCA CTT AAT       96
Thr Val Leu Cys Ile Phe Ile Phe Leu Met Leu Val Phe Ala Leu Asn
            20                  25                  30

AAT ATG ATT ATT ATG TAT GAC AAC TCA ATT AAA GTT TAT AAA GCA AAT      144
Asn Met Ile Ile Met Tyr Asp Asn Ser Ile Lys Val Tyr Lys Ala Asn
        35                  40                  45

ATA GAG AAT AAG ACT AAA TCT ACT GCT CAA AAT AGC GGA GCC AAT GAC      192
Ile Glu Asn Lys Thr Lys Ser Thr Ala Gln Asn Ser Gly Ala Asn Asp
    50                  55                  60

GAT TCA AAT CCT AAT GAA ATA GTT AAT AAG GAA GTG AAT ACT CAA GAT      240
Asp Ser Asn Pro Asn Glu Ile Val Asn Lys Glu Val Asn Thr Gln Asp
65                  70                  75                  80

GTG TCG GAC GGA ATG ACT ACA ATG TCA GGT AAG GAG GTT GGA GTA TAC      288
Val Ser Asp Gly Met Thr Thr Met Ser Gly Lys Glu Val Gly Val Tyr
                85                  90                  95

GAT ATC GCC GAT GGT CAG AAA ACT GAT ATA ACG TCT ACA AAA AAT GAG      336
Asp Ile Ala Asp Gly Gln Lys Thr Asp Ile Thr Ser Thr Lys Asn Glu
            100                 105                 110

CTT GTT ATT ACG TAT CAT GGC AGG CTG AGA AGC TTT TCA GAA GAG GAC      384
Leu Val Ile Thr Tyr His Gly Arg Leu Arg Ser Phe Ser Glu Glu Asp
        115                 120                 125

ACT TAT AAA ATA AAG GCT TGG TTA GAA GAC AAA ATC AAT AGT AAT TTA      432
Thr Tyr Lys Ile Lys Ala Trp Leu Glu Asp Lys Ile Asn Ser Asn Leu
    130                 135                 140

TTG ATA GAA ATG GTT ATT CCT CAG GCA GAC ATC TCT TTC TCT GAC TCT      480
Leu Ile Glu Met Val Ile Pro Gln Ala Asp Ile Ser Phe Ser Asp Ser
145                 150                 155                 160

CTA CGA CTG GGA TAT GAA CGG GGA ATT ATT TTG ATG AAA GAG ATT AAG      528
Leu Arg Leu Gly Tyr Glu Arg Gly Ile Ile Leu Met Lys Glu Ile Lys
                165                 170                 175

AAA ATA TAT CCT GAT GTA GTT ATT GAC ATG AGT GTT AAC TCC GCA GCA      576
Lys Ile Tyr Pro Asp Val Val Ile Asp Met Ser Val Asn Ser Ala Ala
            180                 185                 190

TCA AGT ACA ACG AGT AAA GCT ATT ATC ACG ACT ATT AAT AAA AGG TGT      624
Ser Ser Thr Thr Ser Lys Ala Ile Ile Thr Thr Ile Asn Lys Arg Cys
        195                 200                 205

CAG AGT GAA ATA TAT AAA TCA TTA CCG CTA TTT GTT GTC TGT TCT TTC      672
Gln Ser Glu Ile Tyr Lys Ser Leu Pro Leu Phe Val Val Cys Ser Phe
    210                 215                 220

CTT GCC ATA CTC CCT TTT TTT GCT TTA TCT TTT CCC GGT ATA AGA GAG      720
Leu Ala Ile Leu Pro Phe Phe Ala Leu Ser Phe Pro Gly Ile Arg Glu
225                 230                 235                 240
```

```
TAT GTT TTT GAT AAC TTC ATG GTT TCT GCA ATT TAC AAT GGA GTC ATT      768
Tyr Val Phe Asp Asn Phe Met Val Ser Ala Ile Tyr Asn Gly Val Ile
                245                 250                 255

ATT GCC ATT TAT ATT ACA GGT TCT TTG TGT GCA TTA TTC ACT ATT CTT      816
Ile Ala Ile Tyr Ile Thr Gly Ser Leu Cys Ala Leu Phe Thr Ile Leu
            260                 265                 270

AAA AAT ATT TCA GCA AAA GAC ATA TTA ATA GCT CAG GAC GCC AGT AGA      864
Lys Asn Ile Ser Ala Lys Asp Ile Leu Ile Ala Gln Asp Ala Ser Arg
        275                 280                 285

AAA AAT AGC ATT CTT TCT AAC CTC AAT CAG GTT TTG TTT GCC GGG GAG      912
Lys Asn Ser Ile Leu Ser Asn Leu Asn Gln Val Leu Phe Ala Gly Glu
    290                 295                 300

TCC AAA CAG TGT GAT TTC AAT TTA CTG ATG GAA TTA GAT GAC AAT GTG      960
Ser Lys Gln Cys Asp Phe Asn Leu Leu Met Glu Leu Asp Asp Asn Val
305                 310                 315                 320

TCT ACC GCC CGT AAT CAA CGA TTG TCA TTT ATT ATG AGC TGT AGC AAT     1008
Ser Thr Ala Arg Asn Gln Arg Leu Ser Phe Ile Met Ser Cys Ser Asn
                325                 330                 335

GTG TCG ACG CTT GTT GGC CTG TTG GGG ACG TTT GCG GGT CTG TCT ATT     1056
Val Ser Thr Leu Val Gly Leu Leu Gly Thr Phe Ala Gly Leu Ser Ile
            340                 345                 350

ACG ATT GGT TCA ATC GGG AAC TTA TTG AGC TCG CCA TCA GAT GTT GGC     1104
Thr Ile Gly Ser Ile Gly Asn Leu Leu Ser Ser Pro Ser Asp Val Gly
        355                 360                 365

GGT GAT AAT GCA AGT AAT ACA CTC AAT ATG ATC GTG ACA ATG GTA GCG     1152
Gly Asp Asn Ala Ser Asn Thr Leu Asn Met Ile Val Thr Met Val Ala
    370                 375                 380

TCG CTT TCT GAA CCA TTG AAA GGG ATG AAT ACC GCA TTT GTA TCT TCT     1200
Ser Leu Ser Glu Pro Leu Lys Gly Met Asn Thr Ala Phe Val Ser Ser
385                 390                 395                 400

ATC TAT GGT GTT GTT TGC GCC ATA CTC CTG ACC TCA CAA AGT GTT TTT     1248
Ile Tyr Gly Val Val Cys Ala Ile Leu Leu Thr Ser Gln Ser Val Phe
                405                 410                 415

GTT CGC AGC TCC TAT TCC CTT GTT TCT ACG GAA ATC AAA AAA TTA AAA     1296
Val Arg Ser Ser Tyr Ser Leu Val Ser Thr Glu Ile Lys Lys Leu Lys
            420                 425                 430

ATC ATA AGC AAC AGA GCC AAT AAT AAA CAG CGA AGC CTG CGG GTT GAA     1344
Ile Ile Ser Asn Arg Ala Asn Asn Lys Gln Arg Ser Leu Arg Val Glu
        435                 440                 445

TCA GAG ACG CTT GTA GAA TTT AAA GAG TTG TTT AAA GCG TTT TTT GAT     1392
Ser Glu Thr Leu Val Glu Phe Lys Glu Leu Phe Lys Ala Phe Phe Asp
    450                 455                 460

AAC TAC CTG ACA GTT GAA AAC TTA CGG ACG CAG GAT GAA GAA AAG AAA     1440
Asn Tyr Leu Thr Val Glu Asn Leu Arg Thr Gln Asp Glu Glu Lys Lys
465                 470                 475                 480

CGA GAG ATG CTA TCA GAT AGC TTT GTC ACT TTG CAA AAC CGA CTA TTG     1488
Arg Glu Met Leu Ser Asp Ser Phe Val Thr Leu Gln Asn Arg Leu Leu
                485                 490                 495

GAT AAC TCA GCA AAA CTG GAA CAA ATT TTT ACG CTG ATT GAT GGT TAT     1536
Asp Asn Ser Ala Lys Leu Glu Gln Ile Phe Thr Leu Ile Asp Gly Tyr
            500                 505                 510

CTG GTA AGC AGT AAC GGA AAA TCT CAA AAA ATT ATC TGA                 1575
Leu Val Ser Ser Asn Gly Lys Ser Gln Lys Ile Ile
        515                 520
```

(2) INFORMATION FOR SEQ ID NO:11:

(i) SEQUENCE CHARACTERISTICS:
  (A) LENGTH: 366 bases
  (B) TYPE: nucleotide
  (C) STRANDEDNESS: double stranded (D) TOPOLOGY: linear (ix) FEATURE:
(D) OTHER INFORMATION: the coding nucleotides of SEQ ID NO:11 correspond to nucleotides 2679 through 3044 of SEQ ID NO:2

(xi) SEQUENCE DESCRIPTION: SEQ ID NO:11:

```
ATG AGT ACA ATA CAA AAT ATT ATA GAT AAA AAG AAT GAT TCA ATA ATG       48
Met Ser Thr Ile Gln Asn Ile Ile Asp Lys Lys Asn Asp Ser Ile Met
 1               5                  10                  15

ACA TCA GTT GAT AAA TGT TAT CAG GAA TCT CTT TCA CAT GGT AAG ACC       96
Thr Ser Val Asp Lys Cys Tyr Gln Glu Ser Leu Ser His Gly Lys Thr
            20                  25                  30

ATA AAC GAT ATT GCC GCT GGC AGT GCC GAT ATT TCT CAT ACT CTC GAT      144
Ile Asn Asp Ile Ala Ala Gly Ser Ala Asp Ile Ser His Thr Leu Asp
        35                  40                  45

GGG CTG AGA AAA GAA ATG GAT GAG GAT ATG AAT AAT GTT CAT TTA GCG      192
Gly Leu Arg Lys Glu Met Asp Glu Asp Met Asn Asn Val His Leu Ala
    50                  55                  60

CTA TCC GAT CTA TCG GCT ACT GAT AAA AAG ATT ATT GCC AAT ACT AAA      240
Leu Ser Asp Leu Ser Ala Thr Asp Lys Lys Ile Ile Ala Asn Thr Lys
65                  70                  75                  80

GAG ATT AGT GCT GAA ATG GTT AGC TAC CGT GAT ACC TAT ATG CCA TTA      288
Glu Ile Ser Ala Glu Met Val Ser Tyr Arg Asp Thr Tyr Met Pro Leu
                85                  90                  95

ATG GAA AAA ATA ACA TCT ATG CAT CAG GAA ATA GTA AAG CAA CGT TTG      336
Met Glu Lys Ile Thr Ser Met His Gln Glu Ile Val Lys Gln Arg Leu
            100                 105                 110

TTA AAC AAG GAG GAA AAA AAT GAA GAT TAA                              366
Leu Asn Lys Glu Glu Lys Asn Glu Asp
        115                 120
```

(2) INFORMATION FOR SEQ ID NO:12:

(i) SEQUENCE CHARACTERISTICS:
(A) LENGTH: 1320 bases
(B) TYPE: nucleotide
(C) STRANDEDNESS: double stranded
(D) TOPOLOGY: linear (ix) FEATURE:
(D) OTHER INFORMATION: the coding nucleotides of SEQ ID NO:12 correspond to nucleotides 3034 through 4353 of SEQ ID NO:2

(xi) SEQUENCE DESCRIPTION: SEQ ID NO:12:

```
ATG AAG ATT AAG ATG TTT TTT CTG ACG ACT GCT TTT ATT ACA CAA AGC       48
Met Lys Ile Lys Met Phe Phe Leu Thr Thr Ala Phe Ile Thr Gln Ser
 1               5                  10                  15

ACA TAC GCC AGC GAG CTT CCG GTC ATT CCT CTA AGA GAT TTA GTT AAT       96
Thr Tyr Ala Ser Glu Leu Pro Val Ile Pro Leu Arg Asp Leu Val Asn
            20                  25                  30

GCC GCA TTA ACG CAT CAG CCC TCT GTT GCT GTT TCA TAT TAT GAG ACT      144
Ala Ala Leu Thr His Gln Pro Ser Val Ala Val Ser Tyr Tyr Glu Thr
        35                  40                  45

GAA AAG AAA AAC AGT GAC TTA GAT CTT TCA CGG GCA GCA CTT TAT CCT      192
Glu Lys Lys Asn Ser Asp Leu Asp Leu Ser Arg Ala Ala Leu Tyr Pro
    50                  55                  60

ACC CTG GAT CTA ACA TCT GGC CTT AAT AAT AAC AGG AAA GAG TCA TCA      240
Thr Leu Asp Leu Thr Ser Gly Leu Asn Asn Asn Arg Lys Glu Ser Ser
65                  70                  75                  80

GGT ACC GAG AGG AAC GTT GAA AAT AAG GTG TCT TTA TCA TAC CGA ATA      288
Gly Thr Glu Arg Asn Val Glu Asn Lys Val Ser Leu Ser Tyr Arg Ile
                85                  90                  95
```

```
ACG GAT TTT GGA GTG AGG GGG GCT AAT ATC AGG AAA TCT GAA TAT GAA      336
Thr Asp Phe Gly Val Arg Gly Ala Asn Ile Arg Lys Ser Glu Tyr Glu
            100                 105                 110

AGA GAT AAT AGT AAA ACT GAC TAT GAA AAA ACA AAG AAT ATA GTG TCT      384
Arg Asp Asn Ser Lys Thr Asp Tyr Glu Lys Thr Lys Asn Ile Val Ser
        115                 120                 125

CAG GAG GTT GTG ACA ACC TAT TAC AAC ATC AGT AAA TAT CGT GAA ATG      432
Gln Glu Val Val Thr Thr Tyr Tyr Asn Ile Ser Lys Tyr Arg Glu Met
    130                 135                 140

ATT GAT GGC GTA AAT CTG GAG AAA GAG TTT TAT AAA AAG ATG CTG GAA      480
Ile Asp Gly Val Asn Leu Glu Lys Glu Phe Tyr Lys Lys Met Leu Glu
145                 150                 155                 160

CCT TTT TCG TTG CTG GTA TCT TCC GGT GTA GCT ATG CAA TCT GAT ATG      528
Pro Phe Ser Leu Leu Val Ser Ser Gly Val Ala Met Gln Ser Asp Met
                165                 170                 175

CGT AAA GTA CAA GTA TCT ATC GAT GCA TTA AAT ACC AGA AGC ATT ATG      576
Arg Lys Val Gln Val Ser Ile Asp Ala Leu Asn Thr Arg Ser Ile Met
            180                 185                 190

TAT CAG TCG ATG TTG GAT GAT GAA ATG TAT AAA ATG CAG AAT ATG ACT      624
Tyr Gln Ser Met Leu Asp Asp Glu Met Tyr Lys Met Gln Asn Met Thr
        195                 200                 205

GGT CTG AAT TTA TCG CCA GTT CAG ATT CAA AGC GAT GAA AAA TTC AAC      672
Gly Leu Asn Leu Ser Pro Val Gln Ile Gln Ser Asp Glu Lys Phe Asn
    210                 215                 220

CTC TTC AAA AAA TAT ATC TTT GTC GAA AGC CCT GAA AAA CTT ATG GAC      720
Leu Phe Lys Lys Tyr Ile Phe Val Glu Ser Pro Glu Lys Leu Met Asp
225                 230                 235                 240

ATG GTG ATG AAA TAC AAC GAT GAC TAT AAG ATG CTT GTC AAT ACC CGA      768
Met Val Met Lys Tyr Asn Asp Asp Tyr Lys Met Leu Val Asn Thr Arg
                245                 250                 255

AAA GCC GCG ACC GAA GAT ATT AAT GCC GCA AAA TCA TCC TAT TTT CCG      816
Lys Ala Ala Thr Glu Asp Ile Asn Ala Ala Lys Ser Ser Tyr Phe Pro
            260                 265                 270

ACT GTA GAT CTT GTT TCC AGC TAT GTA CAG AAT AAC CCA AGC GGT AGT      864
Thr Val Asp Leu Val Ser Ser Tyr Val Gln Asn Asn Pro Ser Gly Ser
        275                 280                 285

GCC AAA AAA AGT GAT TAT GAA GAT GAA TTT AAA ACG GGT ATC AAT GTC      912
Ala Lys Lys Ser Asp Tyr Glu Asp Glu Phe Lys Thr Gly Ile Asn Val
    290                 295                 300

AGT TTC AAC ATT TTT AAT GGG TTC AGA AAT TCA GCC CAG GAA AGA AAA      960
Ser Phe Asn Ile Phe Asn Gly Phe Arg Asn Ser Ala Gln Glu Arg Lys
305                 310                 315                 320

ATG GTG GCA AGT TAC TCG CAG GCT AAG CTG CAA ATT GAC GAT TTT TTG     1008
Met Val Ala Ser Tyr Ser Gln Ala Lys Leu Gln Ile Asp Asp Phe Leu
                325                 330                 335

ATT AAA ACG CGT TAT AAC ATT GAT TCA CAA CTT TCA AGA TAC GCC GCT     1056
Ile Lys Thr Arg Tyr Asn Ile Asp Ser Gln Leu Ser Arg Tyr Ala Ala
            340                 345                 350

GCA AAA GAG ACT TAC TCA GTG GCG GAA CGT TCA CAT ACA AAC GCG TTA     1104
Ala Lys Glu Thr Tyr Ser Val Ala Glu Arg Ser His Thr Asn Ala Leu
        355                 360                 365

CAG CTT ACT GAA TTA TAT GAG CAG GAG TTT CAG TTA GGG CAA AAA AGT     1152
Gln Leu Thr Glu Leu Tyr Glu Gln Glu Phe Gln Leu Gly Gln Lys Ser
    370                 375                 380

TTG CTT GAT TTA ATT TCA AGC CGT AAT GAA GCA TTT CAG GCA TAT GTA     1200
Leu Leu Asp Leu Ile Ser Ser Arg Asn Glu Ala Phe Gln Ala Tyr Val
385                 390                 395                 400

AGC ATG ATC GAC AGC AAA TAT AGC CTG TAT ATT TTA AAG CTA CAG CAA     1248
Ser Met Ile Asp Ser Lys Tyr Ser Leu Tyr Ile Leu Lys Leu Gln Gln
                405                 410                 415
```

```
CTC TCA TTG ATT TTT CAT TTA ATG GAT TAT TTA AAA GGA AAT ACT GAA     1296
Leu Ser Leu Ile Phe His Leu Met Asp Tyr Leu Lys Gly Asn Thr Glu
            420                 425                 430

AGT GAG TTA AAT GTA ATG AAA TGA                                     1320
Ser Glu Leu Asn Val Met Lys
        435                 440
```

(2) INFORMATION FOR SEQ ID NO:13:

(i) SEQUENCE CHARACTERISTICS:
(A) LENGTH: 1278 bases
(B) TYPE: nucleotide
(C) STRANDEDNESS: double stranded
(D) TOPOLOGY: linear (ix) FEATURE:
(D) OTHER INFORMATION: the coding nucleotides of SEQ ID NO:13 correspond to nucleotides 4350 through 5627 of SEQ ID NO:2

(xi) SEQUENCE DESCRIPTION: SEQ ID NO:13:

```
ATG AAT AGA AGA CAA AGC GAT CAT CTC ATG ATG ATA ATT ATT TCT TTG       48
Met Asn Arg Arg Gln Ser Asp His Leu Met Met Ile Ile Ile Ser Leu
 1               5                  10                  15

ACG ATC TTA ATT ATT ATC CTT ACC TAC TTT ATA GAA ATT AAT TCA GTG       96
Thr Ile Leu Ile Ile Ile Leu Thr Tyr Phe Ile Glu Ile Asn Ser Val
            20                  25                  30

GTT CAT GGT CAG GGC GTT ATC ACT ACT AAA GAT AAT GCT CAG TTA ATA      144
Val His Gly Gln Gly Val Ile Thr Thr Lys Asp Asn Ala Gln Leu Ile
        35                  40                  45

TCT CTT TCT AAA GGA GGG ACG ATA CAA GAT ATT TAT GTA GCC GAG GGT      192
Ser Leu Ser Lys Gly Gly Thr Ile Gln Asp Ile Tyr Val Ala Glu Gly
    50                  55                  60

GAT ACT GTA AAA AAA GGA GAA CTC CTT GCA AAG GTC GTT AAC CTT GAT      240
Asp Thr Val Lys Lys Gly Glu Leu Leu Ala Lys Val Val Asn Leu Asp
65                  70                  75                  80

CTG CAA AAA GAA TAT CAA AGG TAT AGA ACT CAA AAA GGG TAT CTG GAT      288
Leu Gln Lys Glu Tyr Gln Arg Tyr Arg Thr Gln Lys Gly Tyr Leu Asp
                85                  90                  95

AAA GAT GTT AAC GAA ATA TCT TTC ATT CTT GAT AAA GAA AAT GAG AGT      336
Lys Asp Val Asn Glu Ile Ser Phe Ile Leu Asp Lys Glu Asn Glu Ser
            100                 105                 110

GGG TTG ATT ACC CTG GAT GGC ACC CGT TCT TTA AGC AAT AAA GAG GTA      384
Gly Leu Ile Thr Leu Asp Gly Thr Arg Ser Leu Ser Asn Lys Glu Val
        115                 120                 125

AAA GCG AAT ATT GAA TTA GTG CAT AGT CAG ATA AGA GCT AAA GAG TTA      432
Lys Ala Asn Ile Glu Leu Val His Ser Gln Ile Arg Ala Lys Glu Leu
    130                 135                 140

AAA AAA ACC TCT CTT GAT TCT GAG ATT AGC GGA TTA CAA GAG AAG CTG      480
Lys Lys Thr Ser Leu Asp Ser Glu Ile Ser Gly Leu Gln Glu Lys Leu
145                 150                 155                 160

AGT TCG AAA GAA AAA GAA CTC GCA TTG CTT GCC GAA GAA ATA AAT ATT      528
Ser Ser Lys Glu Lys Glu Leu Ala Leu Leu Ala Glu Glu Ile Asn Ile
                165                 170                 175

CTT TCC CCA CTG GTA AAA AAA GGA ATT AGC CCA TAT ACC AAT TTT CTT      576
Leu Ser Pro Leu Val Lys Lys Gly Ile Ser Pro Tyr Thr Asn Phe Leu
            180                 185                 190

AAC AAG AAA CAG GCG TAT ATA AAA GTT AAG TCT GAA ATT AAT GAT ATT      624
Asn Lys Lys Gln Ala Tyr Ile Lys Val Lys Ser Glu Ile Asn Asp Ile
        195                 200                 205

GAA AGT AGC ATC ACT TTA AAA AAA GAT GAT ATT GAG TTG GTT GTT AAT      672
Glu Ser Ser Ile Thr Leu Lys Lys Asp Asp Ile Glu Leu Val Val Asn
    210                 215                 220
```

```
GAT ATT GAG GCG CTT AAT AAT GAA TTG CGA CTA TCT TTA TCT AAA ATA      720
Asp Ile Glu Ala Leu Asn Asn Glu Leu Arg Leu Ser Leu Ser Lys Ile
225                 230                 235                 240

ATA TCT AAA AAT CTT CAG GAA CTT GAG GTT GTT AAC TCT ACA TTA AAA      768
Ile Ser Lys Asn Leu Gln Glu Leu Glu Val Val Asn Ser Thr Leu Lys
                245                 250                 255

GTA ATA GAG AAG CAG ATA AAT GAG GAG GAT ATC TAT TCA CCG GTT GAC      816
Val Ile Glu Lys Gln Ile Asn Glu Glu Asp Ile Tyr Ser Pro Val Asp
            260                 265                 270

GGT GTA ATT TAT AAA ATC AAT AAA AGT GCC ACT ACT CAT GGT GGT GTG      864
Gly Val Ile Tyr Lys Ile Asn Lys Ser Ala Thr Thr His Gly Gly Val
        275                 280                 285

ATT CAG GCG GCG GAC TTA CTT TTT GAA ATA AAA CCA AAA GTA AGG ACT      912
Ile Gln Ala Ala Asp Leu Leu Phe Glu Ile Lys Pro Lys Val Arg Thr
    290                 295                 300

ATG CTG GCC GAT GTG AAA ATA TTA CCC AAA TAC CGT GAC CAA ATA TAT      960
Met Leu Ala Asp Val Lys Ile Leu Pro Lys Tyr Arg Asp Gln Ile Tyr
305                 310                 315                 320

GTA GAT GAA GCC GTT AAA CTG GAT GTG CAG TCA ATT ATC CAA CCA AAG     1008
Val Asp Glu Ala Val Lys Leu Asp Val Gln Ser Ile Ile Gln Pro Lys
                325                 330                 335

ATA AAA TCG TAT AAT GCG ACT ATC GAT AAT ATT AGC CCT GAT TCC TAT     1056
Ile Lys Ser Tyr Asn Ala Thr Ile Asp Asn Ile Ser Pro Asp Ser Tyr
            340                 345                 350

GAG GAA AAT ACC GGA GGA ACA ATT CAG CGT TAT TAT AAA GTA ATT ATT     1104
Glu Glu Asn Thr Gly Gly Thr Ile Gln Arg Tyr Tyr Lys Val Ile Ile
        355                 360                 365

GCA TTC GAT GTT AAT GAA GAT GAT TTA CGG TGG TTA AAA CCA GGT ATG     1152
Ala Phe Asp Val Asn Glu Asp Asp Leu Arg Trp Leu Lys Pro Gly Met
    370                 375                 380

ACT GTT GAC GCC AGT GTA ATT ACC GGA AAA CAC AGC ATT ATG GAA TAC     1200
Thr Val Asp Ala Ser Val Ile Thr Gly Lys His Ser Ile Met Glu Tyr
385                 390                 395                 400

CTG TTA TCT CCC TTG ATG AAA GGC GTG GAC AAA GCC TTT TCA GAA CCA     1248
Leu Leu Ser Pro Leu Met Lys Gly Val Asp Lys Ala Phe Ser Glu Pro
                405                 410                 415

GTT AAT ACT AAA CGA TTA GAT ACA CCT TGA                             1278
Val Asn Thr Lys Arg Leu Asp Thr Pro
            420                 425
```

(2) INFORMATION FOR SEQ ID NO:14:

(i) SEQUENCE CHARACTERISTICS:
- (A) LENGTH: 393 bases
- (B) TYPE: nucleotide
- (C) STRANDEDNESS: double stranded
- (D) TOPOLOGY: linear (ix) FEATURE:
- (D) OTHER INFORMATION: the coding nucleotides of SEQ ID NO:14 correspond to nucleotides 5644 through 6036 of SEQ ID NO:2

(xi) SEQUENCE DESCRIPTION: SEQ ID NO:14:

```
ATG GGA AAT AAA AGC ATA CAA AAG TTT TTT GCC GAT CAA AAT TCT GTA       48
Met Gly Asn Lys Ser Ile Gln Lys Phe Phe Ala Asp Gln Asn Ser Val
 1               5                  10                  15

ATT GAT TTA TCT TCT TTG GGT AAT GCC AAA GGC GCA AAA GTT TCT CTT       96
Ile Asp Leu Ser Ser Leu Gly Asn Ala Lys Gly Ala Lys Val Ser Leu
            20                  25                  30

TCC GGG CCA GAC ATG AAC ATT ACC ACG CCG CGT GGT TCA GTG ATC ATT      144
Ser Gly Pro Asp Met Asn Ile Thr Thr Pro Arg Gly Ser Val Ile Ile
        35                  40                  45
```

```
GTC AAT GGC GCT CTT TAT TCA AGT ATC AAA GGC AAT AAC CTC GCT GTT      192
Val Asn Gly Ala Leu Tyr Ser Ser Ile Lys Gly Asn Asn Leu Ala Val
    50                  55                  60

AAA TTT AAA GAT AAG ACT ATT ACC GGC GCT AAA ATT CTG GGC AGC GTA      240
Lys Phe Lys Asp Lys Thr Ile Thr Gly Ala Lys Ile Leu Gly Ser Val
65                  70                  75                  80

GAT TTA AAA GAT ATT CAA CTG GAG AGA ATT GAC AGC TCA TTG GTT GAT      288
Asp Leu Lys Asp Ile Gln Leu Glu Arg Ile Asp Ser Ser Leu Val Asp
                85                  90                  95

TCT GCT CAG GTA GAA AAG AAA GGT AAT GGC AAA CGA CGA AAT AAG AAG      336
Ser Ala Gln Val Glu Lys Lys Gly Asn Gly Lys Arg Arg Asn Lys Lys
            100                 105                 110

GAA GAA GAG GAA TTA AAA AGC AGC TTG ACG ATG CTG AAA ACG CAA GAA      384
Glu Glu Glu Glu Leu Lys Ser Ser Leu Thr Met Leu Lys Thr Gln Glu
        115                 120                 125

AGA AGC TGA                                                          393
Arg Ser
    130
```

(2) INFORMATION FOR SEQ ID NO:15:

(i) SEQUENCE CHARACTERISTICS:
(A) LENGTH: 1581 bases
(B) TYPE: nucleotide
(C) STRANDEDNESS: double stranded
(D) TOPOLOGY: linear (ix) FEATURE:
(D) OTHER INFORMATION: the coding nucleotides of SEQ ID NO:15 correspond to nucleotides 6134 through 7714 of SEQ ID NO:2

(xi) SEQUENCE DESCRIPTION: SEQ ID NO:15:

```
ATG CTG CAG AAC TTT TTG GCT GAC AAT GTA GCA AAA GAC AAT CTG GCT       48
Met Leu Gln Asn Phe Leu Ala Asp Asn Val Ala Lys Asp Asn Leu Ala
 1               5                  10                  15

CAG CAA AGC GAT GCT TCC CAG CAA AAT ACA CAG GCT AAA GCA ACG CAG       96
Gln Gln Ser Asp Ala Ser Gln Gln Asn Thr Gln Ala Lys Ala Thr Gln
            20                  25                  30

GCT TCT AAA CAG AAC GAT GCT GAA AAA GTT CTT CCT CAA CCT ATT AAT      144
Ala Ser Lys Gln Asn Asp Ala Glu Lys Val Leu Pro Gln Pro Ile Asn
        35                  40                  45

AAA AAT ACC AGT ACT GGC AAA AGT AAT AGC AGT AAA AAT GAG GAA AAT      192
Lys Asn Thr Ser Thr Gly Lys Ser Asn Ser Ser Lys Asn Glu Glu Asn
    50                  55                  60

AAG CTC GAT GCC GAG TCT GTT AAA GAG CCG CTT AAA GTC ACA TTA GCG      240
Lys Leu Asp Ala Glu Ser Val Lys Glu Pro Leu Lys Val Thr Leu Ala
65                  70                  75                  80

CGT GCG GCC GAG AGT AAC AGC GGT AGC AAA GAT GAT AGT ATA ACT AAT      288
Arg Ala Ala Glu Ser Asn Ser Gly Ser Lys Asp Asp Ser Ile Thr Asn
                85                  90                  95

TTT ACC AAA CCT CAG TTT GTA GTT AGC ACT GCT CCC AAT GCC ACG GTT      336
Phe Thr Lys Pro Gln Phe Val Val Ser Thr Ala Pro Asn Ala Thr Val
            100                 105                 110

ATT ATT AAA ATT AAT GGT ATT GCT GTC GGT CAG GCT GTA ACG GAT AGT      384
Ile Ile Lys Ile Asn Gly Ile Ala Val Gly Gln Ala Val Thr Asp Ser
        115                 120                 125

TTG GGT AAC TTC ACC TTT ACA GCG CCT GAA ACA TTG ACT GAT GGA ACA      432
Leu Gly Asn Phe Thr Phe Thr Ala Pro Glu Thr Leu Thr Asp Gly Thr
    130                 135                 140

TAT AAT CTG GAG GCA GAG GCC AAG ACT GCT GAT GGG AGC GGT AGC GCC      480
Tyr Asn Leu Glu Ala Glu Ala Lys Thr Ala Asp Gly Ser Gly Ser Ala
145                 150                 155                 160
```

```
AAA CTT GTC ATT ACT ATC GAT TCC GTT ACC GAT AAA CCA ACA TTT GAA      528
Lys Leu Val Ile Thr Ile Asp Ser Val Thr Asp Lys Pro Thr Phe Glu
                165                 170                 175

CTT TCG CCT GAA AGT AGT GTG TCC GGT CAT AAG GGC TTA ACG CCG ACC      576
Leu Ser Pro Glu Ser Ser Val Ser Gly His Lys Gly Leu Thr Pro Thr
            180                 185                 190

TTG ACG CCT TCA ATT GTT GGT ACG GCG GAA GAG AAT GCT AAG GTT GAC      624
Leu Thr Pro Ser Ile Val Gly Thr Ala Glu Glu Asn Ala Lys Val Asp
        195                 200                 205

ATT TAT GTA GAT AAT AAA CTG GTT GCC AGC GTT GAT GTC GAT AAA GAT      672
Ile Tyr Val Asp Asn Lys Leu Val Ala Ser Val Asp Val Asp Lys Asp
    210                 215                 220

GGA AAC TGG AGT TAT GAA TTT AAG GAT AAT GAA TTA TCT GAG GGC GAA      720
Gly Asn Trp Ser Tyr Glu Phe Lys Asp Asn Glu Leu Ser Glu Gly Glu
225                 230                 235                 240

AAT AGT ATA AAA GTC GTT GCT GTA GAT AAA GCA GGT AAT AAA AAC GAA      768
Asn Ser Ile Lys Val Val Ala Val Asp Lys Ala Gly Asn Lys Asn Glu
                245                 250                 255

ACG ACG GAT AGT ATC ATA ACC GAC ACC ATT GCT CCA GAA AAG CCG ACG      816
Thr Thr Asp Ser Ile Ile Thr Asp Thr Ile Ala Pro Glu Lys Pro Thr
            260                 265                 270

ATT GAG CTG GAT GAT AGT AGT GAT TCC GGC ATT AAA AAT GAC AAC ATT      864
Ile Glu Leu Asp Asp Ser Ser Asp Ser Gly Ile Lys Asn Asp Asn Ile
        275                 280                 285

ACA AAT AGC ACC CTG CCA ACA TTT ATT GGT GTG GCG GAA CCC GGT TCT      912
Thr Asn Ser Thr Leu Pro Thr Phe Ile Gly Val Ala Glu Pro Gly Ser
    290                 295                 300

ACA GTC TCT ATT TAT CTT GGA CTT AAA CAT CTT GGT GAG GTC ATT GTT      960
Thr Val Ser Ile Tyr Leu Gly Leu Lys His Leu Gly Glu Val Ile Val
305                 310                 315                 320

GCT AAA GAT GGG ACA TGG AGC TAT ACG CTT ACT ACG CCG CTC AAG GAT     1008
Ala Lys Asp Gly Thr Trp Ser Tyr Thr Leu Thr Thr Pro Leu Lys Asp
                325                 330                 335

GGC GAA TAC AAT ATA ACA GCA ACA GCT ACT GAT ATT GCC GGG CAT ACC     1056
Gly Glu Tyr Asn Ile Thr Ala Thr Ala Thr Asp Ile Ala Gly His Thr
            340                 345                 350

TCA GCG ACG GCA AAT CTG CCT TTT ACT ATT GAT ACA CGT ATC AGC TAT     1104
Ser Ala Thr Ala Asn Leu Pro Phe Thr Ile Asp Thr Arg Ile Ser Tyr
        355                 360                 365

TTC AGC GCT GAG ATT GAA ACG ACG AAT GAT AGC GGT ATT GTC GGA GAT     1152
Phe Ser Ala Glu Ile Glu Thr Thr Asn Asp Ser Gly Ile Val Gly Asp
    370                 375                 380

AAC GTT ACT AAC AAT ACT CGC CCA ACC TTT ACA GGT AAA ACT GAG CCA     1200
Asn Val Thr Asn Asn Thr Arg Pro Thr Phe Thr Gly Lys Thr Glu Pro
385                 390                 395                 400

AAT GCT ATT ATC AGT GTC ATA AAT AGT GAG ACT GGC GAA GAG GTT ATT     1248
Asn Ala Ile Ile Ser Val Ile Asn Ser Glu Thr Gly Glu Glu Val Ile
                405                 410                 415

TTT AAA GCG AAT GAC AAG GGC GAA TGG ACG TTC AAT TTC ACT TCC GAC     1296
Phe Lys Ala Asn Asp Lys Gly Glu Trp Thr Phe Asn Phe Thr Ser Asp
            420                 425                 430

TCA GTG GAA GGG ATT AAC AAT CTT ACG TTC ACT GTT GAA GAT GTC GCT     1344
Ser Val Glu Gly Ile Asn Asn Leu Thr Phe Thr Val Glu Asp Val Ala
        435                 440                 445

GGC AAC AAA AAG GAT TTT TCC TTT AGT TAC GTT ATT GAT ACT ATT GCC     1392
Gly Asn Lys Lys Asp Phe Ser Phe Ser Tyr Val Ile Asp Thr Ile Ala
    450                 455                 460

CCT GTA CCT CCG ACG GCT TCT TTG GAG GAT TAT GTT GTT TTG CCG AAT     1440
Pro Val Pro Pro Thr Ala Ser Leu Glu Asp Tyr Val Val Leu Pro Asn
465                 470                 475                 480
```

```
GGT ATA ATT TTA TCA GGG AAT GAT TTA CCG GCT TTA GTC GGT ACG GCA     1488
Gly Ile Ile Leu Ser Gly Asn Asp Leu Pro Ala Leu Val Gly Thr Ala
                485                 490                 495

GAA CCA AAG TCT ACC ATC TTA TTG ATG CGA GAT GGT AAA TTA TAT GAC     1536
Glu Pro Lys Ser Thr Ile Leu Leu Met Arg Asp Gly Lys Leu Tyr Asp
            500                 505                 510

AGC ATT GAA GTT GAC TCA AAC GGG ACC TGG AAA TTA TCA GTT TAG         1581
Ser Ile Glu Val Asp Ser Asn Gly Thr Trp Lys Leu Ser Val
        515                 520                 525
```

(2) INFORMATION FOR SEQ ID NO:16:

(i) SEQUENCE CHARACTERISTICS:
(A) LENGTH: 1134 bases
(B) TYPE: nucleotide
(C) STRANDEDNESS: double stranded
(D) TOPOLOGY: linear (ix) FEATURE:
(D) OTHER INFORMATION: the coding nucleotides of SEQ ID NO:16 correspond to nucleotides 8128 through 9261 of SEQ ID NO:2

(xi) SEQUENCE DESCRIPTION: SEQ ID NO:16:

```
ATG TTG CAT GAT AGC GCT GAC TCT GGC GTT AAA GGC GAT ATG ATT ACT       48
Met Leu His Asp Ser Ala Asp Ser Gly Val Lys Gly Asp Met Ile Thr
 1               5                  10                  15

AAA ATT AAT ACA CCG TTG TTT ACC GGG ATG GCT GAA GCT AAT GCT AAG       96
Lys Ile Asn Thr Pro Leu Phe Thr Gly Met Ala Glu Ala Asn Ala Lys
            20                  25                  30

GTT TCC ATC TAT GTT GAC GGT GTG TTA AGT GGT GAG GCT ATT GCT GGC      144
Val Ser Ile Tyr Val Asp Gly Val Leu Ser Gly Glu Ala Ile Ala Gly
        35                  40                  45

GAT GAT GGT GTA TGG AAT TTT CAA TTT ACC ACA GCG TTA TCC GAT GGC      192
Asp Asp Gly Val Trp Asn Phe Gln Phe Thr Thr Ala Leu Ser Asp Gly
    50                  55                  60

TCG CAT GAC GTA ACG GTA AAG GTA GAA GAT ATT GCC GGT AAT ACT GCC      240
Ser His Asp Val Thr Val Lys Val Glu Asp Ile Ala Gly Asn Thr Ala
65                  70                  75                  80

TCC TCA TCA GCG TAT AAT TTC CAA ATC GTA ACG CAA ACG CAA AAA CCA      288
Ser Ser Ser Ala Tyr Asn Phe Gln Ile Val Thr Gln Thr Gln Lys Pro
                85                  90                  95

ACA ATA GAG TTG GTC AAC GAT ACG GGG GTT GAT AAT ACA GAC CAT ATT      336
Thr Ile Glu Leu Val Asn Asp Thr Gly Val Asp Asn Thr Asp His Ile
            100                 105                 110

ATT AAT GAA AAG AAT CCT GCA CTG ACA GGA ACC GCT GCA CCC TAT TCA      384
Ile Asn Glu Lys Asn Pro Ala Leu Thr Gly Thr Ala Ala Pro Tyr Ser
        115                 120                 125

ACG GTT AAA CTC TAT ATT GAT GGT GCA CTG ATC GCT GAG GTC AGA ACA      432
Thr Val Lys Leu Tyr Ile Asp Gly Ala Leu Ile Ala Glu Val Arg Thr
    130                 135                 140

AAT AAA GAT GGC AGA TGG GAG TAT ACC CTG AAA GCC GAT CAA GGT TTG      480
Asn Lys Asp Gly Arg Trp Glu Tyr Thr Leu Lys Ala Asp Gln Gly Leu
145                 150                 155                 160

GTT GAT GGC GAT CAT AGA ATA ACC GCT TCA GTT GAA GAT ATC GCT GGC      528
Val Asp Gly Asp His Arg Ile Thr Ala Ser Val Glu Asp Ile Ala Gly
                165                 170                 175

AAC ATT GCT CAT TCG GAT CCT TTC TTA ATT AGC GTC GAT ACT GCT ATT      576
Asn Ile Ala His Ser Asp Pro Phe Leu Ile Ser Val Asp Thr Ala Ile
            180                 185                 190

TCA ATA CCG ATA GTT TCA TTG AGC CCG GAT TCA GAT TCG GGA ATT TCA      624
Ser Ile Pro Ile Val Ser Leu Ser Pro Asp Ser Asp Ser Gly Ile Ser
        195                 200                 205
```

```
GAT GAT AAT TTA ACG AAT ATC GTT AAA CCT ACC TTG CAC CTA AAA GAT      672
Asp Asp Asn Leu Thr Asn Ile Val Lys Pro Thr Leu His Leu Lys Asp
    210                 215                 220

ATT GAT CCG GAC ATT ATC AGT GTT CAG GTA TGG GAT GCC ATG TCT GAT      720
Ile Asp Pro Asp Ile Ile Ser Val Gln Val Trp Asp Ala Met Ser Asp
225                 230                 235                 240

ACG CAG ATC GGT GTT GCC ACG CAA CAA CCT GAT GGT TCA TGG GCC TAT      768
Thr Gln Ile Gly Val Ala Thr Gln Gln Pro Asp Gly Ser Trp Ala Tyr
                245                 250                 255

ACC TTT ACT TCA GAT TTA ACG GAA GGC TTG CAT CAG GTT TAT GTC AAG      816
Thr Phe Thr Ser Asp Leu Thr Glu Gly Leu His Gln Val Tyr Val Lys
            260                 265                 270

GTT GAG GAC ATT GCG GGT AAT AAA GCG AAC AGC GCG ATA TTC GAT TTT      864
Val Glu Asp Ile Ala Gly Asn Lys Ala Asn Ser Ala Ile Phe Asp Phe
        275                 280                 285

ACT ATC GAT ACC ACA GTA TCA ACG CCG GTG ATT TCC CTG CTT TCT AAG      912
Thr Ile Asp Thr Thr Val Ser Thr Pro Val Ile Ser Leu Leu Ser Lys
    290                 295                 300

GAT GAT ACG GGG GTT ACA GGC GAT AAC CTG ACC AAT ATC AAT AAG CCA      960
Asp Asp Thr Gly Val Thr Gly Asp Asn Leu Thr Asn Ile Asn Lys Pro
305                 310                 315                 320

GGT TTT GCT ATT TCC GGT GTT GAT GCC GAT GCG CAT CGG GTC GTC GTA     1008
Gly Phe Ala Ile Ser Gly Val Asp Ala Asp Ala His Arg Val Val Val
                325                 330                 335

CAG GTG ATG CAC AAT GGC GTG AGC GAA GAG ATC GAA CTT TCC CAC CTC     1056
Gln Val Met His Asn Gly Val Ser Glu Glu Ile Glu Leu Ser His Leu
            340                 345                 350

AAT GGG AGT TGG TTA TTT ATA CCA GGG GAA TAC GTG GGC GGA TGG CAG     1104
Asn Gly Ser Trp Leu Phe Ile Pro Gly Glu Tyr Val Gly Gly Trp Gln
        355                 360                 365

CTA CAC GTT AAC GGT GAA AGT AGA AGA TAA                             1134
Leu His Val Asn Gly Glu Ser Arg Arg
    370                 375
```

(2) INFORMATION FOR SEQ ID NO:17:

(i) SEQUENCE CHARACTERISTICS:
- (A) LENGTH: 351 bases
- (B) TYPE: nucleotide
- (C) STRANDEDNESS: double stranded
- (D) TOPOLOGY: linear (ix) FEATURE:
- (D) OTHER INFORMATION: the coding nucleotides of SEQ ID NO:17 correspond to nucleotides 9184 through 9535 of SEQ ID NO:2

(xi) SEQUENCE DESCRIPTION: SEQ ID NO:17:

```
ATG GGA GTT GGT TAT TTA TAC CAG GGG AAT ACG TGG GCG GAT GGC AGC       48
Met Gly Val Gly Tyr Leu Tyr Gln Gly Asn Thr Trp Ala Asp Gly Ser
 1               5                  10                  15

TAC ACG TTA ACG GTG AAA GTA GAA GAT AAG GCA GGA AAT ACC AAC TAC       96
Tyr Thr Leu Thr Val Lys Val Glu Asp Lys Ala Gly Asn Thr Asn Tyr
            20                  25                  30

TCG GCG CCG CTG ACG GTC GTT ATC GAT ACC CAA ATC GCC ATT GAT GGG      144
Ser Ala Pro Leu Thr Val Val Ile Asp Thr Gln Ile Ala Ile Asp Gly
        35                  40                  45

GTG GAA CTG GTC AAC GAT AGC GGC GTG AAA GGC GAT AAT ATG ACC AAC      192
Val Glu Leu Val Asn Asp Ser Gly Val Lys Gly Asp Asn Met Thr Asn
    50                  55                  60

GAC GAC CGT CCC CAC TTT CGT GTG ACG GTA CCT ACG GAT GTC AAT GAA      240
Asp Asp Arg Pro His Phe Arg Val Thr Val Pro Thr Asp Val Asn Glu
65                  70                  75                  80
```

```
GTC CGT CTG AGC ATT GAC GGT GGT AAT TCG TGG GTT CAG GCA ACT CCG      288
Val Arg Leu Ser Ile Asp Gly Gly Asn Ser Trp Val Gln Ala Thr Pro
            85                  90                  95

GGC GTG GCA GGA AGC TGG GAG TAT ATC TGG CCG ACA GAC CTG GCA GAT      336
Gly Val Ala Gly Ser Trp Glu Tyr Ile Trp Pro Thr Asp Leu Ala Asp
            100                 105                 110

GGT CCT ACA CGC TAA                                                  351
Gly Pro Thr Arg
        115
```

(2) INFORMATION FOR SEQ ID NO:18:

(i) SEQUENCE CHARACTERISTICS:
(A) LENGTH: 759 bases
(B) TYPE: nucleotide
(C) STRANDEDNESS: double stranded
(D) TOPOLOGY: linear (ix) FEATURE:
(D) OTHER INFORMATION: the coding nucleotides of SEQ ID NO:18 correspond to nucleotides 9566 through 10324 of SEQ ID NO:2

(xi) SEQUENCE DESCRIPTION: SEQ ID NO:18:

```
ATG ACG AAG ACC ATC GAT TTC GCG GTG GAT ACC ACG CTG TCA GTG CCG       48
Met Thr Lys Thr Ile Asp Phe Ala Val Asp Thr Thr Leu Ser Val Pro
 1               5                  10                  15

GTC ATC GTA CTG GAT AGC GCG GAC GAC ACC GGC ATC CAG GGC GAT AAC       96
Val Ile Val Leu Asp Ser Ala Asp Asp Thr Gly Ile Gln Gly Asp Asn
            20                  25                  30

ATG ACG AAT AGC ACC CAG CCG ACA TTT GCC TTG CAG CAT ATT GAT GAT      144
Met Thr Asn Ser Thr Gln Pro Thr Phe Ala Leu Gln His Ile Asp Asp
        35                  40                  45

GAT GCC GTT CGC GTT ACG GTC AGC GTG GAG CAT GGC GGC GTC ACC ACC      192
Asp Ala Val Arg Val Thr Val Ser Val Glu His Gly Gly Val Thr Thr
    50                  55                  60

ACA TTT GAC GCC ACG AAA GGC ACA GGC GGA TGG ACC TTT ACG CCG CCG      240
Thr Phe Asp Ala Thr Lys Gly Thr Gly Gly Trp Thr Phe Thr Pro Pro
65                  70                  75                  80

ACA TCA TGG GCG GAT GGT GAT TAT ACC CTG AGT GTG TCA GTC GAA GAT      288
Thr Ser Trp Ala Asp Gly Asp Tyr Thr Leu Ser Val Ser Val Glu Asp
                85                  90                  95

AAA GCG GGG AAC ACC AGC CAT TCT GCA TCG CTG ACG GTG ACG GTG GAC      336
Lys Ala Gly Asn Thr Ser His Ser Ala Ser Leu Thr Val Thr Val Asp
            100                 105                 110

ACG CAA ATC GCC ATT AAT AAC ATT GAA CTG GTC AAT GAC AGC GGT ATT      384
Thr Gln Ile Ala Ile Asn Asn Ile Glu Leu Val Asn Asp Ser Gly Ile
        115                 120                 125

CCC GAC GAT AAT CTG ACT AAT AAT GTG CGT CCG CAC TTC CAG GTG ACG      432
Pro Asp Asp Asn Leu Thr Asn Asn Val Arg Pro His Phe Gln Val Thr
    130                 135                 140

GTA CCG ACG GAT GTC AAC GTG GTG CGC CTG AGC ATT GAC GGC GGC AAG      480
Val Pro Thr Asp Val Asn Val Val Arg Leu Ser Ile Asp Gly Gly Lys
145                 150                 155                 160

ACG TGG TTC AAC GCT ACC CAG AGC GCG ACG CCA GGC GTC TGG GAT TAT      528
Thr Trp Phe Asn Ala Thr Gln Ser Ala Thr Pro Gly Val Trp Asp Tyr
                165                 170                 175

ATC TGG CCG GAT GAT GTG GCC GAC GGA GGC TAT ACC CTG ACG GTA GAA      576
Ile Trp Pro Asp Asp Val Ala Asp Gly Gly Tyr Thr Leu Thr Val Glu
            180                 185                 190

GCG ACC GAT GAG GCA GGA AAT AAG GCA ACA CAG ACC TCG ATT TCA CCA      624
Ala Thr Asp Glu Ala Gly Asn Lys Ala Thr Gln Thr Ser Ile Ser Pro
        195                 200                 205
```

```
TCG ATA CCA CTC TGT CTG TGC CGA CCC TCT CGC TGG ACA GCG CAG ATG      672
Ser Ile Pro Leu Cys Leu Cys Arg Pro Ser Arg Trp Thr Ala Gln Met
    210                 215                 220

ACA GCG GCA TCG CGG GCG ATA ATA TCA CCA ATG TTA AAA CGC CGG GCT      720
Thr Ala Ala Ser Arg Ala Ile Ile Ser Pro Met Leu Lys Arg Arg Ala
225                 230                 235                 240

TTA CCC TCA ACA ATA TTG ATA CCG ATG TCA GCC GGG TGA                  759
Leu Pro Ser Thr Ile Leu Ile Pro Met Ser Ala Gly
                245                 250
```

(2) INFORMATION FOR SEQ ID NO:19:

(i) SEQUENCE CHARACTERISTICS:
(A) LENGTH: 381 bases
(B) TYPE: nucleotide
(C) STRANDEDNESS: double stranded
(D) TOPOLOGY: linear (ix) FEATURE:
(D) OTHER INFORMATION: the coding nucleotides of SEQ ID NO:19 correspond to nucleotides 10336 through 10716 of SEQ ID NO:2

(xi) SEQUENCE DESCRIPTION: SEQ ID NO:19:

```
ATG CAC AAT GGC ATT AAG CAG GAG GTG CCA CTG GTT CAG ACC GGC GGA       48
Met His Asn Gly Ile Lys Gln Glu Val Pro Leu Val Gln Thr Gly Gly
 1               5                  10                  15

CAG TGG CGC TTT GCG CCG ACC AGC GAC TGG GCG GAC GGC GAC TAT ATC       96
Gln Trp Arg Phe Ala Pro Thr Ser Asp Trp Ala Asp Gly Asp Tyr Ile
            20                  25                  30

CTG ACG GTG AAG GTA GAA GAT AGG ACC GGA AAT GTG AAG CAG TCC GCG      144
Leu Thr Val Lys Val Glu Asp Arg Thr Gly Asn Val Lys Gln Ser Ala
        35                  40                  45

CCG TTG ACG GTG ACA GTA GAC ACG CAT ATC GCC ATT GAC CGT ATT GAA      192
Pro Leu Thr Val Thr Val Asp Thr His Ile Ala Ile Asp Arg Ile Glu
    50                  55                  60

CTG GTT AAC GAC AGC GGT ATC CCC GGC GAT AAT CTG ACC AAT GAA GCG      240
Leu Val Asn Asp Ser Gly Ile Pro Gly Asp Asn Leu Thr Asn Glu Ala
65                  70                  75                  80

CGC CCG CAC TTT CAG GTG ACA GTA CCG GCG GAT GTT AAC GGC GTA AGA      288
Arg Pro His Phe Gln Val Thr Val Pro Ala Asp Val Asn Gly Val Arg
                85                  90                  95

CTG AGC ATT GAT GGC GGC AAA ACG TGG TTT GAC GCC ACG CAG CAG CGC      336
Leu Ser Ile Asp Gly Gly Lys Thr Trp Phe Asp Ala Thr Gln Gln Arg
            100                 105                 110

GAC GTC GGG CGT CTG GGA TTA CAC CTG GCT GAC GAA TGT GGC TAA          381
Asp Val Gly Arg Leu Gly Leu His Leu Ala Asp Glu Cys Gly
        115                 120                 125
```

(2) INFORMATION FOR SEQ ID NO:20:

(i) SEQUENCE CHARACTERISTICS:
(A) LENGTH: 1197 bases
(B) TYPE: nucleotide
(C) STRANDEDNESS: double stranded
(D) TOPOLOGY: linear (ix) FEATURE:
(D) OTHER INFORMATION: the coding nucleotides of SEQ ID NO:20 correspond to nucleotides 10634 through 11830 of SEQ ID NO:2

(xi) SEQUENCE DESCRIPTION: SEQ ID NO:20:

```
ATG GCG GCA AAA CGT GGT TTG ACG CCA CGC AGC AGC GCG ACG TCG GGC       48
Met Ala Ala Lys Arg Gly Leu Thr Pro Arg Ser Ser Ala Thr Ser Gly
 1               5                  10                  15
```

```
GTC TGG GAT TAC ACC TGG CTG ACG AAT GTG GCT AAC GGC CCT CAC ACC       96
Val Trp Asp Tyr Thr Trp Leu Thr Asn Val Ala Asn Gly Pro His Thr
            20                  25                  30

CTG ATG GTG GAA GCG TCC GAC AAG GCG GGA AAC AAA ACG ACG CAG AAA      144
Leu Met Val Glu Ala Ser Asp Lys Ala Gly Asn Lys Thr Thr Gln Lys
        35                  40                  45

CTG GAC TTC ACC ATC GAT ACC ATT CTG TCA GAA CCG ACG ATT ACC CTG      192
Leu Asp Phe Thr Ile Asp Thr Ile Leu Ser Glu Pro Thr Ile Thr Leu
    50                  55                  60

GAC AGC GCG GAT GAT AGC GCC GCT GGC GAT AAC ATC ACC AAC GTT AAG      240
Asp Ser Ala Asp Asp Ser Ala Ala Gly Asp Asn Ile Thr Asn Val Lys
65                  70                  75                  80

ATG CCA GGC TTT ACC CTC GGT AAT ATC GAC GCC GAC GTG ACC AAA GTG      288
Met Pro Gly Phe Thr Leu Gly Asn Ile Asp Ala Asp Val Thr Lys Val
                85                  90                  95

GTG GTG ACG GTG GCG CAT GAT GGT AAG AAC CAA CAG ATA GAG TTG ATT      336
Val Val Thr Val Ala His Asp Gly Lys Asn Gln Gln Ile Glu Leu Ile
            100                 105                 110

AAG AAC GGC GGT GTG TGG CGC TTT ACG CCG GGC GCA GCC TGG ACC GAT      384
Lys Asn Gly Gly Val Trp Arg Phe Thr Pro Gly Ala Ala Trp Thr Asp
        115                 120                 125

GGC GAC TAT ACG TTG ACG GTA AAG GTA GAA GAT AAG GCG GGT AAT ACA      432
Gly Asp Tyr Thr Leu Thr Val Lys Val Glu Asp Lys Ala Gly Asn Thr
    130                 135                 140

AAT TAT TCT GCG CCG CTG ACG GTG ACT ATC GAT ACG CAA ACG TCT ATT      480
Asn Tyr Ser Ala Pro Leu Thr Val Thr Ile Asp Thr Gln Thr Ser Ile
145                 150                 155                 160

GAT CGC ATT GAG CTT CTT AAT GAC ACG GGT ATT GTC GGG GAT AAC CTG      528
Asp Arg Ile Glu Leu Leu Asn Asp Thr Gly Ile Val Gly Asp Asn Leu
                165                 170                 175

ACC AAT GAA GCA CGT CCA CAG TTT CAT ATT ACG GTA CCG ACG GAC GTG      576
Thr Asn Glu Ala Arg Pro Gln Phe His Ile Thr Val Pro Thr Asp Val
            180                 185                 190

AAC TCT GTG CAA CTG AGT CTT GAT GGC GGC ATC AAC TGG GTT AAC GCA      624
Asn Ser Val Gln Leu Ser Leu Asp Gly Gly Ile Asn Trp Val Asn Ala
        195                 200                 205

ACG CTG ACG TCT GAC GGC GTT TGG GAG TAT ATA TGG CCG ACA GAT CTG      672
Thr Leu Thr Ser Asp Gly Val Trp Glu Tyr Ile Trp Pro Thr Asp Leu
    210                 215                 220

GTC GAA AAT ACG TAT ACC CTG ACA GTG AAA GCA ACC GAT GTT GCA GGC      720
Val Glu Asn Thr Tyr Thr Leu Thr Val Lys Ala Thr Asp Val Ala Gly
225                 230                 235                 240

AAC ACG GCG ACG GAA ACG CTC AAT TTT ACC ATT GAT ACC ACA TTG TCG      768
Asn Thr Ala Thr Glu Thr Leu Asn Phe Thr Ile Asp Thr Thr Leu Ser
                245                 250                 255

ACA CCG ACC ATC ACG CTG GAT AGC GCA GAT GAT AGC GGC ACC GCC AAC      816
Thr Pro Thr Ile Thr Leu Asp Ser Ala Asp Asp Ser Gly Thr Ala Asn
            260                 265                 270

GAT AAT AAG ACT AAC GTT AAA ACG CCG GGT TTT ATT ATC GGC GGT ATT      864
Asp Asn Lys Thr Asn Val Lys Thr Pro Gly Phe Ile Ile Gly Gly Ile
        275                 280                 285

GAT TCT GAC GTG ACT CAG GTC GTC GTG CAG GTG ATG CGC GAT GGT CAC      912
Asp Ser Asp Val Thr Gln Val Val Val Gln Val Met Arg Asp Gly His
    290                 295                 300

AGC GAG GAG GTG GAG CTG ACG CAG ACT AAC GGG CAG TGG CGT TTT GTA      960
Ser Glu Glu Val Glu Leu Thr Gln Thr Asn Gly Gln Trp Arg Phe Val
305                 310                 315                 320

CCC GGC AGC GCG TGG ACT GAT GGC GAC TAT ACG CTG ACG GTA ACG GTG     1008
Pro Gly Ser Ala Trp Thr Asp Gly Asp Tyr Thr Leu Thr Val Thr Val
                325                 330                 335
```

```
AAA GAT GAG GCG GGT AAT ATT CGC CAC TCA GCG CCG TTG ACG GTC ACC     1056
Lys Asp Glu Ala Gly Asn Ile Arg His Ser Ala Pro Leu Thr Val Thr
            340                 345                 350

ATC GAT ACG CAA ATC ACC ATT GAC CAT ATT GAA CTG GTC AAT GAC AGC     1104
Ile Asp Thr Gln Ile Thr Ile Asp His Ile Glu Leu Val Asn Asp Ser
        355                 360                 365

GGT ATT CCG GAC GAT AAT CTG ACT AAT AAT GTG CGT CCG CAA CTT CCA     1152
Gly Ile Pro Asp Asp Asn Leu Thr Asn Asn Val Arg Pro Gln Leu Pro
    370                 375                 380

GGT GAC GGT ACC GAC GGA TGT CAA CGT GGT GCG CCT GAG CAT TGA         1197
Gly Asp Gly Thr Asp Gly Cys Gln Arg Gly Ala Pro Glu His
385                 390                 395
```

(2) INFORMATION FOR SEQ ID NO:21:

(i) SEQUENCE CHARACTERISTICS:
(A) LENGTH: 519 bases
(B) TYPE: nucleotide
(C) STRANDEDNESS: double stranded
(D) TOPOLOGY: linear (ix) FEATURE:
(D) OTHER INFORMATION: the coding nucleotides of SEQ ID NO:21 correspond to nucleotides 11766 through 12284 of SEQ ID NO:2

(xi) SEQUENCE DESCRIPTION: SEQ ID NO:21:

```
ATG TGC GTC CGC AAC TTC CAG GTG ACG GTA CCG ACG GAT GTC AAC GTG       48
Met Cys Val Arg Asn Phe Gln Val Thr Val Pro Thr Asp Val Asn Val
 1               5                  10                  15

GTG CGC CTG AGC ATT GAC GGC GGT AAG ACG TGG TTC AAC GTT ACC CAG       96
Val Arg Leu Ser Ile Asp Gly Gly Lys Thr Trp Phe Asn Val Thr Gln
            20                  25                  30

AGC GCG ACG CCG GGC GTC TGG GAT TAT ACC TGG CTG GCT GAT GTG GGA      144
Ser Ala Thr Pro Gly Val Trp Asp Tyr Thr Trp Leu Ala Asp Val Gly
        35                  40                  45

GAG GGT AAG CAT ACC CTG ACA GTG GAG GCG ACC GAC AAG GCG GGA AAC      192
Glu Gly Lys His Thr Leu Thr Val Glu Ala Thr Asp Lys Ala Gly Asn
    50                  55                  60

AAA ACG ACG CAG CAA CTG GAC TTC ATC ATC GAT ACC CTA CTG TCA GAA      240
Lys Thr Thr Gln Gln Leu Asp Phe Ile Ile Asp Thr Leu Leu Ser Glu
65                  70                  75                  80

CCG ACT ATC GTG CTG GAC AGC ACG GAC GAC AGC GGA ACA AAA GGC GAT      288
Pro Thr Ile Val Leu Asp Ser Thr Asp Asp Ser Gly Thr Lys Gly Asp
                85                  90                  95

CAC CTG ACC AAC GTA AAT AAG CCG ACG TTT TTA CTG GGC AAT ATT GAC      336
His Leu Thr Asn Val Asn Lys Pro Thr Phe Leu Leu Gly Asn Ile Asp
            100                 105                 110

GCA GAC GCG CGG TAT GTC ACG GTT GAG GTA CAG CAT GGC GGC ACG AAA      384
Ala Asp Ala Arg Tyr Val Thr Val Glu Val Gln His Gly Gly Thr Lys
        115                 120                 125

GAG GTG CTG ACG GCC ACC AAA GAC GCG ACC GGC AAC TGG AGC GTG ACA      432
Glu Val Leu Thr Ala Thr Lys Asp Ala Thr Gly Asn Trp Ser Val Thr
    130                 135                 140

CCG ACC GGC ACA TGG GCA GAT GGC GAC TAT ACG CTG ACA GTG AGG GTG      480
Pro Thr Gly Thr Trp Ala Asp Gly Asp Tyr Thr Leu Thr Val Arg Val
145                 150                 155                 160

GAA GAT GAG GCG GGG AAC GAA AAA CAC TCA GGT CGC TGA                 519
Glu Asp Glu Ala Gly Asn Glu Lys His Ser Gly Arg
                165                 170
```

(2) INFORMATION FOR SEQ ID NO:22:

```
    (i) SEQUENCE CHARACTERISTICS:
         (A) LENGTH: 918 bases
         (B) TYPE: nucleotide
         (C) STRANDEDNESS: double stranded
         (D) TOPOLOGY: linear

    (ix) FEATURE:
         (D) OTHER INFORMATION: the coding nucleotides of SEQ ID
              NO:22 correspond to nucleotides 12359 through
              13276 of SEQ ID NO:2

    (xi) SEQUENCE DESCRIPTION: SEQ ID NO:22:

ATG ACT AAC GAC GCC CAT CCG CAG TTC CGC GTG ACG GTA CCG GGG GAC       48
Met Thr Asn Asp Ala His Pro Gln Phe Arg Val Thr Val Pro Gly Asp
 1               5                  10                  15

GTT AAC GAA GTC AGT CTG AGC ATT GAC GGT GGC GTG ACC TGG GTT AAG       96
Val Asn Glu Val Ser Leu Ser Ile Asp Gly Gly Val Thr Trp Val Lys
            20                  25                  30

GCG ACA CAG AGC GCG ACG CCG GGC GTC TGG AAT TAT ACC TGG CCG GGC      144
Ala Thr Gln Ser Ala Thr Pro Gly Val Trp Asn Tyr Thr Trp Pro Gly
        35                  40                  45

ACC GTG CCG GAT GGC GAC TAT ACG CTG AAT GTG AAA GCG ACT GAC AAT      192
Thr Val Pro Asp Gly Asp Tyr Thr Leu Asn Val Lys Ala Thr Asp Asn
    50                  55                  60

GCG GGT AAT ACG GTG ACG GAG ACA CTC CAC TTC ACT ATT GAT ACT ACG      240
Ala Gly Asn Thr Val Thr Glu Thr Leu His Phe Thr Ile Asp Thr Thr
65                  70                  75                  80

TTG TCG ACG CCG GTG ATC GTA CTG GAT AGC GCG GAC GAC AGT GGT GTC      288
Leu Ser Thr Pro Val Ile Val Leu Asp Ser Ala Asp Asp Ser Gly Val
                85                  90                  95

CAT GGC GAT AAC ATG ACG AAT AGC ACC CAG CCG ACA TTT GCC CTG CAG      336
His Gly Asp Asn Met Thr Asn Ser Thr Gln Pro Thr Phe Ala Leu Gln
            100                 105                 110

CAT ATT GAT GAT GAT GCC GTT CGC GTT ACG GTC AGC GTA GAG CAT GGC      384
His Ile Asp Asp Asp Ala Val Arg Val Thr Val Ser Val Glu His Gly
        115                 120                 125

GGC GTC ACC ACC ACA TTT GAC GCC ACG AAA GAC GCA GGC GGA TGG ACC      432
Gly Val Thr Thr Thr Phe Asp Ala Thr Lys Asp Ala Gly Gly Trp Thr
    130                 135                 140

TTT ACG CCG ACA GGG GCG TGG GCG GAT GGT GAT TAT ACC CTG AGT GTG      480
Phe Thr Pro Thr Gly Ala Trp Ala Asp Gly Asp Tyr Thr Leu Ser Val
145                 150                 155                 160

TCA GTC GAA GAT AAA GCG GGG AAC ACC AGC CAT TCT GCA TCG CTG ACG      528
Ser Val Glu Asp Lys Ala Gly Asn Thr Ser His Ser Ala Ser Leu Thr
                165                 170                 175

GTG ACG GTG GAC ACG CAA ATC GCC ATT AAT AAC ATT GAA CTG GTC AAT      576
Val Thr Val Asp Thr Gln Ile Ala Ile Asn Asn Ile Glu Leu Val Asn
            180                 185                 190

GAC AGC GGT ATT CCC GAC GAT AAT CTG ACT AAT AAT GTG CGT CCG CAC      624
Asp Ser Gly Ile Pro Asp Asp Asn Leu Thr Asn Asn Val Arg Pro His
        195                 200                 205

TTC CAG GTG ACG GTA CCG ACG GAT GTC AAC GTG GTG CGC CTG AGC ATT      672
Phe Gln Val Thr Val Pro Thr Asp Val Asn Val Val Arg Leu Ser Ile
    210                 215                 220

GAC GGC GGC AAG ACG TGG TTC AAC GCT ACC CAG AGC GCG ACG CCG GGC      720
Asp Gly Gly Lys Thr Trp Phe Asn Ala Thr Gln Ser Ala Thr Pro Gly
225                 230                 235                 240

GTC TGG GAT TAT ACC TGG CTG GCT GAT GTG GGA GAG GGT AAG CAT ACC      768
Val Trp Asp Tyr Thr Trp Leu Ala Asp Val Gly Glu Gly Lys His Thr
                245                 250                 255

CTG ACA GTG GGG GCG ACC GAC AAG GCG GGA AAC AAA ACG ACG CAG CAA      816
Leu Thr Val Gly Ala Thr Asp Lys Ala Gly Asn Lys Thr Thr Gln Gln
            260                 265                 270
```

```
CTG GAC TTC ATC ATC GAT ACC CTA CTG TCA GAA CCG ACT ATC GTG CTG       864
Leu Asp Phe Ile Ile Asp Thr Leu Leu Ser Glu Pro Thr Ile Val Leu
        275                 280                 285

GAC AAC ACG GAC TAC AGC GGA AAC AAA AGG CGA TCA CCT GAC CAA CGT       912
Asp Asn Thr Asp Tyr Ser Gly Asn Lys Arg Arg Ser Pro Asp Gln Arg
    290                 295                 300

AAA TAA                                                               918
Lys
305
```

(2) INFORMATION FOR SEQ ID NO:23:

(i) SEQUENCE CHARACTERISTICS:
(A) LENGTH: 1002 bases
(B) TYPE: nucleotide
(C) STRANDEDNESS: double stranded
(D) TOPOLOGY: linear (ix) FEATURE:
(D) OTHER INFORMATION: the coding nucleotides of SEQ ID NO:23 correspond to nucleotides 13821 through 14822 of SEQ ID NO:2

(xi) SEQUENCE DESCRIPTION: SEQ ID NO:23:

```
ATG GAT AGC AGG GAC GAT ACA GGT GCC ATT GGC GAT CAT ATT ACG AGC        48
Met Asp Ser Arg Asp Asp Thr Gly Ala Ile Gly Asp His Ile Thr Ser
 1               5                  10                  15

GTC AAA AGA CCG GGC TTT ACT ATT GGC AAT ATT GAC GCC GAT GCG CAC        96
Val Lys Arg Pro Gly Phe Thr Ile Gly Asn Ile Asp Ala Asp Ala His
            20                  25                  30

TCG GTC ATT TTG CGG ATC ACA CAG GGC GGC AAT AGC CAG GAA GTG ACA       144
Ser Val Ile Leu Arg Ile Thr Gln Gly Gly Asn Ser Gln Glu Val Thr
        35                  40                  45

CTA ACC CAG GTT GGA GGA CAG TGG CGC TTT ACG CCA GAT GCT GAC TGG       192
Leu Thr Gln Val Gly Gly Gln Trp Arg Phe Thr Pro Asp Ala Asp Trp
    50                  55                  60

GCG GAC GGT AGC TAT ACG CTG ACG GTA GAG GTA ACG GAT AAC GCA GGA       240
Ala Asp Gly Ser Tyr Thr Leu Thr Val Glu Val Thr Asp Asn Ala Gly
65                  70                  75                  80

AAC GTT CGT CAG TCC ACG CCG CTG GTG GTG ACG GTG GAC ACG CAA ACC       288
Asn Val Arg Gln Ser Thr Pro Leu Val Val Thr Val Asp Thr Gln Thr
                85                  90                  95

AGC ATT ACT GAT ATT ACA TTG GTC AAT GAT CAT GGC GTG CCT GAT GAC       336
Ser Ile Thr Asp Ile Thr Leu Val Asn Asp His Gly Val Pro Asp Asp
            100                 105                 110

AAT CTA ACT AAT AGC ACC CGT CCG CAG TTT GAG ATC ACG GTG CCG GCG       384
Asn Leu Thr Asn Ser Thr Arg Pro Gln Phe Glu Ile Thr Val Pro Ala
        115                 120                 125

GAT GTG AAT TCT GTG CAA CTG AGC ATT GAT GGG GGC GCA AAC TGG GTG       432
Asp Val Asn Ser Val Gln Leu Ser Ile Asp Gly Gly Ala Asn Trp Val
    130                 135                 140

AGC GCG ACG CAG GGT ATC GAA GGC GTC TGG GGC TAT ACC TGG CCA ACG       480
Ser Ala Thr Gln Gly Ile Glu Gly Val Trp Gly Tyr Thr Trp Pro Thr
145                 150                 155                 160

GAT ATG GGC GAT GGA AAA CAC ACC CTA ACC GTC ATG GTC ACC GAC AGA       528
Asp Met Gly Asp Gly Lys His Thr Leu Thr Val Met Val Thr Asp Arg
                165                 170                 175

GCG GGC AAT ACG GCG ACG CAA ACG CTT GAA TTT TTC ATC GAC ACC CGG       576
Ala Gly Asn Thr Ala Thr Gln Thr Leu Glu Phe Phe Ile Asp Thr Arg
            180                 185                 190

TTG TCG ACG CCG ACC ATT GCG CTG GAT AGC ACG GAT GAT ACC GGT ACG       624
Leu Ser Thr Pro Thr Ile Ala Leu Asp Ser Thr Asp Asp Thr Gly Thr
        195                 200                 205
```

```
CCT GGC GAT GAT ATG ACC AAT CGC ACC CGA CCG ACC TTT ATT CTG CAG        672
Pro Gly Asp Asp Met Thr Asn Arg Thr Arg Pro Thr Phe Ile Leu Gln
    210                 215                 220

AAT ATC GAT TCG GAT GTT ATC AAC GTT ACA GTC AGC GTC ACG CAT AAT        720
Asn Ile Asp Ser Asp Val Ile Asn Val Thr Val Ser Val Thr His Asn
225                 230                 235                 240

GGA ACG ACA ACC TCG TTT ACT GCG ACA CAG GGG GCT GGA GGA TGG AGC        768
Gly Thr Thr Thr Ser Phe Thr Ala Thr Gln Gly Ala Gly Gly Trp Ser
                245                 250                 255

TTT ACA CCG CCA GCG CCG TGG GGC GAC GGT GAT TAT ACG CTG ACG GTG        816
Phe Thr Pro Pro Ala Pro Trp Gly Asp Gly Asp Tyr Thr Leu Thr Val
            260                 265                 270

ACA GTG GAG GAT CGG GCG GGA AAT ACG CGT CCG TCT ACG CCG CTG ACG        864
Thr Val Glu Asp Arg Ala Gly Asn Thr Arg Pro Ser Thr Pro Leu Thr
        275                 280                 285

GTG ACA GTG GAT ACG CAA ATA GCC ATT GAT CGT ATT GAA TTA GTC AAC        912
Val Thr Val Asp Thr Gln Ile Ala Ile Asp Arg Ile Glu Leu Val Asn
    290                 295                 300

GAT AGC GGC GTC CCT GGC GAT AAT GTG ACA AAA CAT GTG CGT CCG CAG        960
Asp Ser Gly Val Pro Gly Asp Asn Val Thr Lys His Val Arg Pro Gln
305                 310                 315                 320

TTC CAG ATC TCG GTA CCG GAT GAT GTG GAA AAG TTC TTC TGA               1002
Phe Gln Ile Ser Val Pro Asp Asp Val Glu Lys Phe Phe
                325                 330
```

(2) INFORMATION FOR SEQ ID NO:24:

(i) SEQUENCE CHARACTERISTICS:
(A) LENGTH: 621 bases
(B) TYPE: nucleotide
(C) STRANDEDNESS: double stranded
(D) TOPOLOGY: linear (ix) FEATURE:
(D) OTHER INFORMATION: the coding nucleotides of SEQ ID NO:24 correspond to nucleotides 14903 through 15523 of SEQ ID NO:2

(xi) SEQUENCE DESCRIPTION: SEQ ID NO:24:

```
ATG CCA GAG GGA CAG CAT ACC CTG ACC GTG GAA GTG ACT GAC GGT GCG         48
Met Pro Glu Gly Gln His Thr Leu Thr Val Glu Val Thr Asp Gly Ala
 1               5                  10                  15

GGT AAT AAG ATG ACG GAG ACG CTC AAT TTC ACT ATC GAT ATC ACG TTG         96
Gly Asn Lys Met Thr Glu Thr Leu Asn Phe Thr Ile Asp Ile Thr Leu
            20                  25                  30

TTA ACG CCA ACC ATT GAG CTA GCG CCC GAT CAG GAT ACC GGA CAG AAT        144
Leu Thr Pro Thr Ile Glu Leu Ala Pro Asp Gln Asp Thr Gly Gln Asn
        35                  40                  45

AAG AAC GAT AAT CTG ACC AGC GTC ACT CAG CCG GTA TTT GTG TTG GGG        192
Lys Asn Asp Asn Leu Thr Ser Val Thr Gln Pro Val Phe Val Leu Gly
    50                  55                  60

AGT ATC GAT AAA GAT GTT CGA CAC GTG GAA TTG AGT ATT GAG CAT AAC        240
Ser Ile Asp Lys Asp Val Arg His Val Glu Leu Ser Ile Glu His Asn
65                  70                  75                  80

GGC ACG TTT AAA ACG GTG GTA CTC ACC GAA TCA GCC GAC GGC TGG CGC        288
Gly Thr Phe Lys Thr Val Val Leu Thr Glu Ser Ala Asp Gly Trp Arg
                85                  90                  95

TAT CGA CCG GAT TCT GCT TTG GCG GAC GGT AGC TAC ACA TTC ACC GTG        336
Tyr Arg Pro Asp Ser Ala Leu Ala Asp Gly Ser Tyr Thr Phe Thr Val
            100                 105                 110

ACG GTA ACA GAT GTG GCA GGC AAC CAG CAA ACA TCC GCG CCT TTA AAG        384
Thr Val Thr Asp Val Ala Gly Asn Gln Gln Thr Ser Ala Pro Leu Lys
        115                 120                 125
```

```
GTG ACG ATA GAC GGT ACG TTG ACT ACG CCG GTG ATT GAA CTG GCA GCT      432
Val Thr Ile Asp Gly Thr Leu Thr Thr Pro Val Ile Glu Leu Ala Ala
    130                 135                 140

GGC GAA GAT AGC GGT ACT GTT GGC GAT CGC CTC ACC AAT CAC GAT CGG      480
Gly Glu Asp Ser Gly Thr Val Gly Asp Arg Leu Thr Asn His Asp Arg
145                 150                 155                 160

CCT GTG TTC GAC ATA CAT CAG GTT GAT TCT GAC GTT ACG CGC GTG ATG      528
Pro Val Phe Asp Ile His Gln Val Asp Ser Asp Val Thr Arg Val Met
                165                 170                 175

GTC AAA GTA ACT TAC AAC GGT AAA ACG CAC GAA GAA GCG GCG GTA TTC      576
Val Lys Val Thr Tyr Asn Gly Lys Thr His Glu Glu Ala Ala Val Phe
            180                 185                 190

ACC AAT GGT CAA TGG CGC TTT ACG CCT TCT GCG AAG CTG GGC TGA          621
Thr Asn Gly Gln Trp Arg Phe Thr Pro Ser Ala Lys Leu Gly
        195                 200                 205
```

(2) INFORMATION FOR SEQ ID NO:25:

(i) SEQUENCE CHARACTERISTICS:
(A) LENGTH: 372 bases
(B) TYPE: nucleotide
(C) STRANDEDNESS: double stranded
(D) TOPOLOGY: linear (ix) FEATURE:
(D) OTHER INFORMATION: the coding nucleotides of SEQ ID NO:25 correspond to nucleotides 15483 through 15854 of SEQ ID NO:2

(xi) SEQUENCE DESCRIPTION: SEQ ID NO:25:

```
ATG GTC AAT GGC GCT TTA CGC CTT CTG CGA AGC TGG GCT GAT GGC TCA       48
Met Val Asn Gly Ala Leu Arg Leu Leu Arg Ser Trp Ala Asp Gly Ser
 1               5                  10                  15

TAT CAG TTA GCC GTT GTG GTG GAA GAT CTG GCG GGG AAT GTA AAA GAG       96
Tyr Gln Leu Ala Val Val Val Glu Asp Leu Ala Gly Asn Val Lys Glu
            20                  25                  30

TCT GCG CCG TTT GAG GTG CGT ATT GAT ACC ACG ACA ACC ATT AAC AAT      144
Ser Ala Pro Phe Glu Val Arg Ile Asp Thr Thr Thr Thr Ile Asn Asn
        35                  40                  45

ATC GTA TTG CTT AAT GAT ACC GGC GTG CAG AAT GAT CAA TTA ACG AAT      192
Ile Val Leu Leu Asn Asp Thr Gly Val Gln Asn Asp Gln Leu Thr Asn
    50                  55                  60

GTT GCC AAA CCG TCA TTC AGA ATT GAC GTT CCC GGT GAT GTC GTC CAG      240
Val Ala Lys Pro Ser Phe Arg Ile Asp Val Pro Gly Asp Val Val Gln
65                  70                  75                  80

GTA CGT GTA ACC CTG GAT GGT GGC GCT AAC TGG AAT GTG ATA CGC AAA      288
Val Arg Val Thr Leu Asp Gly Gly Ala Asn Trp Asn Val Ile Arg Lys
                85                  90                  95

AAT GCC GAC GGA CAG TGG ATT TTT GAC AGC CCG AAT ACT CTG GTT GAC      336
Asn Ala Asp Gly Gln Trp Ile Phe Asp Ser Pro Asn Thr Leu Val Asp
            100                 105                 110

GGC ACA TAT ACC CTT CGC GTA GAG GCC ACG GGA TGA                      372
Gly Thr Tyr Thr Leu Arg Val Glu Ala Thr Gly
        115                 120
```

(2) INFORMATION FOR SEQ ID NO:26:

(i) SEQUENCE CHARACTERISTICS:
(A) LENGTH: 3870 bases
(B) TYPE: nucleotide
(C) STRANDEDNESS: double stranded
(D) TOPOLOGY: linear (ix) FEATURE:
(D) OTHER INFORMATION: the coding nucleotides of SEQ ID NO:26 correspond to nucleotides 17102 through 20971 of SEQ ID NO:2

(xi) SEQUENCE DESCRIPTION: SEQ ID NO:26:

```
ATG CTG GAC GAC GCC GGA AAG GAT TCT ACG GAT GGT ATT ACG AAT ATT       48
Met Leu Asp Asp Ala Gly Lys Asp Ser Thr Asp Gly Ile Thr Asn Ile
 1               5                  10                  15

ACC TCT CCA CGT TTT GAA ATT TCA GCC AGA GAA CCG CTG CAG AGC GTG       96
Thr Ser Pro Arg Phe Glu Ile Ser Ala Arg Glu Pro Leu Gln Ser Val
            20                  25                  30

ACG GTA ATT TTA AAC GGG AAA TCC AGC ACA CTG ACT CAG GGG GCA GGT      144
Thr Val Ile Leu Asn Gly Lys Ser Ser Thr Leu Thr Gln Gly Ala Gly
        35                  40                  45

AAT AAA TGG CTG TTT ACC CCT GAT ACA CCG TTA GTG GAT GGA ACT TAC      192
Asn Lys Trp Leu Phe Thr Pro Asp Thr Pro Leu Val Asp Gly Thr Tyr
    50                  55                  60

AAA ATA GAA ATA GTG GCT GAA GAT ATC GCA GGT AAT AAA ATT AGC AAA      240
Lys Ile Glu Ile Val Ala Glu Asp Ile Ala Gly Asn Lys Ile Ser Lys
65                  70                  75                  80

GAG GTA TCA TTC ACA ATA GAC ACT ATT GTT TCT GAT CCC AGT ATT GAT      288
Glu Val Ser Phe Thr Ile Asp Thr Ile Val Ser Asp Pro Ser Ile Asp
                85                  90                  95

TTG CTG GAT GCG GAT GAT ACT GGC GAA AGC GCT GTT GAT AAT ATT ACG      336
Leu Leu Asp Ala Asp Asp Thr Gly Glu Ser Ala Val Asp Asn Ile Thr
            100                 105                 110

AGT GTC ACT ACA CCA CGT TTC GTT ATT GGC AAT GTA CCC GCC GAT ATT      384
Ser Val Thr Thr Pro Arg Phe Val Ile Gly Asn Val Pro Ala Asp Ile
        115                 120                 125

GAT ACT GTT GTT ATC AGA ATT AAC GGC GTT TCT TAT CCG GTT ACG GCA      432
Asp Thr Val Val Ile Arg Ile Asn Gly Val Ser Tyr Pro Val Thr Ala
    130                 135                 140

AAT GGC AAT AAC CTC TGG GAA TTT CAG GTT CCC GTT GCG TTA AAC GAT      480
Asn Gly Asn Asn Leu Trp Glu Phe Gln Val Pro Val Ala Leu Asn Asp
145                 150                 155                 160

GGC GTA TAT GAA GCC GTT GTT GTC TTC AGA GAT ATT GCC GGA AAT ATT      528
Gly Val Tyr Glu Ala Val Val Val Phe Arg Asp Ile Ala Gly Asn Ile
                165                 170                 175

TCT GAA ATT AAG CTG CCC TTT ACC ATT GAT ACC ACG ACA AGC GTC AGT      576
Ser Glu Ile Lys Leu Pro Phe Thr Ile Asp Thr Thr Thr Ser Val Ser
            180                 185                 190

GTC AGA ATG GAG CTA GCG TCT GAT ACC GGA AAT TCC AAT AGC GAT AAC      624
Val Arg Met Glu Leu Ala Ser Asp Thr Gly Asn Ser Asn Ser Asp Asn
        195                 200                 205

CTT ACG AAT AAG CAA AAT CCC AAA TTC GAA GGT ACT GCA GAG CCC AAT      672
Leu Thr Asn Lys Gln Asn Pro Lys Phe Glu Gly Thr Ala Glu Pro Asn
    210                 215                 220

GCG AAA CTG GTG ATT ACC ATT GTT GAC GAT AAG TCA GGT CAG GAG GTT      720
Ala Lys Leu Val Ile Thr Ile Val Asp Asp Lys Ser Gly Gln Glu Val
225                 230                 235                 240

TTA AAA CAA ACG ATT ACG GTT GGC GCT GAT GGC AAC TGG AGT GTG ACG      768
Leu Lys Gln Thr Ile Thr Val Gly Ala Asp Gly Asn Trp Ser Val Thr
                245                 250                 255

CCG AAT ATA CTG CCG GAT GGC ATG TAT ACC ATC AAC GTC GTC GCA ACA      816
Pro Asn Ile Leu Pro Asp Gly Met Tyr Thr Ile Asn Val Val Ala Thr
            260                 265                 270

GAT GTC GCG GGA AAT ACT GCG CAA ACG CAG GAA AGA TTC ACT ATC GAT      864
Asp Val Ala Gly Asn Thr Ala Gln Thr Gln Glu Arg Phe Thr Ile Asp
        275                 280                 285

ACG GTT ACG ATC GAT CCC ACC ATT CGC CTT TCG GAT CCA TCT ATT GAT      912
Thr Val Thr Ile Asp Pro Thr Ile Arg Leu Ser Asp Pro Ser Ile Asp
    290                 295                 300
```

```
GAT CAG CAT GAA GCA ACC AGC CTG CGT CCT GAG TTC AAA GGG TTT GCC      960
Asp Gln His Glu Ala Thr Ser Leu Arg Pro Glu Phe Lys Gly Phe Ala
305                 310                 315                 320

GAA GCG TTC TCG ACG ATT ATG ATT CAG TGG GAT GGG AAA GTG GTC GGC     1008
Glu Ala Phe Ser Thr Ile Met Ile Gln Trp Asp Gly Lys Val Val Gly
                325                 330                 335

TCG GCA AAC GCC AAT GCG AAT GGC GAA TGG AGT TGG ACG CCG CCA TCA     1056
Ser Ala Asn Ala Asn Ala Asn Gly Glu Trp Ser Trp Thr Pro Pro Ser
            340                 345                 350

GTA TTA GCG CCA GGC TCC TAT GTT GTG AGC ATT GTT GCC AAA GAT AAA     1104
Val Leu Ala Pro Gly Ser Tyr Val Val Ser Ile Val Ala Lys Asp Lys
        355                 360                 365

GCG GGT AAT GAT TCG TCG CAG GTC GAC TTT CCT GTC GTA ATA CCT GTT     1152
Ala Gly Asn Asp Ser Ser Gln Val Asp Phe Pro Val Val Ile Pro Val
    370                 375                 380

ATT GAT GTC ACG CCT CCA ACC ATA AAG CTC AGC GAG GAG AGC GAT AGT     1200
Ile Asp Val Thr Pro Pro Thr Ile Lys Leu Ser Glu Glu Ser Asp Ser
385                 390                 395                 400

GGC GCC TTA GGA GAC TTT ACC ACG AAT AAT AAA ACG CCG ACC CTG ATT     1248
Gly Ala Leu Gly Asp Phe Thr Thr Asn Asn Lys Thr Pro Thr Leu Ile
                405                 410                 415

GGG AGC ACG TTA CCT AAT ACG ATT GTG AGT ATT TAT GTG GAT GGC GTG     1296
Gly Ser Thr Leu Pro Asn Thr Ile Val Ser Ile Tyr Val Asp Gly Val
            420                 425                 430

AAG GTC GGC GAG GCG ACA GCG GAT ACA GCG GGT CGA TAT ACT TTC CAG     1344
Lys Val Gly Glu Ala Thr Ala Asp Thr Ala Gly Arg Tyr Thr Phe Gln
        435                 440                 445

TTA TCG GAA ATG AAA GAT GGC CAT TAT GTC GTC CAG GTG GGT ATC GTC     1392
Leu Ser Glu Met Lys Asp Gly His Tyr Val Val Gln Val Gly Ile Val
    450                 455                 460

AAC CCT CGC GAT AAT AGC GAA CTG CGT TCT ACC GCC GTT GAT GTC ACT     1440
Asn Pro Arg Asp Asn Ser Glu Leu Arg Ser Thr Ala Val Asp Val Thr
465                 470                 475                 480

ATC GAT ACC GAG GTT GCT GAA CTG GTA TGG AAT ATA TCT GGA ATG CAT     1488
Ile Asp Thr Glu Val Ala Glu Leu Val Trp Asn Ile Ser Gly Met His
                485                 490                 495

GAG GGC GGA TAT ATC AAT ACG GTG ACG CCG GAG ATT GGC GGC ACC AGT     1536
Glu Gly Gly Tyr Ile Asn Thr Val Thr Pro Glu Ile Gly Gly Thr Ser
            500                 505                 510

GAG CCA AAC AGC AAA ATC ACT ATC TTT GTG AAT GGC GTT GGA AAA GCG     1584
Glu Pro Asn Ser Lys Ile Thr Ile Phe Val Asn Gly Val Gly Lys Ala
        515                 520                 525

ATT GCT TAT ACG ACA GGC GCA GGA CAC TGG GGC GTA GTA TTA CCC GCT     1632
Ile Ala Tyr Thr Thr Gly Ala Gly His Trp Gly Val Val Leu Pro Ala
    530                 535                 540

TTG GGT AAT GAC GGT AAT TAT GAA TTA ACG TTT AAA GTT GAA GAC GTT     1680
Leu Gly Asn Asp Gly Asn Tyr Glu Leu Thr Phe Lys Val Glu Asp Val
545                 550                 555                 560

GCC GGT AAT ATC AGA GAG TTT GGT CCG CAG AAT GTA ATA CTG GAT ACA     1728
Ala Gly Asn Ile Arg Glu Phe Gly Pro Gln Asn Val Ile Leu Asp Thr
                565                 570                 575

GTA ATT TCG CCG TTA ACC GTG GTA TTA CGC GAA GCT GAT GAC AGT GGC     1776
Val Ile Ser Pro Leu Thr Val Val Leu Arg Glu Ala Asp Asp Ser Gly
            580                 585                 590

AAA GTT GGC GAC TGG ATC ACC AAT AAA TCT CAT GTC ACC ATC GAT GGT     1824
Lys Val Gly Asp Trp Ile Thr Asn Lys Ser His Val Thr Ile Asp Gly
        595                 600                 605

ACT GCC GAA GCC GGA AGT ACT TTA ACC ATC AGG AAT CCG CAG GGA GTG     1872
Thr Ala Glu Ala Gly Ser Thr Leu Thr Ile Arg Asn Pro Gln Gly Val
    610                 615                 620
```

```
GTT ATT GCT ACC CTG GTG GTA GGC AAT GAT GGT CGA TGG AGC GCA GAA     1920
Val Ile Ala Thr Leu Val Val Gly Asn Asp Gly Arg Trp Ser Ala Glu
625                 630                 635                 640

TTA GAT CTG CGT GAA GGT AGT AAT GCC TTT GTC GTG GTA TCG GAA GAT     1968
Leu Asp Leu Arg Glu Gly Ser Asn Ala Phe Val Val Val Ser Glu Asp
                645                 650                 655

AAA GCG GGC AAC AGT CAA CAA AAA GAG ATT CTG ATA GAA CAT GAT ACG     2016
Lys Ala Gly Asn Ser Gln Gln Lys Glu Ile Leu Ile Glu His Asp Thr
            660                 665                 670

CAG ATT GAA ATC AGC GAT ATT TCA TTA AGT CGG GAT ACT AAT AGC GGT     2064
Gln Ile Glu Ile Ser Asp Ile Ser Leu Ser Arg Asp Thr Asn Ser Gly
        675                 680                 685

GAT AAA TAT GAT CTG ATT ACC AAT AAT AAG TCT CCG GTA CTG GTT GCC     2112
Asp Lys Tyr Asp Leu Ile Thr Asn Asn Lys Ser Pro Val Leu Val Ala
    690                 695                 700

AGG ACC GAT CCC GGC GCG ACG GTA CAG GTT TAT ATT AAT GGT GTG TTA     2160
Arg Thr Asp Pro Gly Ala Thr Val Gln Val Tyr Ile Asn Gly Val Leu
705                 710                 715                 720

CAA GGC ACA GTA GAG GCG AGT TCG TCA GGT AAT ATT AGC TAT ACC ATG     2208
Gln Gly Thr Val Glu Ala Ser Ser Ser Gly Asn Ile Ser Tyr Thr Met
                725                 730                 735

CCG GCA AAT AGC GCC GAC GGC GAG TAT CAG GTG CAA TTT GTT GCT ACG     2256
Pro Ala Asn Ser Ala Asp Gly Glu Tyr Gln Val Gln Phe Val Ala Thr
            740                 745                 750

GAT ACT GCT GGT AAC CGG GTT GAG TCT GCG ATT ACA ACC GTG ACA ATC     2304
Asp Thr Ala Gly Asn Arg Val Glu Ser Ala Ile Thr Thr Val Thr Ile
        755                 760                 765

GAT TCT CAA ATT GCT GTC TTT GAT ATT GAT GAA GAT TCA TTA CCG GCC     2352
Asp Ser Gln Ile Ala Val Phe Asp Ile Asp Glu Asp Ser Leu Pro Ala
    770                 775                 780

CTC TCT AAT AAC CGA GCG TTG TCA GTC TCA GGT GTC GGG GAG GCT GGT     2400
Leu Ser Asn Asn Arg Ala Leu Ser Val Ser Gly Val Gly Glu Ala Gly
785                 790                 795                 800

TCT CAG GTC AGC ATC TTT GTC GAC GGT AAA TTA GTC AAC GTT GTT ATG     2448
Ser Gln Val Ser Ile Phe Val Asp Gly Lys Leu Val Asn Val Val Met
                805                 810                 815

GTT GAG GCT GAT GGC ACA TGG CGC GCG CCG ATA CTG CTG CAA GAT GAT     2496
Val Glu Ala Asp Gly Thr Trp Arg Ala Pro Ile Leu Leu Gln Asp Asp
            820                 825                 830

GGT ACG TTT AAT ATT CAT TTC AGC ATT ACT GAC GTT GCT GGC AAC ACT     2544
Gly Thr Phe Asn Ile His Phe Ser Ile Thr Asp Val Ala Gly Asn Thr
        835                 840                 845

GAA GTG AGC AAG GAT TAT AGC GTG GAT GTC GAT TCA TCA ACC GAC TTC     2592
Glu Val Ser Lys Asp Tyr Ser Val Asp Val Asp Ser Ser Thr Asp Phe
    850                 855                 860

CCA ACG CTC AAC CTT GAA GAT GCA AGC AAC TCT GGT TCA CTT GAC GAT     2640
Pro Thr Leu Asn Leu Glu Asp Ala Ser Asn Ser Gly Ser Leu Asp Asp
865                 870                 875                 880

CTG ATT ACT AAT CAC AAC AAG CCT GTA TTA GTT GGC ACC GCA GAA GCG     2688
Leu Ile Thr Asn His Asn Lys Pro Val Leu Val Gly Thr Ala Glu Ala
                885                 890                 895

GGA GCC ACA ATC CAT ATT TAT GTG GAT GAA AAG ATC GTG GCA AAT GTT     2736
Gly Ala Thr Ile His Ile Tyr Val Asp Glu Lys Ile Val Ala Asn Val
            900                 905                 910

CTT GTG CTT GAA GAT GGA ACC TGG TCC TAT CAG TTT GAT AAT GCG TTA     2784
Leu Val Leu Glu Asp Gly Thr Trp Ser Tyr Gln Phe Asp Asn Ala Leu
        915                 920                 925

AAA GAT GGT GAA TAT TCT ATC CGT GTG GTT GCC GAA GAC CCG GCA GGT     2832
Lys Asp Gly Glu Tyr Ser Ile Arg Val Val Ala Glu Asp Pro Ala Gly
    930                 935                 940
```

```
AAT ACG GCA GAA TCG CCT CGC TTA CTC GTC ACG ATA GAT ACC AGT ACG      2880
Asn Thr Ala Glu Ser Pro Arg Leu Leu Val Thr Ile Asp Thr Ser Thr
945                 950                 955                 960

TTT ATC GAT AAT CCT GCT ATG GTG GCA GGT TCT GAT AAT GGT ATT TTC      2928
Phe Ile Asp Asn Pro Ala Met Val Ala Gly Ser Asp Asn Gly Ile Phe
                965                 970                 975

AGT AAT GAT AGT ATA ACG AGT CAG ACC CGG CCT ACG TTT AGT ATT TTT      2976
Ser Asn Asp Ser Ile Thr Ser Gln Thr Arg Pro Thr Phe Ser Ile Phe
            980                 985                 990

GGA GAA ATG AAC CAG AGT GTT CAG ATT TTC ATT GAT GGA GTG CTA GTC      3024
Gly Glu Met Asn Gln Ser Val Gln Ile Phe Ile Asp Gly Val Leu Val
        995                1000                1005

GAT ACG ATC ACG GTG ACC GAC AGA AAT CAA GTT TAT CGA CCT GAG TCA      3072
Asp Thr Ile Thr Val Thr Asp Arg Asn Gln Val Tyr Arg Pro Glu Ser
    1010                1015                1020

CCG TTG GGC GAT GGT TCC CAT AGC ATT TAT TAT GTT ATC ACC GAT AAA      3120
Pro Leu Gly Asp Gly Ser His Ser Ile Tyr Tyr Val Ile Thr Asp Lys
1025                1030                1035                1040

GCA GGC AAC ACG GCT ACC TCG AAA ACG CTA AAC TTT ACT ATC GAT ACC      3168
Ala Gly Asn Thr Ala Thr Ser Lys Thr Leu Asn Phe Thr Ile Asp Thr
                1045                1050                1055

TTT AAT ACG ACG CCT GTC GCC ATT GAT TCT ATC GGT GGA CAA ACG TTA      3216
Phe Asn Thr Thr Pro Val Ala Ile Asp Ser Ile Gly Gly Gln Thr Leu
            1060                1065                1070

GCA GAG ATG ACC GGT AGT GAT GGC AAA ATA TAT ATA ACG GAC ACG ACG      3264
Ala Glu Met Thr Gly Ser Asp Gly Lys Ile Tyr Ile Thr Asp Thr Thr
        1075                1080                1085

CGT AAC TTA TTG TTT AGT GGC AGT GCC GAG CCC AAT AGC AAA ATA GAA      3312
Arg Asn Leu Leu Phe Ser Gly Ser Ala Glu Pro Asn Ser Lys Ile Glu
    1090                1095                1100

ATC ATC ATT AAT GGC TTA AAT GTG GGG GAA GTT TGG GTT AAT GAA AAA      3360
Ile Ile Ile Asn Gly Leu Asn Val Gly Glu Val Trp Val Asn Glu Lys
1105                1110                1115                1120

GGC CAC TGG CAG ATG CCG GTG AAC CCG CTT TAT TTC ACA GAA GGC CAA      3408
Gly His Trp Gln Met Pro Val Asn Pro Leu Tyr Phe Thr Glu Gly Gln
                1125                1130                1135

CTG GAT ATC ACT GTT AAA TCT ACG GAC CGT GCT GGT AAC GTA AAT CAG      3456
Leu Asp Ile Thr Val Lys Ser Thr Asp Arg Ala Gly Asn Val Asn Gln
            1140                1145                1150

GAA AAG TAT TCC ATT TGG GTT GAT ACG CAT ATC AAG GTA TTT ACC AGC      3504
Glu Lys Tyr Ser Ile Trp Val Asp Thr His Ile Lys Val Phe Thr Ser
        1155                1160                1165

GAG CTT GAT GAC AAT AAA TCA TCA TCG AAA ACG GAA TGG TGG AGT AAT      3552
Glu Leu Asp Asp Asn Lys Ser Ser Ser Lys Thr Glu Trp Trp Ser Asn
    1170                1175                1180

AGC GAT CTC ATT ACC ATG CGA GGC ACG GGT GAA ATT GGC GCT ACG GTA      3600
Ser Asp Leu Ile Thr Met Arg Gly Thr Gly Glu Ile Gly Ala Thr Val
1185                1190                1195                1200

TCA TTA ATC GTG GCT GGC GTC ACG CTG GCA ACT GCT GTT GTG GCG GCA      3648
Ser Leu Ile Val Ala Gly Val Thr Leu Ala Thr Ala Val Val Ala Ala
                1205                1210                1215

ACA GGA CGA TGG GAA TTA TCA ACA GAC AAG CTT CCA GAA GGG ACT TAC      3696
Thr Gly Arg Trp Glu Leu Ser Thr Asp Lys Leu Pro Glu Gly Thr Tyr
            1220                1225                1230

GAT ATT AGT TTG GTC ATT GAA GAT AGC CCG GAA ATC GTT GGG AAG ATG      3744
Asp Ile Ser Leu Val Ile Glu Asp Ser Pro Glu Ile Val Gly Lys Met
        1235                1240                1245

TGC GTG AAA TAT TTA TTG ACC GAA CCC GCC AAA TGC TCC GGT CGT AAC      3792
Cys Val Lys Tyr Leu Leu Thr Glu Pro Ala Lys Cys Ser Gly Arg Asn
    1250                1255                1260
```

```
GTA TTC AGA TAT TGT CAA CGA TCT AAT TAT TAT GCA GGG GAC GGC GGA     3840
Val Phe Arg Tyr Cys Gln Arg Ser Asn Tyr Tyr Ala Gly Asp Gly Gly
1265                1270                1275                1280

AGC CAA ATC TCA GCT AAT AAT AAC CGA TAG                             3870
Ser Gln Ile Ser Ala Asn Asn Asn Arg
                1285
```

(2) INFORMATION FOR SEQ ID NO:27:

(i) SEQUENCE CHARACTERISTICS:
(A) LENGTH: 1392 bases
(B) TYPE: nucleotide
(C) STRANDEDNESS: double stranded
(D) TOPOLOGY: linear (ix) FEATURE:
(D) OTHER INFORMATION: the coding nucleotides of SEQ ID NO:27 correspond to nucleotides 20925 through 22316 of SEQ ID NO:2

(xi) SEQUENCE DESCRIPTION: SEQ ID NO:27:

```
ATG CAG GGG ACG GCG GAA GCC AAA TCT CAG CTA ATA ATA ACC GAT AGT       48
Met Gln Gly Thr Ala Glu Ala Lys Ser Gln Leu Ile Ile Thr Asp Ser
 1               5                  10                  15

GAG GGG AAT ACT TAT ACG TTA ACC GTT CCT GAT AAT GGT AAA TGG AGT       96
Glu Gly Asn Thr Tyr Thr Leu Thr Val Pro Asp Asn Gly Lys Trp Ser
            20                  25                  30

ATG GCT ATC CCG TAT CCA TCA GAA GGG AAG TTT ACC ATT ACG AGT GTG      144
Met Ala Ile Pro Tyr Pro Ser Glu Gly Lys Phe Thr Ile Thr Ser Val
        35                  40                  45

GAT GCT ATT GGT AAC CGG AGT GAT GAT GTC CCT CTC GAT ATC ATG AAA      192
Asp Ala Ile Gly Asn Arg Ser Asp Asp Val Pro Leu Asp Ile Met Lys
    50                  55                  60

GAG GTT CCC GTT ATT TCA TTA TCT CCA GAC TCA GAC AGT GGT ACG GTG      240
Glu Val Pro Val Ile Ser Leu Ser Pro Asp Ser Asp Ser Gly Thr Val
65                  70                  75                  80

GGC GAT AAT ATT ACG CGA GAT AAG CAA CCT ACC TTT ATT ATC GGG AAT      288
Gly Asp Asn Ile Thr Arg Asp Lys Gln Pro Thr Phe Ile Ile Gly Asn
                85                  90                  95

CTG GAA AGC GAT GTT GTG GTC GTT CAG GTC GAT ATC AAT GGG ACC GTA      336
Leu Glu Ser Asp Val Val Val Val Gln Val Asp Ile Asn Gly Thr Val
            100                 105                 110

TAT AAT GCT GAA AAA AAT GCC GAT GGC GTT TGG TTC TTT ACG CCA GGT      384
Tyr Asn Ala Glu Lys Asn Ala Asp Gly Val Trp Phe Phe Thr Pro Gly
        115                 120                 125

ACA CCG TTA GCT GAT GGT TCC TAT ACG ATA TCG GTA ATC GCA AGC GAT      432
Thr Pro Leu Ala Asp Gly Ser Tyr Thr Ile Ser Val Ile Ala Ser Asp
    130                 135                 140

GCC GCG GGT AAT CAG AAA AAC TCG TTA CCC ATT ACT GTC ACG ATC GAC      480
Ala Ala Gly Asn Gln Lys Asn Ser Leu Pro Ile Thr Val Thr Ile Asp
145                 150                 155                 160

AGC ACG CTG ACG GTG CCG GAG ATT GCG TTG GCA GCA GGT GAA GAC AAT      528
Ser Thr Leu Thr Val Pro Glu Ile Ala Leu Ala Ala Gly Glu Asp Asn
                165                 170                 175

GGC GCT TCA GAC AGC GAT AAC GTG ACG AAT CAC ACC CAG CCT AAG TTC      576
Gly Ala Ser Asp Ser Asp Asn Val Thr Asn His Thr Gln Pro Lys Phe
            180                 185                 190

ACG CTG CAG CAT ATT GAT GCT GAT GTG ACC GGG GTG ACC GTA AAC GTG      624
Thr Leu Gln His Ile Asp Ala Asp Val Thr Gly Val Thr Val Asn Val
        195                 200                 205

ACG CAT AAT GGC GTG ACA GAC ATC TAT CAG GCG ACG CAA GGC GCG GAT      672
Thr His Asn Gly Val Thr Asp Ile Tyr Gln Ala Thr Gln Gly Ala Asp
    210                 215                 220
```

```
GGC TGG ACC TTC ACG CCG CCA GCC GCC TGG AAT GAC GGT AAC TAC ACG      720
Gly Trp Thr Phe Thr Pro Pro Ala Ala Trp Asn Asp Gly Asn Tyr Thr
225                 230                 235                 240

CTG AGC GTG ACG GTG GTG GAT CGC GCG GGG AAT TCA CAG CAA TCT GCT      768
Leu Ser Val Thr Val Val Asp Arg Ala Gly Asn Ser Gln Gln Ser Ala
                245                 250                 255

TCG CTA GCG GTG ACG GTT GAC TCA ACG GTG ACG GTA ACA GCG GAT AGC      816
Ser Leu Ala Val Thr Val Asp Ser Thr Val Thr Val Thr Ala Asp Ser
            260                 265                 270

CAG CAT GAC GAT GCG AGC GAT GAC GCC ACG GCA ACA GCG GTT ACT CCA      864
Gln His Asp Asp Ala Ser Asp Asp Ala Thr Ala Thr Ala Val Thr Pro
        275                 280                 285

CCG GAG TCT GAA ACA GTG AAT GCC GAA AGC GCT ACG CAT CTT CGT ACA      912
Pro Glu Ser Glu Thr Val Asn Ala Glu Ser Ala Thr His Leu Arg Thr
    290                 295                 300

GAG CCG TCT GCG GCG GAA GAA AGC GTG GTG AAG GTG ACA GCC TAT AGT      960
Glu Pro Ser Ala Ala Glu Glu Ser Val Val Lys Val Thr Ala Tyr Ser
305                 310                 315                 320

ATT ACA TTG TTA AAC GCT GAC TCT GGG GAT GAA ATA GAT CGT TCA ATT     1008
Ile Thr Leu Leu Asn Ala Asp Ser Gly Asp Glu Ile Asp Arg Ser Ile
                325                 330                 335

AGT CAG ACA CCT TCT TTT GAA ATA TCA GTA CCT GAG AAT ATT GTT AAT     1056
Ser Gln Thr Pro Ser Phe Glu Ile Ser Val Pro Glu Asn Ile Val Asn
            340                 345                 350

GTC AGT ATT ATG TTT GAA GGA GAA GAG TTT ACT CTG CCG ATA ACT AAC     1104
Val Ser Ile Met Phe Glu Gly Glu Glu Phe Thr Leu Pro Ile Thr Asn
        355                 360                 365

CAG AAA GCA ATA TTC GAA GTT CCG CTA TCT TTG GAA GAT GGT GAA TAT     1152
Gln Lys Ala Ile Phe Glu Val Pro Leu Ser Leu Glu Asp Gly Glu Tyr
    370                 375                 380

ACT ATG GAC GTG AAA TTC ATT GAT AAA GAC AAT GAT TTC CTG ATT AAG     1200
Thr Met Asp Val Lys Phe Ile Asp Lys Asp Asn Asp Phe Leu Ile Lys
385                 390                 395                 400

GAG AAA ACA TTC TCA GTC GAT CAC TCC TCG GCG GAT ATT GTG AAC GCA     1248
Glu Lys Thr Phe Ser Val Asp His Ser Ser Ala Asp Ile Val Asn Ala
                405                 410                 415

ATG AAT GTA AGA GGA AAG ACC GAG GAT GAT ATT AAT GAT TCC CCT TCC     1296
Met Asn Val Arg Gly Lys Thr Glu Asp Asp Ile Asn Asp Ser Pro Ser
            420                 425                 430

ACG AGT TCT GTA GGG CAC AAC AAT AAC GGC GCT ATT GAT GTT TTC GCC     1344
Thr Ser Ser Val Gly His Asn Asn Asn Gly Ala Ile Asp Val Phe Ala
        435                 440                 445

GTT AAT GAA GTT ACG CTA CCT GTA GAT AAT CAA GAA GAA CAC GCA TAA     1392
Val Asn Glu Val Thr Leu Pro Val Asp Asn Gln Glu Glu His Ala
    450                 455                 460
```

(2) INFORMATION FOR SEQ ID NO:28:

(i) SEQUENCE CHARACTERISTICS:
(A) LENGTH: 1797 bases
(B) TYPE: nucleotide
(C) STRANDEDNESS: double stranded
(D) TOPOLOGY: linear (ix) FEATURE:
(D) OTHER INFORMATION: the coding nucleotides of SEQ ID NO:28 correspond to nucleotides 22630 through 24426 of SEQ ID NO:2

(xi) SEQUENCE DESCRIPTION: SEQ ID NO:28:

```
ATG GTG TGT GTG AGT GGC GGG CAA AAA ATA AAG TTG GTA AAC GCG CGC       48
Met Val Cys Val Ser Gly Gly Gln Lys Ile Lys Leu Val Asn Ala Arg
 1               5                  10                  15
```

```
GGT GAA CTC TGT TAT GTT GAA ATT GAA GAT GAA TAT TTA AAA GAG TTA       96
Gly Glu Leu Cys Tyr Val Glu Ile Glu Asp Glu Tyr Leu Lys Glu Leu
            20                  25                  30

TCT GCA TTT AGT ATA CTA CCT TTA AAT AAA GTT GTT GAT AGT ATA AGA      144
Ser Ala Phe Ser Ile Leu Pro Leu Asn Lys Val Val Asp Ser Ile Arg
        35                  40                  45

GTA AAA AAT ATC ATA AAA AAC TCT TTA TCG ATG AAC AAG ATT TTT TAT      192
Val Lys Asn Ile Ile Lys Asn Ser Leu Ser Met Asn Lys Ile Phe Tyr
    50                  55                  60

ACT AAA TAC TTT TTT TCA TCT CTT TTT ATG GCA ATT TTT GCG TTA ACT      240
Thr Lys Tyr Phe Phe Ser Ser Leu Phe Met Ala Ile Phe Ala Leu Thr
65                  70                  75                  80

ATC CCA GTA TTT AGT AAT CTG TTC TAT GAT AAG CTT GTT CCA AGC GCT      288
Ile Pro Val Phe Ser Asn Leu Phe Tyr Asp Lys Leu Val Pro Ser Ala
                85                  90                  95

TCG GTT TCA TCT TTA TTT GGC GTG GCT ATA ATT GTT GCT GTA TTT ATT      336
Ser Val Ser Ser Leu Phe Gly Val Ala Ile Ile Val Ala Val Phe Ile
            100                 105                 110

GTT TTT GAG TTT ATC CTT CGT ACT TCG AAA GAT ATT TAT CAG TCT ATC      384
Val Phe Glu Phe Ile Leu Arg Thr Ser Lys Asp Ile Tyr Gln Ser Ile
        115                 120                 125

ACA GCA AGG CAG GAT GAC GTC GAT ATT GAT ATC GCA TTT CTT GAA GCG      432
Thr Ala Arg Gln Asp Asp Val Asp Ile Asp Ile Ala Phe Leu Glu Ala
    130                 135                 140

GTA CTT TAT AGT AAA AAG AAA AAT GGC AGA TCC ATG TCA TCA GCA TTT      480
Val Leu Tyr Ser Lys Lys Lys Asn Gly Arg Ser Met Ser Ser Ala Phe
145                 150                 155                 160

GTG CTA TGG AAT GAG TTT CAG AAA ATT AAA CCC GTT TTA TTA AAC TCG      528
Val Leu Trp Asn Glu Phe Gln Lys Ile Lys Pro Val Leu Leu Asn Ser
                165                 170                 175

ATC TTT CAA CGT ATA GCC GAT ATT CCA ATA TTT ATT ATA TTT CTC ATT      576
Ile Phe Gln Arg Ile Ala Asp Ile Pro Ile Phe Ile Ile Phe Leu Ile
            180                 185                 190

GTT ATA TAT GTA AAT TTA GGT CTG GTT GTT ATT GTA CCT ATT ACC ATG      624
Val Ile Tyr Val Asn Leu Gly Leu Val Val Ile Val Pro Ile Thr Met
        195                 200                 205

TTT ATC GTC TCT ATT ATT ATT TCC CTC GTT AAC CAC CAT TAT ACT AAT      672
Phe Ile Val Ser Ile Ile Ile Ser Leu Val Asn His His Tyr Thr Asn
    210                 215                 220

GAG TTA ATG AAC AAA CAA AAA GAA GGA CAG AAG AAC AGG AAT ATT TTT      720
Glu Leu Met Asn Lys Gln Lys Glu Gly Gln Lys Asn Arg Asn Ile Phe
225                 230                 235                 240

ATC TCA GAA GTT TTC TTA TCT ATT AAA ATG ATC CAT ACC TTA AAT AAT      768
Ile Ser Glu Val Phe Leu Ser Ile Lys Met Ile His Thr Leu Asn Asn
                245                 250                 255

CAA GGT TTA CTT TTT GAT TGG GTT AAT ACA TCA AAT GAA CAG TCG TAT      816
Gln Gly Leu Leu Phe Asp Trp Val Asn Thr Ser Asn Glu Gln Ser Tyr
            260                 265                 270

CTT AAC CTG AAG ATA AGG AAA TTA AAT CTT ATC TAT CAA TCT ATA TTG      864
Leu Asn Leu Lys Ile Arg Lys Leu Asn Leu Ile Tyr Gln Ser Ile Leu
        275                 280                 285

GGG AGT ATG TCA TCT ATT ACC CAA ATA ACT ATT ATG GTA ATA GCC TTT      912
Gly Ser Met Ser Ser Ile Thr Gln Ile Thr Ile Met Val Ile Ala Phe
    290                 295                 300

TTT ATG GTA ATC AAG GGT GAT GTT ACT ACT GGC GCA ATT GTT TCA TCT      960
Phe Met Val Ile Lys Gly Asp Val Thr Thr Gly Ala Ile Val Ser Ser
305                 310                 315                 320

GTC ATT GTC TCT GGC CGT ATT TCC GGG ATC ATT TCG AAT TTT TCT TCT     1008
Val Ile Val Ser Gly Arg Ile Ser Gly Ile Ile Ser Asn Phe Ser Ser
                325                 330                 335
```

```
ACA TTA ATC TCT ATT TTA TCA GCA GAA AAA ACC GGT AAG GAT CTG CTT      1056
Thr Leu Ile Ser Ile Leu Ser Ala Glu Lys Thr Gly Lys Asp Leu Leu
            340                 345                 350

TCT TTT TTT GAT GAA GAT CAG GCA GAA AAA ACA CCG GCA TTA CAG TCA      1104
Ser Phe Phe Asp Glu Asp Gln Ala Glu Lys Thr Pro Ala Leu Gln Ser
        355                 360                 365

ATA TCA AAG TGC AAT GGC GAT ATC TCT ATC CGG GGC GTG AGT TAT CAG      1152
Ile Ser Lys Cys Asn Gly Asp Ile Ser Ile Arg Gly Val Ser Tyr Gln
    370                 375                 380

TAT GAT GCT CAA TCT CCG ATG ATT ATT AAC CGA CTG TCT ATA GAC ATA      1200
Tyr Asp Ala Gln Ser Pro Met Ile Ile Asn Arg Leu Ser Ile Asp Ile
385                 390                 395                 400

CCT GCG GGG CAA CGT GTC GCG GTG GTA GGC GAA TGC GGA GCA GGA AAA      1248
Pro Ala Gly Gln Arg Val Ala Val Val Gly Glu Cys Gly Ala Gly Lys
                405                 410                 415

AGC TCA TTA CTG GGA ATG CTA TCT GGC TAC CTT TCG CCA ACA GAC GGT      1296
Ser Ser Leu Leu Gly Met Leu Ser Gly Tyr Leu Ser Pro Thr Asp Gly
            420                 425                 430

GCC ATT TTA TAT GAT GGA TAT AAC TTA GGA CAT TTA TCG CAG AAC TTT      1344
Ala Ile Leu Tyr Asp Gly Tyr Asn Leu Gly His Leu Ser Gln Asn Phe
        435                 440                 445

TTT TCT CAG CAT TTA AGC GTG GTG ACG ACA CAT GAT GTT TTA TTC ACC      1392
Phe Ser Gln His Leu Ser Val Val Thr Thr His Asp Val Leu Phe Thr
    450                 455                 460

GGA ACC ATT GAA AGT AAT TTC GCG TTA AAA CCG CAA AAC GAC AGG GGC      1440
Gly Thr Ile Glu Ser Asn Phe Ala Leu Lys Pro Gln Asn Asp Arg Gly
465                 470                 475                 480

CGG GTA CTC AAG GCG CTT CAG CTG GCG AAC TGT GGT TTT ATC TTG CAA      1488
Arg Val Leu Lys Ala Leu Gln Leu Ala Asn Cys Gly Phe Ile Leu Gln
                485                 490                 495

CAT CCT ATG GGG CTG AAG TTT CCG GTG AAT TTT ATG GCT AAA AAC CTG      1536
His Pro Met Gly Leu Lys Phe Pro Val Asn Phe Met Ala Lys Asn Leu
            500                 505                 510

TCA TCC GGA CAG CAG CAG CAG TTA TTA TTA GCA CGT AGT CTG AGT AGT      1584
Ser Ser Gly Gln Gln Gln Gln Leu Leu Leu Ala Arg Ser Leu Ser Ser
        515                 520                 525

GAC GCC AGC GTC TTT TTA TGG GAT GAA CCA ACA TCA AAT CTG GAT GAG      1632
Asp Ala Ser Val Phe Leu Trp Asp Glu Pro Thr Ser Asn Leu Asp Glu
    530                 535                 540

AAT ACC GAG AAG CAA ATT TTT GAT AAC TTA GAT GAG TTT ATT CAT GGG      1680
Asn Thr Glu Lys Gln Ile Phe Asp Asn Leu Asp Glu Phe Ile His Gly
545                 550                 555                 560

AAA ACG TTG ATC ATG GTG ACG CAT CGT CGA TAT CTG ATA AAG TAT TTT      1728
Lys Thr Leu Ile Met Val Thr His Arg Arg Tyr Leu Ile Lys Tyr Phe
                565                 570                 575

GAC CGG GTC CTG GTA ATG AAA GGT GGA AAA ATA ATC CGT GAT TGT TCT      1776
Asp Arg Val Leu Val Met Lys Gly Gly Lys Ile Ile Arg Asp Cys Ser
            580                 585                 590

CCG GAT AAA TTA TTA ATG TAA                                          1797
Pro Asp Lys Leu Leu Met
        595
```

(2) INFORMATION FOR SEQ ID NO:29:

(i) SEQUENCE CHARACTERISTICS:
- (A) LENGTH: 516 bases
- (B) TYPE: nucleotide
- (C) STRANDEDNESS: double stranded
- (D) TOPOLOGY: linear (ix) FEATURE:
- (D) OTHER INFORMATION: the coding nucleotides of SEQ ID NO:29 correspond to nucleotides 11963 through 12478 of SEQ ID NO:3

(xi) SEQUENCE DESCRIPTION: SEQ ID NO:29:

```
ATG CTC TAC GCT GAC CGT AAC GCG AAC GGC ATC ATC ATC AAT ATG CTG       48
Met Leu Tyr Ala Asp Arg Asn Ala Asn Gly Ile Ile Ile Asn Met Leu
 1               5                  10                  15

CAG GGC AAA TGT CGG CTG GGT GCT ATT CGT CAT GTT ATC GCC ATG GAC       96
Gln Gly Lys Cys Arg Leu Gly Ala Ile Arg His Val Ile Ala Met Asp
            20                  25                  30

ACC ACT GTC GTC CGC GCT ATC CAG TAC GAT CAC CGG CGT CGA CAA CGT      144
Thr Thr Val Val Arg Ala Ile Gln Tyr Asp His Arg Arg Arg Gln Arg
        35                  40                  45

AGT ATC AAT AGT GAA GTG GAG TGT CTC CGT CAC CGT ATT ACC CGC ATT      192
Ser Ile Asn Ser Glu Val Glu Cys Leu Arg His Arg Ile Thr Arg Ile
    50                  55                  60

GTC AGT CGC TTT CAC ATT CAG CGT ATA GTC GCC ATC CGG CAC GGT GCC      240
Val Ser Arg Phe His Ile Gln Arg Ile Val Ala Ile Arg His Gly Ala
65                  70                  75                  80

CGG CCA GGT ATA ATT CCA GAC GCC CGG CGT CGC GCT CTG TGT CGC CTT      288
Arg Pro Gly Ile Ile Pro Asp Ala Arg Arg Arg Ala Leu Cys Arg Leu
                85                  90                  95

AAC CCA GGT CAC GCC ACC GTC AAT GCT CAG ACT GAC TTC GTT AAC GTC      336
Asn Pro Gly His Ala Thr Val Asn Ala Gln Thr Asp Phe Val Asn Val
            100                 105                 110

CCC CGG TAC CGT CAC GCG GAA CTG CGG ATG GGC GTC GTT AGT CAT ATT      384
Pro Arg Tyr Arg His Ala Glu Leu Arg Met Gly Val Val Ser His Ile
        115                 120                 125

GTC GCC GGG AAT ACC GTT ATC ATT AAC CAG TTC AAT AAC ATC AAT GGT      432
Val Ala Gly Asn Thr Val Ile Ile Asn Gln Phe Asn Asn Ile Asn Gly
    130                 135                 140

GAT TTG GGT ATC AAC AGT GAC CGT CAG CGA CCT GAG TGT TTT TCG TTC      480
Asp Leu Gly Ile Asn Ser Asp Arg Gln Arg Pro Glu Cys Phe Ser Phe
145                 150                 155                 160

CCC GCC TCA TCT TCC ACC CTC ACT GTC AGC GTA TAG                      516
Pro Ala Ser Ser Ser Thr Leu Thr Val Ser Val
                165                 170
```

(2) INFORMATION FOR SEQ ID NO:30:

(i) SEQUENCE CHARACTERISTICS:
(A) LENGTH: 312 bases
(B) TYPE: nucleotide
(C) STRANDEDNESS: double stranded
(D) TOPOLOGY: linear (ix) FEATURE:
(D) OTHER INFORMATION: the coding nucleotides of SEQ ID NO:30 correspond to nucleotides 12273 through 12584 of SEQ ID NO:3

(xi) SEQUENCE DESCRIPTION: SEQ ID NO:30:

```
ATG CTC AGA CTG ACT TCG TTA ACG TCC CCC GGT ACC GTC ACG CGG AAC       48
Met Leu Arg Leu Thr Ser Leu Thr Ser Pro Gly Thr Val Thr Arg Asn
 1               5                  10                  15

TGC GGA TGG GCG TCG TTA GTC ATA TTG TCG CCG GGA ATA CCG TTA TCA       96
Cys Gly Trp Ala Ser Leu Val Ile Leu Ser Pro Gly Ile Pro Leu Ser
            20                  25                  30

TTA ACC AGT TCA ATA ACA TCA ATG GTG ATT TGG GTA TCA ACA GTG ACC      144
Leu Thr Ser Ser Ile Thr Ser Met Val Ile Trp Val Ser Thr Val Thr
        35                  40                  45

GTC AGC GAC CTG AGT GTT TTT CGT TCC CCG CCT CAT CTT CCA CCC TCA      192
Val Ser Asp Leu Ser Val Phe Arg Ser Pro Pro His Leu Pro Pro Ser
    50                  55                  60
```

```
CTG TCA GCG TAT AGT CGC CAT CTG CCC ATG TGC CGG TCG GTG TCA CGC      240
Leu Ser Ala Tyr Ser Arg His Leu Pro Met Cys Arg Ser Val Ser Arg
65                  70                  75                  80

TCC AGT TGC CGG TCG CGT CTT TGG TGG CCG TCA GCA CCT CTT TCG TGC      288
Ser Ser Cys Arg Ser Arg Leu Trp Trp Pro Ser Ala Pro Leu Ser Cys
                85                  90                  95

CGC CAT GCT GTA CCT CAA CCG TGA                                      312
Arg His Ala Val Pro Gln Pro
            100
```

(2) INFORMATION FOR SEQ ID NO:31:

(i) SEQUENCE CHARACTERISTICS:
(A) LENGTH: 384 bases
(B) TYPE: nucleotide
(C) STRANDEDNESS: double stranded
(D) TOPOLOGY: linear (ix) FEATURE:
(D) OTHER INFORMATION: the coding nucleotides of SEQ ID NO:31 correspond to nucleotides 13514 through 13897 of SEQ ID NO:3

(xi) SEQUENCE DESCRIPTION: SEQ ID NO:31:

```
ATG AAA CTG TGG ACG TGC TTC ATT GGT CAG GTT ATC CCC GAC AAT ACC       48
Met Lys Leu Trp Thr Cys Phe Ile Gly Gln Val Ile Pro Asp Asn Thr
 1               5                  10                  15

CGT GTC ATT AAG AAG CTC AAT GCG ATC AAT AGA CGT TTG CGT ATC GAT       96
Arg Val Ile Lys Lys Leu Asn Ala Ile Asn Arg Arg Leu Arg Ile Asp
            20                  25                  30

AGT CAC CGT CAG CGG CGC AGA ATA ATT TGT ATT ACC CGC CTT ATC TTC      144
Ser His Arg Gln Arg Arg Arg Ile Ile Cys Ile Thr Arg Leu Ile Phe
        35                  40                  45

TAC CTT TAC CGT CAA CGT ATA GTC GCC ATC GGT CCA GGC TGC GCC CGG      192
Tyr Leu Tyr Arg Gln Arg Ile Val Ala Ile Gly Pro Gly Cys Ala Arg
    50                  55                  60

CGT AAA GCG CCA CAC ACC GCC GTT CTT AAT CAA CTC TAT CTG TTG GTT      240
Arg Lys Ala Pro His Thr Ala Val Leu Asn Gln Leu Tyr Leu Leu Val
65                  70                  75                  80

CTT ACC ATC ATG CGC CAC CGT CAC CAC CAC TTT GGT CAC GTC GGC GTC      288
Leu Thr Ile Met Arg His Arg His His His Phe Gly His Val Gly Val
                85                  90                  95

GAT ATT ACC GAG GGT AAA GCC TGG CAT CTT AAC GTT GGT GAT GTT ATC      336
Asp Ile Thr Glu Gly Lys Ala Trp His Leu Asn Val Gly Asp Val Ile
            100                 105                 110

GCC AGC GGC GCT ATC ATC CGC GCT GTC CAG GGT AAT CGT CGG TTC TGA      384
Ala Ser Gly Ala Ile Ile Arg Ala Val Gln Gly Asn Arg Arg Phe
        115                 120                 125
```

(2) INFORMATION FOR SEQ ID NO:32:

(i) SEQUENCE CHARACTERISTICS:
(A) LENGTH: 384 bases
(B) TYPE: nucleotide
(C) STRANDEDNESS: double stranded
(D) TOPOLOGY: linear (ix) FEATURE:
(D) OTHER INFORMATION: the coding nucleotides of SEQ ID NO:32 correspond to nucleotides 14196 through 14579 of SEQ ID NO:3

(xi) SEQUENCE DESCRIPTION: SEQ ID NO:32:

```
ATG CGT GTC TAC TGT CAC CGT CAA CGG CGC GGA CTG CTT CAC ATT TCC       48
Met Arg Val Tyr Cys His Arg Gln Arg Arg Gly Leu Leu His Ile Ser
 1               5                  10                  15
```

```
GGT CCT ATC TTC TAC CTT CAC CGT CAG GAT ATA GTC GCC GTC CGC CCA       96
Gly Pro Ile Phe Tyr Leu His Arg Gln Asp Ile Val Ala Val Arg Pro
            20                  25                  30

GTC GCT GGT CGG CGC AAA GCG CCA CTG TCC GCC GGT CTG AAC CAG TGG      144
Val Ala Gly Arg Arg Lys Ala Pro Leu Ser Ala Gly Leu Asn Gln Trp
        35                  40                  45

CAC CTC CTG CTT AAT GCC ATT GTG CAT TAC CTC CAC TAT CAC CCG GCT      192
His Leu Leu Leu Asn Ala Ile Val His Tyr Leu His Tyr His Pro Ala
    50                  55                  60

GAC ATC GGT ATC AAT ATT GTT GAG GGT AAA GCC CGG CGT TTT AAC ATT      240
Asp Ile Gly Ile Asn Ile Val Glu Gly Lys Ala Arg Arg Phe Asn Ile
65                  70                  75                  80

GGT GAT ATT ATC GCC CGC GAT GCC GCT GTC ATC TGC GCT GTC CAG CGA      288
Gly Asp Ile Ile Ala Arg Asp Ala Ala Val Ile Cys Ala Val Gln Arg
                85                  90                  95

GAG GGT CGG CAC AGA CAG AGT GGT ATC GAT GGT GAA ATC GAG GTC TGT      336
Glu Gly Arg His Arg Gln Ser Gly Ile Asp Gly Glu Ile Glu Val Cys
            100                 105                 110

GTT GCC TTA TTT CCT GCC TCA TCG GTC GCT TCT ACC GTC AGG GTA TAG      384
Val Ala Leu Phe Pro Ala Ser Ser Val Ala Ser Thr Val Arg Val
        115                 120                 125
```

(2) INFORMATION FOR SEQ ID NO:33:

(i) SEQUENCE CHARACTERISTICS:
(A) LENGTH: 348 bases
(B) TYPE: nucleotide
(C) STRANDEDNESS: double stranded
(D) TOPOLOGY: linear (ix) FEATURE:
(D) OTHER INFORMATION: the coding nucleotides of SEQ ID NO:33 correspond to nucleotides 17516 through 17863 of SEQ ID NO:3

(xi) SEQUENCE DESCRIPTION: SEQ ID NO:33:

```
ATG CCC GGC AAT ATC AGT AGC TGT TGC TGT TAT ATT GTA TTC GCC ATC       48
Met Pro Gly Asn Ile Ser Ser Cys Cys Cys Tyr Ile Val Phe Ala Ile
 1               5                  10                  15

CTT GAG CGG CGT AGT AAG CGT ATA GCT CCA TGT CCC ATC TTT AGC AAC       96
Leu Glu Arg Arg Ser Lys Arg Ile Ala Pro Cys Pro Ile Phe Ser Asn
            20                  25                  30

AAT GAC CTC ACC AAG ATG TTT AAG TCC AAG ATA AAT AGA GAC TGT AGA      144
Asn Asp Leu Thr Lys Met Phe Lys Ser Lys Ile Asn Arg Asp Cys Arg
        35                  40                  45

ACC GGG TTC CGC CAC ACC AAT AAA TGT TGG CAG GGT GCT ATT TGT AAT      192
Thr Gly Phe Arg His Thr Asn Lys Cys Trp Gln Gly Ala Ile Cys Asn
    50                  55                  60

GTT GTC ATT TTT AAT GCC GGA ATC ACT ACT ATC ATC CAG CTC AAT CGT      240
Val Val Ile Phe Asn Ala Gly Ile Thr Thr Ile Ile Gln Leu Asn Arg
65                  70                  75                  80

CGG CTT TTC TGG AGC AAT GGT GTC GGT TAT GAT ACT ATC CGT CGT TTC      288
Arg Leu Phe Trp Ser Asn Gly Val Gly Tyr Asp Thr Ile Arg Arg Phe
                85                  90                  95

GTT TTT ATT ACC TGC TTT ATC TAC AGC AAC GAC TTT TAT ACT ATT TTC      336
Val Phe Ile Thr Cys Phe Ile Tyr Ser Asn Asp Phe Tyr Thr Ile Phe
            100                 105                 110

GCC CTC AGA TAA                                                      348
Ala Leu Arg
        115
```

(2) INFORMATION FOR SEQ ID NO:34:

```
    (i) SEQUENCE CHARACTERISTICS:
         (A) LENGTH: 324 bases
         (B) TYPE: nucleotide
         (C) STRANDEDNESS: double stranded
         (D) TOPOLOGY: linear

   (ix) FEATURE:
         (D) OTHER INFORMATION: the coding nucleotides of SEQ ID
              NO:34 correspond to nucleotides 18011 through
              18334 of SEQ ID NO:3

   (xi) SEQUENCE DESCRIPTION: SEQ ID NO:34:

ATG ACC GGA CAC ACT ACT TTC AGG CGA AAG TTC AAA TGT TGG TTT ATC        48
Met Thr Gly His Thr Thr Phe Arg Arg Lys Phe Lys Cys Trp Phe Ile
 1               5                  10                  15

GGT AAC GGA ATC GAT AGT AAT GAC AAG TTT GGC GCT ACC GCT CCC ATC        96
Gly Asn Gly Ile Asp Ser Asn Asp Lys Phe Gly Ala Thr Ala Pro Ile
            20                  25                  30

AGC AGT CTT GGC CTC TGC CTC CAG ATT ATA TGT TCC ATC AGT CAA TGT       144
Ser Ser Leu Gly Leu Cys Leu Gln Ile Ile Cys Ser Ile Ser Gln Cys
        35                  40                  45

TTC AGG CGC TGT AAA GGT GAA GTT ACC CAA ACT ATC CGT TAC AGC CTG       192
Phe Arg Arg Cys Lys Gly Glu Val Thr Gln Thr Ile Arg Tyr Ser Leu
    50                  55                  60

ACC GAC AGC AAT ACC ATT AAT TTT AAT AAT AAC CGT GGC ATT GGG AGC       240
Thr Asp Ser Asn Thr Ile Asn Phe Asn Asn Asn Arg Gly Ile Gly Ser
65                  70                  75                  80

AGT GCT AAC TAC AAA CTG AGG TTT GGT AAA ATT AGT TAT ACT ATC ATC       288
Ser Ala Asn Tyr Lys Leu Arg Phe Gly Lys Ile Ser Tyr Thr Ile Ile
                85                  90                  95

TTT GCT ACC GCT GTT ACT CTC GGC CGC ACG CGC TAA                       324
Phe Ala Thr Ala Val Thr Leu Gly Arg Thr Arg
            100                 105


(2) INFORMATION FOR SEQ ID NO:35:

    (i) SEQUENCE CHARACTERISTICS:
         (A) LENGTH: 524 amino acids
         (B) TYPE: amino acid
         (D) TOPOLOGY: linear

   (xi) SEQUENCE DESCRIPTION: SEQ ID NO:35:

Met Glu Asp Glu Ser Asn Pro Trp Pro Ser Phe Val Asp Thr Phe Ser
 1               5                  10                  15

Thr Val Leu Cys Ile Phe Ile Phe Leu Met Leu Val Phe Ala Leu Asn
            20                  25                  30

Asn Met Ile Ile Met Tyr Asp Asn Ser Ile Lys Val Tyr Lys Ala Asn
        35                  40                  45

Ile Glu Asn Lys Thr Lys Ser Thr Ala Gln Asn Ser Gly Ala Asn Asp
    50                  55                  60

Asp Ser Asn Pro Asn Glu Ile Val Asn Lys Glu Val Asn Thr Gln Asp
65                  70                  75                  80

Val Ser Asp Gly Met Thr Thr Met Ser Gly Lys Glu Val Gly Val Tyr
                85                  90                  95

Asp Ile Ala Asp Gly Gln Lys Thr Asp Ile Thr Ser Thr Lys Asn Glu
            100                 105                 110

Leu Val Ile Thr Tyr His Gly Arg Leu Arg Ser Phe Ser Glu Glu Asp
        115                 120                 125

Thr Tyr Lys Ile Lys Ala Trp Leu Glu Asp Lys Ile Asn Ser Asn Leu
    130                 135                 140

Leu Ile Glu Met Val Ile Pro Gln Ala Asp Ile Ser Phe Ser Asp Ser
145                 150                 155                 160
```

```
Leu Arg Leu Gly Tyr Glu Arg Gly Ile Ile Leu Met Lys Glu Ile Lys
                165                 170                 175

Lys Ile Tyr Pro Asp Val Val Ile Asp Met Ser Val Asn Ser Ala Ala
            180                 185                 190

Ser Ser Thr Thr Ser Lys Ala Ile Ile Thr Thr Ile Asn Lys Arg Cys
        195                 200                 205

Gln Ser Glu Ile Tyr Lys Ser Leu Pro Leu Phe Val Val Cys Ser Phe
    210                 215                 220

Leu Ala Ile Leu Pro Phe Phe Ala Leu Ser Phe Pro Gly Ile Arg Glu
225                 230                 235                 240

Tyr Val Phe Asp Asn Phe Met Val Ser Ala Ile Tyr Asn Gly Val Ile
                245                 250                 255

Ile Ala Ile Tyr Ile Thr Gly Ser Leu Cys Ala Leu Phe Thr Ile Leu
            260                 265                 270

Lys Asn Ile Ser Ala Lys Asp Ile Leu Ile Ala Gln Asp Ala Ser Arg
        275                 280                 285

Lys Asn Ser Ile Leu Ser Asn Leu Asn Gln Val Leu Phe Ala Gly Glu
    290                 295                 300

Ser Lys Gln Cys Asp Phe Asn Leu Leu Met Glu Leu Asp Asp Asn Val
305                 310                 315                 320

Ser Thr Ala Arg Asn Gln Arg Leu Ser Phe Ile Met Ser Cys Ser Asn
                325                 330                 335

Val Ser Thr Leu Val Gly Leu Leu Gly Thr Phe Ala Gly Leu Ser Ile
            340                 345                 350

Thr Ile Gly Ser Ile Gly Asn Leu Leu Ser Ser Pro Ser Asp Val Gly
        355                 360                 365

Gly Asp Asn Ala Ser Asn Thr Leu Asn Met Ile Val Thr Met Val Ala
    370                 375                 380

Ser Leu Ser Glu Pro Leu Lys Gly Met Asn Thr Ala Phe Val Ser Ser
385                 390                 395                 400

Ile Tyr Gly Val Val Cys Ala Ile Leu Leu Thr Ser Gln Ser Val Phe
                405                 410                 415

Val Arg Ser Ser Tyr Ser Leu Val Ser Thr Glu Ile Lys Lys Leu Lys
            420                 425                 430

Ile Ile Ser Asn Arg Ala Asn Asn Lys Gln Arg Ser Leu Arg Val Glu
        435                 440                 445

Ser Glu Thr Leu Val Glu Phe Lys Glu Leu Phe Lys Ala Phe Phe Asp
    450                 455                 460

Asn Tyr Leu Thr Val Glu Asn Leu Arg Thr Gln Asp Glu Glu Lys Lys
465                 470                 475                 480

Arg Glu Met Leu Ser Asp Ser Phe Val Thr Leu Gln Asn Arg Leu Leu
                485                 490                 495

Asp Asn Ser Ala Lys Leu Glu Gln Ile Phe Thr Leu Ile Asp Gly Tyr
            500                 505                 510

Leu Val Ser Ser Asn Gly Lys Ser Gln Lys Ile Ile
        515                 520
```

(2) INFORMATION FOR SEQ ID NO:36:

(i) SEQUENCE CHARACTERISTICS:
(A) LENGTH: 121 amino acids
(B) TYPE: amino acid
(D) TOPOLOGY: linear (xi) SEQUENCE DESCRIPTION: SEQ ID NO:36:

```
Met Ser Thr Ile Gln Asn Ile Ile Asp Lys Lys Asn Asp Ser Ile Met
 1               5                  10                  15

Thr Ser Val Asp Lys Cys Tyr Gln Glu Ser Leu Ser His Gly Lys Thr
            20                  25                  30

Ile Asn Asp Ile Ala Ala Gly Ser Ala Asp Ile Ser His Thr Leu Asp
        35                  40                  45

Gly Leu Arg Lys Glu Met Asp Glu Asp Met Asn Asn Val His Leu Ala
    50                  55                  60

Leu Ser Asp Leu Ser Ala Thr Asp Lys Lys Ile Ile Ala Asn Thr Lys
65                  70                  75                  80

Glu Ile Ser Ala Glu Met Val Ser Tyr Arg Asp Thr Tyr Met Pro Leu
                85                  90                  95

Met Glu Lys Ile Thr Ser Met His Gln Glu Ile Val Lys Gln Arg Leu
            100                 105                 110

Leu Asn Lys Glu Glu Lys Asn Glu Asp
        115                 120
```

(2) INFORMATION FOR SEQ ID NO:37:

(i) SEQUENCE CHARACTERISTICS:
(A) LENGTH: 439 amino acids
(B) TYPE: amino acid
(D) TOPOLOGY: linear (xi) SEQUENCE DESCRIPTION: SEQ ID NO:37:

```
Met Lys Ile Lys Met Phe Phe Leu Thr Thr Ala Phe Ile Thr Gln Ser
 1               5                  10                  15

Thr Tyr Ala Ser Glu Leu Pro Val Ile Pro Leu Arg Asp Leu Val Asn
            20                  25                  30

Ala Ala Leu Thr His Gln Pro Ser Val Ala Val Ser Tyr Tyr Glu Thr
        35                  40                  45

Glu Lys Lys Asn Ser Asp Leu Asp Leu Ser Arg Ala Ala Leu Tyr Pro
    50                  55                  60

Thr Leu Asp Leu Thr Ser Gly Leu Asn Asn Asn Arg Lys Glu Ser Ser
65                  70                  75                  80

Gly Thr Glu Arg Asn Val Glu Asn Lys Val Ser Leu Ser Tyr Arg Ile
                85                  90                  95

Thr Asp Phe Gly Val Arg Gly Ala Asn Ile Arg Lys Ser Glu Tyr Glu
            100                 105                 110

Arg Asp Asn Ser Lys Thr Asp Tyr Glu Lys Thr Lys Asn Ile Val Ser
        115                 120                 125

Gln Glu Val Val Thr Thr Tyr Tyr Asn Ile Ser Lys Tyr Arg Glu Met
    130                 135                 140

Ile Asp Gly Val Asn Leu Glu Lys Glu Phe Tyr Lys Lys Met Leu Glu
145                 150                 155                 160

Pro Phe Ser Leu Leu Val Ser Ser Gly Val Ala Met Gln Ser Asp Met
                165                 170                 175

Arg Lys Val Gln Val Ser Ile Asp Ala Leu Asn Thr Arg Ser Ile Met
            180                 185                 190

Tyr Gln Ser Met Leu Asp Asp Glu Met Tyr Lys Met Gln Asn Met Thr
        195                 200                 205

Gly Leu Asn Leu Ser Pro Val Gln Ile Gln Ser Asp Glu Lys Phe Asn
    210                 215                 220

Leu Phe Lys Lys Tyr Ile Phe Val Glu Ser Pro Glu Lys Leu Met Asp
225                 230                 235                 240

Met Val Met Lys Tyr Asn Asp Asp Tyr Lys Met Leu Val Asn Thr Arg
```

```
            245                 250                 255

Lys Ala Ala Thr Glu Asp Ile Asn Ala Ala Lys Ser Ser Tyr Phe Pro
            260                 265                 270

Thr Val Asp Leu Val Ser Ser Tyr Val Gln Asn Asn Pro Ser Gly Ser
        275                 280                 285

Ala Lys Lys Ser Asp Tyr Glu Asp Glu Phe Lys Thr Gly Ile Asn Val
    290                 295                 300

Ser Phe Asn Ile Phe Asn Gly Phe Arg Asn Ser Ala Gln Glu Arg Lys
305                 310                 315                 320

Met Val Ala Ser Tyr Ser Gln Ala Lys Leu Gln Ile Asp Asp Phe Leu
            325                 330                 335

Ile Lys Thr Arg Tyr Asn Ile Asp Ser Gln Leu Ser Arg Tyr Ala Ala
            340                 345                 350

Ala Lys Glu Thr Tyr Ser Val Ala Glu Arg Ser His Thr Asn Ala Leu
        355                 360                 365

Gln Leu Thr Glu Leu Tyr Glu Gln Glu Phe Gln Leu Gly Gln Lys Ser
    370                 375                 380

Leu Leu Asp Leu Ile Ser Ser Arg Asn Glu Ala Phe Gln Ala Tyr Val
385                 390                 395                 400

Ser Met Ile Asp Ser Lys Tyr Ser Leu Tyr Ile Leu Lys Leu Gln Gln
            405                 410                 415

Leu Ser Leu Ile Phe His Leu Met Asp Tyr Leu Lys Gly Asn Thr Glu
            420                 425                 430

Ser Glu Leu Asn Val Met Lys
        435
```

(2) INFORMATION FOR SEQ ID NO:38:

(i) SEQUENCE CHARACTERISTICS:
(A) LENGTH: 425 amino acids
(B) TYPE: amino acid
(D) TOPOLOGY: linear (xi) SEQUENCE DESCRIPTION: SEQ ID NO:38:

```
Met Asn Arg Arg Gln Ser Asp His Leu Met Met Ile Ile Ile Ser Leu
 1               5                  10                  15

Thr Ile Leu Ile Ile Ile Leu Thr Tyr Phe Ile Glu Ile Asn Ser Val
            20                  25                  30

Val His Gly Gln Gly Val Ile Thr Thr Lys Asp Asn Ala Gln Leu Ile
        35                  40                  45

Ser Leu Ser Lys Gly Gly Thr Ile Gln Asp Ile Tyr Val Ala Glu Gly
    50                  55                  60

Asp Thr Val Lys Lys Gly Glu Leu Leu Ala Lys Val Val Asn Leu Asp
65                  70                  75                  80

Leu Gln Lys Glu Tyr Gln Arg Tyr Arg Thr Gln Lys Gly Tyr Leu Asp
            85                  90                  95

Lys Asp Val Asn Glu Ile Ser Phe Ile Leu Asp Lys Glu Asn Glu Ser
            100                 105                 110

Gly Leu Ile Thr Leu Asp Gly Thr Arg Ser Leu Ser Asn Lys Glu Val
        115                 120                 125

Lys Ala Asn Ile Glu Leu Val His Ser Gln Ile Arg Ala Lys Glu Leu
    130                 135                 140

Lys Lys Thr Ser Leu Asp Ser Glu Ile Ser Gly Leu Gln Glu Lys Leu
145                 150                 155                 160

Ser Ser Lys Glu Lys Glu Leu Ala Leu Leu Ala Glu Glu Ile Asn Ile
            165                 170                 175
```

```
Leu Ser Pro Leu Val Lys Lys Gly Ile Ser Pro Tyr Thr Asn Phe Leu
            180                 185                 190

Asn Lys Lys Gln Ala Tyr Ile Lys Val Lys Ser Glu Ile Asn Asp Ile
        195                 200                 205

Glu Ser Ser Ile Thr Leu Lys Lys Asp Asp Ile Glu Leu Val Val Asn
    210                 215                 220

Asp Ile Glu Ala Leu Asn Asn Glu Leu Arg Leu Ser Leu Ser Lys Ile
225                 230                 235                 240

Ile Ser Lys Asn Leu Gln Glu Leu Glu Val Val Asn Ser Thr Leu Lys
                245                 250                 255

Val Ile Glu Lys Gln Ile Asn Glu Glu Asp Ile Tyr Ser Pro Val Asp
            260                 265                 270

Gly Val Ile Tyr Lys Ile Asn Lys Ser Ala Thr Thr His Gly Gly Val
        275                 280                 285

Ile Gln Ala Ala Asp Leu Leu Phe Glu Ile Lys Pro Lys Val Arg Thr
    290                 295                 300

Met Leu Ala Asp Val Lys Ile Leu Pro Lys Tyr Arg Asp Gln Ile Tyr
305                 310                 315                 320

Val Asp Glu Ala Val Lys Leu Asp Val Gln Ser Ile Ile Gln Pro Lys
                325                 330                 335

Ile Lys Ser Tyr Asn Ala Thr Ile Asp Asn Ile Ser Pro Asp Ser Tyr
            340                 345                 350

Glu Glu Asn Thr Gly Gly Thr Ile Gln Arg Tyr Tyr Lys Val Ile Ile
        355                 360                 365

Ala Phe Asp Val Asn Glu Asp Asp Leu Arg Trp Leu Lys Pro Gly Met
    370                 375                 380

Thr Val Asp Ala Ser Val Ile Thr Gly Lys His Ser Ile Met Glu Tyr
385                 390                 395                 400

Leu Leu Ser Pro Leu Met Lys Gly Val Asp Lys Ala Phe Ser Glu Pro
                405                 410                 415

Val Asn Thr Lys Arg Leu Asp Thr Pro
            420                 425
```

(2) INFORMATION FOR SEQ ID NO:39:

(i) SEQUENCE CHARACTERISTICS:
(A) LENGTH: 130 amino acids
(B) TYPE: amino acid
(D) TOPOLOGY: linear (xi) SEQUENCE DESCRIPTION: SEQ ID NO:39:

```
Met Gly Asn Lys Ser Ile Gln Lys Phe Phe Ala Asp Gln Asn Ser Val
 1               5                  10                  15

Ile Asp Leu Ser Ser Leu Gly Asn Ala Lys Gly Ala Lys Val Ser Leu
            20                  25                  30

Ser Gly Pro Asp Met Asn Ile Thr Thr Pro Arg Gly Ser Val Ile Ile
        35                  40                  45

Val Asn Gly Ala Leu Tyr Ser Ser Ile Lys Gly Asn Asn Leu Ala Val
    50                  55                  60

Lys Phe Lys Asp Lys Thr Ile Thr Gly Ala Lys Ile Leu Gly Ser Val
65                  70                  75                  80

Asp Leu Lys Asp Ile Gln Leu Glu Arg Ile Asp Ser Ser Leu Val Asp
                85                  90                  95

Ser Ala Gln Val Glu Lys Lys Gly Asn Gly Lys Arg Arg Asn Lys Lys
            100                 105                 110
```

```
Glu Glu Glu Glu Leu Lys Ser Ser Leu Thr Met Leu Lys Thr Gln Glu
        115                 120                 125

Arg Ser
    130
```

(2) INFORMATION FOR SEQ ID NO:40:

(i) SEQUENCE CHARACTERISTICS:
(A) LENGTH: 526 amino acids
(B) TYPE: amino acid
(D) TOPOLOGY: linear (xi) SEQUENCE DESCRIPTION: SEQ ID NO:40:

```
Met Leu Gln Asn Phe Leu Ala Asp Asn Val Ala Lys Asp Asn Leu Ala
 1               5                  10                  15

Gln Gln Ser Asp Ala Ser Gln Gln Asn Thr Gln Ala Lys Ala Thr Gln
            20                  25                  30

Ala Ser Lys Gln Asn Asp Ala Glu Lys Val Leu Pro Gln Pro Ile Asn
        35                  40                  45

Lys Asn Thr Ser Thr Gly Lys Ser Asn Ser Ser Lys Asn Glu Glu Asn
    50                  55                  60

Lys Leu Asp Ala Glu Ser Val Lys Glu Pro Leu Lys Val Thr Leu Ala
65                  70                  75                  80

Arg Ala Ala Glu Ser Asn Ser Gly Ser Lys Asp Asp Ser Ile Thr Asn
                85                  90                  95

Phe Thr Lys Pro Gln Phe Val Val Ser Thr Ala Pro Asn Ala Thr Val
            100                 105                 110

Ile Ile Lys Ile Asn Gly Ile Ala Val Gly Gln Ala Val Thr Asp Ser
        115                 120                 125

Leu Gly Asn Phe Thr Phe Thr Ala Pro Glu Thr Leu Thr Asp Gly Thr
    130                 135                 140

Tyr Asn Leu Glu Ala Glu Ala Lys Thr Ala Asp Gly Ser Gly Ser Ala
145                 150                 155                 160

Lys Leu Val Ile Thr Ile Asp Ser Val Thr Asp Lys Pro Thr Phe Glu
                165                 170                 175

Leu Ser Pro Glu Ser Ser Val Ser Gly His Lys Gly Leu Thr Pro Thr
            180                 185                 190

Leu Thr Pro Ser Ile Val Gly Thr Ala Glu Glu Asn Ala Lys Val Asp
        195                 200                 205

Ile Tyr Val Asp Asn Lys Leu Val Ala Ser Val Asp Val Asp Lys Asp
    210                 215                 220

Gly Asn Trp Ser Tyr Glu Phe Lys Asp Asn Glu Leu Ser Glu Gly Glu
225                 230                 235                 240

Asn Ser Ile Lys Val Val Ala Val Asp Lys Ala Gly Asn Lys Asn Glu
                245                 250                 255

Thr Thr Asp Ser Ile Ile Thr Asp Thr Ile Ala Pro Glu Lys Pro Thr
            260                 265                 270

Ile Glu Leu Asp Asp Ser Ser Asp Ser Gly Ile Lys Asn Asp Asn Ile
        275                 280                 285

Thr Asn Ser Thr Leu Pro Thr Phe Ile Gly Val Ala Glu Pro Gly Ser
    290                 295                 300

Thr Val Ser Ile Tyr Leu Gly Leu Lys His Leu Gly Glu Val Ile Val
305                 310                 315                 320

Ala Lys Asp Gly Thr Trp Ser Tyr Thr Leu Thr Thr Pro Leu Lys Asp
                325                 330                 335

Gly Glu Tyr Asn Ile Thr Ala Thr Ala Thr Asp Ile Ala Gly His Thr
```

```
            340                 345                 350

Ser Ala Thr Ala Asn Leu Pro Phe Thr Ile Asp Thr Arg Ile Ser Tyr
        355                 360                 365

Phe Ser Ala Glu Ile Glu Thr Thr Asn Asp Ser Gly Ile Val Gly Asp
    370                 375                 380

Asn Val Thr Asn Asn Thr Arg Pro Thr Phe Thr Gly Lys Thr Glu Pro
385                 390                 395                 400

Asn Ala Ile Ile Ser Val Ile Asn Ser Glu Thr Gly Glu Glu Val Ile
                405                 410                 415

Phe Lys Ala Asn Asp Lys Gly Glu Trp Thr Phe Asn Phe Thr Ser Asp
            420                 425                 430

Ser Val Glu Gly Ile Asn Asn Leu Thr Phe Thr Val Glu Asp Val Ala
        435                 440                 445

Gly Asn Lys Lys Asp Phe Ser Phe Ser Tyr Val Ile Asp Thr Ile Ala
    450                 455                 460

Pro Val Pro Pro Thr Ala Ser Leu Glu Asp Tyr Val Val Leu Pro Asn
465                 470                 475                 480

Gly Ile Ile Leu Ser Gly Asn Asp Leu Pro Ala Leu Val Gly Thr Ala
                485                 490                 495

Glu Pro Lys Ser Thr Ile Leu Leu Met Arg Asp Gly Lys Leu Tyr Asp
            500                 505                 510

Ser Ile Glu Val Asp Ser Asn Gly Thr Trp Lys Leu Ser Val
        515                 520                 525
```

(2) INFORMATION FOR SEQ ID NO:41:

(i) SEQUENCE CHARACTERISTICS:
(A) LENGTH: 377 amino acids
(B) TYPE: amino acid
(D) TOPOLOGY: linear (xi) SEQUENCE DESCRIPTION: SEQ ID NO:41:

```
Met Leu His Asp Ser Ala Asp Ser Gly Val Lys Gly Asp Met Ile Thr
 1               5                  10                  15

Lys Ile Asn Thr Pro Leu Phe Thr Gly Met Ala Glu Ala Asn Ala Lys
            20                  25                  30

Val Ser Ile Tyr Val Asp Gly Val Leu Ser Gly Glu Ala Ile Ala Gly
        35                  40                  45

Asp Asp Gly Val Trp Asn Phe Gln Phe Thr Thr Ala Leu Ser Asp Gly
    50                  55                  60

Ser His Asp Val Thr Val Lys Val Glu Asp Ile Ala Gly Asn Thr Ala
65                  70                  75                  80

Ser Ser Ser Ala Tyr Asn Phe Gln Ile Val Thr Gln Thr Gln Lys Pro
                85                  90                  95

Thr Ile Glu Leu Val Asn Asp Thr Gly Val Asp Asn Thr Asp His Ile
            100                 105                 110

Ile Asn Glu Lys Asn Pro Ala Leu Thr Gly Thr Ala Ala Pro Tyr Ser
        115                 120                 125

Thr Val Lys Leu Tyr Ile Asp Gly Ala Leu Ile Ala Glu Val Arg Thr
    130                 135                 140

Asn Lys Asp Gly Arg Trp Glu Tyr Thr Leu Lys Ala Asp Gln Gly Leu
145                 150                 155                 160

Val Asp Gly Asp His Arg Ile Thr Ala Ser Val Glu Asp Ile Ala Gly
                165                 170                 175

Asn Ile Ala His Ser Asp Pro Phe Leu Ile Ser Val Asp Thr Ala Ile
            180                 185                 190
```

```
Ser Ile Pro Ile Val Ser Leu Ser Pro Asp Ser Asp Ser Gly Ile Ser
        195                 200                 205

Asp Asp Asn Leu Thr Asn Ile Val Lys Pro Thr Leu His Leu Lys Asp
    210                 215                 220

Ile Asp Pro Asp Ile Ile Ser Val Gln Val Trp Asp Ala Met Ser Asp
225                 230                 235                 240

Thr Gln Ile Gly Val Ala Thr Gln Gln Pro Asp Gly Ser Trp Ala Tyr
                245                 250                 255

Thr Phe Thr Ser Asp Leu Thr Glu Gly Leu His Gln Val Tyr Val Lys
            260                 265                 270

Val Glu Asp Ile Ala Gly Asn Lys Ala Asn Ser Ala Ile Phe Asp Phe
        275                 280                 285

Thr Ile Asp Thr Thr Val Ser Thr Pro Val Ile Ser Leu Leu Ser Lys
    290                 295                 300

Asp Asp Thr Gly Val Thr Gly Asp Asn Leu Thr Asn Ile Asn Lys Pro
305                 310                 315                 320

Gly Phe Ala Ile Ser Gly Val Asp Ala Asp Ala His Arg Val Val Val
                325                 330                 335

Gln Val Met His Asn Gly Val Ser Glu Glu Ile Glu Leu Ser His Leu
            340                 345                 350

Asn Gly Ser Trp Leu Phe Ile Pro Gly Glu Tyr Val Gly Gly Trp Gln
        355                 360                 365

Leu His Val Asn Gly Glu Ser Arg Arg
    370                 375
```

(2) INFORMATION FOR SEQ ID NO:42:

(i) SEQUENCE CHARACTERISTICS:
(A) LENGTH: 116 amino acids
(B) TYPE: amino acid
(D) TOPOLOGY: linear (xi) SEQUENCE DESCRIPTION: SEQ ID NO:42:

```
Met Gly Val Gly Tyr Leu Tyr Gln Gly Asn Thr Trp Ala Asp Gly Ser
 1               5                  10                  15

Tyr Thr Leu Thr Val Lys Val Glu Asp Lys Ala Gly Asn Thr Asn Tyr
            20                  25                  30

Ser Ala Pro Leu Thr Val Val Ile Asp Thr Gln Ile Ala Ile Asp Gly
        35                  40                  45

Val Glu Leu Val Asn Asp Ser Gly Val Lys Gly Asp Asn Met Thr Asn
    50                  55                  60

Asp Asp Arg Pro His Phe Arg Val Thr Val Pro Thr Asp Val Asn Glu
65                  70                  75                  80

Val Arg Leu Ser Ile Asp Gly Gly Asn Ser Trp Val Gln Ala Thr Pro
                85                  90                  95

Gly Val Ala Gly Ser Trp Glu Tyr Ile Trp Pro Thr Asp Leu Ala Asp
            100                 105                 110

Gly Pro Thr Arg
        115
```

(2) INFORMATION FOR SEQ ID NO:43:

(i) SEQUENCE CHARACTERISTICS:
(A) LENGTH: 252 amino acids
(B) TYPE: amino acid
(D) TOPOLOGY: linear (xi) SEQUENCE DESCRIPTION: SEQ ID NO:43:

```
Met Thr Lys Thr Ile Asp Phe Ala Val Asp Thr Thr Leu Ser Val Pro
 1               5                  10                  15

Val Ile Val Leu Asp Ser Ala Asp Asp Thr Gly Ile Gln Gly Asp Asn
            20                  25                  30

Met Thr Asn Ser Thr Gln Pro Thr Phe Ala Leu Gln His Ile Asp Asp
        35                  40                  45

Asp Ala Val Arg Val Thr Val Ser Val Glu His Gly Gly Val Thr Thr
    50                  55                  60

Thr Phe Asp Ala Thr Lys Gly Thr Gly Gly Trp Thr Phe Thr Pro Pro
65                  70                  75                  80

Thr Ser Trp Ala Asp Gly Asp Tyr Thr Leu Ser Val Ser Val Glu Asp
                85                  90                  95

Lys Ala Gly Asn Thr Ser His Ser Ala Ser Leu Thr Val Thr Val Asp
            100                 105                 110

Thr Gln Ile Ala Ile Asn Asn Ile Glu Leu Val Asn Asp Ser Gly Ile
        115                 120                 125

Pro Asp Asp Asn Leu Thr Asn Asn Val Arg Pro His Phe Gln Val Thr
    130                 135                 140

Val Pro Thr Asp Val Asn Val Val Arg Leu Ser Ile Asp Gly Gly Lys
145                 150                 155                 160

Thr Trp Phe Asn Ala Thr Gln Ser Ala Thr Pro Gly Val Trp Asp Tyr
                165                 170                 175

Ile Trp Pro Asp Asp Val Ala Asp Gly Gly Tyr Thr Leu Thr Val Glu
            180                 185                 190

Ala Thr Asp Glu Ala Gly Asn Lys Ala Thr Gln Thr Ser Ile Ser Pro
        195                 200                 205

Ser Ile Pro Leu Cys Leu Cys Arg Pro Ser Arg Trp Thr Ala Gln Met
    210                 215                 220

Thr Ala Ala Ser Arg Ala Ile Ile Ser Pro Met Leu Lys Arg Arg Ala
225                 230                 235                 240

Leu Pro Ser Thr Ile Leu Ile Pro Met Ser Ala Gly
                245                 250
```

(2) INFORMATION FOR SEQ ID NO:44:

(i) SEQUENCE CHARACTERISTICS:
(A) LENGTH: 126 amino acids
(B) TYPE: amino acid
(D) TOPOLOGY: linear (xi) SEQUENCE DESCRIPTION: SEQ ID NO:44:

```
Met His Asn Gly Ile Lys Gln Glu Val Pro Leu Val Gln Thr Gly Gly
 1               5                  10                  15

Gln Trp Arg Phe Ala Pro Thr Ser Asp Trp Ala Asp Gly Asp Tyr Ile
            20                  25                  30

Leu Thr Val Lys Val Glu Asp Arg Thr Gly Asn Val Lys Gln Ser Ala
        35                  40                  45

Pro Leu Thr Val Thr Val Asp Thr His Ile Ala Ile Asp Arg Ile Glu
    50                  55                  60

Leu Val Asn Asp Ser Gly Ile Pro Gly Asp Asn Leu Thr Asn Glu Ala
65                  70                  75                  80

Arg Pro His Phe Gln Val Thr Val Pro Ala Asp Val Asn Gly Val Arg
                85                  90                  95

Leu Ser Ile Asp Gly Gly Lys Thr Trp Phe Asp Ala Thr Gln Gln Arg
            100                 105                 110
```

```
Asp Val Gly Arg Leu Gly Leu His Leu Ala Asp Glu Cys Gly
        115                 120                 125
```

(2) INFORMATION FOR SEQ ID NO:45:

(i) SEQUENCE CHARACTERISTICS:
(A) LENGTH: 398 amino acids
(B) TYPE: amino acid
(D) TOPOLOGY: linear (xi) SEQUENCE DESCRIPTION: SEQ ID NO:45:

```
Met Ala Ala Lys Arg Gly Leu Thr Pro Arg Ser Ser Ala Thr Ser Gly
 1               5                  10                  15

Val Trp Asp Tyr Thr Trp Leu Thr Asn Val Ala Asn Gly Pro His Thr
            20                  25                  30

Leu Met Val Glu Ala Ser Asp Lys Ala Gly Asn Lys Thr Thr Gln Lys
        35                  40                  45

Leu Asp Phe Thr Ile Asp Thr Ile Leu Ser Glu Pro Thr Ile Thr Leu
    50                  55                  60

Asp Ser Ala Asp Asp Ser Ala Ala Gly Asp Asn Ile Thr Asn Val Lys
65                  70                  75                  80

Met Pro Gly Phe Thr Leu Gly Asn Ile Asp Ala Asp Val Thr Lys Val
                85                  90                  95

Val Val Thr Val Ala His Asp Gly Lys Asn Gln Gln Ile Glu Leu Ile
            100                 105                 110

Lys Asn Gly Gly Val Trp Arg Phe Thr Pro Gly Ala Ala Trp Thr Asp
        115                 120                 125

Gly Asp Tyr Thr Leu Thr Val Lys Val Glu Asp Lys Ala Gly Asn Thr
    130                 135                 140

Asn Tyr Ser Ala Pro Leu Thr Val Thr Ile Asp Thr Gln Thr Ser Ile
145                 150                 155                 160

Asp Arg Ile Glu Leu Leu Asn Asp Thr Gly Ile Val Gly Asp Asn Leu
                165                 170                 175

Thr Asn Glu Ala Arg Pro Gln Phe His Ile Thr Val Pro Thr Asp Val
            180                 185                 190

Asn Ser Val Gln Leu Ser Leu Asp Gly Gly Ile Asn Trp Val Asn Ala
        195                 200                 205

Thr Leu Thr Ser Asp Gly Val Trp Glu Tyr Ile Trp Pro Thr Asp Leu
    210                 215                 220

Val Glu Asn Thr Tyr Thr Leu Thr Val Lys Ala Thr Asp Val Ala Gly
225                 230                 235                 240

Asn Thr Ala Thr Glu Thr Leu Asn Phe Thr Ile Asp Thr Thr Leu Ser
                245                 250                 255

Thr Pro Thr Ile Thr Leu Asp Ser Ala Asp Asp Ser Gly Thr Ala Asn
            260                 265                 270

Asp Asn Lys Thr Asn Val Lys Thr Pro Gly Phe Ile Ile Gly Gly Ile
        275                 280                 285

Asp Ser Asp Val Thr Gln Val Val Val Gln Val Met Arg Asp Gly His
    290                 295                 300

Ser Glu Glu Val Glu Leu Thr Gln Thr Asn Gly Gln Trp Arg Phe Val
305                 310                 315                 320

Pro Gly Ser Ala Trp Thr Asp Gly Asp Tyr Thr Leu Thr Val Thr Val
                325                 330                 335

Lys Asp Glu Ala Gly Asn Ile Arg His Ser Ala Pro Leu Thr Val Thr
            340                 345                 350

Ile Asp Thr Gln Ile Thr Ile Asp His Ile Glu Leu Val Asn Asp Ser
```

```
        355                 360                 365

Gly Ile Pro Asp Asp Asn Leu Thr Asn Asn Val Arg Pro Gln Leu Pro
    370                 375                 380

Gly Asp Gly Thr Asp Gly Cys Gln Arg Gly Ala Pro Glu His
385                 390                 395
```

(2) INFORMATION FOR SEQ ID NO:46:

(i) SEQUENCE CHARACTERISTICS:
(A) LENGTH: 172 amino acids
(B) TYPE: amino acid
(D) TOPOLOGY: linear (xi) SEQUENCE DESCRIPTION: SEQ ID NO:46:

```
Met Cys Val Arg Asn Phe Gln Val Thr Val Pro Thr Asp Val Asn Val
 1               5                  10                  15

Val Arg Leu Ser Ile Asp Gly Gly Lys Thr Trp Phe Asn Val Thr Gln
            20                  25                  30

Ser Ala Thr Pro Gly Val Trp Asp Tyr Thr Trp Leu Ala Asp Val Gly
        35                  40                  45

Glu Gly Lys His Thr Leu Thr Val Glu Ala Thr Asp Lys Ala Gly Asn
    50                  55                  60

Lys Thr Thr Gln Gln Leu Asp Phe Ile Ile Asp Thr Leu Leu Ser Glu
65                  70                  75                  80

Pro Thr Ile Val Leu Asp Ser Thr Asp Asp Ser Gly Thr Lys Gly Asp
                85                  90                  95

His Leu Thr Asn Val Asn Lys Pro Thr Phe Leu Leu Gly Asn Ile Asp
            100                 105                 110

Ala Asp Ala Arg Tyr Val Thr Val Glu Val Gln His Gly Gly Thr Lys
        115                 120                 125

Glu Val Leu Thr Ala Thr Lys Asp Ala Thr Gly Asn Trp Ser Val Thr
    130                 135                 140

Pro Thr Gly Thr Trp Ala Asp Gly Asp Tyr Thr Leu Thr Val Arg Val
145                 150                 155                 160

Glu Asp Glu Ala Gly Asn Glu Lys His Ser Gly Arg
                165                 170
```

(2) INFORMATION FOR SEQ ID NO:47:

(i) SEQUENCE CHARACTERISTICS:
(A) LENGTH: 305 amino acids
(B) TYPE: amino acid
(D) TOPOLOGY: linear (xi) SEQUENCE DESCRIPTION: SEQ ID NO:47:

```
Met Thr Asn Asp Ala His Pro Gln Phe Arg Val Thr Val Pro Gly Asp
 1               5                  10                  15

Val Asn Glu Val Ser Leu Ser Ile Asp Gly Gly Val Thr Trp Val Lys
            20                  25                  30

Ala Thr Gln Ser Ala Thr Pro Gly Val Trp Asn Tyr Thr Trp Pro Gly
        35                  40                  45

Thr Val Pro Asp Gly Asp Tyr Thr Leu Asn Val Lys Ala Thr Asp Asn
    50                  55                  60

Ala Gly Asn Thr Val Thr Glu Thr Leu His Phe Thr Ile Asp Thr Thr
65                  70                  75                  80

Leu Ser Thr Pro Val Ile Val Leu Asp Ser Ala Asp Asp Ser Gly Val
                85                  90                  95

His Gly Asp Asn Met Thr Asn Ser Thr Gln Pro Thr Phe Ala Leu Gln
```

```
            100                 105                 110

His Ile Asp Asp Asp Ala Val Arg Val Thr Val Ser Val Glu His Gly
        115                 120                 125

Gly Val Thr Thr Thr Phe Asp Ala Thr Lys Asp Ala Gly Gly Trp Thr
    130                 135                 140

Phe Thr Pro Thr Gly Ala Trp Ala Asp Gly Asp Tyr Thr Leu Ser Val
145                 150                 155                 160

Ser Val Glu Asp Lys Ala Gly Asn Thr Ser His Ser Ala Ser Leu Thr
                165                 170                 175

Val Thr Val Asp Thr Gln Ile Ala Ile Asn Asn Ile Glu Leu Val Asn
            180                 185                 190

Asp Ser Gly Ile Pro Asp Asp Asn Leu Thr Asn Asn Val Arg Pro His
        195                 200                 205

Phe Gln Val Thr Val Pro Thr Asp Val Asn Val Val Arg Leu Ser Ile
    210                 215                 220

Asp Gly Gly Lys Thr Trp Phe Asn Ala Thr Gln Ser Ala Thr Pro Gly
225                 230                 235                 240

Val Trp Asp Tyr Thr Trp Leu Ala Asp Val Gly Glu Gly Lys His Thr
                245                 250                 255

Leu Thr Val Gly Ala Thr Asp Lys Ala Gly Asn Lys Thr Thr Gln Gln
            260                 265                 270

Leu Asp Phe Ile Ile Asp Thr Leu Leu Ser Glu Pro Thr Ile Val Leu
        275                 280                 285

Asp Asn Thr Asp Tyr Ser Gly Asn Lys Arg Arg Ser Pro Asp Gln Arg
    290                 295                 300

Lys
305
```

(2) INFORMATION FOR SEQ ID NO:48:

(i) SEQUENCE CHARACTERISTICS:
(A) LENGTH: 333 amino acids
(B) TYPE: amino acid
(D) TOPOLOGY: linear (xi) SEQUENCE DESCRIPTION: SEQ ID NO:48:

```
Met Asp Ser Arg Asp Asp Thr Gly Ala Ile Gly Asp His Ile Thr Ser
 1               5                  10                  15

Val Lys Arg Pro Gly Phe Thr Ile Gly Asn Ile Asp Ala Asp Ala His
            20                  25                  30

Ser Val Ile Leu Arg Ile Thr Gln Gly Gly Asn Ser Gln Glu Val Thr
        35                  40                  45

Leu Thr Gln Val Gly Gly Gln Trp Arg Phe Thr Pro Asp Ala Asp Trp
    50                  55                  60

Ala Asp Gly Ser Tyr Thr Leu Thr Val Glu Val Thr Asp Asn Ala Gly
65                  70                  75                  80

Asn Val Arg Gln Ser Thr Pro Leu Val Val Thr Val Asp Thr Gln Thr
                85                  90                  95

Ser Ile Thr Asp Ile Thr Leu Val Asn Asp His Gly Val Pro Asp Asp
            100                 105                 110

Asn Leu Thr Asn Ser Thr Arg Pro Gln Phe Glu Ile Thr Val Pro Ala
        115                 120                 125

Asp Val Asn Ser Val Gln Leu Ser Ile Asp Gly Gly Ala Asn Trp Val
    130                 135                 140

Ser Ala Thr Gln Gly Ile Glu Gly Val Trp Gly Tyr Thr Trp Pro Thr
145                 150                 155                 160
```

```
Asp Met Gly Asp Gly Lys His Thr Leu Thr Val Met Val Thr Asp Arg
                165                 170                 175

Ala Gly Asn Thr Ala Thr Gln Thr Leu Glu Phe Phe Ile Asp Thr Arg
            180                 185                 190

Leu Ser Thr Pro Thr Ile Ala Leu Asp Ser Thr Asp Asp Thr Gly Thr
        195                 200                 205

Pro Gly Asp Asp Met Thr Asn Arg Thr Arg Pro Thr Phe Ile Leu Gln
    210                 215                 220

Asn Ile Asp Ser Asp Val Ile Asn Val Thr Val Ser Val Thr His Asn
225                 230                 235                 240

Gly Thr Thr Thr Ser Phe Thr Ala Thr Gln Gly Ala Gly Gly Trp Ser
                245                 250                 255

Phe Thr Pro Pro Ala Pro Trp Gly Asp Gly Asp Tyr Thr Leu Thr Val
            260                 265                 270

Thr Val Glu Asp Arg Ala Gly Asn Thr Arg Pro Ser Thr Pro Leu Thr
        275                 280                 285

Val Thr Val Asp Thr Gln Ile Ala Ile Asp Arg Ile Glu Leu Val Asn
    290                 295                 300

Asp Ser Gly Val Pro Gly Asp Asn Val Thr Lys His Val Arg Pro Gln
305                 310                 315                 320

Phe Gln Ile Ser Val Pro Asp Asp Val Glu Lys Phe Phe
                325                 330
```

(2) INFORMATION FOR SEQ ID NO:49:

(i) SEQUENCE CHARACTERISTICS:
- (A) LENGTH: 206 amino acids
- (B) TYPE: amino acid
- (D) TOPOLOGY: linear (xi) SEQUENCE DESCRIPTION: SEQ ID NO:49:

```
Met Pro Glu Gly Gln His Thr Leu Thr Val Glu Val Thr Asp Gly Ala
 1               5                  10                  15

Gly Asn Lys Met Thr Glu Thr Leu Asn Phe Thr Ile Asp Ile Thr Leu
            20                  25                  30

Leu Thr Pro Thr Ile Glu Leu Ala Pro Asp Gln Asp Thr Gly Gln Asn
        35                  40                  45

Lys Asn Asp Asn Leu Thr Ser Val Thr Gln Pro Val Phe Val Leu Gly
    50                  55                  60

Ser Ile Asp Lys Asp Val Arg His Val Glu Leu Ser Ile Glu His Asn
65                  70                  75                  80

Gly Thr Phe Lys Thr Val Val Leu Thr Glu Ser Ala Asp Gly Trp Arg
                85                  90                  95

Tyr Arg Pro Asp Ser Ala Leu Ala Asp Gly Ser Tyr Thr Phe Thr Val
            100                 105                 110

Thr Val Thr Asp Val Ala Gly Asn Gln Gln Thr Ser Ala Pro Leu Lys
        115                 120                 125

Val Thr Ile Asp Gly Thr Leu Thr Thr Pro Val Ile Glu Leu Ala Ala
    130                 135                 140

Gly Glu Asp Ser Gly Thr Val Gly Asp Arg Leu Thr Asn His Asp Arg
145                 150                 155                 160

Pro Val Phe Asp Ile His Gln Val Asp Ser Asp Val Thr Arg Val Met
                165                 170                 175

Val Lys Val Thr Tyr Asn Gly Lys Thr His Glu Glu Ala Ala Val Phe
            180                 185                 190
```

```
Thr Asn Gly Gln Trp Arg Phe Thr Pro Ser Ala Lys Leu Gly
        195                 200                 205
```

(2) INFORMATION FOR SEQ ID NO:50:

(i) SEQUENCE CHARACTERISTICS:
(A) LENGTH: 123 amino acids
(B) TYPE: amino acid
(D) TOPOLOGY: linear (xi) SEQUENCE DESCRIPTION: SEQ ID NO:50:

```
Met Val Asn Gly Ala Leu Arg Leu Leu Arg Ser Trp Ala Asp Gly Ser
 1               5                  10                  15

Tyr Gln Leu Ala Val Val Val Glu Asp Leu Ala Gly Asn Val Lys Glu
            20                  25                  30

Ser Ala Pro Phe Glu Val Arg Ile Asp Thr Thr Thr Thr Ile Asn Asn
        35                  40                  45

Ile Val Leu Leu Asn Asp Thr Gly Val Gln Asn Asp Gln Leu Thr Asn
    50                  55                  60

Val Ala Lys Pro Ser Phe Arg Ile Asp Val Pro Gly Asp Val Val Gln
65                  70                  75                  80

Val Arg Val Thr Leu Asp Gly Gly Ala Asn Trp Asn Val Ile Arg Lys
                85                  90                  95

Asn Ala Asp Gly Gln Trp Ile Phe Asp Ser Pro Asn Thr Leu Val Asp
            100                 105                 110

Gly Thr Tyr Thr Leu Arg Val Glu Ala Thr Gly
        115                 120
```

(2) INFORMATION FOR SEQ ID NO:51:

(i) SEQUENCE CHARACTERISTICS:
(A) LENGTH: 1289 amino acids
(B) TYPE: amino acid
(D) TOPOLOGY: linear (xi) SEQUENCE DESCRIPTION: SEQ ID NO:51:

```
Met Leu Asp Asp Ala Gly Lys Asp Ser Thr Asp Gly Ile Thr Asn Ile
 1               5                  10                  15

Thr Ser Pro Arg Phe Glu Ile Ser Ala Arg Glu Pro Leu Gln Ser Val
            20                  25                  30

Thr Val Ile Leu Asn Gly Lys Ser Ser Thr Leu Thr Gln Gly Ala Gly
        35                  40                  45

Asn Lys Trp Leu Phe Thr Pro Asp Thr Pro Leu Val Asp Gly Thr Tyr
    50                  55                  60

Lys Ile Glu Ile Val Ala Glu Asp Ile Ala Gly Asn Lys Ile Ser Lys
65                  70                  75                  80

Glu Val Ser Phe Thr Ile Asp Thr Ile Val Ser Asp Pro Ser Ile Asp
                85                  90                  95

Leu Leu Asp Ala Asp Asp Thr Gly Glu Ser Ala Val Asp Asn Ile Thr
            100                 105                 110

Ser Val Thr Thr Pro Arg Phe Val Ile Gly Asn Val Pro Ala Asp Ile
        115                 120                 125

Asp Thr Val Val Ile Arg Ile Asn Gly Val Ser Tyr Pro Val Thr Ala
    130                 135                 140

Asn Gly Asn Asn Leu Trp Glu Phe Gln Val Pro Val Ala Leu Asn Asp
145                 150                 155                 160

Gly Val Tyr Glu Ala Val Val Val Phe Arg Asp Ile Ala Gly Asn Ile
                165                 170                 175
```

```
Ser Glu Ile Lys Leu Pro Phe Thr Ile Asp Thr Thr Thr Ser Val Ser
            180                 185                 190

Val Arg Met Glu Leu Ala Ser Asp Thr Gly Asn Ser Asn Ser Asp Asn
        195                 200                 205

Leu Thr Asn Lys Gln Asn Pro Lys Phe Glu Gly Thr Ala Glu Pro Asn
    210                 215                 220

Ala Lys Leu Val Ile Thr Ile Val Asp Asp Lys Ser Gly Gln Glu Val
225                 230                 235                 240

Leu Lys Gln Thr Ile Thr Val Gly Ala Asp Gly Asn Trp Ser Val Thr
                245                 250                 255

Pro Asn Ile Leu Pro Asp Gly Met Tyr Thr Ile Asn Val Val Ala Thr
            260                 265                 270

Asp Val Ala Gly Asn Thr Ala Gln Thr Gln Glu Arg Phe Thr Ile Asp
        275                 280                 285

Thr Val Thr Ile Asp Pro Thr Ile Arg Leu Ser Asp Pro Ser Ile Asp
    290                 295                 300

Asp Gln His Glu Ala Thr Ser Leu Arg Pro Glu Phe Lys Gly Phe Ala
305                 310                 315                 320

Glu Ala Phe Ser Thr Ile Met Ile Gln Trp Asp Gly Lys Val Val Gly
                325                 330                 335

Ser Ala Asn Ala Asn Ala Asn Gly Glu Trp Ser Trp Thr Pro Pro Ser
            340                 345                 350

Val Leu Ala Pro Gly Ser Tyr Val Val Ser Ile Val Ala Lys Asp Lys
        355                 360                 365

Ala Gly Asn Asp Ser Ser Gln Val Asp Phe Pro Val Val Ile Pro Val
    370                 375                 380

Ile Asp Val Thr Pro Pro Thr Ile Lys Leu Ser Glu Glu Ser Asp Ser
385                 390                 395                 400

Gly Ala Leu Gly Asp Phe Thr Thr Asn Asn Lys Thr Pro Thr Leu Ile
                405                 410                 415

Gly Ser Thr Leu Pro Asn Thr Ile Val Ser Ile Tyr Val Asp Gly Val
            420                 425                 430

Lys Val Gly Glu Ala Thr Ala Asp Thr Ala Gly Arg Tyr Thr Phe Gln
        435                 440                 445

Leu Ser Glu Met Lys Asp Gly His Tyr Val Val Gln Val Gly Ile Val
    450                 455                 460

Asn Pro Arg Asp Asn Ser Glu Leu Arg Ser Thr Ala Val Asp Val Thr
465                 470                 475                 480

Ile Asp Thr Glu Val Ala Glu Leu Val Trp Asn Ile Ser Gly Met His
                485                 490                 495

Glu Gly Gly Tyr Ile Asn Thr Val Thr Pro Glu Ile Gly Gly Thr Ser
            500                 505                 510

Glu Pro Asn Ser Lys Ile Thr Ile Phe Val Asn Gly Val Gly Lys Ala
        515                 520                 525

Ile Ala Tyr Thr Thr Gly Ala Gly His Trp Gly Val Val Leu Pro Ala
    530                 535                 540

Leu Gly Asn Asp Gly Asn Tyr Glu Leu Thr Phe Lys Val Glu Asp Val
545                 550                 555                 560

Ala Gly Asn Ile Arg Glu Phe Gly Pro Gln Asn Val Ile Leu Asp Thr
                565                 570                 575

Val Ile Ser Pro Leu Thr Val Val Leu Arg Glu Ala Asp Asp Ser Gly
            580                 585                 590

Lys Val Gly Asp Trp Ile Thr Asn Lys Ser His Val Thr Ile Asp Gly
        595                 600                 605
```

```
Thr Ala Glu Ala Gly Ser Thr Leu Thr Ile Arg Asn Pro Gln Gly Val
    610                 615                 620

Val Ile Ala Thr Leu Val Val Gly Asn Asp Gly Arg Trp Ser Ala Glu
625                 630                 635                 640

Leu Asp Leu Arg Glu Gly Ser Asn Ala Phe Val Val Val Ser Glu Asp
                645                 650                 655

Lys Ala Gly Asn Ser Gln Gln Lys Glu Ile Leu Ile Glu His Asp Thr
            660                 665                 670

Gln Ile Glu Ile Ser Asp Ile Ser Leu Ser Arg Asp Thr Asn Ser Gly
        675                 680                 685

Asp Lys Tyr Asp Leu Ile Thr Asn Asn Lys Ser Pro Val Leu Val Ala
    690                 695                 700

Arg Thr Asp Pro Gly Ala Thr Val Gln Val Tyr Ile Asn Gly Val Leu
705                 710                 715                 720

Gln Gly Thr Val Glu Ala Ser Ser Ser Gly Asn Ile Ser Tyr Thr Met
                725                 730                 735

Pro Ala Asn Ser Ala Asp Gly Glu Tyr Gln Val Gln Phe Val Ala Thr
            740                 745                 750

Asp Thr Ala Gly Asn Arg Val Glu Ser Ala Ile Thr Thr Val Thr Ile
        755                 760                 765

Asp Ser Gln Ile Ala Val Phe Asp Ile Asp Glu Asp Ser Leu Pro Ala
    770                 775                 780

Leu Ser Asn Asn Arg Ala Leu Ser Val Ser Gly Val Gly Glu Ala Gly
785                 790                 795                 800

Ser Gln Val Ser Ile Phe Val Asp Gly Lys Leu Val Asn Val Val Met
                805                 810                 815

Val Glu Ala Asp Gly Thr Trp Arg Ala Pro Ile Leu Leu Gln Asp Asp
            820                 825                 830

Gly Thr Phe Asn Ile His Phe Ser Ile Thr Asp Val Ala Gly Asn Thr
        835                 840                 845

Glu Val Ser Lys Asp Tyr Ser Val Asp Val Asp Ser Ser Thr Asp Phe
    850                 855                 860

Pro Thr Leu Asn Leu Glu Asp Ala Ser Asn Ser Gly Ser Leu Asp Asp
865                 870                 875                 880

Leu Ile Thr Asn His Asn Lys Pro Val Leu Val Gly Thr Ala Glu Ala
                885                 890                 895

Gly Ala Thr Ile His Ile Tyr Val Asp Glu Lys Ile Val Ala Asn Val
            900                 905                 910

Leu Val Leu Glu Asp Gly Thr Trp Ser Tyr Gln Phe Asp Asn Ala Leu
        915                 920                 925

Lys Asp Gly Glu Tyr Ser Ile Arg Val Val Ala Glu Asp Pro Ala Gly
    930                 935                 940

Asn Thr Ala Glu Ser Pro Arg Leu Leu Val Thr Ile Asp Thr Ser Thr
945                 950                 955                 960

Phe Ile Asp Asn Pro Ala Met Val Ala Gly Ser Asp Asn Gly Ile Phe
                965                 970                 975

Ser Asn Asp Ser Ile Thr Ser Gln Thr Arg Pro Thr Phe Ser Ile Phe
            980                 985                 990

Gly Glu Met Asn Gln Ser Val Gln Ile Phe Ile Asp Gly Val Leu Val
        995                1000                1005

Asp Thr Ile Thr Val Thr Asp Arg Asn Gln Val Tyr Arg Pro Glu Ser
    1010                1015                1020

Pro Leu Gly Asp Gly Ser His Ser Ile Tyr Tyr Val Ile Thr Asp Lys
```

```
1025                1030                1035                1040

Ala Gly Asn Thr Ala Thr Ser Lys Thr Leu Asn Phe Thr Ile Asp Thr
                1045                1050                1055

Phe Asn Thr Thr Pro Val Ala Ile Asp Ser Ile Gly Gly Gln Thr Leu
            1060                1065                1070

Ala Glu Met Thr Gly Ser Asp Gly Lys Ile Tyr Ile Thr Asp Thr Thr
        1075                1080                1085

Arg Asn Leu Leu Phe Ser Gly Ser Ala Glu Pro Asn Ser Lys Ile Glu
    1090                1095                1100

Ile Ile Ile Asn Gly Leu Asn Val Gly Glu Val Trp Val Asn Glu Lys
1105                1110                1115                1120

Gly His Trp Gln Met Pro Val Asn Pro Leu Tyr Phe Thr Glu Gly Gln
                1125                1130                1135

Leu Asp Ile Thr Val Lys Ser Thr Asp Arg Ala Gly Asn Val Asn Gln
            1140                1145                1150

Glu Lys Tyr Ser Ile Trp Val Asp Thr His Ile Lys Val Phe Thr Ser
        1155                1160                1165

Glu Leu Asp Asp Asn Lys Ser Ser Ser Lys Thr Glu Trp Trp Ser Asn
    1170                1175                1180

Ser Asp Leu Ile Thr Met Arg Gly Thr Gly Glu Ile Gly Ala Thr Val
1185                1190                1195                1200

Ser Leu Ile Val Ala Gly Val Thr Leu Ala Thr Ala Val Val Ala Ala
                1205                1210                1215

Thr Gly Arg Trp Glu Leu Ser Thr Asp Lys Leu Pro Glu Gly Thr Tyr
            1220                1225                1230

Asp Ile Ser Leu Val Ile Glu Asp Ser Pro Glu Ile Val Gly Lys Met
        1235                1240                1245

Cys Val Lys Tyr Leu Leu Thr Glu Pro Ala Lys Cys Ser Gly Arg Asn
    1250                1255                1260

Val Phe Arg Tyr Cys Gln Arg Ser Asn Tyr Tyr Ala Gly Asp Gly Gly
1265                1270                1275                1280

Ser Gln Ile Ser Ala Asn Asn Asn Arg
                1285
```

(2) INFORMATION FOR SEQ ID NO:52:

(i) SEQUENCE CHARACTERISTICS:
(A) LENGTH: 463 amino acids
(B) TYPE: amino acid
(D) TOPOLOGY: linear (xi) SEQUENCE DESCRIPTION: SEQ ID NO:52:

```
Met Gln Gly Thr Ala Glu Ala Lys Ser Gln Leu Ile Ile Thr Asp Ser
 1               5                  10                  15

Glu Gly Asn Thr Tyr Thr Leu Thr Val Pro Asp Asn Gly Lys Trp Ser
            20                  25                  30

Met Ala Ile Pro Tyr Pro Ser Glu Gly Lys Phe Thr Ile Thr Ser Val
        35                  40                  45

Asp Ala Ile Gly Asn Arg Ser Asp Asp Val Pro Leu Asp Ile Met Lys
    50                  55                  60

Glu Val Pro Val Ile Ser Leu Ser Pro Asp Ser Asp Ser Gly Thr Val
65                  70                  75                  80

Gly Asp Asn Ile Thr Arg Asp Lys Gln Pro Thr Phe Ile Ile Gly Asn
                85                  90                  95

Leu Glu Ser Asp Val Val Val Val Gln Val Asp Ile Asn Gly Thr Val
            100                 105                 110
```

```
Tyr Asn Ala Glu Lys Asn Ala Asp Gly Val Trp Phe Phe Thr Pro Gly
        115                 120                 125

Thr Pro Leu Ala Asp Gly Ser Tyr Thr Ile Ser Val Ile Ala Ser Asp
    130                 135                 140

Ala Ala Gly Asn Gln Lys Asn Ser Leu Pro Ile Thr Val Thr Ile Asp
145                 150                 155                 160

Ser Thr Leu Thr Val Pro Glu Ile Ala Leu Ala Ala Gly Glu Asp Asn
                165                 170                 175

Gly Ala Ser Asp Ser Asp Asn Val Thr Asn His Thr Gln Pro Lys Phe
            180                 185                 190

Thr Leu Gln His Ile Asp Ala Asp Val Thr Gly Val Thr Val Asn Val
        195                 200                 205

Thr His Asn Gly Val Thr Asp Ile Tyr Gln Ala Thr Gln Gly Ala Asp
    210                 215                 220

Gly Trp Thr Phe Thr Pro Pro Ala Ala Trp Asn Asp Gly Asn Tyr Thr
225                 230                 235                 240

Leu Ser Val Thr Val Val Asp Arg Ala Gly Asn Ser Gln Gln Ser Ala
                245                 250                 255

Ser Leu Ala Val Thr Val Asp Ser Thr Val Thr Val Thr Ala Asp Ser
            260                 265                 270

Gln His Asp Asp Ala Ser Asp Asp Ala Thr Ala Thr Ala Val Thr Pro
        275                 280                 285

Pro Glu Ser Glu Thr Val Asn Ala Glu Ser Ala Thr His Leu Arg Thr
    290                 295                 300

Glu Pro Ser Ala Ala Glu Glu Ser Val Val Lys Val Thr Ala Tyr Ser
305                 310                 315                 320

Ile Thr Leu Leu Asn Ala Asp Ser Gly Asp Glu Ile Asp Arg Ser Ile
                325                 330                 335

Ser Gln Thr Pro Ser Phe Glu Ile Ser Val Pro Glu Asn Ile Val Asn
            340                 345                 350

Val Ser Ile Met Phe Glu Gly Glu Glu Phe Thr Leu Pro Ile Thr Asn
        355                 360                 365

Gln Lys Ala Ile Phe Glu Val Pro Leu Ser Leu Glu Asp Gly Glu Tyr
    370                 375                 380

Thr Met Asp Val Lys Phe Ile Asp Lys Asp Asn Asp Phe Leu Ile Lys
385                 390                 395                 400

Glu Lys Thr Phe Ser Val Asp His Ser Ser Ala Asp Ile Val Asn Ala
                405                 410                 415

Met Asn Val Arg Gly Lys Thr Glu Asp Asp Ile Asn Asp Ser Pro Ser
            420                 425                 430

Thr Ser Ser Val Gly His Asn Asn Asn Gly Ala Ile Asp Val Phe Ala
        435                 440                 445

Val Asn Glu Val Thr Leu Pro Val Asp Asn Gln Glu Glu His Ala
    450                 455                 460
```

(2) INFORMATION FOR SEQ ID NO:53:

(i) SEQUENCE CHARACTERISTICS:
(A) LENGTH: 598 amino acids
(B) TYPE: amino acid
(D) TOPOLOGY: linear (xi) SEQUENCE DESCRIPTION: SEQ ID NO:53:

```
Met Val Cys Val Ser Gly Gly Gln Lys Ile Lys Leu Val Asn Ala Arg
 1               5                  10                  15
```

```
Gly Glu Leu Cys Tyr Val Glu Ile Glu Asp Glu Tyr Leu Lys Glu Leu
            20                  25                  30

Ser Ala Phe Ser Ile Leu Pro Leu Asn Lys Val Val Asp Ser Ile Arg
        35                  40                  45

Val Lys Asn Ile Ile Lys Asn Ser Leu Ser Met Asn Lys Ile Phe Tyr
    50                  55                  60

Thr Lys Tyr Phe Phe Ser Ser Leu Phe Met Ala Ile Phe Ala Leu Thr
65                  70                  75                  80

Ile Pro Val Phe Ser Asn Leu Phe Tyr Asp Lys Leu Val Pro Ser Ala
                85                  90                  95

Ser Val Ser Ser Leu Phe Gly Val Ala Ile Ile Val Ala Val Phe Ile
            100                 105                 110

Val Phe Glu Phe Ile Leu Arg Thr Ser Lys Asp Ile Tyr Gln Ser Ile
        115                 120                 125

Thr Ala Arg Gln Asp Asp Val Asp Ile Asp Ile Ala Phe Leu Glu Ala
    130                 135                 140

Val Leu Tyr Ser Lys Lys Lys Asn Gly Arg Ser Met Ser Ser Ala Phe
145                 150                 155                 160

Val Leu Trp Asn Glu Phe Gln Lys Ile Lys Pro Val Leu Leu Asn Ser
                165                 170                 175

Ile Phe Gln Arg Ile Ala Asp Ile Pro Ile Phe Ile Ile Phe Leu Ile
            180                 185                 190

Val Ile Tyr Val Asn Leu Gly Leu Val Val Ile Val Pro Ile Thr Met
        195                 200                 205

Phe Ile Val Ser Ile Ile Ile Ser Leu Val Asn His His Tyr Thr Asn
    210                 215                 220

Glu Leu Met Asn Lys Gln Lys Glu Gly Gln Lys Asn Arg Asn Ile Phe
225                 230                 235                 240

Ile Ser Glu Val Phe Leu Ser Ile Lys Met Ile His Thr Leu Asn Asn
                245                 250                 255

Gln Gly Leu Leu Phe Asp Trp Val Asn Thr Ser Asn Glu Gln Ser Tyr
            260                 265                 270

Leu Asn Leu Lys Ile Arg Lys Leu Asn Leu Ile Tyr Gln Ser Ile Leu
        275                 280                 285

Gly Ser Met Ser Ser Ile Thr Gln Ile Thr Ile Met Val Ile Ala Phe
    290                 295                 300

Phe Met Val Ile Lys Gly Asp Val Thr Thr Gly Ala Ile Val Ser Ser
305                 310                 315                 320

Val Ile Val Ser Gly Arg Ile Ser Gly Ile Ile Ser Asn Phe Ser Ser
                325                 330                 335

Thr Leu Ile Ser Ile Leu Ser Ala Glu Lys Thr Gly Lys Asp Leu Leu
            340                 345                 350

Ser Phe Phe Asp Glu Asp Gln Ala Glu Lys Thr Pro Ala Leu Gln Ser
        355                 360                 365

Ile Ser Lys Cys Asn Gly Asp Ile Ser Ile Arg Gly Val Ser Tyr Gln
    370                 375                 380

Tyr Asp Ala Gln Ser Pro Met Ile Ile Asn Arg Leu Ser Ile Asp Ile
385                 390                 395                 400

Pro Ala Gly Gln Arg Val Ala Val Val Gly Glu Cys Gly Ala Gly Lys
                405                 410                 415

Ser Ser Leu Leu Gly Met Leu Ser Gly Tyr Leu Ser Pro Thr Asp Gly
            420                 425                 430

Ala Ile Leu Tyr Asp Gly Tyr Asn Leu Gly His Leu Ser Gln Asn Phe
        435                 440                 445
```

```
Phe Ser Gln His Leu Ser Val Val Thr Thr His Asp Val Leu Phe Thr
    450                 455                 460

Gly Thr Ile Glu Ser Asn Phe Ala Leu Lys Pro Gln Asn Asp Arg Gly
465                 470                 475                 480

Arg Val Leu Lys Ala Leu Gln Leu Ala Asn Cys Gly Phe Ile Leu Gln
                485                 490                 495

His Pro Met Gly Leu Lys Phe Pro Val Asn Phe Met Ala Lys Asn Leu
            500                 505                 510

Ser Ser Gly Gln Gln Gln Gln Leu Leu Leu Ala Arg Ser Leu Ser Ser
        515                 520                 525

Asp Ala Ser Val Phe Leu Trp Asp Glu Pro Thr Ser Asn Leu Asp Glu
    530                 535                 540

Asn Thr Glu Lys Gln Ile Phe Asp Asn Leu Asp Glu Phe Ile His Gly
545                 550                 555                 560

Lys Thr Leu Ile Met Val Thr His Arg Arg Tyr Leu Ile Lys Tyr Phe
                565                 570                 575

Asp Arg Val Leu Val Met Lys Gly Gly Lys Ile Ile Arg Asp Cys Ser
            580                 585                 590

Pro Asp Lys Leu Leu Met
        595
```

(2) INFORMATION FOR SEQ ID NO:54:

(i) SEQUENCE CHARACTERISTICS:
(A) LENGTH: 171 amino acids
(B) TYPE: amino acid
(D) TOPOLOGY: linear (xi) SEQUENCE DESCRIPTION: SEQ ID NO:54:

```
Met Leu Tyr Ala Asp Arg Asn Ala Asn Gly Ile Ile Ile Asn Met Leu
 1               5                  10                  15

Gln Gly Lys Cys Arg Leu Gly Ala Ile Arg His Val Ile Ala Met Asp
            20                  25                  30

Thr Thr Val Val Arg Ala Ile Gln Tyr Asp His Arg Arg Arg Gln Arg
        35                  40                  45

Ser Ile Asn Ser Glu Val Glu Cys Leu Arg His Arg Ile Thr Arg Ile
    50                  55                  60

Val Ser Arg Phe His Ile Gln Arg Ile Val Ala Ile Arg His Gly Ala
65                  70                  75                  80

Arg Pro Gly Ile Ile Pro Asp Ala Arg Arg Arg Ala Leu Cys Arg Leu
                85                  90                  95

Asn Pro Gly His Ala Thr Val Asn Ala Gln Thr Asp Phe Val Asn Val
            100                 105                 110

Pro Arg Tyr Arg His Ala Glu Leu Arg Met Gly Val Val Ser His Ile
        115                 120                 125

Val Ala Gly Asn Thr Val Ile Ile Asn Gln Phe Asn Asn Ile Asn Gly
    130                 135                 140

Asp Leu Gly Ile Asn Ser Asp Arg Gln Arg Pro Glu Cys Phe Ser Phe
145                 150                 155                 160

Pro Ala Ser Ser Ser Thr Leu Thr Val Ser Val
                165                 170
```

(2) INFORMATION FOR SEQ ID NO:55:

(i) SEQUENCE CHARACTERISTICS:
(A) LENGTH: 103 amino acids
(B) TYPE: amino acid (D) TOPOLOGY: linear (xi) SEQUENCE DESCRIPTION: SEQ ID NO:55:

```
Met Leu Arg Leu Thr Ser Leu Thr Ser Pro Gly Thr Val Thr Arg Asn
 1               5                  10                  15

Cys Gly Trp Ala Ser Leu Val Ile Leu Ser Pro Gly Ile Pro Leu Ser
            20                  25                  30

Leu Thr Ser Ser Ile Thr Ser Met Val Ile Trp Val Ser Thr Val Thr
        35                  40                  45

Val Ser Asp Leu Ser Val Phe Arg Ser Pro Pro His Leu Pro Pro Ser
    50                  55                  60

Leu Ser Ala Tyr Ser Arg His Leu Pro Met Cys Arg Ser Val Ser Arg
65                  70                  75                  80

Ser Ser Cys Arg Ser Arg Leu Trp Trp Pro Ser Ala Pro Leu Ser Cys
                85                  90                  95

Arg His Ala Val Pro Gln Pro
            100
```

(2) INFORMATION FOR SEQ ID NO:56:

(i) SEQUENCE CHARACTERISTICS:
(A) LENGTH: 127 amino acids
(B) TYPE: amino acid
(D) TOPOLOGY: linear (xi) SEQUENCE DESCRIPTION: SEQ ID NO:56:

```
Met Lys Leu Trp Thr Cys Phe Ile Gly Gln Val Ile Pro Asp Asn Thr
 1               5                  10                  15

Arg Val Ile Lys Lys Leu Asn Ala Ile Asn Arg Arg Leu Arg Ile Asp
            20                  25                  30

Ser His Arg Gln Arg Arg Arg Ile Ile Cys Ile Thr Arg Leu Ile Phe
        35                  40                  45

Tyr Leu Tyr Arg Gln Arg Ile Val Ala Ile Gly Pro Gly Cys Ala Arg
    50                  55                  60

Arg Lys Ala Pro His Thr Ala Val Leu Asn Gln Leu Tyr Leu Leu Val
65                  70                  75                  80

Leu Thr Ile Met Arg His Arg His His His Phe Gly His Val Gly Val
                85                  90                  95

Asp Ile Thr Glu Gly Lys Ala Trp His Leu Asn Val Gly Asp Val Ile
            100                 105                 110

Ala Ser Gly Ala Ile Ile Arg Ala Val Gln Gly Asn Arg Arg Phe
        115                 120                 125
```

(2) INFORMATION FOR SEQ ID NO:57:

(i) SEQUENCE CHARACTERISTICS:
(A) LENGTH: 127 amino acids
(B) TYPE: amino acid
(D) TOPOLOGY: linear (xi) SEQUENCE DESCRIPTION: SEQ ID NO:57:

```
Met Arg Val Tyr Cys His Arg Gln Arg Arg Gly Leu Leu His Ile Ser
 1               5                  10                  15

Gly Pro Ile Phe Tyr Leu His Arg Gln Asp Ile Val Ala Val Arg Pro
            20                  25                  30

Val Ala Gly Arg Arg Lys Ala Pro Leu Ser Ala Gly Leu Asn Gln Trp
        35                  40                  45

His Leu Leu Leu Asn Ala Ile Val His Tyr Leu His Tyr His Pro Ala
    50                  55                  60
```

```
Asp Ile Gly Ile Asn Ile Val Glu Gly Lys Ala Arg Arg Phe Asn Ile
65                  70                  75                  80

Gly Asp Ile Ile Ala Arg Asp Ala Ala Val Ile Cys Ala Val Gln Arg
                85                  90                  95

Glu Gly Arg His Arg Gln Ser Gly Ile Asp Gly Glu Ile Glu Val Cys
            100                 105                 110

Val Ala Leu Phe Pro Ala Ser Ser Val Ala Ser Thr Val Arg Val
        115                 120                 125
```

(2) INFORMATION FOR SEQ ID NO:58:

(i) SEQUENCE CHARACTERISTICS:
(A) LENGTH: 115 amino acids
(B) TYPE: amino acid
(D) TOPOLOGY: linear (xi) SEQUENCE DESCRIPTION: SEQ ID NO:58:

```
Met Pro Gly Asn Ile Ser Ser Cys Cys Cys Tyr Ile Val Phe Ala Ile
 1               5                  10                  15

Leu Glu Arg Arg Ser Lys Arg Ile Ala Pro Cys Pro Ile Phe Ser Asn
            20                  25                  30

Asn Asp Leu Thr Lys Met Phe Lys Ser Lys Ile Asn Arg Asp Cys Arg
        35                  40                  45

Thr Gly Phe Arg His Thr Asn Lys Cys Trp Gln Gly Ala Ile Cys Asn
    50                  55                  60

Val Val Ile Phe Asn Ala Gly Ile Thr Thr Ile Ile Gln Leu Asn Arg
65                  70                  75                  80

Arg Leu Phe Trp Ser Asn Gly Val Gly Tyr Asp Thr Ile Arg Arg Phe
                85                  90                  95

Val Phe Ile Thr Cys Phe Ile Tyr Ser Asn Asp Phe Tyr Thr Ile Phe
            100                 105                 110

Ala Leu Arg
        115
```

(2) INFORMATION FOR SEQ ID NO:59:

(i) SEQUENCE CHARACTERISTICS:
(A) LENGTH: 107 amino acids
(B) TYPE: amino acid
(D) TOPOLOGY: linear (xi) SEQUENCE DESCRIPTION: SEQ ID NO:59:

```
Met Thr Gly His Thr Thr Phe Arg Arg Lys Phe Lys Cys Trp Phe Ile
 1               5                  10                  15

Gly Asn Gly Ile Asp Ser Asn Asp Lys Phe Gly Ala Thr Ala Pro Ile
            20                  25                  30

Ser Ser Leu Gly Leu Cys Leu Gln Ile Ile Cys Ser Ile Ser Gln Cys
        35                  40                  45

Phe Arg Arg Cys Lys Gly Glu Val Thr Gln Thr Ile Arg Tyr Ser Leu
    50                  55                  60

Thr Asp Ser Asn Thr Ile Asn Phe Asn Asn Asn Arg Gly Ile Gly Ser
65                  70                  75                  80

Ser Ala Asn Tyr Lys Leu Arg Phe Gly Lys Ile Ser Tyr Thr Ile Ile
                85                  90                  95

Phe Ala Thr Ala Val Thr Leu Gly Arg Thr Arg
            100                 105
```

(2) INFORMATION FOR SEQ ID NO:60:

(i) SEQUENCE CHARACTERISTICS:
(A) LENGTH: 24701 bases
(B) TYPE: nucleotide
(C) STRANDEDNESS: single stranded
(D) TOPOLOGY: linear (xi) SEQUENCE DESCRIPTION: SEQ ID NO:60:

```
ACUCAAAGCG UUAUUUGCAU UUUCGCUAUA GUUCUCGUCU GCUGAAAUGC CUGGUGUAAA     60

CCAGGCAUUU UCUUACCUGG UAUUAUUGUC UUUGUAUCCC UUUCAAAAAA GAGAAGCGCA    120

UAUCUUACGG AAAAAUGUCG CUUAUCGCCU CUGGCCGACU CGCCUCGGCA CAUCAUUAUC    180

CAGCCGAAGU UCAUAAAUGU ACUGCAAUAA CCCGGAUUGU CUUAAAUAUG AAAGAGAAAU    240

CUCAUCUGCA AAAUAUAUAA UUUAUAGCCA UUUUUUGACA ACAAAAAGAU AUUAUAAAAU    300

AACGGUAGAG AAUGGUCGGU AUUAUCAAUG GUUAAUUAAA UGUUUGCUUU AGCUUGUGAU    360

GAGCUCAAAU AUGAUAUGUG UAUCUUGCUU UAUUUUUAAU UGCUGAAGAU AAAAUUGUUA    420

CUUAUAGCUG GCUUUAUAUA AAAAAUGGUU UUAUUUGUGU AUUUUUUUAC ACAAUUCUGA    480

UUUUUUACUC CCCACUUAUU AUAUUUUCAA UGAUUUAAGU UAUAUUGAAG UCCAUAUGAC    540

CCUAUGUUUU AAUUGUGAAA AUUAAUUUUA UCCUCUGGAG GCAAAUUUAU UAAAUACGUA    600

UGGUUAUAAC GCGUAUUAAA AAGAAAUAUG UCCUUAAAAU GAUUUAGAGU UUCAAUGAUU    660

AGCUAACAAA UCUAUUUAUC GGCGGGUGGU UUUAAUUUGC UGAUGACUAU UUUUUAUUUA    720

UGAGUUGAGA GCUUAUGCGA UACCUAUUAU UGGGGAGGAU AUAGUUAGUG CAAUAAUUGA    780

UGUCUACCUA AUUAAAAAAA UGAAGAGUGU UUUUAAUUAA AGCACUCAUC UUUGUUGUGG    840

GCGCAUAAAA AUGGCGUCGU UGUUUUUAUU UUUCUGAUUA CGAGAUGUAA GAAAACUGAA    900

AUCUAUAAAG CGUAUUGGUA GCAGGAAGCC AAGGGCGGUA GCGUUCACUU UCUGAAUAAG    960

UUGAGCAUCC UUUAUCCUUU CUAAUCCACA AAAACAUUUU AUUCACAAUG UAAUAUCAGG   1020

AGACAACAUG GAAGACGAAA GUAAUCCGUG GCCUAGUUUU GUUGAUACAU UCUCUACGGU   1080

AUUGUGCAUU UUUAUAUUUC UUAUGUUGGU GUUUGCACUU AAUAAUAUGA UUAUUAUGUA   1140

UGACAACUCA AUUAAAGUUU AUAAAGCAAA UAUAGAGAAU AAGACUAAAU CUACUGCUCA   1200

AAAUAGCGGA GCCAAUGACG AUUCAAAUCC UAAUGAAAUA GUUAAUAAGG AAGUGAAUAC   1260

UCAAGAUGUG UCGGACGGAA UGACUACAAU GUCAGGUAAG GAGGUUGGAG UAUACGAUAU   1320

CGCCGAUGGU CAGAAAACUG AUAUAACGUC UACAAAAAAU GAGCUUGUUA UUACGUAUCA   1380

UGGCAGGCUG AGAAGCUUUU CAGAAGAGGA CACUUAUAAA AUAAAGGCUU GGUUAGAAGA   1440

CAAAAUCAAU AGUAAUUUAU UGAUAGAAAU GGUUAUUCCU CAGGCAGACA UCUCUUUCUC   1500

UGACUCUCUA CGACUGGGAU AUGAACGGGG AAUUAUUUUG AUGAAAGAGA UUAAGAAAAU   1560

AUAUCCUGAU GUAGUUAUUG ACAUGAGUGU UAACUCCGCA GCAUCAAGUA CAACGAGUAA   1620

AGCUAUUAUC ACGACUAUUA AUAAAAGGUG UCAGAGUGAA AUAUAUAAAU CAUUACCGCU   1680

AUUUGUUGUC UGUUCUUUCC UUGCCAUACU CCCUUUUUUU GCUUUAUCUU UUCCCGGUAU   1740

AAGAGAGUAU GUUUUUGAUA ACUUCAUGGU UUCUGCAAUU UACAAUGGAG UCAUUAUUGC   1800

CAUUUAUAUU ACAGGUUCUU UGUGUGCAUU AUUCACUAUU CUUAAAAAUA UUUCAGCAAA   1860

AGACAUAUUA AUAGCUCAGG ACGCCAGUAG AAAAAAUAGC AUUCUUUCUA ACCUCAAUCA   1920

GGUUUUGUUU GCCGGGGAGU CCAAACAGUG UGAUUUCAAU UUACUGAUGG AAUUAGAUGA   1980

CAAUGUGUCU ACCGCCCGUA AUCAACGAUU GUCAUUUAUU AUGAGCUGUA GCAAUGUGUC   2040

GACGCUUGUU GGCCUGUUGG GGACGUUUGC GGGUCUGUCU AUUACGAUUG GUUCAAUCGG   2100

GAACUUAUUG AGCUCGCCAU CAGAUGUUGG CGGUGAUAAU GCAAGUAAUA CACUCAAUAU   2160
```

```
GAUCGUGACA AUGGUAGCGU CGCUUUCUGA ACCAUUGAAA GGGAUGAAUA CCGCAUUUGU 2220
AUCUUCUAUC UAUGGUGUUG UUUGCGCCAU ACUCCUGACC UCACAAAGUG UUUUUGUUCG 2280
CAGCUCCUAU UCCCUUGUUU CUACGGAAAU CAAAAAAUUA AAAAUCAUAA GCAACAGAGC 2340
CAAUAAUAAA CAGCGAAGCC UGCGGGUUGA AUCAGAGACG CUUGUAGAAU UUAAAGAGUU 2400
GUUUAAAGCG UUUUUUGAUA ACUACCUGAC AGUUGAAAAC UUACGGACGC AGGAUGAAGA 2460
AAAGAAACGA GAGAUGCUAU CAGAUAGCUU UGUCACUUUG CAAAACCGAC UAUUGGAUAA 2520
CUCAGCAAAA CUGGAACAAA UUUUUACGCU GAUUGAUGGU UAUCUGGUAA GCAGUAACGG 2580
AAAAUCUCAA AAAAUUAUCU GACGGUGUAA UAACAAUUAC CUCUCGUUUA UCUGAAGGUA 2640
AUAUCCUGCU UGCUGAUAAU AAUGCACGAC UGGAGGCAAU GAGUACAAUA CAAAAUAUUA 2700
UAGAUAAAAA GAAUGAUUCA AUAAUGACAU CAGUUGAUAA AUGUUAUCAG GAAUCUCUUU 2760
CACAUGGUAA GACCAUAAAC GAUAUUGCCG CUGGCAGUGC CGAUAUUUCU CAUACUCUCG 2820
AUGGGCUGAG AAAAGAAAUG GAUGAGGAUA UGAAUAAUGU UCAUUUAGCG CUAUCCGAUC 2880
UAUCGGCUAC UGAUAAAAAG AUUAUUGCCA AUACUAAAGA GAUUAGUGCU GAAAUGGUUA 2940
GCUACCGUGA UACCUAUAUG CCAUUAAUGG AAAAAAUAAC AUCUAUGCAU CAGGAAAUAG 3000
UAAAGCAACG UUUGUUAAAC AAGGAGGAAA AAAAUGAAGA UUAAGAUGUU UUUUCUGACG 3060
ACUGCUUUUA UUACACAAAG CACAUACGCC AGCGAGCUUC CGGUCAUUCC UCUAAGAGAU 3120
UUAGUUAAUG CCGCAUUAAC GCAUCAGCCC UCUGUUGCUG UUUCAUAUUA UGAGACUGAA 3180
AAGAAAAACA GUGACUUAGA UCUUUCACGG GCAGCACUUU AUCCUACCCU GGAUCUAACA 3240
UCUGGCCUUA AUAAUAACAG GAAAGAGUCA UCAGGUACCG AGAGGAACGU UGAAAAUAAG 3300
GUGUCUUUAU CAUACCGAAU AACGGAUUUU GGAGUGAGGG GGCUAAUAU CAGGAAAUCU 3360
GAAUAUGAAA GAGAUAAUAG UAAAACUGAC UAUGAAAAAA CAAAGAAUAU AGUGUCUCAG 3420
GAGGUUGUGA CAACCUAUUA CAACAUCAGU AAAUAUCGUG AAAUGAUUGA UGGCGUAAAU 3480
CUGGAGAAAG AGUUUUAUAA AAAGAUGCUG GAACCUUUUU CGUUGCUGGU AUCUUCCGGU 3540
GUAGCUAUGC AAUCUGAUAU GCGUAAAGUA CAAGUAUCUA UCGAUGCAUU AAAUACCAGA 3600
AGCAUUAUGU AUCAGUCGAU GUUGGAUGAU GAAAUGUAUA AAAUGCAGAA UAUGACUGGU 3660
CUGAAUUUAU CGCCAGUUCA GAUUCAAAGC GAUGAAAAAU UCAACCUCUU CAAAAAAUAU 3720
AUCUUUGUCG AAAGCCCUGA AAAACUUAUG GACAUGGUGA UGAAAUACAA CGAUGACUAU 3780
AAGAUGCUUG UCAAUACCCG AAAAGCCGCG ACCGAAGAUA UUAAUGCCGC AAAAUCAUCC 3840
UAUUUUCCGA CUGUAGAUCU UGUUUCCAGC UAUGUACAGA AUAACCCAAG CGGUAGUGCC 3900
AAAAAAAGUG AUUAUGAAGA UGAAUUUAAA ACGGGUAUCA AUGUCAGUUU CAACAUUUUU 3960
AAUGGGUUCA GAAAUUCAGC CCAGGAAAGA AAAAUGGUGG CAAGUUACUC GCAGGCUAAG 4020
CUGCAAAUUG ACGAUUUUUU GAUUAAAACG CGUUAUAACA UUGAUUCACA ACUUUCAAGA 4080
UACGCCGCUG CAAAAGAGAC UUACUCAGUG GCGGAACGUU CACAUACAAA CGCGUUACAG 4140
CUUACUGAAU UAUAUGAGCA GGAGUUUCAG UUAGGGCAAA AAAGUUUGCU UGAUUUAAUU 4200
UCAAGCCGUA AUGAAGCAUU UCAGGCAUAU GUAAGCAUGA UCGACAGCAA AUAUAGCCUG 4260
UAUAUUUUAA AGCUACAGCA ACUCUCAUUG AUUUUUCAUU UAAUGGAUUA UUUAAAAGGA 4320
AAUACUGAAA GUGAGUUAAA UGUAAUGAAA UGAAUAGAAG ACAAAGCGAU CAUCUCAUGA 4380
UGAUAAUUAU UUCUUUGACG AUCUUAAUUA UUAUCCUUAC CUACUUUAUA GAAAUUAAUU 4440
CAGUGGUUCA UGGUCAGGGC GUUAUCACUA CUAAAGAUAA UGCUCAGUUA AUAUCUCUUU 4500
CUAAAGGAGG GACGAUACAA GAUAUUUAUG UAGCCGAGGG UGAUACUGUA AAAAAAGGAG 4560
```

```
AACUCCUUGC AAAGGUCGUU AACCUUGAUC UGCAAAAAGA AUAUCAAAGG UAUAGAACUC   4620
AAAAAGGGUA UCUGGAUAAA GAUGUUAACG AAAUAUCUUU CAUUCUUGAU AAAGAAAAUG   4680
AGAGUGGGUU GAUUACCCUG GAUGGCACCC GUUCUUUAAG CAAUAAAGAG GUAAAAGCGA   4740
AUAUUGAAUU AGUGCAUAGU CAGAUAAGAG CUAAAGAGUU AAAAAAAACC UCUCUUGAUU   4800
CUGAGAUUAG CGGAUUACAA GAGAAGCUGA GUUCGAAAGA AAAAGAACUC GCAUUGCUUG   4860
CCGAAGAAAU AAAUAUUCUU UCCCCACUGG UAAAAAAAGG AAUUAGCCCA UAUACCAAUU   4920
UUCUUAACAA GAAACAGGCG UAUAUAAAAG UUAAGUCUGA AAUUAAUGAU AUUGAAAGUA   4980
GCAUCACUUU AAAAAAAGAU GAUAUUGAGU UGGUUGUUAA UGAUAUUGAG GCGCUUAAUA   5040
AUGAAUUGCG ACUAUCUUUA UCUAAAAUAA UAUCUAAAAA UCUUCAGGAA CUUGAGGUUG   5100
UUAACUCUAC AUUAAAAGUA AUAGAGAAGC AGAUAAAUGA GGAGGAUAUC UAUUCACCGG   5160
UUGACGGUGU AAUUUAUAAA AUCAAUAAAA GUGCCACUAC UCAUGGUGGU GUGAUUCAGG   5220
CGGCGGACUU ACUUUUUGAA AUAAAACCAA AAGUAAGGAC UAUGCUGGCC GAUGUGAAAA   5280
UAUUACCCAA AUACCGUGAC CAAAUAUAUG UAGAUGAAGC CGUUAAACUG GAUGUGCAGU   5340
CAAUUAUCCA ACCAAAGAUA AAAUCGUAUA AUGCGACUAU CGAUAAUAUU AGCCCUGAUU   5400
CCUAUGAGGA AAAUACCGGA GGAACAAUUC AGCGUUAUUA UAAAGUAAUU AUUGCAUUCG   5460
AUGUUAAUGA AGAUGAUUUA CGGUGGUUAA AACCAGGUAU GACUGUUGAC GCCAGUGUAA   5520
UUACCGGAAA ACACAGCAUU AUGGAAUACC UGUUAUCUCC CUUGAUGAAA GGCGUGGACA   5580
AAGCCUUUUC AGAACCAGUU AAUACUAAAC GAUUAGAUAC ACCUUGAGAG UGAAUAUAAU   5640
AUUAUGGGAA AUAAAAGCAU ACAAAAGUUU UUUGCCGAUC AAAAUUCUGU AAUUGAUUUA   5700
UCUUCUUUGG GUAAUGCCAA AGGCGCAAAA GUUUCUCUUU CCGGGCCAGA CAUGAACAUU   5760
ACCACGCCGC GUGGUUCAGU GAUCAUUGUC AAUGGCGCUC UUUAUUCAAG UAUCAAAGGC   5820
AAUAACCUCG CUGUUAAAUU UAAAGAUAAG ACUAUUACCG GCGCUAAAAU UCUGGGCAGC   5880
GUAGAUUUAA AAGAUAUUCA ACUGGAGAGA AUUGACAGCU CAUUGGUUGA UUCUGCUCAG   5940
GUAGAAAAGA AAGGUAAUGG CAAACGACGA AAUAAGAAGG AAGAAGAGGA AUUAAAAAGC   6000
AGCUUGACGA UGCUGAAAAC GCAAGAAAGA AGCUGAUAAG GCGAAGGAAG AAGCAGAGAA   6060
AGCUAAGGAG GCUGCAGAAA AAGCGCUCAA UGAAGCGUUU GAAGUACAGA ACUCGUCAAA   6120
GCAAAUUGAA GAAAUGCUGC AGAACUUUUU GGCUGACAAU GUAGCAAAAG ACAAUCUGGC   6180
UCAGCAAAGC GAUGCUUCCC AGCAAAAUAC ACAGGCUAAA GCAACGCAGG CUUCUAAACA   6240
GAACGAUGCU GAAAAAGUUC UUCCUCAACC UAUUAAUAAA AAUACCAGUA CUGGCAAAAG   6300
UAAUAGCAGU AAAAAUGAGG AAAAUAAGCU CGAUGCCGAG UCUGUUAAAG AGCCGCUUAA   6360
AGUCACAUUA GCGCGUGCGG CCGAGAGUAA CAGCGGUAGC AAAGAUGAUA GUAUAACUAA   6420
UUUUACCAAA CCUCAGUUUG UAGUUAGCAC UGCUCCCAAU GCCACGGUUA UUAUUAAAAU   6480
UAAUGGUAUU GCUGUCGGUC AGGCUGUAAC GGAUAGUUUG GGUAACUUCA CCUUUACAGC   6540
GCCUGAAACA UUGACUGAUG GAACAUAUAA UCUGGAGGCA GAGGCCAAGA CUGCUGAUGG   6600
GAGCGGUAGC GCCAAACUUG UCAUUACUAU CGAUUCCGUU ACCGAUAAAC CAACAUUUGA   6660
ACUUUCGCCU GAAAGUAGUG UGUCCGGUCA UAAGGGCUUA ACGCCGACCU UGACGCCUUC   6720
AAUUGUUGGU ACGGCGGAAG AGAAUGCUAA GGUUGACAUU UAUGUAGAUA AUAAACUGGU   6780
UGCCAGCGUU GAUGUCGAUA AAGAUGGAAA CUGGAGUUAU GAAUUUAAGG AUAAUGAAUU   6840
AUCUGAGGGC GAAAAUAGUA UAAAAGUCGU UGCUGUAGAU AAAGCAGGUA AUAAAAACGA   6900
AACGACGGAU AGUAUCAUAA CCGACACCAU UGCUCCAGAA AAGCCGACGA UUGAGCUGGA   6960
```

```
UGAUAGUAGU GAUUCCGGCA UUAAAAAUGA CAACAUUACA AAUAGCACCC UGCCAACAUU   7020
UAUUGGUGUG GCGGAACCCG GUUCUACAGU CUCUAUUUAU CUUGGACUUA AACAUCUUGG   7080
UGAGGUCAUU GUUGCUAAAG AUGGGACAUG GAGCUAUACG CUUACUACGC CGCUCAAGGA   7140
UGGCGAAUAC AAUAUAACAG CAACAGCUAC UGAUAUUGCC GGGCAUACCU CAGCGACGGC   7200
AAAUCUGCCU UUUACUAUUG AUACACGUAU CAGCUAUUUC AGCGCUGAGA UUGAAACGAC   7260
GAAUGAUAGC GGUAUUGUCG GAGAUAACGU UACUAACAAU ACUCGCCCAA CCUUUACAGG   7320
UAAAACUGAG CCAAAUGCUA UUAUCAGUGU CAUAAAUAGU GAGACUGGCG AAGAGGUUAU   7380
UUUUAAAGCG AAUGACAAGG GCGAAUGGAC GUUCAAUUUC ACUUCCGACU CAGUGGAAGG   7440
GAUUAACAAU CUUACGUUCA CUGUUGAAGA UGUCGCUGGC AACAAAAAGG AUUUUUCCUU   7500
UAGUUACGUU AUUGAUACUA UUGCCCCUGU ACCUCCGACG GCUUCUUUGG AGGAUUAUGU   7560
UGUUUUGCCG AAUGGUAUAA UUUUAUCAGG GAAUGAUUUA CCGGCUUUAG UCGGUACGGC   7620
AGAACCAAAG UCUACCAUCU UAUUGAUGCG AGAUGGUAAA UUAUAUGACA GCAUUGAAGU   7680
UGACUCAAAC GGGACCUGGA AAUUAUCAGU UUAGUAAUAA AUUCUUCAGG GCGCCUAUGA   7740
UAUUGAAAUC AUUCUCAGGA UGCCGCCGGC AAUAAAUCCU CUACUGUUAA AUAUUCUUUU   7800
ACUAUUCAAA CUGAAGUUGU ACCUCCAAAA GCGGAACUCG AUGCCAGUGA UGAUUCCGGU   7860
GCAAAAGGCG ACUGGAUUAC CAAUAAACAU AAUGCUCUGA CAUUACUGGG AACAGCGGAU   7920
AGGUUUGCUA CCGUAAAUAU CCUUAUUGAC GGUAAAACGA UAGGCGUGAC GACUGCGGAU   7980
GCAGACGGUA ACUGGAAUUU UGAUAUUUCC AGAAAUCUGU CUGACAAUGU UUAUAAGAUU   8040
ACGGUUGAAU CCAUCGAUCC UUUAGGAAGA ACGUCAUCUG UAGAUUAUCA GCUUACCAUU   8100
GAUAGCUUUA CGCCGAUCCC UACUGUUAUG UUGCAUGAUA GCGCUGACUC UGGCGUUAAA   8160
GGCGAUAUGA UUACUAAAAU UAAUACACCG UUGUUUACCG GGAUGGCUGA AGCUAAUGCU   8220
AAGGUUUCCA UCUAUGUUGA CGGUGUGUUA AGUGGUGAGG CUAUUGCUGG CGAUGAUGGU   8280
GUAUGGAAUU UUCAAUUUAC CACAGCGUUA UCCGAUGGCU CGCAUGACGU AACGGUAAAG   8340
GUAGAAGAUA UUGCCGGUAA UACUGCCUCC UCAUCAGCGU AUAAUUUCCA AAUCGUAACG   8400
CAAACGCAAA AACCAACAAU AGAGUUGGUC AACGAUACGG GGUUGAUAA UACAGACCAU    8460
AUUAUUAAUG AAAAGAAUCC UGCACUGACA GGAACCGCUG CACCCUAUUC AACGGUUAAA   8520
CUCUAUAUUG AUGGUGCACU GAUCGCUGAG GUCAGAACAA AUAAAGAUGG CAGAUGGGAG   8580
UAUACCCUGA AAGCCGAUCA AGGUUUGGUU GAUGGCGAUC AUAGAAUAAC CGCUUCAGUU   8640
GAAGAUAUCG CUGGCAACAU UGCUCAUUCG GAUCCUUUCU UAAUUAGCGU CGAUACUGCU   8700
AUUUCAAUAC CGAUAGUUUC AUUGAGCCCG GAUUCAGAUU CGGGAAUUUC AGAUGAUAAU   8760
UUAACGAAUA UCGUUAAACC UACCUUGCAC CUAAAAGAUA UUGAUCCGGA CAUUAUCAGU   8820
GUUCAGGUAU GGGAUGCCAU GUCUGAUACG CAGAUCGGUG UUGCCACGCA ACAACCUGAU   8880
GGUUCAUGGG CCUAUACCUU UACUUCAGAU UUAACGGAAG GCUUGCAUCA GGUUUAUGUC   8940
AAGGUUGAGG ACAUUGCGGG UAAUAAAGCG AACAGCGCGA UAUUCGAUUU UACUAUCGAU   9000
ACCACAGUAU CAACGCCGGU GAUUUCCCUG CUUUCUAAGG AUGAUACGGG GGUUACAGGC   9060
GAUAACCUGA CCAAUAUCAA UAAGCCAGGU UUUGCUAUUU CCGGUGUUGA UGCCGAUGCG   9120
CAUCGGGUCG UCGUACAGGU GAUGCACAAU GGCGUGAGCG AAGAGAUCGA ACUUUCCCAC   9180
CUCAAUGGGA GUUGGUUAUU UAUACCAGGG GAAUACGUGG GCGGAUGGCA GCUACACGUU   9240
AACGGUGAAA GUAGAAGAUA AGGCAGGAAA UACCAACUAC UCGGCGCCGC UGACGGUCGU   9300
UAUCGAUACC CAAAUCGCCA UUGAUGGGGU GGAACUGGUC AACGAUAGCG GCGUGAAAGG   9360
```

```
CGAUAAUAUG ACCAACGACG ACCGUCCCCA CUUUCGUGUG ACGGUACCUA CGGAUGUCAA   9420
UGAAGUCCGU CUGAGCAUUG ACGGUGGUAA UUCGUGGGUU CAGGCAACUC CGGGCGUGGC   9480
AGGAAGCUGG GAGUAUAUCU GGCCGACAGA CCUGGCAGAU GGUCCUACAC GCUAACGGUG   9540
GAAGCGACUG AUAAAGCAGC AAUACAUGAC GAAGACCAUC GAUUUCGCGG UGGAUACCAC   9600
GCUGUCAGUG CCGGUCAUCG UACUGGAUAG CGCGGACGAC ACCGGCAUCC AGGGCGAUAA   9660
CAUGACGAAU AGCACCCAGC CGACAUUUGC CUUGCAGCAU AUUGAUGAUG AUGCCGUUCG   9720
CGUUACGGUC AGCGUGGAGC AUGGCGGCGU CACCACCACA UUUGACGCCA CGAAAGGCAC   9780
AGGCGGAUGG ACCUUUACGC CGCCGACAUC AUGGGCGGAU GGUGAUUAUA CCCUGAGUGU   9840
GUCAGUCGAA GAUAAAGCGG GGAACACCAG CCAUUCUGCA UCGCUGACGG UGACGGUGGA   9900
CACGCAAAUC GCCAUUAAUA ACAUUGAACU GGUCAAUGAC AGCGGUAUUC CCGACGAUAA   9960
UCUGACUAAU AAUGUGCGUC CGCACUUCCA GGUGACGGUA CCGACGGAUG UCAACGUGGU  10020
GCGCCUGAGC AUUGACGGCG GCAAGACGUG GUUCAACGCU ACCCAGAGCG CGACGCCAGG  10080
CGUCUGGGAU UAUAUCUGGC CGGAUGAUGU GGCCGACGGA GGCUAUACCC UGACGGUAGA  10140
AGCGACCGAU GAGGCAGGAA AUAAGGCAAC ACAGACCUCG AUUUCACCAU CGAUACCACU  10200
CUGUCUGUGC CGACCCUCUC GCUGGACAGC GCAGAUGACA GCGGCAUCGC GGGCGAUAAU  10260
AUCACCAAUG UUAAAACGCC GGGCUUUACC CUCAACAAUA UUGAUACCGA UGUCAGCCGG  10320
GUGAUAGUGG AGGUAAUGCA CAAUGGCAUU AAGCAGGAGG UGCCACUGGU UCAGACCGGC  10380
GGACAGUGGC GCUUUGCGCC GACCAGCGAC UGGGCGGACG GCGACUAUAU CCUGACGGUG  10440
AAGGUAGAAG AUAGGACCGG AAAUGUGAAG CAGUCCGCGC CGUUGACGGU GACAGUAGAC  10500
ACGCAUAUCG CCAUUGACCG UAUUGAACUG GUUAACGACA GCGGUAUCCC CGGCGAUAAU  10560
CUGACCAAUG AAGCGCGCCC GCACUUUCAG GUGACAGUAC CGGCGGAUGU UAACGGCGUA  10620
AGACUGAGCA UUGAUGGCGG CAAAACGUGG UUUGACGCCA CGCAGCAGCG CGACGUCGGG  10680
CGUCUGGGAU UACACCUGGC UGACGAAUGU GGCUAACGGC CCUCACACCC UGAUGGUGGA  10740
AGCGUCCGAC AAGGCGGGAA ACAAAACGAC GCAGAAACUG GACUUCACCA UCGAUACCAU  10800
UCUGUCAGAA CCGACGAUUA CCCUGGACAG CGCGGAUGAU AGCGCCGCUG GCGAUAACAU  10860
CACCAACGUU AAGAUGCCAG GCUUUACCCU CGGUAAUAUC GACGCCGACG UGACCAAAGU  10920
GGUGGUGACG GUGGCGCAUG AUGGUAAGAA CCAACAGAUA GAGUUGAUUA AGAACGGCGG  10980
UGUGUGGCGC UUUACGCCGG GCGCAGCCUG GACCGAUGGC GACUAUACGU UGACGGUAAA  11040
GGUAGAAGAU AAGGCGGGUA AUACAAAUUA UUCUGCGCCG CUGACGGUGA CUAUCGAUAC  11100
GCAAACGUCU AUUGAUCGCA UUGAGCUUCU UAAUGACACG GGUAUUGUCG GGGAUAACCU  11160
GACCAAUGAA GCACGUCCAC AGUUUCAUAU UACGGUACCG ACGGACGUGA ACUCUGUGCA  11220
ACUGAGUCUU GAUGGCGGCA UCAACUGGGU UAACGCAACG CUGACGUCUG ACGGCGUUUG  11280
GGAGUAUAUA UGGCCGACAG AUCUGGUCGA AAAUACGUAU ACCCUGACAG UGAAAGCAAC  11340
CGAUGUUGCA GGCAACACGG CGACGGAAAC GCUCAAUUUU ACCAUUGAUA CCACAUUGUC  11400
GACACCGACC AUCACGCUGG AUAGCGCAGA UGAUAGCGGC ACCGCCAACG AUAAUAAGAC  11460
UAACGUUAAA ACGCCGGGUU UUAUUAUCGG CGGUAUUGAU UCUGACGUGA CUCAGGUCGU  11520
CGUGCAGGUG AUGCGCGAUG GUCACAGCGA GGAGGUGGAG CUGACGCAGA CUAACGGGCA  11580
GUGGCGUUUU GUACCCGGCA GCGCGUGGAC UGAUGGCGAC UAUACGCUGA CGGUAACGGU  11640
GAAAGAUGAG GCGGGUAAUA UUCGCCACUC AGCGCCGUUG ACGGUCACCA UCGAUACGCA  11700
AAUCACCAUU GACCAUAUUG AACUGGUCAA UGACAGCGGU AUUCCGGACG AUAAUCUGAC  11760
```

```
UAAUAAUGUG CGUCCGCAAC UUCCAGGUGA CGGUACCGAC GGAUGUCAAC GUGGUGCGCC  11820
UGAGCAUUGA CGGCGGUAAG ACGUGGUUCA ACGUUACCCA GAGCGCGACG CCGGGCGUCU  11880
GGGAUUAUAC CUGGCUGGCU GAUGUGGGAG AGGGUAAGCA UACCCUGACA GUGGAGGCGA  11940
CCGACAAGGC GGGAAACAAA ACGACGCAGC AACUGGACUU CAUCAUCGAU ACCCUACUGU  12000
CAGAACCGAC UAUCGUGCUG GACAGCACGG ACGACAGCGG AACAAAAGGC GAUCACCUGA  12060
CCAACGUAAA UAAGCCGACG UUUUUACUGG GCAAUAUUGA CGCAGACGCG CGGUAUGUCA  12120
CGGUUGAGGU ACAGCAUGGC GGCACGAAAG AGGUGCUGAC GGCCACCAAA GACGCGACCG  12180
GCAACUGGAG CGUGACACCG ACCGGCACAU GGGCAGAUGG CGACUAUACG CUGACAGUGA  12240
GGGUGGAAGA UGAGGCGGGG AACGAAAAAC ACUCAGGUCG CUGACGGUCA CUGUUGAUAC  12300
CCAAAUCACC AUUGAUGUUA UUGAACUGGU UAAUGAUAAC GGUAUUCCCG GCGACAAUAU  12360
GACUAACGAC GCCCAUCCGC AGUUCCGCGU GACGGUACCG GGGGACGUUA ACGAAGUCAG  12420
UCUGAGCAUU GACGGUGGCG UGACCUGGGU UAAGGCGACA CAGAGCGCGA CGCCGGGCGU  12480
CUGGAAUUAU ACCUGGCCGG GCACCGUGCC GGAUGGCGAC UAUACGCUGA AUGUGAAAGC  12540
GACUGACAAU GCGGGUAAUA CGGUGACGGA GACACUCCAC UUCACUAUUG AUACUACGUU  12600
GUCGACGCCG GUGAUCGUAC UGGAUAGCGC GGACGACAGU GGUGUCCAUG GCGAUAACAU  12660
GACGAAUAGC ACCCAGCCGA CAUUUGCCCU GCAGCAUAUU GAUGAUGAUG CCGUUCGCGU  12720
UACGGUCAGC GUAGAGCAUG GCGGCGUCAC CACCACAUUU GACGCCACGA AAGACGCAGG  12780
CGGAUGGACC UUUACGCCGA CAGGGGCGUG GCGGAUGGU GAUUAUACCC UGAGUGUGUC  12840
AGUCGAAGAU AAAGCGGGGA ACACCAGCCA UUCUGCAUCG CUGACGGUGA CGGUGGACAC  12900
GCAAAUCGCC AUUAAUAACA UUGAACUGGU CAAUGACAGC GGUAUUCCCG ACGAUAAUCU  12960
GACUAAUAAU GUGCGUCCGC ACUUCCAGGU GACGGUACCG ACGGAUGUCA ACGUGGUGCG  13020
CCUGAGCAUU GACGGCGGCA AGACGUGGUU CAACGCUACC CAGAGCGCGA CGCCGGGCGU  13080
CUGGGAUUAU ACCUGGCUGG CUGAUGUGGG AGAGGGUAAG CAUACCCUGA CAGUGGGGGC  13140
GACCGACAAG GCGGGAAACA AAACGACGCA GCAACUGGAC UUCAUCAUCG AUACCCUACU  13200
GUCAGAACCG ACUAUCGUGC UGGACAACAC GGACUACAGC GGAAACAAAA GGCGAUCACC  13260
UGACCAACGU AAAUAAGCCG ACGUUUUUAC UGGGCAAUAU UGACGCAGAC GCGCGGUAUG  13320
UCACGGUUGA GGUGCAACAU GGCGGCACGA AAGAAGUGCU GACGGCCACC AAAGGCGCGA  13380
CCGGCAUCUG GAGCGUGACA CCGACCGGCA CAUGGGCAGA UGGCGACUAU ACGCUGACGG  13440
UGAGGGUGGA GGAUGAUGCG GGGAACGUAA AAUACUCAGC GCCGCUGACG GUCACGGUUG  13500
ACACCCAAAU CACCAUCGAU GUUAUUGAAC UGGUUAAUGA UAACGGUAUU CCCGGCGACA  13560
ACCUGACCAA UGACGUUCGU CCACACUUCC GCGUCACGGU GCCAGGGGAU GUCAACGAAG  13620
UACGUCUGAG UAUCGACGGC GGUAAUACGU GGGUUCGUGC AACACAGGGC ACGGCAGGGA  13680
UCUGGGAUUA CACCUGGCCG AAAGAUGUGA CCGACGGGCU ACAUACCCUG ACGGUAGAAG  13740
CGACCGAUAA GGCGGGAAAU AAGACGACGC AGACGCUCGA UUUUACCAUU GAUACCCGGC  13800
UGUCAACGCC UACCAUCGCU AUGGAUAGCA GGGACGAUAC AGGUGCCAUU GGCGAUCAUA  13860
UUACGAGCGU CAAAAGACCG GGCUUUACUA UUGGCAAUAU UGACGCCGAU GCGCACUCGG  13920
UCAUUUUGCG GAUCACACAG GGCGGCAAUA GCCAGGAAGU GACACUAACC CAGGUUGGAG  13980
GACAGUGGCG CUUUACGCCA GAUGCUGACU GGGCGGACGG UAGCUAUACG CUGACGGUAG  14040
AGGUAACGGA UAACGCAGGA AACGUUCGUC AGUCCACGCC GCUGGUGGUG ACGGUGGACA  14100
CGCAAACCAG CAUUACUGAU AUUACAUUGG UCAAUGAUCA UGGCGUGCCU GAUGACAAUC  14160
```

```
UAACUAAUAG CACCCGUCCG CAGUUUGAGA UCACGGUGCC GGCGGAUGUG AAUUCUGUGC  14220
AACUGAGCAU UGAUGGGGGC GCAAACUGGG UGAGCGCGAC GCAGGGUAUC GAAGGCGUCU  14280
GGGGCUAUAC CUGGCCAACG GAUAUGGGCG AUGGAAAACA CACCCUAACC GUCAUGGUCA  14340
CCGACAGAGC GGGCAAUACG GCGACGCAAA CGCUUGAAUU UUUCAUCGAC ACCCGGUUGU  14400
CGACGCCGAC CAUUGCGCUG GAUAGCACGG AUGAUACCGG UACGCCUGGC GAUGAUAUGA  14460
CCAAUCGCAC CCGACCGACC UUUAUUCUGC AGAAUAUCGA UUCGGAUGUU AUCAACGUUA  14520
CAGUCAGCGU CACGCAUAAU GGAACGACAA CCUCGUUUAC UGCGACACAG GGGGCUGGAG  14580
GAUGGAGCUU UACACCGCCA GCGCCGUGGG GCGACGGUGA UUAUACGCUG ACGGUGACAG  14640
UGGAGGAUCG GGCGGGAAAU ACGCGUCCGU CUACGCCGCU GACGGUGACA GUGGAUACGC  14700
AAAUAGCCAU UGAUCGUAUU GAAUUAGUCA ACGAUAGCGG CGUCCCUGGC GAUAAUGUGA  14760
CAAAACAUGU GCGUCCGCAG UUCCAGAUCU CGGUACCGGA UGAUGUGGAA AAGUUCUUCU  14820
GAGUAUUGAC GGCGGCACGA CCUGGGUUAC UGCAAUCAAG AGUUCGACGG CUGGCAUUUG  14880
GGAUUACACC UGGCCGACGG AUAUGCCAGA GGGACAGCAU ACCCUGACCG UGGAAGUGAC  14940
UGACGGUGCG GGUAAUAAGA UGACGGAGAC GCUCAAUUUC ACUAUCGAUA UCACGUUGUU  15000
AACGCCAACC AUUGAGCUAG CGCCCGAUCA GGAUACCGGA CAGAAUAAGA ACGAUAAUCU  15060
GACCAGCGUC ACUCAGCCGG UAUUUGUGUU GGGGAGUAUC GAUAAAGAUG UUCGACACGU  15120
GGAAUUGAGU AUUGAGCAUA ACGGCACGUU UAAAACGGUG GUACUCACCG AAUCAGCCGA  15180
CGGCUGGCGC UAUCGACCGG AUUCUGCUUU GGCGGACGGU AGCUACACAU UCACCGUGAC  15240
GGUAACAGAU GUGGCAGGCA ACCAGCAAAC AUCCGCGCCU UUAAAGGUGA CGAUAGACGG  15300
UACGUUGACU ACGCCGGUGA UUGAACUGGC AGCUGGCGAA GAUAGCGGUA CUGUUGGCGA  15360
UCGCCUCACC AAUCACGAUC GGCCUGUGUU CGACAUACAU CAGGUUGAUU CUGACGUUAC  15420
GCGCGUGAUG GUCAAAGUAA CUUACAACGG UAAAACGCAC GAAGAAGCGG CGGUAUUCAC  15480
CAAUGGUCAA UGGCGCUUUA CGCCUUCUGC GAAGCUGGGC UGAUGGCUCA UAUCAGUUAG  15540
CCGUUGUGGU GGAAGAUCUG GCGGGGAAUG UAAAAGAGUC UGCGCCGUUU GAGGUGCGUA  15600
UUGAUACCAC GACAACCAUU AACAAUAUCG UAUUGCUUAA UGAUACCGGC GUGCAGAAUG  15660
AUCAAUUAAC GAAUGUUGCC AAACCGUCAU UCAGAAUUGA CGUUCCCGGU GAUGUCGUCC  15720
AGGUACGUGU AACCCUGGAU GGUGGCGCUA ACUGGAAUGU GAUACGCAAA AAUGCCGACG  15780
GACAGUGGAU UUUUGACAGC CCGAAUACUC UGGUUGACGG CACAUAUACC CUUCGCGUAG  15840
AGGCCACGGG AUGAGGCAGG UAAUAUUGCG AAUAAAGAUU UAGUAUUUAA UAUCGAUACU  15900
AAUAUACAGG UUCCUACUAU UGCUUUAGAC GCAGGACAAG AUACCGGAGC GAAUACCGCC  15960
GAUAAUAUUA CUAAUAUUUC ACGACCCACC UUUACGAUUG GUAAUGUUGA CCCCGAUGUU  16020
AUCAAAGUCG UGGUGACGAU UGAUGGUCAU GAUUAUAACG CGACUAAGGU UGGGGCUGGU  16080
UGGCAAUUUA CACCAGGCAA UGCCAUUCCG GAUGGCUCUU AUAAUAUUAC CGUUACGGUU  16140
GAAGAUAAGG CCGGAAAUAC CGCGACAUCG AAACCAUUAC CUGUUGUGAU AGAUACGACG  16200
GCUGAAAUUG AAAGCGUCAC GUUGGUUACA GAUAGCGGUG AUAGCGAUGU AGAUAACAUU  16260
ACCAAAGUCG ACAGCCGCAG UUUAGUAUUG UUACCGCUGA UGAUAUAACC CAUGUGCGCG  16320
UUAAAAUCGA UAACGCCGCU AAUUGGAUUG AACUCACAAA AGGAGGGAUG GCCGCUGGAU  16380
AUUUAAUGUC GGUUCGGCAU UACCUGAUGG GCAACACACU CUCUUGGUUG AUGUGACUGA  16440
UAUCGCCGGC AACGUUGCGC AAGAAACGCU GCAGUUUACG AUUGAUACGA CUCUGCGAGA  16500
GCCGACAAUU GUACUCGAUC CCACCCAUGA UACUGGUGAU GAUACUAAUG AUAAUCUUAC  16560
```

```
CAGGAUUAAC AAACCGGUGU UUAUUAUCGG UAAUGUCGAU AAUGAUGUAU CACACAUUGU  16620

GGUUCAUAUU GAUGGUCGGG AUUACACCAU UGAAAACACA GGGGGGAAUU UAACCUUUAC  16680

GCCGGAUCAA CCGCUGUCUG ACGGUCAGCA UACGAUCUCU GUUACCGUAA CGGAUAUUGC  16740

UGGUAAUACC AAAACAUCGG CCGAACUGCG GAUUGAAAUC GACACGCAGG UUCAGAUUGA  16800

CAGUGUUACG UUAACAACAG AUAGCGGCGU CAACGAUCAC GAUAAUGUCA CCAAUGCUAC  16860

CCGUCCCUCU UUUGAAAUUG CAACGCCUGA UGAUGUGACA UCGGUGCUGG UUUCUUUCGA  16920

UGGCGUAAAC UGGACGCCCA UCAGUAAAAA UGCGGCCGGG CAGUGGGAAU UUACUGCAGG  16980

UAGCGCAUUG CCUGAUGGUC AUUAUACUCU CCAUGUCCAG GCGACGGAUC GGGCAGGGAA  17040

UACGGCAAAU UCCACGCUGG GCUUCACCGU GGAUACGCAG AUUGACGGCC UGAGCGUCGU  17100

GAUGCUGGAC GACGCCGGAA AGGAUUCUAC GGAUGGUAUU ACGAAUAUUA CCUCUCCACG  17160

UUUUGAAAUU UCAGCCAGAG AACCGCUGCA GAGCGUGACG GUAAUUUUAA ACGGGAAAUC  17220

CAGCACACUG ACUCAGGGGG CAGGUAAUAA AUGGCUGUUU ACCCCUGAUA CACCGUUAGU  17280

GGAUGGAACU UACAAAAUAG AAAUAGUGGC UGAAGAUAUC GCAGGUAAUA AAAUUAGCAA  17340

AGAGGUAUCA UUCACAAUAG ACACUAUUGU UUCUGAUCCC AGUAUUGAUU UGCUGGAUGC  17400

GGAUGAUACU GGCGAAAGCG CUGUUGAUAA UAUUACGAGU GUCACUACAC CACGUUUCGU  17460

UAUUGGCAAU GUACCCGCCG AUAUUGAUAC UGUUGUUAUC AGAAUUAACG GCGUUUCUUA  17520

UCCGGUUACG GCAAAUGGCA AUAACCUCUG GGAAUUUCAG GUUCCCGUUG CGUUAAACGA  17580

UGGCGUAUAU GAAGCCGUUG UUGUCUUCAG AGAUAUUGCC GGAAAUAUUU CUGAAAUUAA  17640

GCUGCCCUUU ACCAUUGAUA CCACGACAAG CGUCAGUGUC AGAAUGGAGC UAGCGUCUGA  17700

UACCGGAAAU UCCAAUAGCG AUAACCUUAC GAAUAAGCAA AAUCCCAAAU UCGAAGGUAC  17760

UGCAGAGCCC AAUGCGAAAC UGGUGAUUAC CAUUGUUGAC GAUAAGUCAG GUCAGGAGGU  17820

UUUAAAACAA ACGAUUACGG UUGGCGCUGA UGGCAACUGG AGUGUGACGC CGAAUAUACU  17880

GCCGGAUGGC AUGUAUACCA UCAACGUCGU CGCAACAGAU GUCGCGGGAA AUACUGCGCA  17940

AACGCAGGAA AGAUUCACUA UCGAUACGGU UACGAUCGAU CCCACCAUUC GCCUUUCGGA  18000

UCCAUCUAUU GAUGAUCAGC AUGAAGCAAC CAGCCUGCGU CCUGAGUUCA AAGGGUUUGC  18060

CGAAGCGUUC UCGACGAUUA UGAUUCAGUG GGAUGGGAAA GUGGUCGGCU CGGCAAACGC  18120

CAAUGCGAAU GGCGAAUGGA GUUGGACGCC GCCAUCAGUA UUAGCGCCAG GCUCCUAUGU  18180

UGUGAGCAUU GUUGCCAAAG AUAAAGCGGG UAAUGAUUCG UCGCAGGUCG ACUUUCCUGU  18240

CGUAAUACCU GUUAUUGAUG UCACGCCUCC AACCAUAAAG CUCAGCGAGG AGAGCGAUAG  18300

UGGCGCCUUA GGAGACUUUA CCACGAAUAA UAAAACGCCG ACCCUGAUUG GGAGCACGUU  18360

ACCUAAUACG AUUGUGAGUA UUUAUGUGGA UGGCGUGAAG GUCGGCGAGG CGACAGCGGA  18420

UACAGCGGGU CGAUAUACUU UCCAGUUAUC GGAAAUGAAA GAUGGCCAUU AUGUCGUCCA  18480

GGUGGGUAUC GUCAACCCUC GCGAUAAUAG CGAACUGCGU UCUACCGCCG UUGAUGUCAC  18540

UAUCGAUACC GAGGUUGCUG AACUGGUAUG GAAUAUAUCU GGAAUGCAUG AGGGCGGAUA  18600

UAUCAAUACG GUGACGCCGG AGAUUGGCGG CACCAGUGAG CCAAACAGCA AAAUCACUAU  18660

CUUUGUGAAU GGCGUUGGAA AAGCGAUUGC UUAUACGACA GGCGCAGGAC ACUGGGGCGU  18720

AGUAUUACCC GCUUUGGGUA AUGACGGUAA UUAUGAAUUA ACGUUUAAAG UUGAAGACGU  18780

UGCCGGUAAU AUCAGAGAGU UUGGUCCGCA GAAUGUAAUA CUGGAUACAG UAAUUUCGCC  18840

GUUAACCGUG GUAUUACGCG AAGCUGAUGA CAGUGGCAAA GUUGGCGACU GGAUCACCAA  18900

UAAAUCUCAU GUCACCAUCG AUGGUACUGC CGAAGCCGGA AGUACUUUAA CCAUCAGGAA  18960
```

UCCGCAGGGA GUGGUUAUUG CUACCCUGGU GGUAGGCAAU GAUGGUCGAU GGAGCGCAGA 19020

AUUAGAUCUG CGUGAAGGUA GUAAUGCCUU UGUCGUGGUA UCGGAAGAUA AAGCGGGCAA 19080

CAGUCAACAA AAAGAGAUUC UGAUAGAACA UGAUACGCAG AUUGAAAUCA GCGAUAUUUC 19140

AUUAAGUCGG GAUACUAAUA GCGGUGAUAA AUAUGAUCUG AUUACCAAUA AUAAGUCUCC 19200

GGUACUGGUU GCCAGGACCG AUCCCGGCGC GACGGUACAG GUUUAUAUUA AUGGUGUGUU 19260

ACAAGGCACA GUAGAGGCGA GUUCGUCAGG UAAUAUUAGC UAUACCAUGC CGGCAAAUAG 19320

CGCCGACGGC GAGUAUCAGG UGCAAUUUGU UGCUACGGAU ACUGCUGGUA ACCGGGUUGA 19380

GUCUGCGAUU ACAACCGUGA CAAUCGAUUC UCAAAUUGCU GUCUUUGAUA UUGAUGAAGA 19440

UUCAUUACCG GCCCUCUCUA AUAACCGAGC GUUGUCAGUC UCAGGUGUCG GGAGGCUGG 19500

UUCUCAGGUC AGCAUCUUUG UCGACGGUAA AUUAGUCAAC GUUGUUAUGG UUGAGGCUGA 19560

UGGCACAUGG CGCGCGCCGA UACUGCUGCA AGAUGAUGGU ACGUUUAAUA UUCAUUUCAG 19620

CAUUACUGAC GUUGCUGGCA ACACUGAAGU GAGCAAGGAU UAUAGCGUGG AUGUCGAUUC 19680

AUCAACCGAC UUCCCAACGC UCAACCUUGA AGAUGCAAGC AACUCUGGUU CACUUGACGA 19740

UCUGAUUACU AAUCACAACA AGCCUGUAUU AGUUGGCACC GCAGAAGCGG GAGCCACAAU 19800

CCAUAUUUAU GUGGAUGAAA AGAUCGUGGC AAAUGUUCUU GUGCUUGAAG AUGGAACCUG 19860

GUCCUAUCAG UUUGAUAAUG CGUUAAAAGA UGGUGAAUAU UCUAUCCGUG UGGUUGCCGA 19920

AGACCCGGCA GGUAAUACGG CAGAAUCGCC UCGCUUACUC GUCACGAUAG AUACCAGUAC 19980

GUUUAUCGAU AAUCCUGCUA UGGUGGCAGG UUCUGAUAAU GGUAUUUUCA GUAAUGAUAG 20040

UAUAACGAGU CAGACCCGGC CUACGUUUAG UAUUUUUGGA GAAAUGAACC AGAGUGUUCA 20100

GAUUUUCAUU GAUGGAGUGC UAGUCGAUAC GAUCACGGUG ACCGACAGAA AUCAAGUUUA 20160

UCGACCUGAG UCACCGUUGG GCGAUGGUUC CCAUAGCAUU UAUUAUGUUA UCACCGAUAA 20220

AGCAGGCAAC ACGGCUACCU CGAAAACGCU AAACUUUACU AUCGAUACCU UUAAUACGAC 20280

GCCUGUCGCC AUUGAUUCUA UCGGUGGACA AACGUUAGCA GAGAUGACCG GUAGUGAUGG 20340

CAAAAUAUAU AUAACGGACA CGACGCGUAA CUUAUUGUUU AGUGGCAGUG CCGAGCCCAA 20400

UAGCAAAAUA GAAAUCAUCA UUAAUGGCUU AAAUGUGGGG GAAGUUUGGG UUAAUGAAAA 20460

AGGCCACUGG CAGAUGCCGG UGAACCCGCU UUAUUUCACA GAAGGCCAAC UGGAUAUCAC 20520

UGUUAAAUCU ACGGACCGUG CUGGUAACGU AAAUCAGGAA AAGUAUUCCA UUUGGGUUGA 20580

UACGCAUAUC AAGGUAUUUA CCAGCGAGCU UGAUGACAAU AAAUCAUCAU CGAAAACGGA 20640

AUGGUGGAGU AAUAGCGAUC UCAUUACCAU GCGAGGCACG GGUGAAAUUG GCGCUACGGU 20700

AUCAUUAAUC GUGGCUGGCG UCACGCUGGC AACUGCUGUU GUGGCGGCAA CAGGACGAUG 20760

GGAAUUAUCA ACAGACAAGC UUCCAGAAGG GACUUACGAU AUUAGUUUGG UCAUUGAAGA 20820

UAGCCCGGAA AUCGUUGGGA AGAUGUGCGU GAAAUAUUUA UUGACCGAAC CCGCCAAAUG 20880

CUCCGGUCGU AACGUAUUCA GAUAUUGUCA ACGAUCUAAU UAUUAUGCAG GGGACGGCGG 20940

AAGCCAAAUC UCAGCUAAUA AUAACCGAUA GUGAGGGGAA UACUUAUACG UUAACCGUUC 21000

CUGAUAAUGG UAAAUGGAGU AUGGCUAUCC CGUAUCCAUC AGAAGGGAAG UUUACCAUUA 21060

CGAGUGUGGA UGCUAUUGGU AACCGGAGUG AUGAUGUCCC UCUCGAUAUC AUGAAAGAGG 21120

UUCCCGUUAU UUCAUUAUCU CCAGACUCAG ACAGUGGUAC GGUGGGCGAU AAUAUUACGC 21180

GAGAUAAGCA ACCUACCUUU AUUAUCGGGA AUCUGGAAAG CGAUGUUGUG GUCGUUCAGG 21240

UCGAUAUCAA UGGGACCGUA UAUAAUGCUG AAAAAAAUGC CGAUGGCGUU UGGUUCUUUA 21300

CGCCAGGUAC ACCGUUAGCU GAUGGUUCCU AUACGAUAUC GGUAAUCGCA AGCGAUGCCG 21360

```
CGGGUAAUCA GAAAAACUCG UUACCCAUUA CUGUCACGAU CGACAGCACG CUGACGGUGC  21420
CGGAGAUUGC GUUGGCAGCA GGUGAAGACA AUGGCGCUUC AGACAGCGAU AACGUGACGA  21480
AUCACACCCA GCCUAAGUUC ACGCUGCAGC AUAUUGAUGC UGAUGUGACC GGGGUGACCG  21540
UAAACGUGAC GCAUAAUGGC GUGACAGACA UCUAUCAGGC GACGCAAGGC GCGGAUGGCU  21600
GGACCUUCAC GCCGCCAGCC GCCUGGAAUG ACGGUAACUA CACGCUGAGC GUGACGGUGG  21660
UGGAUCGCGC GGGGAAUUCA CAGCAAUCUG CUUCGCUAGC GGUGACGGUU GACUCAACGG  21720
UGACGGUAAC AGCGGAUAGC CAGCAUGACG AUGCGAGCGA UGACGCCACG GCAACAGCGG  21780
UUACUCCACC GGAGUCUGAA ACAGUGAAUG CCGAAAGCGC UACGCAUCUU CGUACAGAGC  21840
CGUCUGCGGC GGAAGAAAGC GUGGUGAAGG UGACAGCCUA UAGUAUUACA UUGUUAAACG  21900
CUGACUCUGG GGAUGAAAUA GAUCGUUCAA UUAGUCAGAC ACCUUCUUUU GAAAUAUCAG  21960
UACCUGAGAA UAUUGUUAAU GUCAGUAUUA UGUUUGAAGG AGAAGAGUUU ACUCUGCCGA  22020
UAACUAACCA GAAAGCAAUA UUCGAAGUUC CGCUAUCUUU GGAAGAUGGU GAAUAUACUA  22080
UGGACGUGAA AUUCAUUGAU AAAGACAAUG AUUUCCUGAU UAAGGAGAAA ACAUUCUCAG  22140
UCGAUCACUC CUCGGCGGAU AUUGUGAACG CAAUGAAUGU AAGAGGAAAG ACCGAGGAUG  22200
AUAUUAAUGA UUCCCCUUCC ACGAGUUCUG UAGGGCACAA CAAUAACGGC GCUAUUGAUG  22260
UUUUCGCCGU UAAUGAAGUU ACGCUACCUG UAGAUAAUCA AGAAGAACAC GCAUAAUAAC  22320
GGAGGCCCCU CACCUUUGGG UUGAAGGGGG UUUACUUAUG GAUAAAAAAC UAGAACCUUA  22380
UUAUUUAAGU GCGGAAACGG CAUUAUCUAU AGUGUCUACA AAAUUCAACA UAAAAAUUGA  22440
CAUCCGAGAA GAUGAUAUAC AUUUGAAGAU UUAGAAAGUA CGACUGAAAU AACACUGACG  22500
ACCUAUACGA AUGAAGAAUU UCUUUUUGUC GUUAGGGCUU UCUCUACAGG AUAUAUUAUU  22560
UAAUAAUGGU GAGGAUUUAC UAAAUGAGCC UAUGCCGAUU UUACUAUUAA CACCAGAAAA  22620
UGAAAGUGGA UGGUGUGUGU GAGUGGCGGG CAAAAAAUAA AGUUGGUAAA CGCGCGCGGU  22680
GAACUCUGUU AUGUUGAAAU UGAAGAUGAA UAUUUAAAAG AGUUAUCUGC AUUUAGUAUA  22740
CUACCUUUAA AUAAAGUUGU UGAUAGUAUA AGAGUAAAAA AUAUCAUAAA AAACUCUUUA  22800
UCGAUGAACA AGAUUUUUUA UACUAAAUAC UUUUUUUCAU CUCUUUUUAU GGCAAUUUUU  22860
GCGUUAACUA UCCCAGUAUU UAGUAAUCUG UUCUAUGAUA AGCUUGUUCC AAGCGCUUCG  22920
GUUUCAUCUU UAUUUGGCGU GGCUAUAAUU GUUGCUGUAU UUAUUGUUUU UGAGUUUAUC  22980
CUUCGUACUU CGAAAGAUAU UUAUCAGUCU AUCACAGCAA GGCAGGAUGA CGUCGAUAUU  23040
GAUAUCGCAU UUCUUGAAGC GGUACUUUAU AGUAAAAAGA AAAAUGGCAG AUCCAUGUCA  23100
UCAGCAUUUG UGCUAUGGAA UGAGUUUCAG AAAAUUAAAC CCGUUUUUAUU AAACUCGAUC  23160
UUUCAACGUA UAGCCGAUAU UCCAAUAUUU AUUAUAUUUC UCAUUGUUAU AUAUGUAAAU  23220
UUAGGUCUGG UUGUUAUUGU ACCUAUUACC AUGUUUAUCG UCUCUAUUAU UAUUUCCCUC  23280
GUUAACCACC AUUAUACUAA UGAGUUAAUG AACAAACAAA AAGAAGGACA GAAGAACAGG  23340
AAUAUUUUUA UCUCAGAAGU UUUCUUAUCU AUUAAAAUGA UCCAUACCUU AAAUAAUCAA  23400
GGUUUACUUU UUGAUUGGGU UAAUACAUCA AAUGAACAGU CGUAUCUUAA CCUGAAGAUA  23460
AGGAAAUUAA AUCUUAUCUA UCAAUCUAUA UUGGGGAGUA UGUCAUCUAU UACCCAAAUA  23520
ACUAUUAUGG UAAUAGCCUU UUUUAUGGUA AUCAAGGGUG AUGUUACUAC UGGCGCAAUU  23580
GUUUCAUCUG UCAUUGUCUC UGGCCGUAUU UCCGGGAUCA UUUCGAAUUU UUCUUCUACA  23640
UUAAUCUCUA UUUUAUCAGC AGAAAAAACC GGUAAGGAUC UGCUUUCUUU UUUUGAUGAA  23700
GAUCAGGCAG AAAAAACACC GGCAUUACAG UCAAUAUCAA AGUGCAAUGG CGAUAUCUCU  23760
```

```
AUCCGGGGCG UGAGUUAUCA GUAUGAUGCU CAAUCUCCGA UGAUUAUUAA CCGACUGUCU  23820
AUAGACAUAC CUGCGGGGCA ACGUGUCGCG GUGGUAGGCG AAUGCGGAGC AGGAAAAAGC  23880
UCAUUACUGG GAAUGCUAUC UGGCUACCUU UCGCCAACAG ACGGUGCCAU UUUAUAUGAU  23940
GGAUAUAACU UAGGACAUUU AUCGCAGAAC UUUUUUUCUC AGCAUUUAAG CGUGGUGACG  24000
ACACAUGAUG UUUUAUUCAC CGGAACCAUU GAAAGUAAUU UCGCGUUAAA ACCGCAAAAC  24060
GACAGGGGCC GGGUACUCAA GGCGCUUCAG CUGGCGAACU GUGGUUUUAU CUUGCAACAU  24120
CCUAUGGGGC UGAAGUUUCC GGUGAAUUUU AUGGCUAAAA ACCUGUCAUC CGGACAGCAG  24180
CAGCAGUUAU UAUUAGCACG UAGUCUGAGU AGUGACGCCA GCGUCUUUUU AUGGGAUGAA  24240
CCAACAUCAA AUCUGGAUGA GAAUACCGAG AAGCAAAUUU UUGAUAACUU AGAUGAGUUU  24300
AUUCAUGGGA AAACGUUGAU CAUGGUGACG CAUCGUCGAU AUCUGAUAAA GUAUUUUGAC  24360
CGGGUCCUGG UAAUGAAAGG UGGAAAAAUA AUCCGUGAUU GUUCUCCGGA UAAAUUAUUA  24420
AUGUAAAAUA AGCAGCGCUU GUCGCUGUUA UCAGGUGGUA CUGCUUAAUA AAAAAGACCC  24480
GUUGCACAAA CGGGUCUUUU UUGUCAUUUA ACGGAGUCGG CAACGUCUUC AAUAAGUUUA  24540
GCUCGAUUCU GUUAGGGCUA UUCCACUUGC CAUUUUUGGA UAACCACACC UGGCGGCCUU  24600
CAUCAACGGC AAUGCGAGGG ACGUGAUGGU GCGCAAGGCU AACCCCUGGC GCGCGAUUCC  24660
GCGUUGAGAU AACCGGUGGG CGGCUUCAGC GGCAGCGAUA G                      24701
```

(2) INFORMATION FOR SEQ ID NO:61:

(i) SEQUENCE CHARACTERISTICS:
- (A) LENGTH: 24701 bases
- (B) TYPE: nucleotide
- (C) STRANDEDNESS: single stranded
- (D) TOPOLOGY: linear (xi) SEQUENCE DESCRIPTION: SEQ ID NO:61:

```
CUAUCGCUGC CGCUGAAGCC GCCCACCGGU UAUCUCAACG CGGAAUCGCG CGCCAGGGGU     60
UAGCCUUGCG CACCAUCACG UCCCUCGCAU UGCCGUUGAU GAAGGCCGCC AGGUGUGGUU    120
AUCCAAAAAU GGCAAGUGGA AUAGCCCUAA CAGAAUCGAG CUAAACUUAU UGAAGACGUU    180
GCCGACUCCG UUAAAUGACA AAAAAGACCC GUUUGUGCAA CGGGUCUUUU UUAUUAAGCA    240
GUACCACCUG AUAACAGCGA CAAGCGCUGC UUAUUUUACA UUAAUAAUUU AUCCGGAGAA    300
CAAUCACGGA UUAUUUUUCC ACCUUUCAUU ACCAGGACCC GGUCAAAAUA CUUUAUCAGA    360
UAUCGACGAU GCGUCACCAU GAUCAACGUU UUCCCAUGAA UAAACUCAUC UAAGUUAUCA    420
AAAAUUUGCU UCUCGGUAUU CUCAUCCAGA UUUGAUGUUG GUUCAUCCCA UAAAAAGACG    480
CUGGCGUCAC UACUCAGACU ACGUGCUAAU AAUAACUGCU GCUGCUGUCC GGAUGACAGG    540
UUUUUAGCCA UAAAAUUCAC CGGAAACUUC AGCCCCAUAG GAUGUUGCAA GAUAAAACCA    600
CAGUUCGCCA GCUGAAGCGC CUUGAGUACC CGGCCCCUGU CGUUUUGCGG UUUUAACGCG    660
AAAUUACUUU CAAUGGUUCC GGUGAAUAAA ACAUCAUGUG UCGUCACCAC GCUUAAAUGC    720
UGAGAAAAAA AGUUCUGCGA UAAAUGUCCU AAGUUAUAUC CAUCAUAUAA AAUGGCACCG    780
UCUGUUGGCG AAAGGUAGCC AGAUAGCAUU CCCAGUAAUG AGCUUUUUCC UGCUCCGCAU    840
UCGCCUACCA CCGCGACACG UUGCCCCGCA GGUAUGUCUA UAGACAGUCG GUUAAUAAUC    900
AUCGGAGAUU GAGCAUCAUA CUGAUAACUC ACGCCCCGGA UAGAGAUAUC GCCAUUGCAC    960
UUUGAUAUUG ACUGUAAUGC CGGUGUUUUU UCUGCCUGAU CUUCAUCAAA AAAGAAAGC   1020
AGAUCCUUAC CGGUUUUUUC UGCUGAUAAA AUAGAGAUUA AUGUAGAAGA AAAAUUCGAA   1080
```

-continued

AUGAUCCCGG AAAUACGGCC AGAGACAAUG ACAGAUGAAA CAAUUGCGCC AGUAGUAACA 1140

UCACCCUUGA UUACCAUAAA AAAGGCUAUU ACCAUAAUAG UUAUUUGGGU AAUAGAUGAC 1200

AUACUCCCCA AUAUAGAUUG AUAGAUAAGA UUUAAUUUCC UUAUCUUCAG GUUAAGAUAC 1260

GACUGUUCAU UUGAUGUAUU AACCCAAUCA AAAAGUAAAC CUUGAUUAUU UAAGGUAUGG 1320

AUCAUUUUAA UAGAUAAGAA AACUUCUGAG AUAAAAAUAU UCCUGUUCUU CUGUCCUUCU 1380

UUUUGUUUGU UCAUUAACUC AUUAGUAUAA UGGUGGUUAA CGAGGGAAAU AAUAAUAGAG 1440

ACGAUAAACA UGGUAAUAGG UACAAUAACA ACCAGACCUA AAUUUACAUA UAUAACAAUG 1500

AGAAAUAUAA UAAAUAUUGG AAUAUCGGCU AUACGUUGAA AGAUCGAGUU UAAUAAAACG 1560

GGUUUAAUUU UCUGAAACUC AUUCCAUAGC ACAAAUGCUG AUGACAUGGA UCUGCCAUUU 1620

UUCUUUUUAC UAUAAAGUAC CGCUUCAAGA AAUGCGAUAU CAAUAUCGAC GUCAUCCUGC 1680

CUUGCUGUGA UAGACUGAUA AAUAUCUUUC GAAGUACGAA GGAUAAACUC AAAAACAAUA 1740

AAUACAGCAA CAAUUAUAGC CACGCCAAAU AAAGAUGAAA CCGAAGCGCU UGGAACAAGC 1800

UUAUCAUAGA ACAGAUUACU AAAUACUGGG AUAGUUAACG CAAAAAUUGC CAUAAAAAGA 1860

GAUGAAAAAA AGUAUUUAGU AUAAAAAAUC UUGUUCAUCG AUAAAGAGUU UUUUAUGAUA 1920

UUUUUUACUC UUAUACUAUC AACAACUUUA UUUAAAGGUA GUAUACUAAA UGCAGAUAAC 1980

UCUUUUAAAU AUUCAUCUUC AAUUUCAACA UAACAGAGUU CACCGCGCGC GUUUACCAAC 2040

UUUAUUUUUU GCCCGCCACU CACACACACC AUCCACUUUC AUUUUCUGGU GUUAAUAGUA 2100

AAAUCGGCAU AGGCUCAUUU AGUAAAUCCU CACCAUUAUU AAAUAAUAUA UCCUGUAGAG 2160

AAAGCCCUAA CGACAAAAAG AAAUUCUUCA UUCGUAUAGG UCGUCAGUGU UAUUUCAGUC 2220

GUACUUUCUA AAUCUUCAAA UGUAUAUCAU CUUCUCGGAU GUCAAUUUUU AUGUUGAAUU 2280

UUGUAGACAC UAUAGAUAAU GCCGUUUCCG CACUUAAAUA AUAAGGUUCU AGUUUUUUAU 2340

CCAUAAGUAA ACCCCCUUCA ACCCAAAGGU GAGGGGCCUC CGUUAUUAUG CGUGUUCUUC 2400

UUGAUUAUCU ACAGGUAGCG UAACUUCAUU AACGGCGAAA ACAUCAAUAG CGCCGUUAUU 2460

GUUGUGCCCU ACAGAACUCG UGGAAGGGGA AUCAUUAAUA UCAUCCUCGG UCUUUCCUCU 2520

UACAUUCAUU GCGUUCACAA UAUCCGCCGA GGAGUGAUCG ACUGAGAAUG UUUUCUCCUU 2580

AAUCAGGAAA UCAUUGUCUU UAUCAAUGAA UUUCACGUCC AUAGUAUAUU CACCAUCUUC 2640

CAAAGAUAGC GGAACUUCGA AUAUUGCUUU CUGGUUAGUU AUCGGCAGAG UAAACUCUUC 2700

UCCUUCAAAC AUAAUACUGA CAUUAACAAU AUUCUCAGGU ACUGAUAUUU CAAAAGAAGG 2760

UGUCUGACUA AUUGAACGAU CUAUUUCAUC CCCAGAGUCA GCGUUUAACA AUGUAAUACU 2820

AUAGGCUGUC ACCUUCACCA CGCUUUCUUC CGCCGCAGAC GGCUCUGUAC GAAGAUGCGU 2880

AGCGCUUUCG GCAUUCACUG UUUCAGACUC CGGUGGAGUA ACCGCUGUUG CCGUGGCGUC 2940

AUCGCUCGCA UCGUCAUGCU GGCUAUCCGC UGUUACCGUC ACCGUUGAGU CAACCGUCAC 3000

CGCUAGCGAA GCAGAUUGCU GUGAAUUCCC CGCGCGAUCC ACCACCGUCA CGCUCAGCGU 3060

GUAGUUACCG UCAUUCCAGG CGGCUGGCGG CGUGAAGGUC CAGCCAUCCG CGCCUUGCGU 3120

CGCCUGAUAG AUGUCUGUCA CGCCAUUAUG CGUCACGUUU ACGGUCACCC CGGUCACAUC 3180

AGCAUCAAUA UGCUGCAGCG UGAACUUAGG CUGGGUGUGA UUCGUCACGU UAUCGCUGUC 3240

UGAAGCGCCA UUGUCUUCAC CUGCUGCCAA CGCAAUCUCC GGCACCGUCA GCGUGCUGUC 3300

GAUCGUGACA GUAAUGGGUA ACGAGUUUUU CUGAUUACCC GCGGCAUCGC UUGCGAUUAC 3360

CGAUAUCGUA UAGGAACCAU CAGCUAACGG UGUACCUGGC GUAAAGAACC AAACGCCAUC 3420

GGCAUUUUUU UCAGCAUUAU AUACGGUCCC AUUGAUAUCG ACCUGAACGA CCACAACAUC 3480

```
GCUUUCCAGA UUCCCGAUAA UAAAGGUAGG UUGCUUAUCU CGCGUAAUAU UAUCGCCCAC   3540
CGUACCACUG UCUGAGUCUG GAGAUAAUGA AAUAACGGGA ACCUCUUUCA UGAUAUCGAG   3600
AGGGACAUCA UCACUCCGGU UACCAAUAGC AUCCACACUC GUAAUGGUAA ACUUCCCUUC   3660
UGAUGGAUAC GGGAUAGCCA UACUCCAUUU ACCAUUAUCA GGAACGGUUA ACGUAUAAGU   3720
AUUCCCCUCA CUAUCGGUUA UUAUUAGCUG AGAUUUGGCU UCCGCCGUCC CCUGCAUAAU   3780
AAUUAGAUCG UUGACAAUAU CUGAAUACGU UACGACCGGA GCAUUUGGCG GGUUCGGUCA   3840
AUAAAUAUUU CACGCACAUC UUCCCAACGA UUUCCGGGCU AUCUUCAAUG ACCAAACUAA   3900
UAUCGUAAGU CCCUUCUGGA AGCUUGUCUG UUGAUAAUUC CCAUCGUCCU GUUGCCGCCA   3960
CAACAGCAGU UGCCAGCGUG ACGCCAGCCA CGAUUAAUGA UACCGUAGCG CCAAUUUCAC   4020
CCGUGCCUCG CAUGGUAAUG AGAUCGCUAU UACUCCACCA UUCCGUUUUC GAUGAUGAUU   4080
UAUUGUCAUC AAGCUCGCUG GUAAAUACCU UGAUAUGCGU AUCAACCCAA AUGGAAUACU   4140
UUUCCUGAUU UACGUUACCA GCACGGUCCG UAGAUUUAAC AGUGAUAUCC AGUUGGCCUU   4200
CUGUGAAAUA AAGCGGGUUC ACCGGCAUCU GCCAGUGGCC UUUUUCAUUA ACCCAAACUU   4260
CCCCCACAUU UAAGCCAUUA AUGAUGAUUU CUAUUUUGCU AUUGGGCUCG GCACUGCCAC   4320
UAAACAAUAA GUUACGCGUC GUGUCCGUUA UAUAUAUUUU GCCAUCACUA CCGGUCAUCU   4380
CUGCUAACGU UUGUCCACCG AUAGAAUCAA UGGCGACAGG CGUCGUAUUA AAGGUAUCGA   4440
UAGUAAAGUU UAGCGUUUUC GAGGUAGCCG UGUUGCCUGC UUUAUCGGUG AUAACAUAAU   4500
AAAUGCUAUG GGAACCAUCG CCCAACGGUG ACUCAGGUCG AUAAACUUGA UUUCUGUCGG   4560
UCACCGUGAU CGUAUCGACU AGCACUCCAU CAAUGAAAAU CUGAACACUC UGGUUCAUUU   4620
CUCCAAAAAU ACUAAACGUA GGCCGGGUCU GACUCGUUAU ACUAUCAUUA CUGAAAAUAC   4680
CAUUAUCAGA ACCUGCCACC AUAGCAGGAU UAUCGAUAAA CGUACUGGUA UCUAUCGUGA   4740
CGAGUAAGCG AGGCGAUUCU GCCGUAUUAC CUGCCGGGUC UUCGGCAACC ACACGGAUAG   4800
AAUAUUCACC AUCUUUUAAC GCAUUAUCAA ACUGAUAGGA CCAGGUUCCA UCUUCAAGCA   4860
CAAGAACAUU UGCCACGAUC UUUUCAUCCA CAUAAAUAUG GAUUGUGGCU CCCGCUUCUG   4920
CGGUGCCAAC UAAUACAGGC UUGUUGUGAU UAGUAAUCAG AUCGUCAAGU GAACCAGAGU   4980
UGCUUGCAUC UUCAAGGUUG AGCGUUGGGA AGUCGGUUGA UGAAUCGACA UCCACGCUAU   5040
AAUCCUUGCU CACUUCAGUG UUGCCAGCAA CGUCAGUAAU GCUGAAAUGA AUAUUAAACG   5100
UACCAUCAUC UUGCAGCAGU AUCGGCGCGC GCCAUGUGCC AUCAGCCUCA ACCAUAACAA   5160
CGUUGACUAA UUUACCGUCG ACAAAGAUGC UGACCUGAGA ACCAGCCUCC CCGACACCUG   5220
AGACUGACAA CGCUCGGUUA UUAGAGAGGG CCGGUAAUGA AUCUUCAUCA AUAUCAAAGA   5280
CAGCAAUUUG AGAAUCGAUU GUCACGGUUG UAAUCGCAGA CUCAACCCGG UUACCAGCAG   5340
UAUCCGUAGC AACAAAUUGC ACCUGAUACU CGCCGUCGGC GCUAUUUGCC GGCAUGGUAU   5400
AGCUAAUAUU ACCUGACGAA CUCGCCUCUA CUGUGCCUUG UAACACACCA UUAAUAUAAA   5460
CCUGUACCGU CGCGCCGGGA UCGGUCCUGG CAACCAGUAC CGGAGACUUA UUAUUGGUAA   5520
UCAGAUCAUA UUUAUCACCG CUAUUAGUAU CCCGACUUAA UGAAAUAUCG CUGAUUUCAA   5580
UCUGCGUAUC AUGUUCUAUC AGAAUCUCUU UUUGUUGACU GUUGCCCGCU UUAUCUUCCG   5640
AUACCACGAC AAAGGCAUUA CUACCUUCAC GCAGAUCUAA UUCUGCGCUC CAUCGACCAU   5700
CAUUGCCUAC CACCAGGGUA GCAAUAACCA CUCCCUGCGG AUUCCUGAUG GUUAAAGUAC   5760
UUCCGGCUUC GGCAGUACCA UCGAUGGUGA CAUGAGAUUU AUUGGUGAUC CAGUCGCCAA   5820
CUUUGCCACU GUCAUCAGCU UCGCGUAAUA CCACGGUUAA CGGCGAAAUU ACUGUAUCCA   5880
```

-continued

```
GUAUUACAUU CUGCGGACCA AACUCUCUGA UAUUACCGGC AACGUCUUCA ACUUUAAACG   5940
UUAAUUCAUA AUUACCGUCA UUACCCAAAG CGGGUAAUAC UACGCCCCAG UGUCCUGCGC   6000
CUGUCGUAUA AGCAAUCGCU UUUCCAACGC CAUUCACAAA GAUAGUGAUU UUGCUGUUUG   6060
GCUCACUGGU GCCGCCAAUC UCCGGCGUCA CCGUAUUGAU AUAUCCGCCC UCAUGCAUUC   6120
CAGAUAUAUU CCAUACCAGU UCAGCAACCU CGGUAUCGAU AGUGACAUCA ACGGCGGUAG   6180
AACGCAGUUC GCUAUUAUCG CGAGGGUUGA CGAUACCCAC CUGGACGACA UAAUGGCCAU   6240
CUUUCAUUUC CGAUAACUGG AAAGUAUAUC GACCCGCUGU AUCCGCUGUC GCCUCGCCGA   6300
CCUUCACGCC AUCCACAUAA AUACUCACAA UCGUAUUAGG UAACGUGCUC CCAAUCAGGG   6360
UCGGCGUUUU AUUAUUCGUG GUAAAGUCUC CUAAGGCGCC ACUAUCGCUC UCCUCGCUGA   6420
GCUUUAUGGU UGGAGGCGUG ACAUCAAUAA CAGGUAUUAC GACAGGAAAG UCGACCUGCG   6480
ACGAAUCAUU ACCCGCUUUA UCUUUGGCAA CAAUGCUCAC AACAUAGGAG CCUGGCGCUA   6540
AUACUGAUGG CGGCGUCCAA CUCCAUUCGC CAUUCGCAUU GGCGUUUGCC GAGCCGACCA   6600
CUUUCCCAUC CCACUGAAUC AUAAUCGUCG AGAACGCUUC GGCAAACCCU UUGAACUCAG   6660
GACGCAGGCU GGUUGCUUCA UGCUGAUCAU CAAUAGAUGG AUCCGAAAGG CGAAUGGUGG   6720
GAUCGAUCGU AACCGUAUCG AUAGUGAAUC UUUCCUGCGU UUGCGCAGUA UUUCCCGCGA   6780
CAUCUGUUGC GACGACGUUG AUGGUAUACA UGCCAUCCGG CAGUAUAUUC GGCGUCACAC   6840
UCCAGUUGCC AUCAGCGCCA ACCGUAAUCG UUUGUUUUAA AACCUCCUGA CCUGACUUAU   6900
CGUCAACAAU GGUAAUCACC AGUUUCGCAU UGGGCUCUGC AGUACCUUCG AAUUUGGGAU   6960
UUUGCUUAUU CGUAAGGUUA UCGCUAUUGG AAUUUCCGGU AUCAGACGCU AGCUCCAUUC   7020
UGACACUGAC GCUUGUCGUG GUAUCAAUGG UAAAGGGCAG CUUAAUUUCA GAAAUAUUUC   7080
CGGCAAUAUC UCUGAAGACA ACAACGGCUU CAUAUACGCC AUCGUUUAAC GCAACGGGAA   7140
CCUGAAAUUC CCAGAGGUUA UUGCCAUUUG CCGUAACCGG AUAAGAAACG CCGUUAAUUC   7200
UGAUAACAAC AGUAUCAAUA UCGGCGGGUA CAUUGCCAAU AACGAAACGU GGUGUAGUGA   7260
CACUCGUAAU AUUAUCAACA GCGCUUUCGC CAGUAUCAUC CGCAUCCAGC AAAUCAAUAC   7320
UGGGAUCAGA AACAAUAGUG UCUAUUGUGA AUGAUACCUC UUUGCUAAUU UUAUUACCUG   7380
CGAUAUCUUC AGCCACUAUU UCUAUUUUGU AAGUUCCAUC CACUAACGGU GUAUCAGGGG   7440
UAAACAGCCA UUUAUUACCU GCCCCCUGAG UCAGUGUGCU GGAUUUCCCG UUUAAAAUUA   7500
CCGUCACGCU CUGCAGCGGU UCUCUGGCUG AAAUUUCAAA ACGUGGAGAG GUAAUAUUCG   7560
UAAUACCAUC CGUAGAAUCC UUUCCGGCGU CGUCCAGCAU CACGACGCUC AGGCCGUCAA   7620
UCUGCGUAUC CACGGUGAAG CCCAGCGUGG AAUUUGCCGU AUUCCCUGCC CGAUCCGUCG   7680
CCUGGACAUG GAGAGUAUAA UGACCAUCAG GCAAUGCGCU ACCUGCAGUA AAUUCCCACU   7740
GCCCGGCCGC AUUUUUACUG AUGGGCGUCC AGUUUACGCC AUCGAAAGAA ACCAGCACCG   7800
AUGUCACAUC AUCAGGCGUU GCAAUUUCAA AAGAGGGACG GGUAGCAUUG GUGACAUUAU   7860
CGUGAUCGUU GACGCCGCUA UCUGUUGUUA ACGUAACACU GUCAAUCUGA ACCUGCGUGU   7920
CGAUUUCAAU CCGCAGUUCG GCCGAUGUUU UGGUAUUACC AGCAAUAUCC GUUACGGUAA   7980
CAGAGAUCGU AUGCUGACCG UCAGACAGCG GUUGAUCCGG CGUAAAGGUU AAAUUCCCCC   8040
CUGUGUUUUC AAUGGUGUAA UCCCGACCAU CAAUAUGAAC CACAAUGUGU GAUACAUCAU   8100
UAUCGACAUU ACCGAUAAUA AACACCGGUU UGUUAAUCCU GGUAAGAUUA UCAUUAGUAU   8160
CAUCACCAGU AUCAUGGGUG GGAUCGAGUA CAAUUGUCGG CUCUCGCAGA GUCGUAUCAA   8220
UCGUAAACUG CAGCGUUUCU UGCGCAACGU UGCCGGCGAU AUCAGUCACA UCAACCAAGA   8280
```

-continued

```
GAGUGUGUUG CCCAUCAGGU AAUGCCGAAC CGACAUUAAA UAUCCAGCGG CCAUCCCUCC   8340
UUUUGUGAGU UCAAUCCAAU UAGCGGCGUU AUCGAUUUUA ACGCGCACAU GGGUUAUAUC   8400
AUCAGCGGUA ACAAUACUAA ACUGCGGCUG UCGACUUUGG UAAUGUUAUC UACAUCGCUA   8460
UCACCGCUAU CUGUAACCAA CGUGACGCUU UCAAUUUCAG CCGUCGUAUC UAUCACAACA   8520
GGUAAUGGUU UCGAUGUCGC GGUAUUUCCG GCCUUAUCUU CAACCGUAAC GGUAAUAUUA   8580
UAAGAGCCAU CCGGAAUGGC AUUGCCUGGU GUAAAUUGCC AACCAGCCCC AACCUUAGUC   8640
GCGUUAUAAU CAUGACCAUC AAUCGUCACC ACGACUUUGA UAACAUCGGG GUCAACAUUA   8700
CCAAUCGUAA AGGUGGGUCG UGAAAUAUUA GUAAUAUUAU CGGCGGUAUU CGCUCCGGUA   8760
UCUUGUCCUG CGUCUAAAGC AAUAGUAGGA ACCUGUAUAU UAGUAUCGAU AUUAAAUACU   8820
AAAUCUUUAU UCGCAAUAUU ACCUGCCUCA UCCCGUGGCC UCUACGCGAA GGGUAUAUGU   8880
GCCGUCAACC AGAGUAUUCG GGCUGUCAAA AAUCCACUGU CCGUCGGCAU UUUUGCGUAU   8940
CACAUUCCAG UUAGCGCCAC CAUCCAGGGU UACACGUACC UGGACGACAU CACCGGGAAC   9000
GUCAAUUCUG AAUGACGGUU UGGCAACAUU CGUUAAUUGA UCAUUCUGCA CGCCGGUAUC   9060
AUUAAGCAAU ACGAUAUUGU UAAUGGUUGU CGUGGUAUCA AUACGCACCU CAAACGGCGC   9120
AGACUCUUUU ACAUUCCCCG CCAGAUCUUC CACCACAACG GCUAACUGAU AUGAGCCAUC   9180
AGCCCAGCUU CGCAGAAGGC GUAAAGCGCC AUUGACCAUU GGUGAAUACC GCCGCUUCUU   9240
CGUGCGUUUU ACCGUUGUAA GUUACUUUGA CCAUCACGCG CGUAACGUCA GAAUCAACCU   9300
GAUGUAUGUC GAACACAGGC CGAUCGUGAU UGGUGAGGCG AUCGCCAACA GUACCGCUAU   9360
CUUCGCCAGC UGCCAGUUCA AUCACCGGCG UAGUCAACGU ACCGUCUAUC GUCACCUUUA   9420
AAGGCGCGGA UGUUUGCUGG UUGCCUGCCA CAUCUGUUAC CGUCACGGUG AAUGUGUAGC   9480
UACCGUCCGC CAAAGCAGAA UCCGGUCGAU AGCGCCAGCC GUCGGCUGAU UCGGUGAGUA   9540
CCACCGUUUU AAACGUGCCG UUAUGCUCAA UACUCAAUUC CACGUGUCGA ACAUCUUUAU   9600
CGAUACUCCC CAACACAAAU ACCGGCUGAG UGACGCUGGU CAGAUUAUCG UUCUUAUUCU   9660
GUCCGGUAUC CUGAUCGGGC GCUAGCUCAA UGGUUGGCGU UAACAACGUG AUAUCGAUAG   9720
UGAAAUUGAG CGUCUCCGUC AUCUUAUUAC CCGCACCGUC AGUCACUUCC ACGGUCAGGG   9780
UAUGCUGUCC CUCUGGCAUA UCCGUCGGCC AGGUGUAAUC CCAAAUGCCA GCCGUCGAAC   9840
UCUUGAUUGC AGUAACCCAG GUCGUGCCGC CGUCAAUACU CAGAAGAACU UUUCCACAUC   9900
AUCCGGUACC GAGAUCUGGA ACUGCGGACG CACAUGUUUU GUCACAUUAU CGCCAGGGAC   9960
GCCGCUAUCG UUGACUAAUU CAAUACGAUC AAUGGCUAUU UGCGUAUCCA CUGUCACCGU  10020
CAGCGGCGUA GACGGACGCG UAUUUCCCGC CCGAUCCUCC ACUGUCACCG UCAGCGUAUA  10080
AUCACCGUCG CCCCACGGCG CUGGCGGUGU AAAGCUCCAU CCUCCAGCCC CCUGUGUCGC  10140
AGUAAACGAG GUUGUCGUUC CAUUAUGCGU GACGCUGACU GUAACGUUGA UAACAUCCGA  10200
AUCGAUAUUC UGCAGAAUAA AGGUCGGUCG GGUGCGAUUG GUCAUAUCAU CGCCAGGCGU  10260
ACCGGUAUCA UCCGUGCUAU CCAGCGCAAU GGUCGGCGUC GACAACCGGG UGUCGAUGAA  10320
AAAUUCAAGC GUUUGCGUCG CCGUAUUGCC CGCUCUGUCG GUGACCAUGA CGGUUAGGGU  10380
GUGUUUUCCA UCGCCCAUAU CCGUUGGCCA GGUAUAGCCC CAGACGCCUU CGAUACCCUG  10440
CGUCGCGCUC ACCCAGUUUG CGCCCCCAUC AAUGCUCAGU UGCACAGAAU UCACAUCCGC  10500
CGGCACCGUG AUCUCAAACU GCGGACGGGU GCUAUUAGUU AGAUUGUCAU CAGGCACGCC  10560
AUGAUCAUUG ACCAAUGUAA UAUCAGUAAU GCUGGUUUGC GUGUCCACCG UCACCACCAG  10620
CGGCGUGGAC UGACGAACGU UUCCUGCGUU AUCCGUUACC UCUACCGUCA GCGUAUAGCU  10680
```

-continued

```
ACCGUCCGCC CAGUCAGCAU CUGGCGUAAA GCGCCACUGU CCUCCAACCU GGGUUAGUGU  10740
CACUUCCUGG CUAUUGCCGC CCUGUGUGAU CCGCAAAAUG ACCGAGUGCG CAUCGGCGUC  10800
AAUAUUGCCA AUAGUAAAGC CCGGUCUUUU GACGCUCGUA AUAUGAUCGC CAAUGGCACC  10860
UGUAUCGUCC CUGCUAUCCA UAGCGAUGGU AGGCGUUGAC AGCCGGGUAU CAAUGGUAAA  10920
AUCGAGCGUC UGCGUCGUCU UAUUUCCCGC CUUAUCGGUC GCUUCUACCG UCAGGGUAUG  10980
UAGCCCGUCG GUCACAUCUU UCGGCCAGGU GUAAUCCCAG AUCCCUGCCG UGCCCUGUGU  11040
UGCACGAACC CACGUAUUAC CGCCGUCGAU ACUCAGACGU ACUUCGUUGA CAUCCCCUGG  11100
CACCGUGACG CGGAAGUGUG GACGAACGUC AUUGGUCAGG UUGUCGCCGG GAAUACCGUU  11160
AUCAUUAACC AGUUCAAUAA CAUCGAUGGU GAUUUGGGUG UCAACCGUGA CCGUCAGCGG  11220
CGCUGAGUAU UUUACGUUCC CCGCAUCAUC CUCCACCCUC ACCGUCAGCG UAUAGUCGCC  11280
AUCUGCCCAU GUGCCGGUCG GUGUCACGCU CCAGAUGCCG GUCGCGCCUU UGGUGGCCGU  11340
CAGCACUUCU UUCGUGCCGC CAUGUUGCAC CUCAACCGUG ACAUACCGCG CGUCUGCGUC  11400
AAUAUUGCCC AGUAAAAACG UCGGCUUAUU UACGUUGGUC AGGUGAUCGC CUUUUGUUUC  11460
CGCUGUAGUC CGUGUUGUCC AGCACGAUAG UCGGUUCUGA CAGUAGGGUA UCGAUGAUGA  11520
AGUCCAGUUG CUGCGUCGUU UUGUUUCCCG CCUUGUCGGU CGCCCCCACU GUCAGGGUAU  11580
GCUUACCCUC UCCCACAUCA GCCAGCCAGG UAUAAUCCCA GACGCCCGGC GUCGCGCUCU  11640
GGGUAGCGUU GAACCACGUC UUGCCGCCGU CAAUGCUCAG GCGCACCACG UUGACAUCCG  11700
UCGGUACCGU CACCUGGAAG UGCGGACGCA CAUUAUUAGU CAGAUUAUCG UCGGGAAUAC  11760
CGCUGUCAUU GACCAGUUCA AUGUUAUUAA UGGCGAUUUG CGUGUCCACC GUCACCGUCA  11820
GCGAUGCAGA AUGGCUGGUG UUCCCCGCUU UAUCUUCGAC UGACACACUC AGGGUAUAAU  11880
CACCAUCCGC CCACGCCCCU GUCGGCGUAA AGGUCCAUCC GCCUGCGUCU UUCGUGGCGU  11940
CAAAUGUGGU GGUGACGCCG CCAUGCUCUA CGCUGACCGU AACGCGAACG GCAUCAUCAU  12000
CAAUAUGCUG CAGGGCAAAU GUCGGCUGGG UGCUAUUCGU CAUGUUAUCG CCAUGGACAC  12060
CACUGUCGUC CGCGCUAUCC AGUACGAUCA CCGGCGUCGA CAACGUAGUA UCAAUAGUGA  12120
AGUGGAGUGU CUCCGUCACC GUAUUACCCG CAUUGUCAGU CGCUUUCACA UUCAGCGUAU  12180
AGUCGCCAUC CGGCACGGUG CCCGGCCAGG UAUAAUUCCA GACGCCCGGC GUCGCGCUCU  12240
GUGUCGCCUU AACCCAGGUC ACGCCACCGU CAAUGCUCAG ACUGACUUCG UUAACGUCCC  12300
CCGGUACCGU CACGCGGAAC UGCGGAUGGG CGUCGUUAGU CAUAUUUGUCG CCGGGAAUAC  12360
CGUUAUCAUU AACCAGUUCA AUAACAUCAA UGGUGAUUUG GGUAUCAACA GUGACCGUCA  12420
GCGACCUGAG UGUUUUUCGU UCCCCGCCUC AUCUUCCACC CUCACUGUCA GCGUAUAGUC  12480
GCCAUCUGCC CAUGUGCCGG UCGGUGUCAC GCUCCAGUUG CCGGUCGCGU CUUUGGUGGC  12540
CGUCAGCACC UCUUUCGUGC CGCCAUGCUG UACCUCAACC GUGACAUACC GCGCGUCUGC  12600
GUCAAUAUUG CCCAGUAAAA ACGUCGGCUU AUUUACGUUG GUCAGGUGAU CGCCUUUUGU  12660
UCCGCUGUCG UCCGUGCUGU CCAGCACGAU AGUCGGUUCU GACAGUAGGG UAUCGAUGAU  12720
GAAGUCCAGU UGCUGCGUCG UUUUGUUUCC CGCCUUGUCG GUCGCCUCCA CUGUCAGGGU  12780
AUGCUUACCC UCUCCCACAU CAGCCAGCCA GGUAUAAUCC CAGACGCCCG GCGUCGCGCU  12840
CUGGGUAACG UUGAACCACG UCUUACCGCC GUCAAUGCUC AGGCGCACCA CGUUGACAUC  12900
CGUCGGUACC GUCACCUGGA AGUUGCGGAC GCACAUUAUU AGUCAGAUUA UCGUCCGGAA  12960
UACCGCUGUC AUUGACCAGU UCAAUAUGGU CAAUGGUGAU UUGCGUAUCG AUGGUGACCG  13020
UCAACGGCGC UGAGUGGCGA AUAUUACCCG CCUCAUCUUU CACCGUUACC GUCAGCGUAU  13080
```

```
AGUCGCCAUC AGUCCACGCG CUGCCGGGUA CAAAACGCCA CUGCCCGUUA GUCUGCGUCA  13140
GCUCCACCUC CUCGCUGUGA CCAUCGCGCA UCACCUGCAC GACGACCUGA GUCACGUCAG  13200
AAUCAAUACC GCCGAUAAUA AAACCCGGCG UUUUAACGUU AGUCUUAUUA UCGUUGGCGG  13260
UGCCGCUAUC AUCUGCGCUA UCCAGCGUGA UGGUCGGUGU CGACAAUGUG GUAUCAAUGG  13320
UAAAAUUGAG CGUUUCCGUC GCCGUGUUGC CUGCAACAUC GGUUGCUUUC ACUGUCAGGG  13380
UAUACGUAUU UUCGACCAGA UCUGUCGGCC AUAUAUACUC CCAAACGCCG UCAGACGUCA  13440
GCGUUGCGUU AACCCAGUUG AUGCCGCCAU CAAGACUCAG UUGCACAGAG UUCACGUCCG  13500
UCGGUACCGU AAUAUGAAAC UGUGGACGUG CUUCAUUGGU CAGGUUAUCC CCGACAAUAC  13560
CCGUGUCAUU AAGAAGCUCA AUGCGAUCAA UAGACGUUUG CGUAUCGAUA GUCACCGUCA  13620
GCGGCGCAGA AUAAUUUGUA UUACCCGCCU UAUCUUCUAC CUUUACCGUC AACGUAUAGU  13680
CGCCAUCGGU CCAGGCUGCG CCCGGCGUAA AGCGCCACAC ACCGCCGUUC UUAAUCAACU  13740
CUAUCUGUUG GUUCUUACCA UCAUGCGCCA CCGUCACCAC CACUUUGGUC ACGUCGGCGU  13800
CGAUAUUACC GAGGGUAAAG CCUGGCAUCU UAACGUUGGU GAUGUUAUCG CCAGCGGCGC  13860
UAUCAUCCGC GCUGUCCAGG GUAAUCGUCG GUUCUGACAG AAUGGUAUCG AUGGUGAAGU  13920
CCAGUUUCUG CGUCGUUUUG UUUCCCGCCU UGUCGGACGC UUCCACCAUC AGGGUGUGAG  13980
GGCCGUUAGC CACAUUCGUC AGCCAGGUGU AAUCCCAGAC GCCCGACGUC GCGCUGCUGC  14040
GUGGCGUCAA ACCACGUUUU GCCGCCAUCA AUGCUCAGUC UUACGCCGUU AACAUCCGCC  14100
GGUACUGUCA CCUGAAAGUG CGGGCGCGCU UCAUUGGUCA GAUUAUCGCC GGGGAUACCG  14160
CUGUCGUUAA CCAGUUCAAU ACGGUCAAUG GCGAUAUGCG UGUCUACUGU CACCGUCAAC  14220
GGCGCGGACU GCUUCACAUU UCCGGUCCUA UCUUCUACCU UCACCGUCAG GAUAUAGUCG  14280
CCGUCCGCCC AGUCGCUGGU CGGCGCAAAG CGCCACUGUC CGCCGGUCUG AACCAGUGGC  14340
ACCUCCUGCU UAAUGCCAUU GUGCAUUACC UCCACUAUCA CCCGGCUGAC AUCGGUAUCA  14400
AUAUUGUUGA GGGUAAAGCC CGGCGUUUUA ACAUUGGUGA UAUUAUCGCC CGCGAUGCCG  14460
CUGUCAUCUG CGCUGUCCAG CGAGAGGGUC GGCACAGACA GAGUGGUAUC GAUGGUGAAA  14520
UCGAGGUCUG UGUUGCCUUA UUUCCUGCCU CAUCGGUCGC UUCUACCGUC AGGGUAUAGC  14580
CUCCGUCGGC CACAUCAUCC GGCCAGAUAU AAUCCCAGAC GCCUGGCGUC GCGCUCUGGG  14640
UAGCGUUGAA CCACGUCUUG CCGCCGUCAA UGCUCAGGCG CACCACGUUG ACAUCCGUCG  14700
GUACCGUCAC CUGGAAGUGC GGACGCACAU UAUUAGUCAG AUUAUCGUCG GGAAUACCGC  14760
UGUCAUUGAC CAGUUCAAUG UUAUUAAUGG CGAUUUGCGU GUCCACCGUC ACCGUCAGCG  14820
AUGCAGAAUG GCUGGUGUUC CCCGCUUUAU CUUCGACUGA CACACUCAGG GUAUAAUCAC  14880
CAUCCGCCCA UGAUGUCGGC GGCGUAAAGG UCCAUCCGCC UGUGCCUUUC GUGGCGUCAA  14940
AUGUGGUGGU GACGCCGCCA UGCUCCACGC UGACCGUAAC GCGAACGGCA UCAUCAUCAA  15000
UAUGCUGCAA GGCAAAUGUC GGCUGGGUGC UAUUCGUCAU GUUAUCGCCC UGGAUGCCGG  15060
UGUCGUCCGC GCUAUCCAGU ACGAUGACCG GCACUGACAG CGUGGUAUCC ACCGCGAAAU  15120
CGAUGGUCUU CGUCAUGUAU UGCUGCUUUA UCAGUCGCUU CCACCGUUAG CGUGUAGGAC  15180
CAUCUGCCAG GUCUGUCGGC CAGAUAUACU CCCAGCUUCC UGCCACGCCC GGAGUUGCCU  15240
GAACCCACGA AUUACCACCG UCAAUGCUCA GACGGACUUC AUUGACAUCC GUAGGUACCG  15300
UCACACGAAA GUGGGGACGG UCGUCGUUGG UCAUAUUAUC GCCUUUCACG CCGCUAUCGU  15360
UGACCAGUUC CACCCCAUCA AUGGCGAUUU GGGUAUCGAU AACGACCGUC AGCGGCGCCG  15420
AGUAGUUGGU AUUUCCUGCC UUAUCUUCUA CUUUCACCGU UAACGUGUAG CUGCCAUCCG  15480
```

```
CCCACGUAUU CCCCUGGUAU AAAUAACCAA CUCCCAUUGA GGUGGGAAAG UUCGAUCUCU  15540
UCGCUCACGC CAUUGUGCAU CACCUGUACG ACGACCCGAU GCGCAUCGGC AUCAACACCG  15600
GAAAUAGCAA AACCUGGCUU AUUGAUAUUG GUCAGGUUAU CGCCUGUAAC CCCCGUAUCA  15660
UCCUUAGAAA GCAGGGAAAU CACCGGCGUU GAUACUGUGG UAUCGAUAGU AAAAUCGAAU  15720
AUCGCGCUGU UCGCUUUAUU ACCCGCAAUG UCCUCAACCU UGACAUAAAC CUGAUGCAAG  15780
CCUUCCGUUA AAUCUGAAGU AAAGGUAUAG GCCCAUGAAC CAUCAGGUUG UUGCGUGGCA  15840
ACACCGAUCU GCGUAUCAGA CAUGGCAUCC CAUACCUGAA CACUGAUAAU GUCCGGAUCA  15900
AUAUCUUUUA GGUGCAAGGU AGGUUUAACG AUAUUCGUUA AAUUAUCAUC UGAAAUUCCC  15960
GAAUCUGAAU CCGGGCUCAA UGAAACUAUC GGUAUUGAAA UAGCAGUAUC GACGCUAAUU  16020
AAGAAAGGAU CCGAAUGAGC AAUGUUGCCA GCGAUAUCUU CAACUGAAGC GGUUAUUCUA  16080
UGAUCGCCAU CAACCAAACC UUGAUCGGCU UUCAGGGUAU ACUCCCAUCU GCCAUCUUUA  16140
UUUGUUCUGA CCUCAGCGAU CAGUGCACCA UCAAUAUAGA GUUUAACCGU UGAAUAGGGU  16200
GCAGCGGUUC CUGUCAGUGC AGGAUUCUUU UCAUUAAUAA UAUGGUCUGU AUUAUCAACC  16260
CCCGUAUCGU UGACCAACUC UAUUGUUGGU UUUUGCGUUU GCGUUACGAU UUGGAAAUUA  16320
UACGCUGAUG AGGAGGCAGU AUUACCGGCA AUAUCUUCUA CCUUUACCGU UACGUCAUGC  16380
GAGCCAUCGG AUAACGCUGU GGUAAAUUGA AAAUUCCAUA CACCAUCAUC GCCAGCAAUA  16440
GCCUCACCAC UUAACACACC GUCAACAUAG AUGGAAACCU UAGCAUUAGC UUCAGCCAUC  16500
CCGGUAAACA ACGGUGUAUU AAUUUUAGUA AUCAUAUCGC CUUUAACGCC AGAGUCAGCG  16560
CUAUCAUGCA ACAUAACAGU AGGGAUCGGC GUAAAGCUAU CAAUGGUAAG CUGAUAAUCU  16620
ACAGAUGACG UUCUUCCUAA AGGAUCGAUG GAUUCAACCG UAAUCUUAUA AACAUUGUCA  16680
GACAGAUUUC UGGAAAUAUC AAAAUUCCAG UUACCGUCUG CAUCCGCAGU CGUCACGCCU  16740
AUCGUUUUAC CGUCAAUAAG GAUAUUUACG GUAGCAAACC UAUCCGCUGU UCCCAGUAAU  16800
GUCAGAGCAU UAUGUUUAUU GGUAAUCCAG UCGCCUUUUG CACCGGAAUC AUCACUGGCA  16860
UCGAGUUCCG CUUUUGGAGG UACAACUUCA GUUUGAAUAG UAAAAGAAUA UUUAACAGUA  16920
GAGGAUUUAU UGCCGGCGGC AUCCUGAGAA UGAUUUCAAU AUCAUAGGCG CCCUGAAGAA  16980
UUUAUUACUA AACUGAUAAU UUCCAGGUCC CGUUUGAGUC AACUUCAAUG CUGUCAUAUA  17040
AUUUACCAUC UCGCAUCAAU AAGAUGGUAG ACUUUGGUUC UGCCGUACCG ACUAAAGCCG  17100
GUAAAUCAUU CCCUGAUAAA AUUAUACCAU UCGGCAAAAC AACAUAAUCC UCCAAAGAAG  17160
CCGUCGGAGG UACAGGGGCA AUAGUAUCAA UAACGUAACU AAAGGAAAAA UCCUUUUUGU  17220
UGCCAGCGAC AUCUUCAACA GUGAACGUAA GAUUGUUAAU CCCUUCCACU GAGUCGGAAG  17280
UGAAAUUGAA CGUCCAUUCG CCCUUGUCAU UCGCUUUAAA AAUAACCUCU UCGCCAGUCU  17340
CACUAUUUAU GACACUGAUA AUAGCAUUUG GCUCAGUUUU ACCUGUAAAG GUUGGGCGAG  17400
UAUUGUUAGU AACGUUAUCU CCGACAAUAC CGCUAUCAUU CGUCGUUUCA AUCUCAGCGC  17460
UGAAAUAGCU GAUACGUGUA UCAAUAGUAA AAGGCAGAUU UGCCGUCGCU GAGGUAUGCC  17520
CGGCAAUAUC AGUAGCUGUU GCUGUUAUAU UGUAUUCGCC AUCCUUGAGC GGCGUAGUAA  17580
GCGUAUAGCU CCAUGUCCCA UCUUUAGCAA CAAUGACCUC ACCAAGAUGU UUAAGUCCAA  17640
GAUAAAUAGA GACUGUAGAA CCGGGUUCCG CCACACCAAU AAAUGUUGGC AGGGUGCUAU  17700
UUGUAAUGUU GUCAUUUUUA AUGCCGGAAU CACUACUAUC AUCCAGCUCA AUCGUCGGCU  17760
UUUCUGGAGC AAUGGUGUCG GUUAUGAUAC UAUCCGUCGU UUCGUUUUUA UUACCUGCUU  17820
UAUCUACAGC AACGACUUUU AUACUAUUUU CGCCCUCAGA UAAUUCAUUA UCCUUAAAUU  17880
```

-continued

```
CAUAACUCCA GUUUCCAUCU UUAUCGACAU CAACGCUGGC AACCAGUUUA UUAUCUACAU  17940
AAAUGUCAAC CUUAGCAUUC UCUUCCGCCG UACCAACAAU UGAAGGCGUC AAGGUCGGCG  18000
UUAAGCCCUU AUGACCGGAC ACACUACUUU CAGGCGAAAG UUCAAAUGUU GGUUUAUCGG  18060
UAACGGAAUC GAUAGUAAUG ACAAGUUUGG CGCUACCGCU CCCAUCAGCA GUCUUGGCCU  18120
CUGCCUCCAG AUUAUAUGUU CCAUCAGUCA AUGUUUCAGG CGCUGUAAAG GUGAAGUUAC  18180
CCAAACUAUC CGUUACAGCC UGACCGACAG CAAUACCAUU AAUUUUAAUA AUAACCGUGG  18240
CAUUGGGAGC AGUGCUAACU ACAAACUGAG GUUUGGUAAA AUUAGUUAUA CUAUCAUCUU  18300
UGCUACCGCU GUUACUCUCG GCCGCACGCG CUAAUGUGAC UUUAAGCGGC UCUUUAACAG  18360
ACUCGGCAUC GAGCUUAUUU UCCUCAUUUU UACUGCUAUU ACUUUUGCCA GUACUGGUAU  18420
UUUUAUUAAU AGGUUGAGGA AGAACUUUUU CAGCAUCGUU CUGUUUAGAA GCCUGCGUUG  18480
CUUUAGCCUG UGUAUUUUGC UGGGAAGCAU CGCUUUGCUG AGCCAGAUUG UCUUUUGCUA  18540
CAUUGUCAGC CAAAAAGUUC UGCAGCAUUU CUUCAAUUUG CUUUGACGAG UUCUGUACUU  18600
CAAACGCUUC AUUGAGCGCU UUUUCUGCAG CCUCCUUAGC UUUCUCUGCU UCUUCCUUCG  18660
CCUUAUCAGC UUCUUUCUUG CGUUUUCAGC AUCGUCAAGC UGCUUUUUAA UUCCUCUUCU  18720
UCCUUCUUAU UUCGUCGUUU GCCAUUACCU UUCUUUUCUA CCUGAGCAGA AUCAACCAAU  18780
GAGCUGUCAA UUCUCUCCAG UUGAAUAUCU UUUAAAUCUA CGCUGCCCAG AAUUUUAGCG  18840
CCGGUAAUAG UCUUAUCUUU AAAUUUAACA GCGAGGUUAU UGCCUUUGAU ACUUGAAUAA  18900
AGAGCGCCAU UGACAAUGAU CACUGAACCA CGCGGCGUGG UAAUGUUCAU GUCUGGCCCG  18960
GAAAGAGAAA CUUUUGCGCC UUUGGCAUUA CCCAAAGAAG AUAAAUCAAU UACAGAAUUU  19020
UGAUCGGCAA AAAACUUUUG UAUGCUUUUA UUUCCCAUAA UAUUAUAUUC ACUCUCAAGG  19080
UGUAUCUAAU CGUUUAGUAU UAACUGGUUC UGAAAAGGCU UUGUCCACGC CUUUCAUCAA  19140
GGGAGAUAAC AGGUAUUCCA UAAUGCUGUG UUUUCCGGUA AUUACACUGG CGUCAACAGU  19200
CAUACCUGGU UUUAACCACC GUAAAUCAUC UUCAUUAACA UCGAAUGCAA UAAUUACUUU  19260
AUAAUAACGC UGAAUUGUUC CUCCGGUAUU UUCCUCAUAG GAAUCAGGGC UAAUAUUAUC  19320
GAUAGUCGCA UUAUACGAUU UUAUCUUUGG UUGGAUAAUU GACUGCACAU CCAGUUUAAC  19380
GGCUUCAUCU ACAUAUAUUU GGUCACGGUA UUUGGGUAAU AUUUUCACAU CGGCCAGCAU  19440
AGUCCUUACU UUUGGUUUUA UUUCAAAAAG UAAGUCCGCC GCCUGAAUCA CACCACCAUG  19500
AGUAGUGGCA CUUUUAUUGA UUUUAUAAAU UACACCGUCA ACCGGUGAAU AGAUAUCCUC  19560
CUCAUUUAUC UGCUUCUCUA UUACUUUUAA UGUAGAGUUA ACAACCUCAA GUUCCUGAAG  19620
AUUUUUAGAU AUUAUUUUAG AUAAAGAUAG UCGCAAUUCA UUAUUAAGCG CCUCAAUAUC  19680
AUUAACAACC AACUCAAUAU CAUCUUUUUU UAAAGUGAUG CUACUUUCAA UAUCAUUAAU  19740
UUCAGACUUA ACUUUUAUAU ACGCCUGUUU CUUGUUAAGA AAAUUGGUAU AUGGGCUAAU  19800
UCCUUUUUUU ACCAGUGGGG AAAGAAUAUU UAUUUCUUCG GCAAGCAAUG CGAGUUCUUU  19860
UUCUUUCGAA CUCAGCUUCU CUUGUAAUCC GCUAAUCUCA GAAUCAAGAG AGGUUUUUUU  19920
UAACUCUUUA GCUCUUAUCU GACUAUGCAC UAAUUCAAUA UUCGCUUUUA CCUCUUUAUU  19980
GCUUAAAGAA CGGGUGCCAU CCAGGGUAAU CAACCCACUC UCAUUUUCUU UAUCAAGAAU  20040
GAAAGAUAUU UCGUUAACAU CUUUAUCCAG AUACCCUUUU UGAGUUCUAU ACCUUUGAUA  20100
UUCUUUUUGC AGAUCAAGGU UAACGACCUU UGCAAGGAGU UCUCCUUUUU UUACAGUAUC  20160
ACCCUCGGCU ACAUAAAUAU CUUGUAUCGU CCCUCCUUUA GAAAGAGAUA UUAACUGAGC  20220
AUUAUCUUUA GUAGUGAUAA CGCCCUGACC AUGAACCACU GAAUUAAUUU CUAUAAAGUA  20280
```

-continued

```
GGUAAGGAUA AUAAUUAAGA UCGUCAAAGA AAUAAUUAUC AUCAUGAGAU GAUCGCUUUG  20340
UCUUCUAUUC AUUUCAUUAC AUUUAACUCA CUUUCAGUAU UUCCUUUUAA AUAAUCCAUU  20400
AAAUGAAAAA UCAAUGAGAG UUGCUGUAGC UUUAAAAUAU ACAGGCUAUA UUUGCUGUCG  20460
AUCAUGCUUA CAUAUGCCUG AAAUGCUUCA UUACGGCUUG AAAUUAAAUC AAGCAAACUU  20520
UUUUGCCCUA ACUGAAACUC CUGCUCAUAU AAUUCAGUAA GCUGUAACGC GUUUGUAUGU  20580
GAACGUUCCG CCACUGAGUA AGUCUCUUUU GCAGCGGCGU AUCUUGAAAG UUGUGAAUCA  20640
AUGUUAUAAC GCGUUUUAAU CAAAAAAUCG UCAAUUUGCA GCUUAGCCUG CGAGUAACUU  20700
GCCACCAUUU UUCUUUCCUG GGCUGAAUUU CUGAACCCAU UAAAAAUGUU GAAACUGACA  20760
UUGAUACCCG UUUUAAAUUC AUCUUCAUAA UCACUUUUUU UGGCACUACC GCUUGGGUUA  20820
UUCUGUACAU AGCUGGAAAC AAGAUCUACA GUCGGAAAAU AGGAUGAUUU UGCGGCAUUA  20880
AUAUCUUCGG UCGCGGCUUU UCGGGUAUUG ACAAGCAUCU UAUAGUCAUC GUUGUAUUUC  20940
AUCACCAUGU CCAUAAGUUU UUCAGGGCUU UCGACAAAGA UAUAUUUUUU GAAGAGGUUG  21000
AAUUUUUCAU CGCUUUGAAU CUGAACUGGC GAUAAAUUCA GACCAGUCAU AUUCUGCAUU  21060
UUAUACAUUU CAUCAUCCAA CAUCGACUGA UACAUAAUGC UUCUGGUAUU UAAUGCAUCG  21120
AUAGAUACUU GUACUUUACG CAUAUCAGAU UGCAUAGCUA CACCGGAAGA UACCAGCAAC  21180
GAAAAAGGUU CCAGCAUCUU UUUAUAAAAC UCUUUCUCCA GAUUUACGCC AUCAAUCAUU  21240
UCACGAUAUU UACUGAUGUU GUAAUAGGUU GUCACAACCU CCUGAGACAC UAUAUUCUUU  21300
GUUUUUUCAU AGUCAGUUUU ACUAUUAUCU CUUUCAUAUU CAGAUUUCCU GAUAUUAGCC  21360
CCCCUCACUC CAAAAUCCGU UAUUCGGUAU GAUAAAGACA CCUUAUUUUC AACGUUCCUC  21420
UCGGUACCUG AUGACUCUUU CCUGUUAUUA UUAAGGCCAG AUGUUAGAUC CAGGGUAGGA  21480
UAAAGUGCUG CCCGUGAAAG AUCUAAGUCA CUGUUUUUCU UUUCAGUCUC AUAAUAUGAA  21540
ACAGCAACAG AGGGCUGAUG CGUUAAUGCG GCAUUAACUA AAUCUCUUAG AGGAAUGACC  21600
GGAAGCUCGC UGGCGUAUGU GCUUUGUGUA AUAAAAGCAG UCGUCAGAAA AAACAUCUUA  21660
AUCUUCAUUU UUUUCCUCCU UGUUUAACAA ACGUUGCUUU ACUAUUUCCU GAUGCAUAGA  21720
UGUUAUUUUU UCCAUUAAUG GCAUAUAGGU AUCACGGUAG CUAACCAUUU CAGCACUAAU  21780
CUCUUUAGUA UUGGCAAUAA UCUUUUUAUC AGUAGCCGAU AGAUCGGAUA GCGCUAAAUG  21840
AACAUUAUUC AUAUCCUCAU CCAUUUCUUU UCUCAGCCCA UCGAGAGUAU GAGAAAUAUC  21900
GGCACUGCCA GCGGCAAUAU CGUUUAUGGU CUUACCAUGU GAAAGAGAUU CCUGAUAACA  21960
UUUAUCAACU GAUGUCAUUA UUGAAUCAUU CUUUUUAUCU AUAAUAUUUU GUAUUGUACU  22020
CAUUGCCUCC AGUCGUGCAU UAUUAUCAGC AAGCAGGAUA UUACCUUCAG AUAAACGAGA  22080
GGUAAUUGUU AUUACACCGU CAGAUAAUUU UUUGAGAUUU UCCGUUACUG CUUACCAGAU  22140
AACCAUCAAU CAGCGUAAAA AUUUGUUCCA GUUUUGCUGA GUUAUCCAAU AGUCGGUUUU  22200
GCAAAGUGAC AAAGCUAUCU GAUAGCAUCU CUCGUUUCUU UUCUUCAUCC UGCGUCCGUA  22260
AGUUUUCAAC UGUCAGGUAG UUAUCAAAAA ACGCUUUAAA CAACUCUUUA AAUUCUACAA  22320
GCGUCUCUGA UUCAACCCGC AGGCUUCGCU GUUUAUUAUU GGCUCUGUUG CUUAUGAUUU  22380
UUAAUUUUUU GAUUUCCGUA GAAACAAGGG AAUAGGAGCU GCGAACAAAA ACACUUUGUG  22440
AGGUCAGGAG UAUGGCGCAA ACAACACCAU AGAUAGAAGA UACAAAUGCG GUAUUCAUCC  22500
CUUUCAAUGG UUCAGAAAGC GACGCUACCA UUGUCACGAU CAUAUUGAGU GUAUUACUUG  22560
CAUUAUCACC GCCAACAUCU GAUGGCGAGC UCAAUAAGUU CCCGAUUGAA CCAAUCGUAA  22620
UAGACAGACC CGCAAACGUC CCCAACAGGC CAACAAGCGU CGACACAUUG CUACAGCUCA  22680
```

```
UAAUAAAUGA CAAUCGUUGA UUACGGGCGG UAGACACAUU GUCAUCUAAU UCCAUCAGUA  22740

AAUUGAAAUC ACACUGUUUG GACUCCCCGG CAAACAAAAC CUGAUUGAGG UUAGAAAGAA  22800

UGCUAUUUUU UCUACUGGCG UCCUGAGCUA UUAAUAUGUC UUUUGCUGAA AUAUUUUUAA  22860

GAAUAGUGAA UAAUGCACAC AAAGAACCUG UAAUAUAAAU GGCAAUAAUG ACUCCAUUGU  22920

AAAUUGCAGA AACCAUGAAG UUAUCAAAAA CAUACUCUCU UAUACCGGGA AAAGAUAAAG  22980

CAAAAAAAGG GAGUAUGGCA AGGAAAGAAC AGACAACAAA UAGCGGUAAU GAUUUAUAUA  23040

UUUCACUCUG ACACCUUUUA UUAAUAGUCG UGAUAAUAGC UUUACUCGUU GUACUUGAUG  23100

CUGCGGAGUU AACACUCAUG UCAAUAACUA CAUCAGGAUA UAUUUUCUUA AUCUCUUUCA  23160

UCAAAAUAAU UCCCCGUUCA UAUCCCAGUC GUAGAGAGUC AGAGAAAGAG AUGUCUGCCU  23220

GAGGAAUAAC CAUUUCUAUC AAUAAAUUAC UAUUGAUUUU GUCUUCUAAC CAAGCCUUUA  23280

UUUUAUAAGU GUCCUCUUCU GAAAAGCUUC UCAGCCUGCC AUGAUACGUA AUAACAAGCU  23340

CAUUUUUUGU AGACGUUAUA UCAGUUUUCU GACCAUCGGC GAUAUCGUAU ACUCCAACCU  23400

CCUUACCUGA CAUUGUAGUC AUUCCGUCCG ACACAUCUUG AGUAUUCACU UCCUUAUUAA  23460

CUAUUUCAUU AGGAUUUGAA UCGUCAUUGG CUCCGCUAUU UUGAGCAGUA GAUUUAGUCU  23520

UAUUCUCUAU AUUUGCUUUA UAAACUUUAA UUGAGUUGUC AUACAUAAUA AUCAUAUUAU  23580

UAAGUGCAAA CACCAACAUA AGAAAUAUAA AAAUGCACAA UACCGUAGAG AAUGUAUCAA  23640

CAAAACUAGG CCACGGAUUA CUUUCGUCUU CCAUGUUGUC UCCUGAUAUU ACAUUGUGAA  23700

UAAAAUGUUU UUGUGGAUUA GAAAGGAUAA AGGAUGCUCA ACUUAUUCAG AAAGUGAACG  23760

CUACCGCCCU UGGCUUCCUG CUACCAAUAC GCUUUAUAGA UUUCAGUUUU CUUACAUCUC  23820

GUAAUCAGAA AAAUAAAAAC AACGACGCCA UUUUUAUGCG CCCACAACAA AGAUGAGUGC  23880

UUUAAUUAAA AACACUCUUC AUUUUUUUAA UUAGGUAGAC AUCAAUUAUU GCACUAACUA  23940

UAUCCUCCCC AAUAAUAGGU AUCGCAUAAG CUCUCAACUC AUAAAUAAAA AAUAGUCAUC  24000

AGCAAAUUAA AACCACCCGC CGAUAAAUAG AUUUGUUAGC UAAUCAUUGA AACUCUAAAU  24060

CAUUUUAAGG ACAUAUUUCU UUUUAAUACG CGUUAUAACC AUACGUAUUU AAUAAAUUUG  24120

CCUCCAGAGG AUAAAAUUAA UUUUCACAAU UAAAACAUAG GGUCAUAUGG ACUUCAAUAU  24180

AACUUAAAUC AUUGAAAAUA UAAUAAGUGG GGAGUAAAAA AUCAGAAUUG UGUAAAAAAA  24240

UACACAAAUA AAACCAUUUU UUAUAUAAAG CCAGCUAUAA GUAACAAUUU UAUCUUCAGC  24300

AAUUAAAAAU AAAGCAAGAU ACACAUAUCA UAUUUGAGCU CAUCACAAGC UAAAGCAAAC  24360

AUUUAAUUAA CCAUUGAUAA UACCGACCAU UCUCUACCGU UAUUUUAUAA UAUCUUUUUG  24420

UUGUCAAAAA AUGGCUAUAA AUUAUAUAUU UUGCAGAUGA GAUUUCUCUU UCAUAUUUAA  24480

GACAAUCCGG GUUAUUGCAG UACAUUUAUG AACUUCGGCU GGAUAAUGAU GUGCCGAGGC  24540

GAGUCGGCCA GAGGCGAUAA GCGACAUUUU UCCGUAAGAU AUGCGCUUCU CUUUUUUGAA  24600

AGGGAUACAA AGACAAUAAU ACCAGGUAAG AAAAUGCCUG GUUUACACCA GGCAUUUCAG  24660

CAGACGAGAA CUAUAGCGAA AAUGCAAAUA ACGCUUUGAG U                      24701
```

(2) INFORMATION FOR SEQ ID NO:62:

(i) SEQUENCE CHARACTERISTICS:
- (A) LENGTH: 222 bases
- (B) TYPE: nucleotide
- (C) STRANDEDNESS: single stranded
- (D) TOPOLOGY: linear (xi) SEQUENCE DESCRIPTION: SEQ ID NO:62:

```
AGCUGGGCUG AUGGCUCAUA UCAGUUAGCC GUUGUGGUGG AAGAUCUGGC GGGGAAUGUA     60
```

```
AAAGAGUCUG CGCCGUUUGA GGUGCGUAUU GAUACCACGA CAACCAUUAA CAAUAUCGUA    120

UUGCUUAAUG AUACCGGCGU GCAGAAUGAU CAAUUAACGA AUGUUGCCAA ACCGUCAUUC    180

AGAAUUGACG UUCCCGGUGA UGUCGUCCAG GUACGUGUAA CC                       222
```

(2) INFORMATION FOR SEQ ID NO:63:

(i) SEQUENCE CHARACTERISTICS:
(A) LENGTH: 15512 bases
(B) TYPE: nucleotide
(C) STRANDEDNESS: single stranded
(D) TOPOLOGY: linear (xi) SEQUENCE DESCRIPTION: SEQ ID NO:63:

```
ACUCAAAGCG UUAUUUGCAU UUUCGCUAUA GUUCUCGUCU GCUGAAAUGC CUGGUGUAAA     60

CCAGGCAUUU UCUUACCUGG UAUUAUUGUC UUUGUAUCCC UUUCAAAAAA GAGAAGCGCA    120

UAUCUUACGG AAAAAUGUCG CUUAUCGCCU CUGGCCGACU CGCCUCGGCA CAUCAUUAUC    180

CAGCCGAAGU UCAUAAAUGU ACUGCAAUAA CCCGGAUUGU CUUAAAUAUG AAAGAGAAAU    240

CUCAUCUGCA AAAUAUAUAA UUUAUAGCCA UUUUUUGACA ACAAAAAGAU AUUAUAAAAU    300

AACGGUAGAG AAUGGUCGGU AUUAUCAAUG GUUAAUUAAA UGUUUGCUUU AGCUUGUGAU    360

GAGCUCAAAU AUGAUAUGUG UAUCUUGCUU UAUUUUUAAU UGCUGAAGAU AAAAUUGUUA    420

CUUAUAGCUG GCUUUAUAUA AAAAAUGGUU UUAUUUGUGU AUUUUUUUAC ACAAUUCUGA    480

UUUUUUACUC CCCACUUAUU AUAUUUUCAA UGAUUUAAGU UAUAUUGAAG UCCAUAUGAC    540

CCUAUGUUUU AAUUGUGAAA AUUAAUUUUA UCCUCUGGAG GCAAAUUUAU UAAAUACGUA    600

UGGUUAUAAC GCGUAUUAAA AAGAAAUAUG UCCUUAAAAU GAUUUAGAGU UUCAAUGAUU    660

AGCUAACAAA UCUAUUUAUC GGCGGGUGGU UUUAAUUUGC UGAUGACUAU UUUUUAUUUA    720

UGAGUUGAGA GCUUAUGCGA UACCUAUUAU UGGGGAGGAU AUAGUUAGUG CAAUAAUUGA    780

UGUCUACCUA AUUAAAAAAA UGAAGAGUGU UUUUAAUUAA AGCACUCAUC UUUGUUGUGG    840

GCGCAUAAAA AUGGCGUCGU UGUUUUUAUU UUUCUGAUUA CGAGAUGUAA GAAAACUGAA    900

AUCUAUAAAG CGUAUUGGUA GCAGGAAGCC AAGGGCGGUA GCGUUCACUU UCUGAAUAAG    960

UUGAGCAUCC UUUAUCCUUU CUAAUCCACA AAAACAUUUU AUUCACAAUG UAAUAUCAGG   1020

AGACAACAUG GAAGACGAAA GUAAUCCGUG GCCUAGUUUU GUUGAUACAU UCUCUACGGU   1080

AUUGUGCAUU UUUAUAUUUC UUAUGUUGGU GUUUGCACUU AAUAAUAUGA UUAUUAUGUA   1140

UGACAACUCA AUUAAAGUUU AUAAAGCAAA UAUAGAGAAU AAGACUAAAU CUACUGCUCA   1200

AAAUAGCGGA GCCAAUGACG AUUCAAAUCC UAAUGAAAUA GUUAAUAAGG AAGUGAAUAC   1260

UCAAGAUGUG UCGGACGGAA UGACUACAAU GUCAGGUAAG GAGGUUGGAG UAUACGAUAU   1320

CGCCGAUGGU CAGAAAACUG AUAUAACGUC UACAAAAAAU GAGCUUGUUA UUACGUAUCA   1380

UGGCAGGCUG AGAAGCUUUU CAGAAGAGGA CACUUAUAAA AUAAAGGCUU GGUUAGAAGA   1440

CAAAAUCAAU AGUAAUUUAU UGAUAGAAAU GGUUAUUCCU CAGGCAGACA UCUCUUUCUC   1500

UGACUCUCUA CGACUGGGAU AUGAACGGGG AAUUAUUUUG AUGAAAGAGA UUAAGAAAAU   1560

AUAUCCUGAU GUAGUUAUUG ACAUGAGUGU UAACUCCGCA GCAUCAAGUA CAACGAGUAA   1620

AGCUAUUAUC ACGACUAUUA AUAAAAGGUG UCAGAGUGAA AUAUAUAAAU CAUUACCGCU   1680

AUUUGUUGUC UGUUCUUUCC UUGCCAUACU CCCUUUUUUU GCUUUAUCUU UUCCCGGUAU   1740

AAGAGAGUAU GUUUUUGAUA ACUUCAUGGU UUCUGCAAUU UACAAUGGAG UCAUUAUUGC   1800

CAUUUAUAUU ACAGGUUCUU UGUGUGCAUU AUUCACUAUU CUUAAAAAUA UUUCAGCAAA   1860
```

-continued

```
AGACAUAUUA AUAGCUCAGG ACGCCAGUAG AAAAAAUAGC AUUCUUUCUA ACCUCAAUCA   1920
GGUUUUGUUU GCCGGGGAGU CCAAACAGUG UGAUUUCAAU UUACUGAUGG AAUUAGAUGA   1980
CAAUGUGUCU ACCGCCCGUA AUCAACGAUU GUCAUUUAUU AUGAGCUGUA GCAAUGUGUC   2040
GACGCUUGUU GGCCUGUUGG GGACGUUUGC GGGUCUGUCU AUUACGAUUG GUUCAAUCGG   2100
GAACUUAUUG AGCUCGCCAU CAGAUGUUGG CGGUGAUAAU GCAAGUAAUA CACUCAAUAU   2160
GAUCGUGACA AUGGUAGCGU CGCUUUCUGA ACCAUUGAAA GGGAUGAAUA CCGCAUUUGU   2220
AUCUUCUAUC UAUGGUGUUG UUUGCGCCAU ACUCCUGACC UCACAAAGUG UUUUUGUUCG   2280
CAGCUCCUAU UCCCUUGUUU CUACGGAAAU CAAAAAAUUA AAAAUCAUAA GCAACAGAGC   2340
CAAUAAUAAA CAGCGAAGCC UGCGGGUUGA AUCAGAGACG CUUGUAGAAU UUAAAGAGUU   2400
GUUUAAAGCG UUUUUUGAUA ACUACCUGAC AGUUGAAAAC UUACGGACGC AGGAUGAAGA   2460
AAAGAAACGA GAGAUGCUAU CAGAUAGCUU UGUCACUUUG CAAAACCGAC UAUUGGAUAA   2520
CUCAGCAAAA CUGGAACAAA UUUUUACGCU GAUUGAUGGU UAUCUGGUAA GCAGUAACGG   2580
AAAAUCUCAA AAAAUUAUCU GACGGUGUAA UAACAAUUAC CUCUCGUUUA UCUGAAGGUA   2640
AUAUCCUGCU UGCUGAUAAU AAUGCACGAC UGGAGGCAAU GAGUACAAUA CAAAAUAUUA   2700
UAGAUAAAAA GAAUGAUUCA AUAAUGACAU CAGUUGAUAA AUGUUAUCAG GAAUCUCUUU   2760
CACAUGGUAA GACCAUAAAC GAUAUUGCCG CUGGCAGUGC CGAUAUUUCU CAUACUCUCG   2820
AUGGGCUGAG AAAAGAAAUG GAUGAGGAUA UGAAUAAUGU UCAUUUAGCG CUAUCCGAUC   2880
UAUCGGCUAC UGAUAAAAAG AUUAUUGCCA AUACUAAAGA GAUUAGUGCU GAAAUGGUUA   2940
GCUACCGUGA UACCUAUAUG CCAUUAAUGG AAAAAAUAAC AUCUAUGCAU CAGGAAAUAG   3000
UAAAGCAACG UUUGUUAAAC AAGGAGGAAA AAAAUGAAGA UUAAGAUGUU UUUUCUGACG   3060
ACUGCUUUUA UUACACAAAG CACAUACGCC AGCGAGCUUC CGGUCAUUCC UCUAAGAGAU   3120
UUAGUUAAUG CCGCAUUAAC GCAUCAGCCC UCUGUUGCUG UUUCAUAUUA UGAGACUGAA   3180
AAGAAAAACA GUGACUUAGA UCUUUCACGG GCAGCACUUU AUCCUACCCU GGAUCUAACA   3240
UCUGGCCUUA AUAAUAACAG GAAAGAGUCA UCAGGUACCG AGAGGAACGU UGAAAAUAAG   3300
GUGUCUUUAU CAUACCGAAU AACGGAUUUU GGAGUGAGGG GGCUAAUAU CAGGAAAUCU    3360
GAAUAUGAAA GAGAUAAUAG UAAAACUGAC UAUGAAAAAA CAAAGAAUAU AGUGUCUCAG   3420
GAGGUUGUGA CAACCUAUUA CAACAUCAGU AAAUAUCGUG AAAUGAUUGA UGGCGUAAAU   3480
CUGGAGAAAG AGUUUUAUAA AAAGAUGCUG GAACCUUUUU CGUUGCUGGU AUCUUCCGGU   3540
GUAGCUAUGC AAUCUGAUAU GCGUAAAGUA CAAGUAUCUA UCGAUGCAUU AAAUACCAGA   3600
AGCAUUAUGU AUCAGUCGAU GUUGGAUGAU GAAAUGUAUA AAAUGCAGAA UAUGACUGGU   3660
CUGAAUUUAU CGCCAGUUCA GAUUCAAAGC GAUGAAAAAU UCAACCUCUU CAAAAAAUAU   3720
AUCUUUGUCG AAAGCCCUGA AAAACUUAUG GACAUGGUGA UGAAAUACAA CGAUGACUAU   3780
AAGAUGCUUG UCAAUACCCG AAAAGCCGCG ACCGAAGAUA UUAAUGCCGC AAAAUCAUCC   3840
UAUUUUCCGA CUGUAGAUCU UGUUUCCAGC UAUGUACAGA AUAACCCAAG CGGUAGUGCC   3900
AAAAAAAGUG AUUAUGAAGA UGAAUUUAAA ACGGGUAUCA AUGUCAGUUU CAACAUUUUU   3960
AAUGGGUUCA GAAAUUCAGC CCAGGAAAGA AAAAUGGUGG CAAGUUACUC GCAGGCUAAG   4020
CUGCAAAUUG ACGAUUUUUU GAUUAAAACG CGUUAUAACA UUGAUUCACA ACUUUCAAGA   4080
UACGCCGCUG CAAAAGAGAC UUACUCAGUG GCGGAACGUU CACAUACAAA CGCGUUACAG   4140
CUUACUGAAU UAUAUGAGCA GGAGUUUCAG UUAGGGCAAA AAGUUUGCU UGAUUUAAUU    4200
UCAAGCCGUA AUGAAGCAUU UCAGGCAUAU GUAAGCAUGA UCGACAGCAA AUAUAGCCUG   4260
```

```
UAUAUUUUAA AGCUACAGCA ACUCUCAUUG AUUUUUCAUU UAAUGGAUUA UUUAAAAGGA   4320
AAUACUGAAA GUGAGUUAAA UGUAAUGAAA UGAAUAGAAG ACAAAGCGAU CAUCUCAUGA   4380
UGAUAAUUAU UUCUUUGACG AUCUUAAUUA UUAUCCUUAC CUACUUUAUA GAAAUUAAUU   4440
CAGUGGUUCA UGGUCAGGGC GUUAUCACUA CUAAAGAUAA UGCUCAGUUA AUAUCUCUUU   4500
CUAAAGGAGG GACGAUACAA GAUAUUUAUG UAGCCGAGGG UGAUACUGUA AAAAAAGGAG   4560
AACUCCUUGC AAAGGUCGUU AACCUUGAUC UGCAAAAAGA AUAUCAAAGG UAUAGAACUC   4620
AAAAAGGGUA UCUGGAUAAA GAUGUUAACG AAAUAUCUUU CAUUCUUGAU AAAGAAAAUG   4680
AGAGUGGGUU GAUUACCCUG GAUGGCACCC GUUCUUUAAG CAAUAAAGAG GUAAAAGCGA   4740
AUAUUGAAUU AGUGCAUAGU CAGAUAAGAG CUAAAGAGUU AAAAAAAACC UCUCUUGAUU   4800
CUGAGAUUAG CGGAUUACAA GAGAAGCUGA GUUCGAAAGA AAAAGAACUC GCAUUGCUUG   4860
CCGAAGAAAU AAAUAUUCUU UCCCCACUGG UAAAAAAAGG AAUUAGCCCA UAUACCAAUU   4920
UUCUUAACAA GAAACAGGCG UAUAUAAAAG UUAAGUCUGA AAUUAAUGAU AUUGAAAGUA   4980
GCAUCACUUU AAAAAAAGAU GAUAUUGAGU UGGUUGUUAA UGAUAUUGAG GCGCUUAAUA   5040
AUGAAUUGCG ACUAUCUUUA UCUAAAAUAA UAUCUAAAAA UCUUCAGGAA CUUGAGGUUG   5100
UUAACUCUAC AUUAAAAGUA AUAGAGAAGC AGAUAAAUGA GGAGGAUAUC UAUUCACCGG   5160
UUGACGGUGU AAUUUAUAAA AUCAAUAAAA GUGCCACUAC UCAUGGUGGU GUGAUUCAGG   5220
CGGCGGACUU ACUUUUUGAA AUAAAACCAA AAGUAAGGAC UAUGCUGGCC GAUGUGAAAA   5280
UAUUACCCAA AUACCGUGAC CAAAUAUAUG UAGAUGAAGC CGUUAAACUG GAUGUGCAGU   5340
CAAUUAUCCA ACCAAAGAUA AAAUCGUAUA AUGCGACUAU CGAUAAUAUU AGCCCUGAUU   5400
CCUAUGAGGA AAAUACCGGA GGAACAAUUC AGCGUUAUUA UAAAGUAAUU AUUGCAUUCG   5460
AUGUUAAUGA AGAUGAUUUA CGGUGGUUAA AACCAGGUAU GACUGUUGAC GCCAGUGUAA   5520
UUACCGGAAA ACACAGCAUU AUGGAAUACC UGUUAUCUCC CUUGAUGAAA GGCGUGGACA   5580
AAGCCUUUUC AGAACCAGUU AAUACUAAAC GAUUAGAUAC ACCUUGAGAG UGAAUAUAAU   5640
AUUAUGGGAA AUAAAAGCAU ACAAAAGUUU UUUGCCGAUC AAAAUUCUGU AAUUGAUUUA   5700
UCUUCUUUGG GUAAUGCCAA AGGCGCAAAA GUUUCUCUUU CCGGGCCAGA CAUGAACAUU   5760
ACCACGCCGC GUGGUUCAGU GAUCAUUGUC AAUGGCGCUC UUUAUUCAAG UAUCAAAGGC   5820
AAUAACCUCG CUGUUAAAUU UAAAGAUAAG ACUAUUACCG GCGCUAAAAU UCUGGGCAGC   5880
GUAGAUUUAA AAGAUAUUCA ACUGGAGAGA AUUGACAGCU CAUUGGUUGA UUCUGCUCAG   5940
GUAGAAAAGA AAGGUAAUGG CAAACGACGA AAUAAGAAGG AAGAAGAGGA AUUAAAAAGC   6000
AGCUUGACGA UGCUGAAAAC GCAAGAAAGA AGCUGAUAAG GCGAAGGAAG AAGCAGAGAA   6060
AGCUAAGGAG GCUGCAGAAA AAGCGCUCAA UGAAGCGUUU GAAGUACAGA ACUCGUCAAA   6120
GCAAAUUGAA GAAAUGCUGC AGAACUUUUU GGCUGACAAU GUAGCAAAAG ACAAUCUGGC   6180
UCAGCAAAGC GAUGCUUCCC AGCAAAAUAC ACAGGCUAAA GCAACGCAGG CUUCUAAACA   6240
GAACGAUGCU GAAAAAGUUC UUCCUCAACC UAUUAAUAAA AAUACCAGUA CUGGCAAAAG   6300
UAAUAGCAGU AAAAAUGAGG AAAAUAAGCU CGAUGCCGAG UCUGUUAAAG AGCCGCUUAA   6360
AGUCACAUUA GCGCGUGCGG CCGAGAGUAA CAGCGGUAGC AAAGAUGAUA GUAUAACUAA   6420
UUUUACCAAA CCUCAGUUUG UAGUUAGCAC UGCUCCCAAU GCCACGGUUA UUAUUAAAAU   6480
UAAUGGUAUU GCUGUCGGUC AGGCUGUAAC GGAUAGUUUG GGUAACUUCA CCUUUACAGC   6540
GCCUGAAACA UUGACUGAUG GAACAUAUAA UCUGGAGGCA GAGGCCAAGA CUGCUGAUGG   6600
GAGCGGUAGC GCCAAACUUG UCAUUACUAU CGAUUCCGUU ACCGAUAAAC CAACAUUUGA   6660
```

-continued

```
ACUUUCGCCU GAAAGUAGUG UGUCCGGUCA UAAGGGCUUA ACGCCGACCU UGACGCCUUC   6720
AAUUGUUGGU ACGGCGGAAG AGAAUGCUAA GGUUGACAUU UAUGUAGAUA AUAAACUGGU   6780
UGCCAGCGUU GAUGUCGAUA AAGAUGGAAA CUGGAGUUAU GAAUUUAAGG AUAAUGAAUU   6840
AUCUGAGGGC GAAAAUAGUA UAAAAGUCGU UGCUGUAGAU AAAGCAGGUA AUAAAAACGA   6900
AACGACGGAU AGUAUCAUAA CCGACACCAU UGCUCCAGAA AAGCCGACGA UUGAGCUGGA   6960
UGAUAGUAGU GAUUCCGGCA UUAAAAAUGA CAACAUUACA AAUAGCACCC UGCCAACAUU   7020
UAUUGGUGUG GCGGAACCCG GUUCUACAGU CUCUAUUUAU CUUGGACUUA AACAUCUUGG   7080
UGAGGUCAUU GUUGCUAAAG AUGGGACAUG GAGCUAUACG CUUACUACGC CGCUCAAGGA   7140
UGGCGAAUAC AAUAUAACAG CAACAGCUAC UGAUAUUGCC GGGCAUACCU CAGCGACGGC   7200
AAAUCUGCCU UUUACUAUUG AUACACGUAU CAGCUAUUUC AGCGCUGAGA UUGAAACGAC   7260
GAAUGAUAGC GGUAUUGUCG GAGAUAACGU UACUAACAAU ACUCGCCCAA CCUUUACAGG   7320
UAAAACUGAG CCAAAUGCUA UUAUCAGUGU CAUAAAUAGU GAGACUGGCG AAGAGGUUAU   7380
UUUUAAAGCG AAUGACAAGG GCGAAUGGAC GUUCAAUUUC ACUUCCGACU CAGUGGAAGG   7440
GAUUAACAAU CUUACGUUCA CUGUUGAAGA UGUCGCUGGC AACAAAAAGG AUUUUUCCUU   7500
UAGUUACGUU AUUGAUACUA UUGCCCCUGU ACCUCCGACG GCUUCUUUGG AGGAUUAUGU   7560
UGUUUUGCCG AAUGGUAUAA UUUUAUCAGG GAAUGAUUUA CCGGCUUUAG UCGGUACGGC   7620
AGAACCAAAG UCUACCAUCU UAUUGAUGCG AGAUGGUAAA UUAUAUGACA GCAUUGAAGU   7680
UGACUCAAAC GGGACCUGGA AAUUAUCAGU UUAGUAAUAA AUUCUUCAGG GCGCCUAUGA   7740
UAUUGAAAUC AUUCUCAGGA UGCCGCCGGC AAUAAAUCCU CUACUGUUAA AUAUUCUUUU   7800
ACUAUUCAAA CUGAAGUUGU ACCUCCAAAA GCGGAACUCG AUGCCAGUGA UGAUUCCGGU   7860
GCAAAAGGCG ACUGGAUUAC CAAUAAACAU AAUGCUCUGA CAUUACUGGG AACAGCGGAU   7920
AGGUUUGCUA CCGUAAAUAU CCUUAUUGAC GGUAAAACGA UAGGCGUGAC GACUGCGGAU   7980
GCAGACGGUA ACUGGAAUUU UGAUAUUUCC AGAAAUCUGU CUGACAAUGU UUAUAAGAUU   8040
ACGGUUGAAU CCAUCGAUCC UUUAGGAAGA ACGUCAUCUG UAGAUUAUCA GCUUACCAUU   8100
GAUAGCUUUA CGCCGAUCCC UACUGUUAUG UUGCAUGAUA GCGCUGACUC UGGCGUUAAA   8160
GGCGAUAUGA UUACUAAAAU UAAUACACCG UUGUUUACCG GGAUGGCUGA AGCUAAUGCU   8220
AAGGUUUCCA UCUAUGUUGA CGGUGUGUUA AGUGGUGAGG CUAUUGCUGG CGAUGAUGGU   8280
GUAUGGAAUU UUCAAUUUAC CACAGCGUUA UCCGAUGGCU CGCAUGACGU AACGGUAAAG   8340
GUAGAAGAUA UUGCCGGUAA UACUGCCUCC UCAUCAGCGU AUAAUUUCCA AAUCGUAACG   8400
CAAACGCAAA AACCAACAAU AGAGUUGGUC AACGAUACGG GGGUUGAUAA UACAGACCAU   8460
AUUAUUAAUG AAAAGAAUCC UGCACUGACA GGAACCGCUG CACCCUAUUC AACGGUUAAA   8520
CUCUAUAUUG AUGGUGCACU GAUCGCUGAG GUCAGAACAA AUAAAGAUGG CAGAUGGGAG   8580
UAUACCCUGA AAGCCGAUCA AGGUUUGGUU GAUGGCGAUC AUAGAAUAAC CGCUUCAGUU   8640
GAAGAUAUCG CUGGCAACAU UGCUCAUUCG GAUCCUUUCU UAAUUAGCGU CGAUACUGCU   8700
AUUUCAAUAC CGAUAGUUUC AUUGAGCCCG GAUUCAGAUU CGGGAAUUUC AGAUGAUAAU   8760
UUAACGAAUA UCGUUAAACC UACCUUGCAC CUAAAAGAUA UUGAUCCGGA CAUUAUCAGU   8820
GUUCAGGUAU GGGAUGCCAU GUCUGAUACG CAGAUCGGUG UUGCCACGCA ACAACCUGAU   8880
GGUUCAUGGG CCUAUACCUU UACUUCAGAU UUAACGGAAG GCUUGCAUCA GGUUUAUGUC   8940
AAGGUUGAGG ACAUUGCGGG UAAUAAAGCG AACAGCGCGA UAUUCGAUUU UACUAUCGAU   9000
ACCACAGUAU CAACGCCGGU GAUUUCCCUG CUUUCUAAGG AUGAUACGGG GGUUACAGGC   9060
```

-continued

```
GAUAACCUGA CCAAUAUCAA UAAGCCAGGU UUUGCUAUUU CCGGUGUUGA UGCCGAUGCG   9120
CAUCGGGUCG UCGUACAGGU GAUGCACAAU GGCGUGAGCG AAGAGAUCGA ACUUUCCCAC   9180
CUCAAUGGGA GUUGGUUAUU UAUACCAGGG GAAUACGUGG GCGGAUGGCA GCUACACGUU   9240
AACGGUGAAA GUAGAAGAUA AGGCAGGAAA UACCAACUAC UCGGCGCCGC UGACGGUCGU   9300
UAUCGAUACC CAAAUCGCCA UUGAUGGGGU GGAACUGGUC AACGAUAGCG GCGUGAAAGG   9360
CGAUAAUAUG ACCAACGACG ACCGUCCCCA CUUUCGUGUG ACGGUACCUA CGGAUGUCAA   9420
UGAAGUCCGU CUGAGCAUUG ACGGUGGUAA UUCGUGGGUU CAGGCAACUC CGGGCGUGGC   9480
AGGAAGCUGG GAGUAUAUCU GGCCGACAGA CCUGGCAGAU GGUCCUACAC GCUAACGGUG   9540
GAAGCGACUG AUAAAGCAGC AAUACAUGAC GAAGACCAUC GAUUUCGCGG UGGAUACCAC   9600
GCUGUCAGUG CCGGUCAUCG UACUGGAUAG CGCGGACGAC ACCGGCAUCC AGGGCGAUAA   9660
CAUGACGAAU AGCACCCAGC CGACAUUUGC CUUGCAGCAU AUUGAUGAUG AUGCCGUUCG   9720
CGUUACGGUC AGCGUGGAGC AUGGCGGCGU CACCACCACA UUUGACGCCA CGAAAGGCAC   9780
AGGCGGAUGG ACCUUUACGC CGCCGACAUC AUGGGCGGAU GGUGAUUAUA CCCUGAGUGU   9840
GUCAGUCGAA GAUAAAGCGG GGAACACCAG CCAUUCUGCA UCGCUGACGG UGACGGUGGA   9900
CACGCAAAUC GCCAUUAAUA ACAUUGAACU GGUCAAUGAC AGCGGUAUUC CCGACGAUAA   9960
UCUGACUAAU AAUGUGCGUC CGCACUUCCA GGUGACGGUA CCGACGGAUG UCAACGUGGU  10020
GCGCCUGAGC AUUGACGGCG GCAAGACGUG GUUCAACGCU ACCCAGAGCG CGACGCCAGG  10080
CGUCUGGGAU UAUAUCUGGC CGGAUGAUGU GGCCGACGGA GGCUAUACCC UGACGGUAGA  10140
AGCGACCGAU GAGGCAGGAA AUAAGGCAAC ACAGACCUCG AUUUCACCAU CGAUACCACU  10200
CUGUCUGUGC CGACCCUCUC GCUGGACAGC GCAGAUGACA GCGGCAUCGC GGGCGAUAAU  10260
AUCACCAAUG UUAAAACGCC GGGCUUUACC CUCAACAAUA UUGAUACCGA UGUCAGCCGG  10320
GUGAUAGUGG AGGUAAUGCA CAAUGGCAUU AAGCAGGAGG UGCCACUGGU UCAGACCGGC  10380
GGACAGUGGC GCUUUGCGCC GACCAGCGAC UGGGCGGACG GCGACUAUAU CCUGACGGUG  10440
AAGGUAGAAG AUAGGACCGG AAAUGUGAAG CAGUCCGCGC CGUUGACGGU GACAGUAGAC  10500
ACGCAUAUCG CCAUUGACCG UAUUGAACUG GUUAACGACA GCGGUAUCCC CGGCGAUAAU  10560
CUGACCAAUG AAGCGCGCCC GCACUUUCAG GUGACAGUAC CGGCGGAUGU UAACGGCGUA  10620
AGACUGAGCA UUGAUGGCGG CAAAACGUGG UUUGACGCCA CGCAGCAGCG CGACGUCGGG  10680
CGUCUGGGAU UACACCUGGC UGACGAAUGU GGCUAACGGC CCUCACACCC UGAUGGUGGA  10740
AGCGUCCGAC AAGGCGGGAA ACAAAACGAC GCAGAAACUG GACUUCACCA UCGAUACCAU  10800
UCUGUCAGAA CCGACGAUUA CCCUGGACAG CGCGGAUGAU AGCGCCGCUG GCGAUAACAU  10860
CACCAACGUU AAGAUGCCAG GCUUUACCCU CGGUAAUAUC GACGCCGACG UGACCAAAGU  10920
GGUGGUGACG GUGGCGCAUG AUGGUAAGAA CCAACAGAUA GAGUUGAUUA AGAACGGCGG  10980
UGUGUGGCGC UUUACGCCGG GCGCAGCCUG GACCGAUGGC GACUAUACGU UGACGGUAAA  11040
GGUAGAAGAU AAGGCGGGUA AUACAAAUUA UUCUGCGCCG CUGACGGUGA CUAUCGAUAC  11100
GCAAACGUCU AUUGAUCGCA UUGAGCUUCU UAAUGACACG GGUAUUGUCG GGGAUAACCU  11160
GACCAAUGAA GCACGUCCAC AGUUUCAUAU UACGGUACCG ACGGACGUGA ACUCUGUGCA  11220
ACUGAGUCUU GAUGGCGGCA UCAACUGGGU UAACGCAACG CUGACGUCUG ACGGCGUUUG  11280
GGAGUAUAUA UGGCCGACAG AUCUGGUCGA AAAUACGUAU ACCCUGACAG UGAAAGCAAC  11340
CGAUGUUGCA GGCAACACGG CGACGGAAAC GCUCAAUUUU ACCAUUGAUA CCACAUUGUC  11400
GACACCGACC AUCACGCUGG AUAGCGCAGA UGAUAGCGGC ACCGCCAACG AUAAUAAGAC  11460
```

```
UAACGUUAAA ACGCCGGGUU UUAUUAUCGG CGGUAUUGAU UCUGACGUGA CUCAGGUCGU  11520
CGUGCAGGUG AUGCGCGAUG GUCACAGCGA GGAGGUGGAG CUGACGCAGA CUAACGGGCA  11580
GUGGCGUUUU GUACCCGGCA GCGCGUGGAC UGAUGGCGAC UAUACGCUGA CGGUAACGGU  11640
GAAAGAUGAG GCGGGUAAUA UUCGCCACUC AGCGCCGUUG ACGGUCACCA UCGAUACGCA  11700
AAUCACCAUU GACCAUAUUG AACUGGUCAA UGACAGCGGU AUUCCGGACG AUAAUCUGAC  11760
UAAUAAUGUG CGUCCGCAAC UUCCAGGUGA CGGUACCGAC GGAUGUCAAC GUGGUGCGCC  11820
UGAGCAUUGA CGGCGGUAAG ACGUGGUUCA ACGUUACCCA GAGCGCGACG CCGGGCGUCU  11880
GGGAUUAUAC CUGGCUGGCU GAUGUGGGAG AGGGUAAGCA UACCCUGACA GUGGAGGCGA  11940
CCGACAAGGC GGGAAACAAA ACGACGCAGC AACUGGACUU CAUCAUCGAU ACCCUACUGU  12000
CAGAACCGAC UAUCGUGCUG GACAGCACGG ACGACAGCGG AACAAAAGGC GAUCACCUGA  12060
CCAACGUAAA UAAGCCGACG UUUUUACUGG GCAAUAUUGA CGCAGACGCG CGGUAUGUCA  12120
CGGUUGAGGU ACAGCAUGGC GGCACGAAAG AGGUGCUGAC GGCCACCAAA GACGCGACCG  12180
GCAACUGGAG CGUGACACCG ACCGGCACAU GGGCAGAUGG CGACUAUACG CUGACAGUGA  12240
GGGUGGAAGA UGAGGCGGGG AACGAAAAAC ACUCAGGUCG CUGACGGUCA CUGUUGAUAC  12300
CCAAAUCACC AUUGAUGUUA UUGAACUGGU UAAUGAUAAC GGUAUUCCCG GCGACAAUAU  12360
GACUAACGAC GCCCAUCCGC AGUUCCGCGU GACGGUACCG GGGGACGUUA ACGAAGUCAG  12420
UCUGAGCAUU GACGGUGGCG UGACCUGGGU UAAGGCGACA CAGAGCGCGA CGCCGGGCGU  12480
CUGGAAUUAU ACCUGGCCGG GCACCGUGCC GGAUGGCGAC UAUACGCUGA AUGUGAAAGC  12540
GACUGACAAU GCGGGUAAUA CGGUGACGGA GACACUCCAC UUCACUAUUG AUACUACGUU  12600
GUCGACGCCG GUGAUCGUAC UGGAUAGCGC GGACGACAGU GGUGUCCAUG GCGAUAACAU  12660
GACGAAUAGC ACCCAGCCGA CAUUUGCCCU GCAGCAUAUU GAUGAUGAUG CCGUUCGCGU  12720
UACGGUCAGC GUAGAGCAUG GCGGCGUCAC CACCACAUUU GACGCCACGA AAGACGCAGG  12780
CGGAUGGACC UUUACGCCGA CAGGGGCGUG GCGGAUGGU GAUUAUACCC UGAGUGUGUC  12840
AGUCGAAGAU AAAGCGGGGA ACACCAGCCA UUCUGCAUCG CUGACGGUGA CGGUGGACAC  12900
GCAAAUCGCC AUUAAUAACA UUGAACUGGU CAAUGACAGC GGUAUUCCCG ACGAUAAUCU  12960
GACUAAUAAU GUGCGUCCGC ACUUCCAGGU GACGGUACCG ACGGAUGUCA ACGUGGUGCG  13020
CCUGAGCAUU GACGGCGGCA AGACGUGGUU CAACGCUACC CAGAGCGCGA CGCCGGGCGU  13080
CUGGGAUUAU ACCUGGCUGG CUGAUGUGGG AGAGGGUAAG CAUACCCUGA CAGUGGGGGC  13140
GACCGACAAG GCGGGAAACA AAACGACGCA GCAACUGGAC UUCAUCAUCG AUACCCUACU  13200
GUCAGAACCG ACUAUCGUGC UGGACAACAC GGACUACAGC GGAAACAAAA GGCGAUCACC  13260
UGACCAACGU AAAUAAGCCG ACGUUUUUAC UGGGCAAUAU UGACGCAGAC GCGCGGUAUG  13320
UCACGGUUGA GGUGCAACAU GGCGGCACGA AAGAAGUGCU GACGGCCACC AAAGGCGCGA  13380
CCGGCAUCUG GAGCGUGACA CCGACCGGCA CAUGGGCAGA UGGCGACUAU ACGCUGACGG  13440
UGAGGGUGGA GGAUGAUGCG GGGAACGUAA AAUACUCAGC GCCGCUGACG GUCACGGUUG  13500
ACACCCAAAU CACCAUCGAU GUUAUUGAAC UGGUUAAUGA UAACGGUAUU CCCGGCGACA  13560
ACCUGACCAA UGACGUUCGU CCACACUUCC GCGUCACGGU GCCAGGGGAU GUCAACGAAG  13620
UACGUCUGAG UAUCGACGGC GGUAAUACGU GGGUUCGUGC AACACAGGGC ACGGCAGGGA  13680
UCUGGGAUUA CACCUGGCCG AAAGAUGUGA CCGACGGGCU ACAUACCCUG ACGGUAGAAG  13740
CGACCGAUAA GGCGGGAAAU AAGACGACGC AGACGCUCGA UUUUACCAUU GAUACCCGGC  13800
UGUCAACGCC UACCAUCGCU AUGGAUAGCA GGGACGAUAC AGGUGCCAUU GGCGAUCAUA  13860
```

```
UUACGAGCGU CAAAAGACCG GGCUUUACUA UUGGCAAUAU UGACGCCGAU GCGCACUCGG  13920
UCAUUUUGCG GAUCACACAG GGCGGCAAUA GCCAGGAAGU GACACUAACC CAGGUUGGAG  13980
GACAGUGGCG CUUUACGCCA GAUGCUGACU GGGCGGACGG UAGCUAUACG CUGACGGUAG  14040
AGGUAACGGA UAACGCAGGA AACGUUCGUC AGUCCACGCC GCUGGUGGUG ACGGUGGACA  14100
CGCAAACCAG CAUUACUGAU AUUACAUUGG UCAAUGAUCA UGGCGUGCCU GAUGACAAUC  14160
UAACUAAUAG CACCCGUCCG CAGUUUGAGA UCACGGUGCC GGCGGAUGUG AAUUCUGUGC  14220
AACUGAGCAU UGAUGGGGGC GCAAACUGGG UGAGCGCGAC GCAGGGUAUC GAAGGCGUCU  14280
GGGGCUAUAC CUGGCCAACG GAUAUGGGCG AUGGAAAACA CACCCUAACC GUCAUGGUCA  14340
CCGACAGAGC GGGCAAUACG GCGACGCAAA CGCUUGAAUU UUUCAUCGAC ACCCGGUUGU  14400
CGACGCCGAC CAUUGCGCUG GAUAGCACGG AUGAUACCGG UACGCCUGGC GAUGAUAUGA  14460
CCAAUCGCAC CCGACCGACC UUUAUUCUGC AGAAUAUCGA UUCGGAUGUU AUCAACGUUA  14520
CAGUCAGCGU CACGCAUAAU GGAACGACAA CCUCGUUUAC UGCGACACAG GGGGCUGGAG  14580
GAUGGAGCUU UACACCGCCA GCGCCGUGGG GCGACGGUGA UUAUACGCUG ACGGUGACAG  14640
UGGAGGAUCG GGCGGGAAAU ACGCGUCCGU CUACGCCGCU GACGGUGACA GUGGAUACGC  14700
AAAUAGCCAU UGAUCGUAUU GAAUUAGUCA ACGAUAGCGG CGUCCCUGGC GAUAAUGUGA  14760
CAAAACAUGU GCGUCCGCAG UUCCAGAUCU CGGUACCGGA UGAUGUGGAA AGUUCUUCU  14820
GAGUAUUGAC GGCGGCACGA CCUGGGUUAC UGCAAUCAAG AGUUCGACGG CUGGCAUUUG  14880
GGAUUACACC UGGCCGACGG AUAUGCCAGA GGGACAGCAU ACCCUGACCG UGGAAGUGAC  14940
UGACGGUGCG GGUAAUAAGA UGACGGAGAC GCUCAAUUUC ACUAUCGAUA UCACGUUGUU  15000
AACGCCAACC AUUGAGCUAG CGCCCGAUCA GGAUACCGGA CAGAAUAAGA ACGAUAAUCU  15060
GACCAGCGUC ACUCAGCCGG UAUUUGUGUU GGGGAGUAUC GAUAAAGAUG UUCGACACGU  15120
GGAAUUGAGU AUUGAGCAUA ACGGCACGUU UAAAACGGUG GUACUCACCG AAUCAGCCGA  15180
CGGCUGGCGC UAUCGACCGG AUUCUGCUUU GGCGGACGGU AGCUACACAU UCACCGUGAC  15240
GGUAACAGAU GUGGCAGGCA ACCAGCAAAC AUCCGCGCCU UUAAAGGUGA CGAUAGACGG  15300
UACGUUGACU ACGCCGGUGA UUGAACUGGC AGCUGGCGAA GAUAGCGGUA CUGUUGGCGA  15360
UCGCCUCACC AAUCACGAUC GGCCUGUGUU CGACAUACAU CAGGUUGAUU CUGACGUUAC  15420
GCGCGUGAUG GUCAAAGUAA CUUACAACGG UAAAACGCAC GAAGAAGCGG CGGUAUUCAC  15480
CAAUGGUCAA UGGCGCUUUA CGCCUUCUGC GA                                15512
```

(2) INFORMATION FOR SEQ ID NO:64:

(i) SEQUENCE CHARACTERISTICS:
(A) LENGTH: 8967 bases
(B) TYPE: nucleotide
(C) STRANDEDNESS: single stranded
(D) TOPOLOGY: linear (xi) SEQUENCE DESCRIPTION: SEQ ID NO:64:

```
CUGGAUGGUG GCGCUAACUG GAAUGUGAUA CGCAAAAAUG CCGACGGACA GUGGAUUUUU     60
GACAGCCCGA AUACUCUGGU UGACGGCACA UAUACCCUUC GCGUAGAGGC CACGGGAUGA    120
GGCAGGUAAU AUUGCGAAUA AAGAUUUAGU AUUUAAUAUC GAUACUAAUA UACAGGUUCC    180
UACUAUUGCU UUAGACGCAG GACAAGAUAC CGGAGCGAAU ACCGCCGAUA AUAUUACUAA    240
UAUUUCACGA CCCACCUUUA CGAUUGGUAA UGUUGACCCC GAUGUUAUCA AAGUCGUGGU    300
GACGAUUGAU GGUCAUGAUU AUAACGCGAC UAAGGUUGGG GCUGGUUGGC AAUUUACACC    360
AGGCAAUGCC AUUCCGGAUG GCUCUUAUAA UAUUACCGUU ACGGUUGAAG AUAAGGCCGG    420
```

```
AAAUACCGCG ACAUCGAAAC CAUUACCUGU UGUGAUAGAU ACGACGGCUG AAAUUGAAAG    480
CGUCACGUUG GUUACAGAUA GCGGUGAUAG CGAUGUAGAU AACAUUACCA AAGUCGACAG    540
CCGCAGUUUA GUAUUGUUAC CGCUGAUGAU AUAACCCAUG UGCGCGUUAA AAUCGAUAAC    600
GCCGCUAAUU GGAUUGAACU CACAAAAGGA GGGAUGGCCG CUGGAUAUUU AAUGUCGGUU    660
CGGCAUUACC UGAUGGGCAA CACACUCUCU UGGUUGAUGU GACUGAUAUC GCCGGCAACG    720
UUGCGCAAGA AACGCUGCAG UUUACGAUUG AUACGACUCU GCGAGAGCCG ACAAUUGUAC    780
UCGAUCCCAC CCAUGAUACU GGUGAUGAUA CUAAUGAUAA UCUUACCAGG AUUAACAAAC    840
CGGUGUUUAU UAUCGGUAAU GUCGAUAAUG AUGUAUCACA CAUUGUGGUU CAUAUUGAUG    900
GUCGGGAUUA CACCAUUGAA AACACAGGGG GGAAUUUAAC CUUUACGCCG GAUCAACCGC    960
UGUCUGACGG UCAGCAUACG AUCUCUGUUA CCGUAACGGA UAUUGCUGGU AAUACCAAAA   1020
CAUCGGCCGA ACUGCGGAUU GAAAUCGACA CGCAGGUUCA GAUUGACAGU GUUACGUUAA   1080
CAACAGAUAG CGGCGUCAAC GAUCACGAUA AUGUCACCAA UGCUACCCGU CCCUCUUUUG   1140
AAAUUGCAAC GCCUGAUGAU GUGACAUCGG UGCUGGUUUC UUUCGAUGGC GUAAACUGGA   1200
CGCCCAUCAG UAAAAAUGCG GCCGGGCAGU GGGAAUUUAC UGCAGGUAGC GCAUUGCCUG   1260
AUGGUCAUUA UACUCUCCAU GUCCAGGCGA CGGAUCGGGC AGGGAAUACG GCAAAUUCCA   1320
CGCUGGGCUU CACCGUGGAU ACGCAGAUUG ACGGCCUGAG CGUCGUGAUG CUGGACGACG   1380
CCGGAAAGGA UUCUACGGAU GGUAUUACGA AUAUUACCUC UCCACGUUUU GAAAUUUCAG   1440
CCAGAGAACC GCUGCAGAGC GUGACGGUAA UUUUAAACGG GAAAUCCAGC ACACUGACUC   1500
AGGGGGCAGG UAAUAAAUGG CUGUUUACCC CUGAUACACC GUUAGUGGAU GGAACUUACA   1560
AAAUAGAAAU AGUGGCUGAA GAUAUCGCAG GUAAUAAAAU UAGCAAAGAG GUAUCAUUCA   1620
CAAUAGACAC UAUUGUUUCU GAUCCCAGUA UUGAUUUGCU GGAUGCGGAU GAUACUGGCG   1680
AAAGCGCUGU UGAUAAUAUU ACGAGUGUCA CUACACCACG UUUCGUUAUU GGCAAUGUAC   1740
CCGCCGAUAU UGAUACUGUU GUUAUCAGAA UUAACGGCGU UUCUUAUCCG GUUACGGCAA   1800
AUGGCAAUAA CCUCUGGGAA UUUCAGGUUC CCGUUGCGUU AAACGAUGGC GUAUAUGAAG   1860
CCGUUGUUGU CUUCAGAGAU AUUGCCGGAA AUAUUUCUGA AAUUAAGCUG CCCUUUACCA   1920
UUGAUACCAC GACAAGCGUC AGUGUCAGAA UGGAGCUAGC GUCUGAUACC GGAAAUUCCA   1980
AUAGCGAUAA CCUUACGAAU AAGCAAAAUC CCAAAUUCGA AGGUACUGCA GAGCCCAAUG   2040
CGAAACUGGU GAUUACCAUU GUUGACGAUA AGUCAGGUCA GGAGGUUUUA AAACAAACGA   2100
UUACGGUUGG CGCUGAUGGC AACUGGAGUG UGACGCCGAA UAUACUGCCG GAUGGCAUGU   2160
AUACCAUCAA CGUCGUCGCA ACAGAUGUCG CGGGAAAUAC UGCGCAAACG CAGGAAAGAU   2220
UCACUAUCGA UACGGUUACG AUCGAUCCCA CCAUUCGCCU UUCGGAUCCA UCUAUUGAUG   2280
AUCAGCAUGA AGCAACCAGC CUGCGUCCUG AGUUCAAAGG GUUUGCCGAA GCGUUCUCGA   2340
CGAUUAUGAU UCAGUGGGAU GGGAAAGUGG UCGGCUCGGC AAACGCCAAU GCGAAUGGCG   2400
AAUGGAGUUG GACGCCGCCA UCAGUAUUAG CGCCAGGCUC CUAUGUUGUG AGCAUUGUUG   2460
CCAAAGAUAA AGCGGGUAAU GAUUCGUCGC AGGUCGACUU UCCUGUCGUA AUACCUGUUA   2520
UUGAUGUCAC GCCUCCAACC AUAAAGCUCA GCGAGGAGAG CGAUAGUGGC GCCUUAGGAG   2580
ACUUUACCAC GAAUAAUAAA ACGCCGACCC UGAUUGGGAG CACGUUACCU AAUACGAUUG   2640
UGAGUAUUUA UGUGGAUGGC GUGAAGGUCG GCGAGGCGAC AGCGGAUACA GCGGGUCGAU   2700
AUACUUUCCA GUUAUCGGAA AUGAAAGAUG GCCAUUAUGU CGUCCAGGUG GGUAUCGUCA   2760
ACCCUCGCGA UAAUAGCGAA CUGCGUUCUA CCGCCGUUGA UGUCACUAUC GAUACCGAGG   2820
```

```
UUGCUGAACU GGUAUGGAAU AUAUCUGGAA UGCAUGAGGG CGGAUAUAUC AAUACGGUGA   2880
CGCCGGAGAU UGGCGGCACC AGUGAGCCAA ACAGCAAAAU CACUAUCUUU GUGAAUGGCG   2940
UUGGAAAAGC GAUUGCUUAU ACGACAGGCG CAGGACACUG GGCGUAGUA UUACCCGCUU    3000
UGGGUAAUGA CGGUAAUUAU GAAUUAACGU UUAAAGUUGA AGACGUUGCC GGUAAUAUCA   3060
GAGAGUUUGG UCCGCAGAAU GUAAUACUGG AUACAGUAAU UUCGCCGUUA ACCGUGGUAU   3120
UACGCGAAGC UGAUGACAGU GGCAAAGUUG GCGACUGGAU CACCAAUAAA UCUCAUGUCA   3180
CCAUCGAUGG UACUGCCGAA GCCGGAAGUA CUUUAACCAU CAGGAAUCCG CAGGGAGUGG   3240
UUAUUGCUAC CCUGGUGGUA GGCAAUGAUG GUCGAUGGAG CGCAGAAUUA GAUCUGCGUG   3300
AAGGUAGUAA UGCCUUUGUC GUGGUAUCGG AAGAUAAAGC GGGCAACAGU CAACAAAAAG   3360
AGAUUCUGAU AGAACAUGAU ACGCAGAUUG AAAUCAGCGA UAUUUCAUUA AGUCGGGAUA   3420
CUAAUAGCGG UGAUAAAUAU GAUCUGAUUA CCAAUAAUAA GUCUCCGGUA CUGGUUGCCA   3480
GGACCGAUCC CGGCGCGACG GUACAGGUUU AUAUUAAUGG UGUGUUACAA GGCACAGUAG   3540
AGGCGAGUUC GUCAGGUAAU AUUAGCUAUA CCAUGCCGGC AAAUAGCGCC GACGGCGAGU   3600
AUCAGGUGCA AUUUGUUGCU ACGGAUACUG CUGGUAACCG GGUUGAGUCU GCGAUUACAA   3660
CCGUGACAAU CGAUUCUCAA AUUGCUGUCU UUGAUAUUGA UGAAGAUUCA UUACCGGCCC   3720
UCUCUAAUAA CCGAGCGUUG UCAGUCUCAG GUGUCGGGGA GGCUGGUUCU CAGGUCAGCA   3780
UCUUUGUCGA CGGUAAAUUA GUCAACGUUG UUAUGGUUGA GGCUGAUGGC ACAUGGCGCG   3840
CGCCGAUACU GCUGCAAGAU GAUGGUACGU UUAAUAUUCA UUUCAGCAUU ACUGACGUUG   3900
CUGGCAACAC UGAAGUGAGC AAGGAUUAUA GCGUGGAUGU CGAUUCAUCA ACCGACUUCC   3960
CAACGCUCAA CCUUGAAGAU GCAAGCAACU CUGGUUCACU UGACGAUCUG AUUACUAAUC   4020
ACAACAAGCC UGUAUUAGUU GGCACCGCAG AAGCGGGAGC CACAAUCCAU AUUUAUGUGG   4080
AUGAAAAGAU CGUGGCAAAU GUUCUUGUGC UUGAAGAUGG AACCUGGUCC UAUCAGUUUG   4140
AUAAUGCGUU AAAAGAUGGU GAAUAUUCUA UCCGUGUGGU UGCCGAAGAC CCGGCAGGUA   4200
AUACGGCAGA AUCGCCUCGC UUACUCGUCA CGAUAGAUAC CAGUACGUUU AUCGAUAAUC   4260
CUGCUAUGGU GGCAGGUUCU GAUAAUGGUA UUUUCAGUAA UGAUAGUAUA ACGAGUCAGA   4320
CCCGGCCUAC GUUUAGUAUU UUUGGAGAAA UGAACCAGAG UGUUCAGAUU UUCAUUGAUG   4380
GAGUGCUAGU CGAUACGAUC ACGGUGACCG ACAGAAAUCA AGUUUAUCGA CCUGAGUCAC   4440
CGUUGGGCGA UGGUUCCCAU AGCAUUUAUU AUGUUAUCAC CGAUAAAGCA GGCAACACGG   4500
CUACCUCGAA AACGCUAAAC UUUACUAUCG AUACCUUUAA UACGACGCCU GUCGCCAUUG   4560
AUUCUAUCGG UGGACAAACG UUAGCAGAGA UGACCGGUAG UGAUGGCAAA AUAUAUAUAA   4620
CGGACACGAC GCGUAACUUA UUGUUUAGUG GCAGUGCCGA GCCCAAUAGC AAAAUAGAAA   4680
UCAUCAUUAA UGGCUUAAAU GUGGGGGAAG UUUGGGUUAA UGAAAAAGGC CACUGGCAGA   4740
UGCCGGUGAA CCCGCUUUAU UUCACAGAAG GCCAACUGGA UAUCACUGUU AAAUCUACGG   4800
ACCGUGCUGG UAACGUAAAU CAGGAAAAGU AUUCCAUUUG GGUUGAUACG CAUAUCAAGG   4860
UAUUUACCAG CGAGCUUGAU GACAAUAAAU CAUCAUCGAA AACGGAAUGG UGGAGUAAUA   4920
GCGAUCUCAU UACCAUGCGA GGCACGGGUG AAAUUGGCGC UACGGUAUCA UUAAUCGUGG   4980
CUGGCGUCAC GCUGGCAACU GCUGUUGUGG CGGCAACAGG ACGAUGGGAA UUAUCAACAG   5040
ACAAGCUUCC AGAAGGGACU UACGAUAUUA GUUUGGUCAU UGAAGAUAGC CCGGAAAUCG   5100
UUGGGAAGAU GUGCGUGAAA UAUUUAUUGA CCGAACCCGC CAAAUGCUCC GGUCGUAACG   5160
UAUUCAGAUA UUGUCAACGA UCUAAUUAUU AUGCAGGGGA CGGCGGAAGC CAAAUCUCAG   5220
```

```
CUAAUAAUAA CCGAUAGUGA GGGGAAUACU UAUACGUUAA CCGUUCCUGA UAAUGGUAAA   5280
UGGAGUAUGG CUAUCCCGUA UCCAUCAGAA GGGAAGUUUA CCAUUACGAG UGUGGAUGCU   5340
AUUGGUAACC GGAGUGAUGA UGUCCCUCUC GAUAUCAUGA AAGAGGUUCC CGUUAUUUCA   5400
UUAUCUCCAG ACUCAGACAG UGGUACGGUG GGCGAUAAUA UUACGCGAGA UAAGCAACCU   5460
ACCUUUAUUA UCGGGAAUCU GGAAAGCGAU GUUGUGGUCG UUCAGGUCGA UAUCAAUGGG   5520
ACCGUAUAUA AUGCUGAAAA AAAUGCCGAU GGCGUUUGGU UCUUUACGCC AGGUACACCG   5580
UUAGCUGAUG GUUCCUAUAC GAUAUCGGUA AUCGCAAGCG AUGCCGCGGG UAAUCAGAAA   5640
AACUCGUUAC CCAUUACUGU CACGAUCGAC AGCACGCUGA CGGUGCCGGA GAUUGCGUUG   5700
GCAGCAGGUG AAGACAAUGG CGCUUCAGAC AGCGAUAACG UGACGAAUCA CACCCAGCCU   5760
AAGUUCACGC UGCAGCAUAU UGAUGCUGAU GUGACCGGGG UGACCGUAAA CGUGACGCAU   5820
AAUGGCGUGA CAGACAUCUA UCAGGCGACG CAAGGCGCGG AUGGCUGGAC CUUCACGCCG   5880
CCAGCCGCCU GGAAUGACGG UAACUACACG CUGAGCGUGA CGGUGGUGGA UCGCGCGGGG   5940
AAUUCACAGC AAUCUGCUUC GCUAGCGGUG ACGGUUGACU CAACGGUGAC GGUAACAGCG   6000
GAUAGCCAGC AUGACGAUGC GAGCGAUGAC GCCACGGCAA CAGCGGUUAC UCCACCGGAG   6060
UCUGAAACAG UGAAUGCCGA AAGCGCUACG CAUCUUCGUA CAGAGCCGUC UGCGGCGGAA   6120
GAAAGCGUGG UGAAGGUGAC AGCCUAUAGU AUUACAUUGU UAAACGCUGA CUCUGGGGAU   6180
GAAAUAGAUC GUUCAAUUAG UCAGACACCU UCUUUUGAAA UAUCAGUACC UGAGAAUAUU   6240
GUUAAUGUCA GUAUUAUGUU UGAAGGAGAA GAGUUUACUC UGCCGAUAAC UAACCAGAAA   6300
GCAAUAUUCG AAGUUCCGCU AUCUUUGGAA GAUGGUGAAU AUACUAUGGA CGUGAAAUUC   6360
AUUGAUAAAG ACAAUGAUUU CCUGAUUAAG GAGAAAACAU UCUCAGUCGA UCACUCCUCG   6420
GCGGAUAUUG UGAACGCAAU GAAUGUAAGA GGAAAGACCG AGGAUGAUAU UAAUGAUUCC   6480
CCUUCCACGA GUUCUGUAGG GCACAACAAU AACGGCGCUA UUGAUGUUUU CGCCGUUAAU   6540
GAAGUUACGC UACCUGUAGA UAAUCAAGAA GAACACGCAU AAUAACGGAG GCCCCUCACC   6600
UUUGGGUUGA AGGGGGUUUA CUUAUGGAUA AAAAACUAGA ACCUUAUUAU UUAAGUGCGG   6660
AAACGGCAUU AUCUAUAGUG UCUACAAAAU UCAACAUAAA AAUUGACAUC CGAGAAGAUG   6720
AUAUACAUUU GAAGAUUUAG AAAGUACGAC UGAAAUAACA CUGACGACCU AUACGAAUGA   6780
AGAAUUUCUU UUUGUCGUUA GGGCUUUCUC UACAGGAUAU AUUAUUUAAU AAUGGUGAGG   6840
AUUUACUAAA UGAGCCUAUG CCGAUUUUAC UAUUAACACC AGAAAAUGAA AGUGGAUGGU   6900
GUGUGUGAGU GGCGGGCAAA AAAUAAAGUU GGUAAACGCG CGCGGUGAAC UCUGUUAUGU   6960
UGAAAUUGAA GAUGAAUAUU UAAAAGAGUU AUCUGCAUUU AGUAUACUAC CUUUAAAUAA   7020
AGUUGUUGAU AGUAUAAGAG UAAAAAAUAU CAUAAAAAAC UCUUUAUCGA UGAACAAGAU   7080
UUUUUAUACU AAAUACUUUU UUUCAUCUCU UUUUAUGGCA AUUUUUGCGU UAACUAUCCC   7140
AGUAUUUAGU AAUCUGUUCU AUGAUAAGCU UGUUCCAAGC GCUUCGGUUU CAUCUUUAUU   7200
UGGCGUGGCU AUAAUUGUUG CUGUAUUUAU UGUUUUUGAG UUUAUCCUUC GUACUUCGAA   7260
AGAUAUUUAU CAGUCUAUCA CAGCAAGGCA GGAUGACGUC GAUAUUGAUA UCGCAUUUCU   7320
UGAAGCGGUA CUUUAUAGUA AAAAGAAAAA UGGCAGAUCC AUGUCAUCAG CAUUUGUGCU   7380
AUGGAAUGAG UUUCAGAAAA UUAAACCCGU UUUAUUAAAC UCGAUCUUUC AACGUAUAGC   7440
CGAUAUUCCA AUAUUUAUUA UAUUUCUCAU UGUUAUAUAU GUAAAUUUAG GUCUGGUUGU   7500
UAUUGUACCU AUUACCAUGU UUAUCGUCUC UAUUAUUAUU UCCCUCGUUA ACCACCAUUA   7560
UACUAAUGAG UUAAUGAACA AACAAAAAGA AGGACAGAAG AACAGGAAUA UUUUUAUCUC   7620
```

```
AGAAGUUUUC UUAUCUAUUA AAAUGAUCCA UACCUUAAAU AAUCAAGGUU UACUUUUUGA   7680

UUGGGUUAAU ACAUCAAAUG AACAGUCGUA UCUUAACCUG AAGAUAAGGA AAUUAAAUCU   7740

UAUCUAUCAA UCUAUAUUGG GGAGUAUGUC AUCUAUUACC CAAAUAACUA UUAUGGUAAU   7800

AGCCUUUUUU AUGGUAAUCA AGGGUGAUGU UACUACUGGC GCAAUUGUUU CAUCUGUCAU   7860

UGUCUCUGGC CGUAUUUCCG GGAUCAUUUC GAAUUUUUCU UCUACAUUAA UCUCUAUUUU   7920

AUCAGCAGAA AAAACCGGUA AGGAUCUGCU UUCUUUUUUU GAUGAAGAUC AGGCAGAAAA   7980

AACACCGGCA UUACAGUCAA UAUCAAAGUG CAAUGGCGAU AUCUCUAUCC GGGGCGUGAG   8040

UUAUCAGUAU GAUGCUCAAU CUCCGAUGAU UAUUAACCGA CUGUCUAUAG ACAUACCUGC   8100

GGGGCAACGU GUCGCGGUGG UAGGCGAAUG CGGAGCAGGA AAAGCUCAU UACUGGGAAU   8160

GCUAUCUGGC UACCUUUCGC CAACAGACGG UGCCAUUUUA UAUGAUGGAU AUAACUUAGG   8220

ACAUUUAUCG CAGAACUUUU UUUCUCAGCA UUUAAGCGUG GUGACGACAC AUGAUGUUUU   8280

AUUCACCGGA ACCAUUGAAA GUAAUUUCGC GUUAAAACCG CAAAACGACA GGGGCCGGGU   8340

ACUCAAGGCG CUUCAGCUGG CGAACUGUGG UUUUAUCUUG CAACAUCCUA UGGGGCUGAA   8400

GUUUCCGGUG AAUUUUAUGG CUAAAAACCU GUCAUCCGGA CAGCAGCAGC AGUUAUUAUU   8460

AGCACGUAGU CUGAGUAGUG ACGCCAGCGU CUUUUUAUGG GAUGAACCAA CAUCAAAUCU   8520

GGAUGAGAAU ACCGAGAAGC AAAUUUUUGA UAACUUAGAU GAGUUUAUUC AUGGGAAAAC   8580

GUUGAUCAUG GUGACGCAUC GUCGAUAUCU GAUAAAGUAU UUUGACCGGG UCCUGGUAAU   8640

GAAAGGUGGA AAAAUAAUCC GUGAUUGUUC UCCGGAUAAA UUAUUAAUGU AAAAUAAGCA   8700

GCGCUUGUCG CUGUUAUCAG GUGGUACUGC UUAAUAAAAA AGACCCGUUG CACAAACGGG   8760

UCUUUUUUGU CAUUUAACGG AGUCGGCAAC GUCUUCAAUA AGUUUAGCUC GAUUCUGUUA   8820

GGGCUAUUCC ACUUGCCAUU UUUGGAUAAC CACACCUGGC GGCCUUCAUC AACGGCAAUG   8880

CGAGGGACGU GAUGGUGCGC AAGGCUAACC CCUGGCGCGC GAUUCCGCGU UGAGAUAACC   8940

GGUGGGCGGC UUCAGCGGCA GCGAUAG                                       8967
```

(2) INFORMATION FOR SEQ ID NO:65:

(i) SEQUENCE CHARACTERISTICS:
(A) LENGTH: 222 bases
(B) TYPE: nucleotide
(C) STRANDEDNESS: single stranded
(D) TOPOLOGY: linear (xi) SEQUENCE DESCRIPTION: SEQ ID NO:65:

```
GGUUACACGU ACCUGGACGA CAUCACCGGG AACGUCAAUU CUGAAUGACG GUUUGGCAAC     60

AUUCGUUAAU UGAUCAUUCU GCACGCCGGU AUCAUUAAGC AAUACGAUAU UGUUAAUGGU    120

UGUCGUGGUA UCAAUACGCA CCUCAAACGG CGCAGACUCU UUUACAUUCC CCGCCAGAUC    180

UUCCACCACA ACGGCUAACU GAUAUGAGCC AUCAGCCCAG CU                       222
```

(2) INFORMATION FOR SEQ ID NO:66:

(i) SEQUENCE CHARACTERISTICS:
(A) LENGTH: 15512 bases
(B) TYPE: nucleotide
(C) STRANDEDNESS: single stranded
(D) TOPOLOGY: linear (xi) SEQUENCE DESCRIPTION: SEQ ID NO:66:

```
UCGCAGAAGG CGUAAAGCGC CAUUGACCAU UGGUGAAUAC CGCCGCUUCU UCGUGCGUUU     60

UACCGUUGUA AGUUACUUUG ACCAUCACGC GCGUAACGUC AGAAUCAACC UGAUGUAUGU    120
```

```
CGAACACAGG CCGAUCGUGA UUGGUGAGGC GAUCGCCAAC AGUACCGCUA UCUUCGCCAG    180
CUGCCAGUUC AAUCACCGGC GUAGUCAACG UACCGUCUAU CGUCACCUUU AAAGGCGCGG    240
AUGUUUGCUG GUUGCCUGCC ACAUCUGUUA CCGUCACGGU GAAUGUGUAG CUACCGUCCG    300
CCAAAGCAGA AUCCGGUCGA UAGCGCCAGC CGUCGGCUGA UUCGGUGAGU ACCACCGUUU    360
UAAACGUGCC GUUAUGCUCA AUACUCAAUU CCACGUGUCG AACAUCUUUA UCGAUACUCC    420
CCAACACAAA UACCGGCUGA GUGACGCUGG UCAGAUUAUC GUUCUUAUUC UGUCCGGUAU    480
CCUGAUCGGG CGCUAGCUCA AUGGUUGGCG UUAACAACGU GAUAUCGAUA GUGAAAUUGA    540
GCGUCUCCGU CAUCUUAUUA CCCGCACCGU CAGUCACUUC CACGGUCAGG GUAUGCUGUC    600
CCUCUGGCAU AUCCGUCGGC CAGGUGUAAU CCCAAAUGCC AGCCGUCGAA CUCUUGAUUG    660
CAGUAACCCA GGUCGUGCCG CCGUCAAUAC UCAGAAGAAC UUUUCCACAU CAUCCGGUAC    720
CGAGAUCUGG AACUGCGGAC GCACAUGUUU UGUCACAUUA UCGCCAGGGA CGCCGCUAUC    780
GUUGACUAAU UCAAUACGAU CAAUGGCUAU UUGCGUAUCC ACUGUCACCG UCAGCGGCGU    840
AGACGGACGC GUAUUUCCCG CCCGAUCCUC CACUGUCACC GUCAGCGUAU AAUCACCGUC    900
GCCCCACGGC GCUGGCGGUG UAAAGCUCCA UCCUCCAGCC CCCUGUGUCG CAGUAAACGA    960
GGUUGUCGUU CCAUUAUGCG UGACGCUGAC UGUAACGUUG AUAACAUCCG AAUCGAUAUU   1020
CUGCAGAAUA AAGGUCGGUC GGGUGCGAUU GGUCAUAUCA UCGCCAGGCG UACCGGUAUC   1080
AUCCGUGCUA UCCAGCGCAA UGGUCGGCGU CGACAACCGG GUGUCGAUGA AAAAUUCAAG   1140
CGUUUGCGUC GCCGUAUUGC CCGCUCUGUC GGUGACCAUG ACGGUUAGGG UGUGUUUUCC   1200
AUCGCCCAUA UCCGUUGGCC AGGUAUAGCC CCAGACGCCU UCGAUACCCU GCGUCGCGCU   1260
CACCCAGUUU GCGCCCCCAU CAAUGCUCAG UUGCACAGAA UUCACAUCCG CCGGCACCGU   1320
GAUCUCAAAC UGCGGACGGG UGCUAUUAGU UAGAUUGUCA UCAGGCACGC CAUGAUCAUU   1380
GACCAAUGUA AUAUCAGUAA UGCUGGUUUG CGUGUCCACC GUCACCACCA GCGGCGUGGA   1440
CUGACGAACG UUUCCUGCGU UAUCCGUUAC CUCUACCGUC AGCGUAUAGC UACCGUCCGC   1500
CCAGUCAGCA UCUGGCGUAA AGCGCCACUG UCCUCCAACC UGGGUUAGUG UCACUUCCUG   1560
GCUAUUGCCG CCCUGUGUGA UCCGCAAAAU GACCGAGUGC GCAUCGGCGU CAAUAUUGCC   1620
AAUAGUAAAG CCCGGUCUUU UGACGCUCGU AAUAUGAUCG CCAAUGGCAC CUGUAUCGUC   1680
CCUGCUAUCC AUAGCGAUGG UAGGCGUUGA CAGCCGGGUA UCAAUGGUAA AAUCGAGCGU   1740
CUGCGUCGUC UUAUUUCCCG CCUUAUCGGU CGCUUCUACC GUCAGGGUAU GUAGCCCGUC   1800
GGUCACAUCU UUCGGCCAGG UGUAAUCCCA GAUCCCUGCC GUGCCCUGUG UUGCACGAAC   1860
CCACGUAUUA CCGCCGUCGA UACUCAGACG UACUUCGUUG ACAUCCCCUG GCACCGUGAC   1920
GCGGAAGUGU GGACGAACGU CAUUGGUCAG GUUGUCGCCG GGAAUACCGU UAUCAUUAAC   1980
CAGUUCAAUA ACAUCGAUGG UGAUUUGGGU GUCAACCGUG ACCGUCAGCG GCGCUGAGUA   2040
UUUUACGUUC CCCGCAUCAU CCUCCACCCU CACCGUCAGC GUAUAGUCGC CAUCUGCCCA   2100
UGUGCCGGUC GGUGUCACGC UCCAGAUGCC GGUCGCGCCU UUGGUGGCCG UCAGCACUUC   2160
UUUCGUGCCG CCAUGUUGCA CCUCAACCGU GACAUACCGC GCGUCUGCGU CAAUAUUGCC   2220
CAGUAAAAAC GUCGGCUUAU UUACGUUGGU CAGGUGAUCG CCUUUUGUUU CCGCUGUAGU   2280
CCGUGUUGUC CAGCACGAUA GUCGGUUCUG ACAGUAGGGU AUCGAUGAUG AAGUCCAGUU   2340
GCUGCGUCGU UUUGUUUCCC GCCUUGUCGG UCGCCCCCAC UGUCAGGGUA UGCUUACCCU   2400
CUCCCACAUC AGCCAGCCAG GUAUAAUCCC AGACGCCCGG CGUCGCGCUC UGGGUAGCGU   2460
UGAACCACGU CUUGCCGCCG UCAAUGCUCA GGCGCACCAC GUUGACAUCC GUCGGUACCG   2520
```

-continued

```
UCACCUGGAA GUGCGGACGC ACAUUAUUAG UCAGAUUAUC GUCGGGAAUA CCGCUGUCAU   2580
UGACCAGUUC AAUGUUAUUA AUGGCGAUUU GCGUGUCCAC CGUCACCGUC AGCGAUGCAG   2640
AAUGGCUGGU GUUCCCCGCU UUAUCUUCGA CUGACACACU CAGGGUAUAA UCACCAUCCG   2700
CCCACGCCCC UGUCGGCGUA AAGGUCCAUC CGCCUGCGUC UUUCGUGGCG UCAAAUGUGG   2760
UGGUGACGCC GCCAUGCUCU ACGCUGACCG UAACGCGAAC GGCAUCAUCA UCAAUAUGCU   2820
GCAGGGCAAA UGUCGGCUGG GUGCUAUUCG UCAUGUUAUC GCCAUGGACA CCACUGUCGU   2880
CCGCGCUAUC CAGUACGAUC ACCGGCGUCG ACAACGUAGU AUCAAUAGUG AAGUGGAGUG   2940
UCUCCGUCAC CGUAUUACCC GCAUUGUCAG UCGCUUUCAC AUUCAGCGUA UAGUCGCCAU   3000
CCGGCACGGU GCCCGGCCAG GUAUAAUUCC AGACGCCCGG CGUCGCGCUC UGUGUCGCCU   3060
UAACCCAGGU CACGCCACCG UCAAUGCUCA GACUGACUUC GUUAACGUCC CCCGGUACCG   3120
UCACGCGGAA CUGCGGAUGG GCGUCGUUAG UCAUAUUGUC GCCGGGAAUA CCGUUAUCAU   3180
UAACCAGUUC AAUAACAUCA AUGGUGAUUU GGGUAUCAAC AGUGACCGUC AGCGACCUGA   3240
GUGUUUUUCG UUCCCCGCCU CAUCUUCCAC CCUCACUGUC AGCGUAUAGU CGCCAUCUGC   3300
CCAUGUGCCG GUCGGUGUCA CGCUCCAGUU GCCGGUCGCG UCUUUGGUGG CCGUCAGCAC   3360
CUCUUUCGUG CCGCCAUGCU GUACCUCAAC CGUGACAUAC CGCGCGUCUG CGUCAAUAUU   3420
GCCCAGUAAA AACGUCGGCU UAUUUACGUU GGUCAGGUGA UCGCCUUUUG UUCCGCUGUC   3480
GUCCGUGCUG UCCAGCACGA UAGUCGGUUC UGACAGUAGG GUAUCGAUGA UGAAGUCCAG   3540
UUGCUGCGUC GUUUUGUUUC CCGCCUUGUC GGUCGCCUCC ACUGUCAGGG UAUGCUUACC   3600
CUCUCCCACA UCAGCCAGCC AGGUAUAAUC CCAGACGCCC GGCGUCGCGC UCUGGGUAAC   3660
GUUGAACCAC GUCUUACCGC CGUCAAUGCU CAGGCGCACC ACGUUGACAU CCGUCGGUAC   3720
CGUCACCUGG AAGUUGCGGA CGCACAUUAU UAGUCAGAUU AUCGUCCGGA AUACCGCUGU   3780
CAUUGACCAG UUCAAUAUGG UCAAUGGUGA UUUGCGUAUC GAUGGUGACC GUCAACGGCG   3840
CUGAGUGGCG AAUAUUACCC GCCUCAUCUU UCACCGUUAC CGUCAGCGUA UAGUCGCCAU   3900
CAGUCCACGC GCUGCCGGGU ACAAAACGCC ACUGCCCGUU AGUCUGCGUC AGCUCCACCU   3960
CCUCGCUGUG ACCAUCGCGC AUCACCUGCA CGACGACCUG AGUCACGUCA GAAUCAAUAC   4020
CGCCGAUAAU AAAACCCGGC GUUUUAACGU UAGUCUUAUU AUCGUUGGCG GUGCCGCUAU   4080
CAUCUGCGCU AUCCAGCGUG AUGGUCGGUG UCGACAAUGU GGUAUCAAUG GUAAAAUUGA   4140
GCGUUUCCGU CGCCGUGUUG CCUGCAACAU CGGUUGCUUU CACUGUCAGG GUAUACGUAU   4200
UUUCGACCAG AUCUGUCGGC CAUAUAUACU CCCAAACGCC GUCAGACGUC AGCGUUGCGU   4260
UAACCCAGUU GAUGCCGCCA UCAAGACUCA GUUGCACAGA GUUCACGUCC GUCGGUACCG   4320
UAAUAUGAAA CUGUGGACGU GCUUCAUUGG UCAGGUUAUC CCCGACAAUA CCCGUGUCAU   4380
UAAGAAGCUC AAUGCGAUCA AUAGACGUUU GCGUAUCGAU AGUCACCGUC AGCGGCGCAG   4440
AAUAAUUUGU AUUACCCGCC UUAUCUUCUA CCUUUACCGU CAACGUAUAG UCGCCAUCGG   4500
UCCAGGCUGC GCCCGGCGUA AAGCGCCACA CACCGCCGUU CUUAAUCAAC UCUAUCUGUU   4560
GGUUCUUACC AUCAUGCGCC ACCGUCACCA CCACUUUGGU CACGUCGGCG UCGAUAUUAC   4620
CGAGGGUAAA GCCUGGCAUC UUAACGUUGG UGAUGUUAUC GCCAGCGGCG CUAUCAUCCG   4680
CGCUGUCCAG GGUAAUCGUC GGUUCUGACA GAAUGGUAUC GAUGGUGAAG UCCAGUUUCU   4740
GCGUCGUUUU GUUUCCCGCC UUGUCGGACG CUUCCACCAU CAGGGUGUGA GGGCCGUUAG   4800
CCACAUUCGU CAGCCAGGUG UAAUCCCAGA CGCCCGACGU CGCGCUGCUG CGUGGCGUCA   4860
AACCACGUUU UGCCGCCAUC AAUGCUCAGU CUUACGCCGU UAACAUCCGC CGGUACUGUC   4920
```

```
ACCUGAAAGU GCGGGCGCGC UUCAUUGGUC AGAUUAUCGC CGGGGAUACC GCUGUCGUUA   4980

ACCAGUUCAA UACGGUCAAU GGCGAUAUGC GUGUCUACUG UCACCGUCAA CGGCGCGGAC   5040

UGCUUCACAU UUCCGGUCCU AUCUUCUACC UUCACCGUCA GGAUAUAGUC GCCGUCCGCC   5100

CAGUCGCUGG UCGGCGCAAA GCGCCACUGU CCGCCGGUCU GAACCAGUGG CACCUCCUGC   5160

UUAAUGCCAU UGUGCAUUAC CUCCACUAUC ACCCGGCUGA CAUCGGUAUC AAUAUUGUUG   5220

AGGGUAAAGC CCGGCGUUUU AACAUUGGUG AUAUUAUCGC CCGCGAUGCC GCUGUCAUCU   5280

GCGCUGUCCA GCGAGAGGGU CGGCACAGAC AGAGUGGUAU CGAUGGUGAA AUCGAGGUCU   5340

GUGUUGCCUU AUUUCCUGCC UCAUCGGUCG CUUCUACCGU CAGGGUAUAG CCUCCGUCGG   5400

CCACAUCAUC CGGCCAGAUA UAAUCCCAGA CGCCUGGCGU CGCGCUCUGG GUAGCGUUGA   5460

ACCACGUCUU GCCGCCGUCA AUGCUCAGGC GCACCACGUU GACAUCCGUC GGUACCGUCA   5520

CCUGGAAGUG CGGACGCACA UUAUUAGUCA GAUUAUCGUC GGGAAUACCG CUGUCAUUGA   5580

CCAGUUCAAU GUUAUUAAUG GCGAUUUGCG UGUCCACCGU CACCGUCAGC GAUGCAGAAU   5640

GGCUGGUGUU CCCCGCUUUA UCUUCGACUG ACACACUCAG GGUAUAAUCA CCAUCCGCCC   5700

AUGAUGUCGG CGGCGUAAAG GUCCAUCCGC CUGUGCCUUU CGUGGCGUCA AAUGUGGUGG   5760

UGACGCCGCC AUGCUCCACG CUGACCGUAA CGCGAACGGC AUCAUCAUCA AUAUGCUGCA   5820

AGGCAAAUGU CGGCUGGGUG CUAUUCGUCA UGUUAUCGCC CUGGAUGCCG GUGUCGUCCG   5880

CGCUAUCCAG UACGAUGACC GGCACUGACA GCGUGGUAUC CACCGCGAAA UCGAUGGUCU   5940

UCGUCAUGUA UUGCUGCUUU AUCAGUCGCU UCCACCGUUA GCGUGUAGGA CCAUCUGCCA   6000

GGUCUGUCGG CCAGAUAUAC UCCCAGCUUC CUGCCACGCC CGGAGUUGCC UGAACCCACG   6060

AAUUACCACC GUCAAUGCUC AGACGGACUU CAUUGACAUC CGUAGGUACC GUCACACGAA   6120

AGUGGGGACG GUCGUCGUUG GUCAUAUUAU CGCCUUUCAC GCCGCUAUCG UUGACCAGUU   6180

CCACCCCAUC AAUGGCGAUU UGGGUAUCGA UAACGACCGU CAGCGGCGCC GAGUAGUUGG   6240

UAUUUCCUGC CUUAUCUUCU ACUUUCACCG UUAACGUGUA GCUGCCAUCC GCCCACGUAU   6300

UCCCCUGGUA UAAAUAACCA ACUCCCAUUG AGGUGGGAAA GUUCGAUCUC UUCGCUCACG   6360

CCAUUGUGCA UCACCUGUAC GACGACCCGA UGCGCAUCGG CAUCAACACC GGAAAUAGCA   6420

AAACCUGGCU UAUUGAUAUU GGUCAGGUUA UCGCCUGUAA CCCCCGUAUC AUCCUUAGAA   6480

AGCAGGGAAA UCACCGGCGU UGAUACUGUG GUAUCGAUAG UAAAAUCGAA UAUCGCGCUG   6540

UUCGCUUUAU UACCCGCAAU GUCCUCAACC UUGACAUAAA CCUGAUGCAA GCCUUCCGUU   6600

AAAUCUGAAG UAAAGGUAUA GGCCCAUGAA CCAUCAGGUU GUUGCGUGGC AACACCGAUC   6660

UGCGUAUCAG ACAUGGCAUC CCAUACCUGA ACACUGAUAA UGUCCGGAUC AAUAUCUUUU   6720

AGGUGCAAGG UAGGUUUAAC GAUAUUCGUU AAAUUAUCAU CUGAAAUUCC CGAAUCUGAA   6780

UCCGGGCUCA AUGAAACUAU CGGUAUUGAA AUAGCAGUAU CGACGCUAAU UAAGAAAGGA   6840

UCCGAAUGAG CAAUGUUGCC AGCGAUAUCU UCAACUGAAG CGGUUAUUCU AUGAUCGCCA   6900

UCAACCAAAC CUUGAUCGGC UUUCAGGGUA UACUCCCAUC UGCCAUCUUU AUUUGUUCUG   6960

ACCUCAGCGA UCAGUGCACC AUCAAUAUAG AGUUUAACCG UUGAAUAGGG UGCAGCGGUU   7020

CCUGUCAGUG CAGGAUUCUU UUCAUUAAUA AUAUGGUCUG UAUUAUCAAC CCCCGUAUCG   7080

UUGACCAACU CUAUUGUUGG UUUUUGCGUU UGCGUUACGA UUUGGAAAUU AUACGCUGAU   7140

GAGGAGGCAG UAUUACCGGC AAUAUCUUCU ACCUUUACCG UUACGUCAUG CGAGCCAUCG   7200

GAUAACGCUG UGGUAAAUUG AAAAUUCCAU ACACCAUCAU CGCCAGCAAU AGCCUCACCA   7260

CUUAACACAC CGUCAACAUA GAUGGAAACC UUAGCAUUAG CUUCAGCCAU CCCGGUAAAC   7320
```

```
AACGGUGUAU UAAUUUUAGU AAUCAUAUCG CCUUUAACGC CAGAGUCAGC GCUAUCAUGC   7380
AACAUAACAG UAGGGAUCGG CGUAAAGCUA UCAAUGGUAA GCUGAUAAUC UACAGAUGAC   7440
GUUCUUCCUA AAGGAUCGAU GGAUUCAACC GUAAUCUUAU AAACAUUGUC AGACAGAUUU   7500
CUGGAAAUAU CAAAAUUCCA GUUACCGUCU GCAUCCGCAG UCGUCACGCC UAUCGUUUUA   7560
CCGUCAAUAA GGAUAUUUAC GGUAGCAAAC CUAUCCGCUG UUCCCAGUAA UGUCAGAGCA   7620
UUAUGUUUAU UGGUAAUCCA GUCGCCUUUU GCACCGGAAU CAUCACUGGC AUCGAGUUCC   7680
GCUUUUGGAG GUACAACUUC AGUUUGAAUA GUAAAAGAAU AUUUAACAGU AGAGGAUUUA   7740
UUGCCGGCGG CAUCCUGAGA AUGAUUUCAA UAUCAUAGGC GCCCUGAAGA AUUUAUUACU   7800
AAACUGAUAA UUUCCAGGUC CCGUUUGAGU CAACUUCAAU GCUGUCAUAU AAUUUACCAU   7860
CUCGCAUCAA UAAGAUGGUA GACUUUGGUU CUGCCGUACC GACUAAAGCC GGUAAAUCAU   7920
UCCCUGAUAA AAUUAUACCA UUCGGCAAAA CAACAUAAUC CUCCAAAGAA GCCGUCGGAG   7980
GUACAGGGGC AAUAGUAUCA AUAACGUAAC UAAAGGAAAA AUCCUUUUUG UUGCCAGCGA   8040
CAUCUUCAAC AGUGAACGUA AGAUUGUUAA UCCCUUCCAC UGAGUCGGAA GUGAAAUUGA   8100
ACGUCCAUUC GCCCUUGUCA UUCGCUUUAA AAAUAACCUC UUCGCCAGUC UCACUAUUUA   8160
UGACACUGAU AAUAGCAUUU GGCUCAGUUU UACCUGUAAA GGUUGGGCGA GUAUUGUUAG   8220
UAACGUUAUC UCCGACAAUA CCGCUAUCAU UCGUCGUUUC AAUCUCAGCG CUGAAAUAGC   8280
UGAUACGUGU AUCAAUAGUA AAAGGCAGAU UUGCCGUCGC UGAGGUAUGC CCGGCAAUAU   8340
CAGUAGCUGU UGCUGUUAUA UUGUAUUCGC CAUCCUUGAG CGGCGUAGUA AGCGUAUAGC   8400
UCCAUGUCCC AUCUUUAGCA ACAAUGACCU CACCAAGAUG UUUAAGUCCA AGAUAAAUAG   8460
AGACUGUAGA ACCGGGUUCC GCCACACCAA UAAAUGUUGG CAGGGUGCUA UUUGUAAUGU   8520
UGUCAUUUUU AAUGCCGGAA UCACUACUAU CAUCCAGCUC AAUCGUCGGC UUUUCUGGAG   8580
CAAUGGUGUC GGUUAUGAUA CUAUCCGUCG UUUCGUUUUU AUUACCUGCU UUAUCUACAG   8640
CAACGACUUU UAUACUAUUU UCGCCCUCAG AUAAUUCAUU AUCCUUAAAU UCAUAACUCC   8700
AGUUUCCAUC UUUAUCGACA UCAACGCUGG CAACCAGUUU AUUAUCUACA UAAAUGUCAA   8760
CCUUAGCAUU CUCUUCCGCC GUACCAACAA UUGAAGGCGU CAAGGUCGGC GUUAAGCCCU   8820
UAUGACCGGA CACACUACUU UCAGGCGAAA GUUCAAAUGU UGGUUUAUCG GUAACGGAAU   8880
CGAUAGUAAU GACAAGUUUG GCGCUACCGC UCCCAUCAGC AGUCUUGGCC UCUGCCUCCA   8940
GAUUAUAUGU UCCAUCAGUC AAUGUUUCAG GCGCUGUAAA GGUGAAGUUA CCCAAACUAU   9000
CCGUUACAGC CUGACCGACA GCAAUACCAU UAAUUUUAAU AAUAACCGUG GCAUUGGGAG   9060
CAGUGCUAAC UACAAACUGA GGUUUGGUAA AAUUAGUUAU ACUAUCAUCU UUGCUACCGC   9120
UGUUACUCUC GGCCGCACGC GCUAAUGUGA CUUUAAGCGG CUCUUUAACA GACUCGGCAU   9180
CGAGCUUAUU UUCCUCAUUU UUACUGCUAU UACUUUUGCC AGUACUGGUA UUUUUAUUAA   9240
UAGGUUGAGG AAGAACUUUU UCAGCAUCGU UCUGUUUAGA AGCCUGCGUU GCUUUAGCCU   9300
GUGUAUUUUG CUGGGAAGCA UCGCUUUGCU GAGCCAGAUU GUCUUUUGCU ACAUUGUCAG   9360
CCAAAAAGUU CUGCAGCAUU UCUUCAAUUU GCUUUGACGA GUUCUGUACU UCAAACGCUU   9420
CAUUGAGCGC UUUUUCUGCA GCCUCCUUAG CUUUCUCUGC UUCUUCCUUC GCCUUAUCAG   9480
CUUCUUUCUU GCGUUUUCAG CAUCGUCAAG CUGCUUUUUA AUUCCUCUUC UUCCUUCUUA   9540
UUUCGUCGUU UGCCAUUACC UUUCUUUUCU ACCUGAGCAG AAUCAACCAA UGAGCUGUCA   9600
AUUCUCUCCA GUUGAAUAUC UUUUAAAUCU ACGCUGCCCA GAAUUUUAGC GCCGGUAAUA   9660
GUCUUAUCUU UAAAUUUAAC AGCGAGGUUA UUGCCUUUGA UACUUGAAUA AAGAGCGCCA   9720
```

```
UUGACAAUGA UCACUGAACC ACGCGGCGUG GUAAUGUUCA UGUCUGGCCC GGAAAGAGAA   9780
ACUUUUGCGC CUUUGGCAUU ACCCAAAGAA GAUAAAUCAA UUACAGAAUU UUGAUCGGCA   9840
AAAAACUUUU GUAUGCUUUU AUUUCCCAUA AUAUUAUAUU CACUCUCAAG GUGUAUCUAA   9900
UCGUUUAGUA UUAACUGGUU CUGAAAAGGC UUUGUCCACG CCUUUCAUCA AGGGAGAUAA   9960
CAGGUAUUCC AUAAUGCUGU GUUUUCCGGU AAUUACACUG GCGUCAACAG UCAUACCUGG  10020
UUUUAACCAC CGUAAAUCAU CUUCAUUAAC AUCGAAUGCA AUAAUUACUU UAUAAUAACG  10080
CUGAAUUGUU CCUCCGGUAU UUUCCUCAUA GGAAUCAGGG CUAAUAUUAU CGAUAGUCGC  10140
AUUAUACGAU UUUAUCUUUG GUUGGAUAAU UGACUGCACA UCCAGUUUAA CGGCUUCAUC  10200
UACAUAUAUU UGGUCACGGU AUUUGGGUAA UAUUUUCACA UCGGCCAGCA UAGUCCUUAC  10260
UUUUGGUUUU AUUUCAAAAA GUAAGUCCGC CGCCUGAAUC ACACCACCAU GAGUAGUGGC  10320
ACUUUUAUUG AUUUUAUAAA UUACACCGUC AACCGGUGAA UAGAUAUCCU CCUCAUUUAU  10380
CUGCUUCUCU AUUACUUUUA AUGUAGAGUU AACAACCUCA AGUUCCUGAA GAUUUUUAGA  10440
UAUUAUUUUA GAUAAAGAUA GUCGCAAUUC AUUAUUAAGC GCCUCAAUAU CAUUAACAAC  10500
CAACUCAAUA UCAUCUUUUU UUAAAGUGAU GCUACUUUCA AUAUCAUUAA UUUCAGACUU  10560
AACUUUUAUA UACGCCUGUU UCUUGUUAAG AAAAUUGGUA UAUGGGCUAA UUCCUUUUUU  10620
UACCAGUGGG GAAAGAAUAU UUAUUUCUUC GGCAAGCAAU GCGAGUUCUU UUUCUUUCGA  10680
ACUCAGCUUC UCUUGUAAUC CGCUAAUCUC AGAAUCAAGA GAGGUUUUUU UUAACUCUUU  10740
AGCUCUUAUC UGACUAUGCA CUAAUUCAAU AUUCGCUUUU ACCUCUUUAU UGCUUAAAGA  10800
ACGGGUGCCA UCCAGGGUAA UCAACCCACU CUCAUUUUCU UUAUCAAGAA UGAAAGAUAU  10860
UUCGUUAACA UCUUUAUCCA GAUACCCUUU UUGAGUUCUA UACCUUUGAU AUUCUUUUUG  10920
CAGAUCAAGG UUAACGACCU UUGCAAGGAG UUCUCCUUUU UUUACAGUAU CACCCUCGGC  10980
UACAUAAAUA UCUUGUAUCG UCCCUCCUUU AGAAAGAGAU AUUAACUGAG CAUUAUCUUU  11040
AGUAGUGAUA ACGCCCUGAC CAUGAACCAC UGAAUUAAUU UCUAUAAAGU AGGUAAGGAU  11100
AAUAAUUAAG AUCGUCAAAG AAAUAAUUAU CAUCAUGAGA UGAUCGCUUU GUCUUCUAUU  11160
CAUUUCAUUA CAUUUAACUC ACUUUCAGUA UUUCCUUUUA AAUAAUCCAU UAAAUGAAAA  11220
AUCAAUGAGA GUUGCUGUAG CUUUAAAAUA UACAGGCUAU AUUUGCUGUC GAUCAUGCUU  11280
ACAUAUGCCU GAAAUGCUUC AUUACGGCUU GAAAUUAAAU CAAGCAAACU UUUUUGCCCU  11340
AACUGAAACU CCUGCUCAUA UAAUUCAGUA AGCUGUAACG CGUUUGUAUG UGAACGUUCC  11400
GCCACUGAGU AAGUCUCUUU UGCAGCGGCG UAUCUUGAAA GUUGUGAAUC AAUGUUAUAA  11460
CGCGUUUUAA UCAAAAAAUC GUCAAUUUGC AGCUUAGCCU GCGAGUAACU UGCCACCAUU  11520
UUUCUUUCCU GGGCUGAAUU UCUGAACCCA UUAAAAAUGU UGAAACUGAC AUUGAUACCC  11580
GUUUUAAAUU CAUCUUCAUA AUCACUUUUU UUGGCACUAC CGCUUGGGUU AUUCUGUACA  11640
UAGCUGGAAA CAAGAUCUAC AGUCGGAAAA UAGGAUGAUU UUGCGGCAUU AAUAUCUUCG  11700
GUCGCGGCUU UUCGGGUAUU GACAAGCAUC UUAUAGUCAU CGUUGUAUUU CAUCACCAUG  11760
UCCAUAAGUU UUUCAGGGCU UUCGACAAAG AUAUAUUUUU UGAAGAGGUU GAAUUUUUCA  11820
UCGCUUUGAA UCUGAACUGG CGAUAAAUUC AGACCAGUCA UAUUCUGCAU UUUAUACAUU  11880
UCAUCAUCCA ACAUCGACUG AUACAUAAUG CUUCUGGUAU UUAAUGCAUC GAUAGAUACU  11940
UGUACUUUAC GCAUAUCAGA UUGCAUAGCU ACACCGGAAG AUACCAGCAA CGAAAAAGGU  12000
UCCAGCAUCU UUUUAUAAAA CUCUUUCUCC AGAUUUACGC CAUCAAUCAU UUCACGAUAU  12060
UUACUGAUGU UGUAAUAGGU UGUCACAACC UCCUGAGACA CUAUAUUCUU UGUUUUUUCA  12120
```

```
UAGUCAGUUU UACUAUUAUC UCUUUCAUAU UCAGAUUUCC UGAUAUUAGC CCCCCUCACU  12180
CCAAAAUCCG UUAUUCGGUA UGAUAAAGAC ACCUUAUUUU CAACGUUCCU CUCGGUACCU  12240
GAUGACUCUU UCCUGUUAUU AUUAAGGCCA GAUGUUAGAU CCAGGGUAGG AUAAAGUGCU  12300
GCCCGUGAAA GAUCUAAGUC ACUGUUUUUC UUUUCAGUCU CAUAAUAUGA AACAGCAACA  12360
GAGGGCUGAU GCGUUAAUGC GGCAUUAACU AAAUCUCUUA GAGGAAUGAC CGGAAGCUCG  12420
CUGGCGUAUG UGCUUUGUGU AAUAAAAGCA GUCGUCAGAA AAAACAUCUU AAUCUUCAUU  12480
UUUUUCCUCC UUGUUUAACA AACGUUGCUU UACUAUUUCC UGAUGCAUAG AUGUUAUUUU  12540
UUCCAUUAAU GGCAUAUAGG UAUCACGGUA GCUAACCAUU UCAGCACUAA UCUCUUUAGU  12600
AUUGGCAAUA AUCUUUUUAU CAGUAGCCGA UAGAUCGGAU AGCGCUAAAU GAACAUUAUU  12660
CAUAUCCUCA UCCAUUUCUU UUCUCAGCCC AUCGAGAGUA UGAGAAAUAU CGGCACUGCC  12720
AGCGGCAAUA UCGUUUAUGG UCUUACCAUG UGAAAGAGAU UCCUGAUAAC AUUUAUCAAC  12780
UGAUGUCAUU AUUGAAUCAU UCUUUUUAUC UAUAAUAUUU UGUAUUGUAC UCAUUGCCUC  12840
CAGUCGUGCA UUAUUAUCAG CAAGCAGGAU AUUACCUUCA GAUAAACGAG AGGUAAUUGU  12900
UAUUACACCG UCAGAUAAUU UUUUGAGAUU UUCCGUUACU GCUUACCAGA UAACCAUCAA  12960
UCAGCGUAAA AAUUUGUUCC AGUUUUGCUG AGUUAUCCAA UAGUCGGUUU UGCAAAGUGA  13020
CAAAGCUAUC UGAUAGCAUC UCUCGUUUCU UUUCUUCAUC CUGCGUCCGU AAGUUUUCAA  13080
CUGUCAGGUA GUUAUCAAAA AACGCUUUAA ACAACUCUUU AAAUUCUACA AGCGUCUCUG  13140
AUUCAACCCG CAGGCUUCGC UGUUUAUUAU UGGCUCUGUU GCUUAUGAUU UUUAAUUUUU  13200
UGAUUUCCGU AGAAACAAGG GAAUAGGAGC UGCGAACAAA AACACUUUGU GAGGUCAGGA  13260
GUAUGGCGCA AACAACACCA UAGAUAGAAG AUACAAAUGC GGUAUUCAUC CCUUUCAAUG  13320
GUUCAGAAAG CGACGCUACC AUUGUCACGA UCAUAUUGAG UGUAUUACUU GCAUUAUCAC  13380
CGCCAACAUC UGAUGGCGAG CUCAAUAAGU UCCCGAUUGA ACCAAUCGUA AUAGACAGAC  13440
CCGCAAACGU CCCCAACAGG CCAACAAGCG UCGACACAUU GCUACAGCUC AUAAUAAAUG  13500
ACAAUCGUUG AUUACGGGCG GUAGACACAU UGUCAUCUAA UUCCAUCAGU AAAUUGAAAU  13560
CACACUGUUU GGACUCCCCG GCAAACAAAA CCUGAUUGAG GUUAGAAAGA AUGCUAUUUU  13620
UUCUACUGGC GUCCUGAGCU AUUAAUAUGU CUUUUGCUGA AAUAUUUUUA AGAAUAGUGA  13680
AUAAUGCACA CAAAGAACCU GUAAUAUAAA UGGCAAUAAU GACUCCAUUG UAAAUUGCAG  13740
AAACCAUGAA GUUAUCAAAA ACAUACUCUC UUAUACCGGG AAAAGAUAAA GCAAAAAAAG  13800
GGAGUAUGGC AAGGAAAGAA CAGACAACAA AUAGCGGUAA UGAUUUAUAU AUUUCACUCU  13860
GACACCUUUU AUUAAUAGUC GUGAUAAUAG CUUUACUCGU UGUACUUGAU GCUGCGGAGU  13920
UAACACUCAU GUCAAUAACU ACAUCAGGAU AUAUUUUCUU AAUCUCUUUC AUCAAAAUAA  13980
UUCCCCGUUC AUAUCCCAGU CGUAGAGAGU CAGAGAAAGA GAUGUCUGCC UGAGGAAUAA  14040
CCAUUUCUAU CAAUAAAUUA CUAUUGAUUU UGUCUUCUAA CCAAGCCUUU AUUUUAUAAG  14100
UGUCCUCUUC UGAAAAGCUU CUCAGCCUGC CAUGAUACGU AAUAACAAGC UCAUUUUUUG  14160
UAGACGUUAU AUCAGUUUUC UGACCAUCGG CGAUAUCGUA UACUCCAACC UCCUUACCUG  14220
ACAUUGUAGU CAUUCCGUCC GACACAUCUU GAGUAUUCAC UUCCUUAUUA ACUAUUUCAU  14280
UAGGAUUUGA AUCGUCAUUG GCUCCGCUAU UUUGAGCAGU AGAUUUAGUC UUAUUCUCUA  14340
UAUUUGCUUU AUAAACUUUA AUUGAGUUGU CAUACAUAAU AAUCAUAUUA UUAAGUGCAA  14400
ACACCAACAU AAGAAAUAUA AAAAUGCACA AUACCGUAGA GAAUGUAUCA ACAAAACUAG  14460
GCCACGGAUU ACUUUCGUCU UCCAUGUUGU CUCCUGAUAU UACAUUGUGA AUAAAAUGUU  14520
```

UUUGUGGAUU AGAAAGGAUA AAGGAUGCUC AACUUAUUCA GAAAGUGAAC GCUACCGCCC 14580

UUGGCUUCCU GCUACCAAUA CGCUUUAUAG AUUUCAGUUU UCUUACAUCU CGUAAUCAGA 14640

AAAAUAAAAA CAACGACGCC AUUUUUAUGC GCCCACAACA AAGAUGAGUG CUUUAAUUAA 14700

AAACACUCUU CAUUUUUUUA AUUAGGUAGA CAUCAAUUAU UGCACUAACU AUAUCCUCCC 14760

CAAUAAUAGG UAUCGCAUAA GCUCUCAACU CAUAAAUAAA AAAUAGUCAU CAGCAAAUUA 14820

AAACCACCCG CCGAUAAAUA GAUUUGUUAG CUAAUCAUUG AAACUCUAAA UCAUUUUAAG 14880

GACAUAUUUC UUUUUAAUAC GCGUUAUAAC CAUACGUAUU UAAUAAAUUU GCCUCCAGAG 14940

GAUAAAAUUA AUUUUCACAA UUAAAACAUA GGGUCAUAUG GACUUCAAUA UAACUUAAAU 15000

CAUUGAAAAU AUAAUAAGUG GGGAGUAAAA AAUCAGAAUU GUGUAAAAAA AUACACAAAU 15060

AAAACCAUUU UUUAUAUAAA GCCAGCUAUA AGUAACAAUU UUAUCUUCAG CAAUUAAAAA 15120

UAAAGCAAGA UACACAUAUC AUAUUUGAGC UCAUCACAAG CUAAAGCAAA CAUUUAAUUA 15180

ACCAUUGAUA AUACCGACCA UUCUCUACCG UUAUUUUAUA AUAUCUUUUU GUUGUCAAAA 15240

AAUGGCUAUA AAUUAUAUAU UUUGCAGAUG AGAUUUCUCU UUCAUAUUUA AGACAAUCCG 15300

GGUUAUUGCA GUACAUUUAU GAACUUCGGC UGGAUAAUGA UGUGCCGAGG CGAGUCGGCC 15360

AGAGGCGAUA AGCGACAUUU UUCCGUAAGA UAUGCGCUUC UCUUUUUUGA AAGGGAUACA 15420

AAGACAAUAA UACCAGGUAA GAAAAUGCCU GGUUUACACC AGGCAUUUCA GCAGACGAGA 15480

ACUAUAGCGA AAAUGCAAAU AACGCUUUGA GU 15512

(2) INFORMATION FOR SEQ ID NO:67:

(i) SEQUENCE CHARACTERISTICS:
(A) LENGTH: 8967 bases
(B) TYPE: nucleotide
(C) STRANDEDNESS: single stranded
(D) TOPOLOGY: linear (xi) SEQUENCE DESCRIPTION: SEQ ID NO:67:

CUAUCGCUGC CGCUGAAGCC GCCCACCGGU UAUCUCAACG CGGAAUCGCG CGCCAGGGGU 60

UAGCCUUGCG CACCAUCACG UCCCUCGCAU UGCCGUUGAU GAAGGCCGCC AGGUGUGGUU 120

AUCCAAAAAU GGCAAGUGGA AUAGCCCUAA CAGAAUCGAG CUAAACUUAU UGAAGACGUU 180

GCCGACUCCG UUAAAUGACA AAAAAGACCC GUUUGUGCAA CGGGUCUUUU UUAUUAAGCA 240

GUACCACCUG AUAACAGCGA CAAGCGCUGC UUAUUUUACA UUAAUAAUUU AUCCGGAGAA 300

CAAUCACGGA UUAUUUUUCC ACCUUUCAUU ACCAGGACCC GGUCAAAAUA CUUUAUCAGA 360

UAUCGACGAU GCGUCACCAU GAUCAACGUU UUCCCAUGAA UAAACUCAUC UAAGUUAUCA 420

AAAAUUUGCU UCUCGGUAUU CUCAUCCAGA UUUGAUGUUG GUUCAUCCCA UAAAAAGACG 480

CUGGCGUCAC UACUCAGACU ACGUGCUAAU AAUAACUGCU GCUGCUGUCC GGAUGACAGG 540

UUUUUAGCCA UAAAAUUCAC CGGAAACUUC AGCCCCAUAG GAUGUUGCAA GAUAAAACCA 600

CAGUUCGCCA GCUGAAGCGC CUUGAGUACC CGGCCCCUGU CGUUUUGCGG UUUUAACGCG 660

AAAUUACUUU CAAUGGUUCC GGUGAAUAAA ACAUCAUGUG UCGUCACCAC GCUUAAAUGC 720

UGAGAAAAAA AGUUCUGCGA UAAAUGUCCU AAGUUAUAUC CAUCAUAUAA AAUGGCACCG 780

UCUGUUGGCG AAAGGUAGCC AGAUAGCAUU CCCAGUAAUG AGCUUUUUCC UGCUCCGCAU 840

UCGCCUACCA CCGCGACACG UUGCCCCGCA GGUAUGUCUA UAGACAGUCG GUUAAUAAUC 900

AUCGGAGAUU GAGCAUCAUA CUGAUAACUC ACGCCCCGGA UAGAGAUAUC GCCAUUGCAC 960

UUUGAUAUUG ACUGUAAUGC CGGUGUUUUU UCUGCCUGAU CUUCAUCAAA AAAAGAAAGC 1020

-continued

```
AGAUCCUUAC CGGUUUUUUC UGCUGAUAAA AUAGAGAUUA AUGUAGAAGA AAAAUUCGAA   1080
AUGAUCCCGG AAAUACGGCC AGAGACAAUG ACAGAUGAAA CAAUUGCGCC AGUAGUAACA   1140
UCACCCUUGA UUACCAUAAA AAAGGCUAUU ACCAUAAUAG UUAUUUGGGU AAUAGAUGAC   1200
AUACUCCCCA AUAUAGAUUG AUAGAUAAGA UUUAAUUUCC UUAUCUUCAG GUUAAGAUAC   1260
GACUGUUCAU UUGAUGUAUU AACCCAAUCA AAAAGUAAAC CUUGAUUAUU UAAGGUAUGG   1320
AUCAUUUUAA UAGAUAAGAA AACUUCUGAG AUAAAAAUAU UCCUGUUCUU CUGUCCUUCU   1380
UUUUGUUUGU UCAUUAACUC AUUAGUAUAA UGGUGGUUAA CGAGGGAAAU AAUAAUAGAG   1440
ACGAUAAACA UGGUAAUAGG UACAAUAACA ACCAGACCUA AAUUUACAUA UAUAACAAUG   1500
AGAAAUAUAA UAAAUAUUGG AAUAUCGGCU AUACGUUGAA AGAUCGAGUU UAAUAAAACG   1560
GGUUUAAUUU UCUGAAACUC AUUCCAUAGC ACAAAUGCUG AUGACAUGGA UCUGCCAUUU   1620
UUCUUUUUAC UAUAAAGUAC CGCUUCAAGA AAUGCGAUAU CAAUAUCGAC GUCAUCCUGC   1680
CUUGCUGUGA UAGACUGAUA AAUAUCUUUC GAAGUACGAA GGAUAAACUC AAAAACAAUA   1740
AAUACAGCAA CAAUUAUAGC CACGCCAAAU AAAGAUGAAA CCGAAGCGCU UGGAACAAGC   1800
UUAUCAUAGA ACAGAUUACU AAAUACUGGG AUAGUUAACG CAAAAAUUGC CAUAAAAAGA   1860
GAUGAAAAAA AGUAUUUAGU AUAAAAAAUC UUGUUCAUCG AUAAAGAGUU UUUUAUGAUA   1920
UUUUUUACUC UUAUACUAUC AACAACUUUA UUUAAAGGUA GUAUACUAAA UGCAGAUAAC   1980
UCUUUUAAAU AUUCAUCUUC AAUUUCAACA UAACAGAGUU CACCGCGCGC GUUUACCAAC   2040
UUUAUUUUUU GCCCGCCACU CACACACACC AUCCACUUUC AUUUUCUGGU GUUAAUAGUA   2100
AAAUCGGCAU AGGCUCAUUU AGUAAAUCCU CACCAUUAUU AAAUAAUAUA UCCUGUAGAG   2160
AAAGCCCUAA CGACAAAAAG AAAUUCUUCA UUCGUAUAGG UCGUCAGUGU UAUUUCAGUC   2220
GUACUUUCUA AAUCUUCAAA UGUAUAUCAU CUUCUCGGAU GUCAAUUUUU AUGUUGAAUU   2280
UUGUAGACAC UAUAGAUAAU GCCGUUUCCG CACUUAAAUA AUAAGGUUCU AGUUUUUUAU   2340
CCAUAAGUAA ACCCCCUUCA ACCCAAAGGU GAGGGGCCUC CGUUAUUAUG CGUGUUCUUC   2400
UUGAUUAUCU ACAGGUAGCG UAACUUCAUU AACGGCGAAA ACAUCAAUAG CGCCGUUAUU   2460
GUUGUGCCCU ACAGAACUCG UGGAAGGGGA AUCAUUAAUA UCAUCCUCGG UCUUUCCUCU   2520
UACAUUCAUU GCGUUCACAA UAUCCGCCGA GGAGUGAUCG ACUGAGAAUG UUUUCUCCUU   2580
AAUCAGGAAA UCAUUGUCUU UAUCAAUGAA UUUCACGUCC AUAGUAUAUU CACCAUCUUC   2640
CAAAGAUAGC GGAACUUCGA AUAUUGCUUU CUGGUUAGUU AUCGGCAGAG UAAACUCUUC   2700
UCCUUCAAAC AUAAUACUGA CAUUAACAAU AUUCUCAGGU ACUGAUAUUU CAAAAGAAGG   2760
UGUCUGACUA AUUGAACGAU CUAUUUCAUC CCCAGAGUCA GCGUUUAACA AUGUAAUACU   2820
AUAGGCUGUC ACCUUCACCA CGCUUUCUUC CGCCGCAGAC GGCUCUGUAC GAAGAUGCGU   2880
AGCGCUUUCG GCAUUCACUG UUUCAGACUC CGGUGGAGUA ACCGCUGUUG CCGUGGCGUC   2940
AUCGCUCGCA UCGUCAUGCU GGCUAUCCGC UGUUACCGUC ACCGUUGAGU CAACCGUCAC   3000
CGCUAGCGAA GCAGAUUGCU GUGAAUUCCC CGCGCGAUCC ACCACCGUCA CGCUCAGCGU   3060
GUAGUUACCG UCAUUCCAGG CGGCUGGCGG CGUGAAGGUC CAGCCAUCCG CGCCUUGCGU   3120
CGCCUGAUAG AUGUCUGUCA CGCCAUUAUG CGUCACGUUU ACGGUCACCC CGGUCACAUC   3180
AGCAUCAAUA UGCUGCAGCG UGAACUUAGG CUGGGUGUGA UUCGUCACGU UAUCGCUGUC   3240
UGAAGCGCCA UUGUCUUCAC CUGCUGCCAA CGCAAUCUCC GGCACCGUCA GCGUGCUGUC   3300
GAUCGUGACA GUAAUGGGUA ACGAGUUUUU CUGAUUACCC GCGGCAUCGC UUGCGAUUAC   3360
CGAUAUCGUA UAGGAACCAU CAGCUAACGG UGUACCUGGC GUAAAGAACC AAACGCCAUC   3420
```

-continued

```
GGCAUUUUUU UCAGCAUUAU AUACGGUCCC AUUGAUAUCG ACCUGAACGA CCACAACAUC   3480

GCUUUCCAGA UUCCCGAUAA UAAAGGUAGG UUGCUUAUCU CGCGUAAUAU UAUCGCCCAC   3540

CGUACCACUG UCUGAGUCUG GAGAUAAUGA AAUAACGGGA ACCUCUUUCA UGAUAUCGAG   3600

AGGGACAUCA UCACUCCGGU UACCAAUAGC AUCCACACUC GUAAUGGUAA ACUUCCCUUC   3660

UGAUGGAUAC GGGAUAGCCA UACUCCAUUU ACCAUUAUCA GGAACGGUUA ACGUAUAAGU   3720

AUUCCCCUCA CUAUCGGUUA UUAUUAGCUG AGAUUUGGCU UCCGCCGUCC CCUGCAUAAU   3780

AAUUAGAUCG UUGACAAUAU CUGAAUACGU UACGACCGGA GCAUUUGGCG GGUUCGGUCA   3840

AUAAAUAUUU CACGCACAUC UUCCCAACGA UUUCCGGGCU AUCUUCAAUG ACCAAACUAA   3900

UAUCGUAAGU CCCUUCUGGA AGCUUGUCUG UUGAUAAUUC CCAUCGUCCU GUUGCCGCCA   3960

CAACAGCAGU UGCCAGCGUG ACGCCAGCCA CGAUUAAUGA UACCGUAGCG CCAAUUUCAC   4020

CCGUGCCUCG CAUGGUAAUG AGAUCGCUAU UACUCCACCA UUCCGUUUUC GAUGAUGAUU   4080

UAUUGUCAUC AAGCUCGCUG GUAAAUACCU UGAUAUGCGU AUCAACCCAA AUGGAAUACU   4140

UUUCCUGAUU UACGUUACCA GCACGGUCCG UAGAUUUAAC AGUGAUAUCC AGUUGGCCUU   4200

CUGUGAAAUA AAGCGGGUUC ACCGGCAUCU GCCAGUGGCC UUUUUCAUUA ACCCAAACUU   4260

CCCCCACAUU UAAGCCAUUA AUGAUGAUUU CUAUUUUGCU AUUGGGCUCG GCACUGCCAC   4320

UAAACAAUAA GUUACGCGUC GUGUCCGUUA UAUAUAUUUU GCCAUCACUA CCGGUCAUCU   4380

CUGCUAACGU UUGUCCACCG AUAGAAUCAA UGGCGACAGG CGUCGUAUUA AAGGUAUCGA   4440

UAGUAAAGUU UAGCGUUUUC GAGGUAGCCG UGUUGCCUGC UUUAUCGGUG AUAACAUAAU   4500

AAAUGCUAUG GGAACCAUCG CCCAACGGUG ACUCAGGUCG AUAAACUUGA UUUCUGUCGG   4560

UCACCGUGAU CGUAUCGACU AGCACUCCAU CAAUGAAAAU CUGAACACUC UGGUUCAUUU   4620

CUCCAAAAAU ACUAAACGUA GGCCGGGUCU GACUCGUUAU ACUAUCAUUA CUGAAAAUAC   4680

CAUUAUCAGA ACCUGCCACC AUAGCAGGAU UAUCGAUAAA CGUACUGGUA UCUAUCGUGA   4740

CGAGUAAGCG AGGCGAUUCU GCCGUAUUAC CUGCCGGGUC UUCGGCAACC ACACGGAUAG   4800

AAUAUUCACC AUCUUUUAAC GCAUUAUCAA ACUGAUAGGA CCAGGUUCCA UCUUCAAGCA   4860

CAAGAACAUU UGCCACGAUC UUUUCAUCCA CAUAAAUAUG GAUUGUGGCU CCCGCUUCUG   4920

CGGUGCCAAC UAAUACAGGC UUGUUGUGAU UAGUAAUCAG AUCGUCAAGU GAACCAGAGU   4980

UGCUUGCAUC UUCAAGGUUG AGCGUUGGGA AGUCGGUUGA UGAAUCGACA UCCACGCUAU   5040

AAUCCUUGCU CACUUCAGUG UUGCCAGCAA CGUCAGUAAU GCUGAAAUGA AUAUUAAACG   5100

UACCAUCAUC UUGCAGCAGU AUCGGCGCGC GCCAUGUGCC AUCAGCCUCA ACCAUAACAA   5160

CGUUGACUAA UUUACCGUCG ACAAAGAUGC UGACCUGAGA ACCAGCCUCC CCGACACCUG   5220

AGACUGACAA CGCUCGGUUA UUAGAGAGGG CCGGUAAUGA AUCUUCAUCA AUAUCAAAGA   5280

CAGCAAUUUG AGAAUCGAUU GUCACGGUUG UAAUCGCAGA CUCAACCCGG UUACCAGCAG   5340

UAUCCGUAGC AACAAAUUGC ACCUGAUACU CGCCGUCGGC GCUAUUUGCC GGCAUGGUAU   5400

AGCUAAUAUU ACCUGACGAA CUCGCCUCUA CUGUGCCUUG UAACACACCA UUAAUAUAAA   5460

CCUGUACCGU CGCGCCGGGA UCGGUCCUGG CAACCAGUAC CGGAGACUUA UUAUUGGUAA   5520

UCAGAUCAUA UUUAUCACCG CUAUUAGUAU CCCGACUUAA UGAAAUAUCG CUGAUUUCAA   5580

UCUGCGUAUC AUGUUCUAUC AGAAUCUCUU UUUGUUGACU GUUGCCCGCU UUAUCUUCCG   5640

AUACCACGAC AAAGGCAUUA CUACCUUCAC GCAGAUCUAA UUCUGCGCUC CAUCGACCAU   5700

CAUUGCCUAC CACCAGGGUA GCAAUAACCA CUCCCUGCGG AUUCCUGAUG GUUAAAGUAC   5760

UUCCGGCUUC GGCAGUACCA UCGAUGGUGA CAUGAGAUUU AUUGGUGAUC CAGUCGCCAA   5820
```

```
CUUUGCCACU GUCAUCAGCU UCGCGUAAUA CCACGGUUAA CGGCGAAAUU ACUGUAUCCA   5880
GUAUUACAUU CUGCGGACCA AACUCUCUGA UAUUACCGGC AACGUCUUCA ACUUUAAACG   5940
UUAAUUCAUA AUUACCGUCA UUACCCAAAG CGGGUAAUAC UACGCCCCAG UGUCCUGCGC   6000
CUGUCGUAUA AGCAAUCGCU UUUCCAACGC CAUUCACAAA GAUAGUGAUU UUGCUGUUUG   6060
GCUCACUGGU GCCGCCAAUC UCCGGCGUCA CCGUAUUGAU AUAUCCGCCC UCAUGCAUUC   6120
CAGAUAUAUU CCAUACCAGU UCAGCAACCU CGGUAUCGAU AGUGACAUCA ACGGCGGUAG   6180
AACGCAGUUC GCUAUUAUCG CGAGGGUUGA CGAUACCCAC CUGGACGACA UAAUGGCCAU   6240
CUUUCAUUUC CGAUAACUGG AAAGUAUAUC GACCCGCUGU AUCCGCUGUC GCCUCGCCGA   6300
CCUUCACGCC AUCCACAUAA AUACUCACAA UCGUAUUAGG UAACGUGCUC CCAAUCAGGG   6360
UCGGCGUUUU AUUAUUCGUG GUAAAGUCUC CUAAGGCGCC ACUAUCGCUC UCCUCGCUGA   6420
GCUUUAUGGU UGGAGGCGUG ACAUCAAUAA CAGGUAUUAC GACAGGAAAG UCGACCUGCG   6480
ACGAAUCAUU ACCCGCUUUA UCUUUGGCAA CAAUGCUCAC AACAUAGGAG CCUGGCGCUA   6540
AUACUGAUGG CGGCGUCCAA CUCCAUUCGC CAUUCGCAUU GGCGUUUGCC GAGCCGACCA   6600
CUUUCCCAUC CCACUGAAUC AUAAUCGUCG AGAACGCUUC GGCAAACCCU UUGAACUCAG   6660
GACGCAGGCU GGUUGCUUCA UGCUGAUCAU CAAUAGAUGG AUCCGAAAGG CGAAUGGUGG   6720
GAUCGAUCGU AACCGUAUCG AUAGUGAAUC UUUCCUGCGU UUGCGCAGUA UUUCCCGCGA   6780
CAUCUGUUGC GACGACGUUG AUGGUAUACA UGCCAUCCGG CAGUAUAUUC GGCGUCACAC   6840
UCCAGUUGCC AUCAGCGCCA ACCGUAAUCG UUUGUUUUAA AACCUCCUGA CCUGACUUAU   6900
CGUCAACAAU GGUAAUCACC AGUUUCGCAU UGGGCUCUGC AGUACCUUCG AAUUUGGGAU   6960
UUUGCUUAUU CGUAAGGUUA UCGCUAUUGG AAUUUCCGGU AUCAGACGCU AGCUCCAUUC   7020
UGACACUGAC GCUUGUCGUG GUAUCAAUGG UAAAGGGCAG CUUAAUUUCA GAAAUAUUUC   7080
CGGCAAUAUC UCUGAAGACA ACAACGGCUU CAUAUACGCC AUCGUUUAAC GCAACGGGAA   7140
CCUGAAAUUC CCAGAGGUUA UUGCCAUUUG CCGUAACCGG AUAAGAAACG CCGUUAAUUC   7200
UGAUAACAAC AGUAUCAAUA UCGGCGGGUA CAUUGCCAAU AACGAAACGU GGUGUAGUGA   7260
CACUCGUAAU AUUAUCAACA GCGCUUUCGC CAGUAUCAUC CGCAUCCAGC AAAUCAAUAC   7320
UGGGAUCAGA AACAAUAGUG UCUAUUGUGA AUGAUACCUC UUUGCUAAUU UUAUUACCUG   7380
CGAUAUCUUC AGCCACUAUU UCUAUUUUGU AAGUUCCAUC CACUAACGGU GUAUCAGGGG   7440
UAAACAGCCA UUUAUUACCU GCCCCCUGAG UCAGUGUGCU GGAUUUCCCG UUUAAAAUUA   7500
CCGUCACGCU CUGCAGCGGU UCUCUGGCUG AAAUUUCAAA ACGUGGAGAG GUAAUAUUCG   7560
UAAUACCAUC CGUAGAAUCC UUUCCGGCGU CGUCCAGCAU CACGACGCUC AGGCCGUCAA   7620
UCUGCGUAUC CACGGUGAAG CCCAGCGUGG AAUUUGCCGU AUUCCCUGCC CGAUCCGUCG   7680
CCUGGACAUG GAGAGUAUAA UGACCAUCAG GCAAUGCGCU ACCUGCAGUA AAUUCCCACU   7740
GCCCGGCCGC AUUUUUACUG AUGGGCGUCC AGUUUACGCC AUCGAAAGAA ACCAGCACCG   7800
AUGUCACAUC AUCAGGCGUU GCAAUUUCAA AAGAGGGACG GGUAGCAUUG GUGACAUUAU   7860
CGUGAUCGUU GACGCCGCUA UCUGUUGUUA ACGUAACACU GUCAAUCUGA ACCUGCGUGU   7920
CGAUUUCAAU CCGCAGUUCG GCCGAUGUUU UGGUAUUACC AGCAAUAUCC GUUACGGUAA   7980
CAGAGAUCGU AUGCUGACCG UCAGACAGCG GUUGAUCCGG CGUAAAGGUU AAAUUCCCCC   8040
CUGUGUUUUC AAUGGUGUAA UCCCGACCAU CAAUAUGAAC CACAAUGUGU GAUACAUCAU   8100
UAUCGACAUU ACCGAUAAUA AACACCGGUU UGUUAAUCCU GGUAAGAUUA UCAUUAGUAU   8160
CAUCACCAGU AUCAUGGGUG GGAUCGAGUA CAAUUGUCGG CUCUCGCAGA GUCGUAUCAA   8220
```

-continued

```
UCGUAAACUG CAGCGUUUCU UGCGCAACGU UGCCGGCGAU AUCAGUCACA UCAACCAAGA    8280

GAGUGUGUUG CCCAUCAGGU AAUGCCGAAC CGACAUUAAA UAUCCAGCGG CCAUCCCUCC    8340

UUUUGUGAGU UCAAUCCAAU UAGCGGCGUU AUCGAUUUUA ACGCGCACAU GGGUUAUAUC    8400

AUCAGCGGUA ACAAUACUAA ACUGCGGCUG UCGACUUUGG UAAUGUUAUC UACAUCGCUA    8460

UCACCGCUAU CUGUAACCAA CGUGACGCUU UCAAUUUCAG CCGUCGUAUC UAUCACAACA    8520

GGUAAUGGUU UCGAUGUCGC GGUAUUUCCG GCCUUAUCUU CAACCGUAAC GGUAAUAUUA    8580

UAAGAGCCAU CCGGAAUGGC AUUGCCUGGU GUAAAUUGCC AACCAGCCCC AACCUUAGUC    8640

GCGUUAUAAU CAUGACCAUC AAUCGUCACC ACGACUUUGA UAACAUCGGG GUCAACAUUA    8700

CCAAUCGUAA AGGUGGGUCG UGAAAUAUUA GUAAUAUUAU CGGCGGUAUU CGCUCCGGUA    8760

UCUUGUCCUG CGUCUAAAGC AAUAGUAGGA ACCUGUAUAU UAGUAUCGAU AUUAAAUACU    8820

AAAUCUUUAU UCGCAAUAUU ACCUGCCUCA UCCCGUGGCC UCUACGCGAA GGGUAUAUGU    8880

GCCGUCAACC AGAGUAUUCG GGCUGUCAAA AAUCCACUGU CCGUCGGCAU UUUUGCGUAU    8940

CACAUUCCAG UUAGCGCCAC CAUCCAG                                       8967
```